(12) United States Patent

Cha et al.

(10) Patent No.: US 10,873,035 B2
(45) Date of Patent: Dec. 22, 2020

(54) HETEROCYCLIC COMPOUND AND ORGANIC LIGHT EMITTING DIODE CONTAINING SAME

(71) Applicant: LG Chem, Ltd., Seoul (KR)

(72) Inventors: Yongbum Cha, Daejeon (KR); Seongmi Cho, Daejeon (KR); Jungbum Kim, Daejeon (KR); Sung Kil Hong, Daejeon (KR); Jiwon Kwak, Daejeon (KR)

(73) Assignee: LG Chem, Ltd.

( * ) Notice: Subject to any disclaimer, the term of this patent is extended or adjusted under 35 U.S.C. 154(b) by 323 days.

(21) Appl. No.: 15/761,657

(22) PCT Filed: Feb. 23, 2017

(86) PCT No.: PCT/KR2017/001977
§ 371 (c)(1),
(2) Date: Mar. 20, 2018

(87) PCT Pub. No.: WO2017/146474
PCT Pub. Date: Aug. 31, 2017

(65) Prior Publication Data
US 2018/0351111 A1 Dec. 6, 2018

(30) Foreign Application Priority Data
Feb. 23, 2016 (KR) .................. 10-2016-0021349

(51) Int. Cl.
*H01L 51/00* (2006.01)
*C07D 307/91* (2006.01)
(Continued)

(52) U.S. Cl.
CPC ........ *H01L 51/0073* (2013.01); *C07D 307/91* (2013.01); *C07D 307/93* (2013.01); *C07D 405/04* (2013.01); *C07D 405/10* (2013.01); *C07D 405/12* (2013.01); *C07D 405/14* (2013.01); *C07D 407/04* (2013.01); *C07D 407/12* (2013.01); *C07D 409/04* (2013.01); *C07D 409/12* (2013.01); *C09K 11/06* (2013.01); *H01L 51/006* (2013.01);
(Continued)

(58) Field of Classification Search
None
See application file for complete search history.

(56) References Cited

U.S. PATENT DOCUMENTS

2004/0251816 A1  12/2004  Leo et al.
2009/0309488 A1  12/2009  Kato et al.
(Continued)

FOREIGN PATENT DOCUMENTS

JP  2014028819 A  2/2014
JP  2014224047 A  12/2014
(Continued)

OTHER PUBLICATIONS

Search report from International Application No. PCT/KR2017/001977, dated Jun. 5, 2017.

*Primary Examiner* — Robert S Loewe
(74) *Attorney, Agent, or Firm* — Lerner, David, Littenberg, Krumholz & Mentlik, LLP

(57) ABSTRACT

The present specification relates to a hetero-cyclic compound and an organic light emitting device including the same.

15 Claims, 4 Drawing Sheets

(51) Int. Cl.
*C09K 11/06* (2006.01)
*C07D 409/12* (2006.01)
*C07D 405/12* (2006.01)
*C07D 407/04* (2006.01)
*C07D 409/04* (2006.01)
*C07D 407/12* (2006.01)
*C07D 405/04* (2006.01)
*C07D 307/93* (2006.01)
*C07D 405/10* (2006.01)
*C07D 405/14* (2006.01)
*H01L 51/50* (2006.01)
*H01L 51/56* (2006.01)

(52) U.S. Cl.
CPC ...... *H01L 51/0052* (2013.01); *H01L 51/0054* (2013.01); *H01L 51/0059* (2013.01); *H01L 51/0061* (2013.01); *H01L 51/0067* (2013.01); *H01L 51/0072* (2013.01); *C09K 2211/1007* (2013.01); *C09K 2211/1088* (2013.01); *H01L 51/001* (2013.01); *H01L 51/0074* (2013.01); *H01L 51/5012* (2013.01); *H01L 51/5016* (2013.01); *H01L 51/5056* (2013.01); *H01L 51/5072* (2013.01); *H01L 51/5096* (2013.01); *H01L 51/56* (2013.01); *H01L 2251/558* (2013.01)

(56) References Cited

U.S. PATENT DOCUMENTS

| | | | |
|---|---|---|---|
| 2012/0104940 | A1 | 5/2012 | Shin et al. |
| 2015/0144938 | A1* | 5/2015 | Lee .................... H01L 51/0073 257/40 |
| 2015/0236262 | A1 | 8/2015 | Cho et al. |
| 2016/0351816 | A1* | 12/2016 | Kim .................... H01L 51/0073 |
| 2016/0351817 | A1* | 12/2016 | Kim .................... H01L 51/0052 |
| 2016/0351818 | A1* | 12/2016 | Kim .................... H01L 51/0073 |
| 2018/0127385 | A1* | 5/2018 | Jung .................... C07D 251/24 |
| 2018/0269405 | A1* | 9/2018 | Mun .................... C07D 403/04 |

FOREIGN PATENT DOCUMENTS

| | | | |
|---|---|---|---|
| JP | 2015534258 A | 11/2015 | |
| KR | 20140018825 A | 2/2014 | |
| KR | 20140049186 A | 4/2014 | |
| KR | 20150096593 A | 8/2015 | |
| KR | 20160141360 A | 12/2016 | |
| WO | 2014061963 A1 | 4/2014 | |
| WO | WO-2014061963 A1 * | 4/2014 | .......... C07D 333/76 |

\* cited by examiner

[Figure 1]
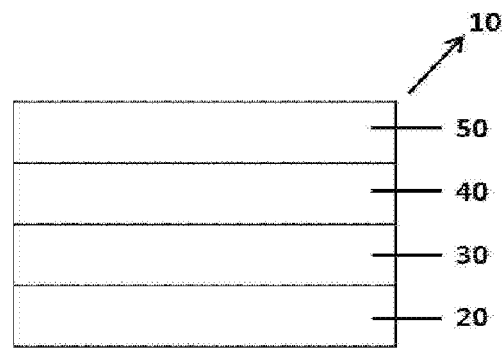
[Figure 2]
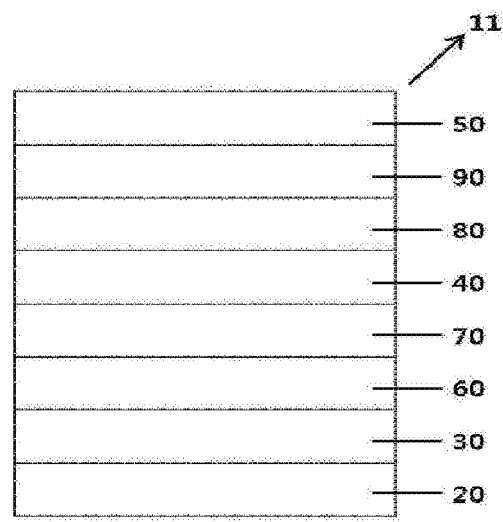

[Figure 3]
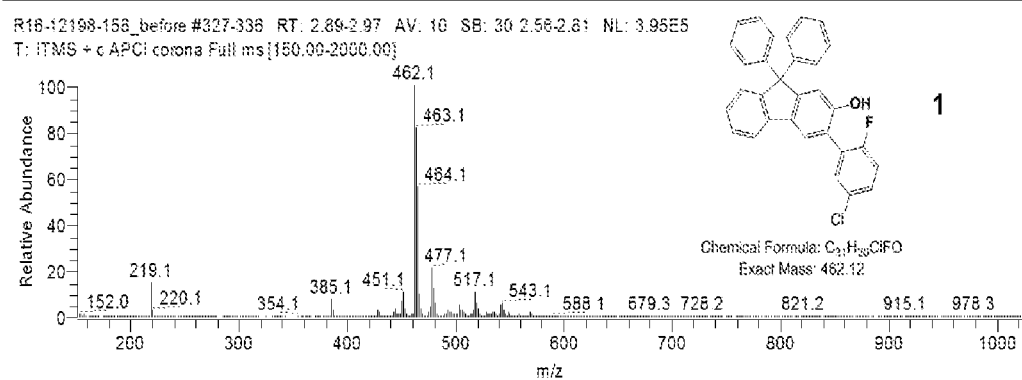
[Figure 4]
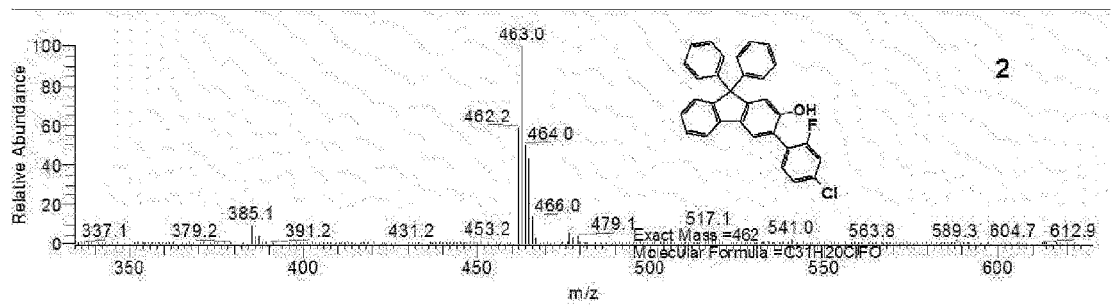
[Figure 5]
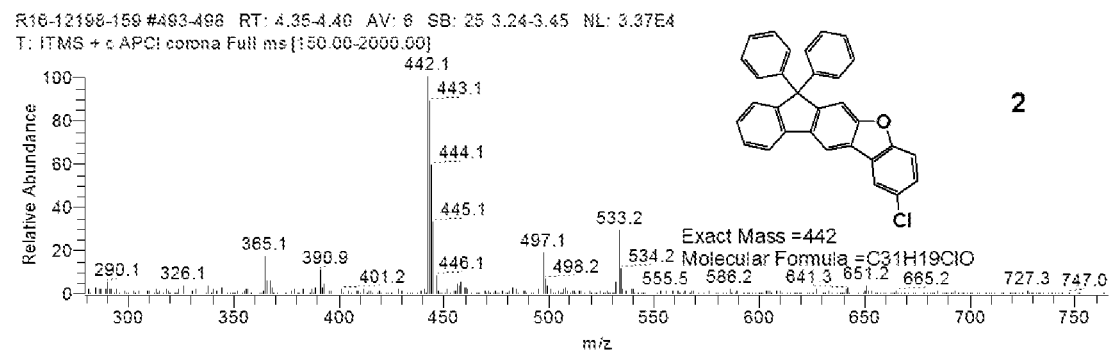

[Figure 6]
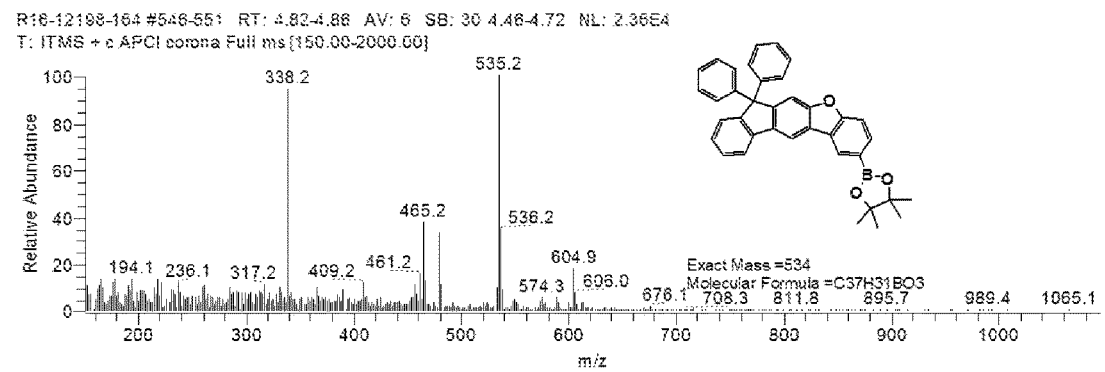
[Figure 7]
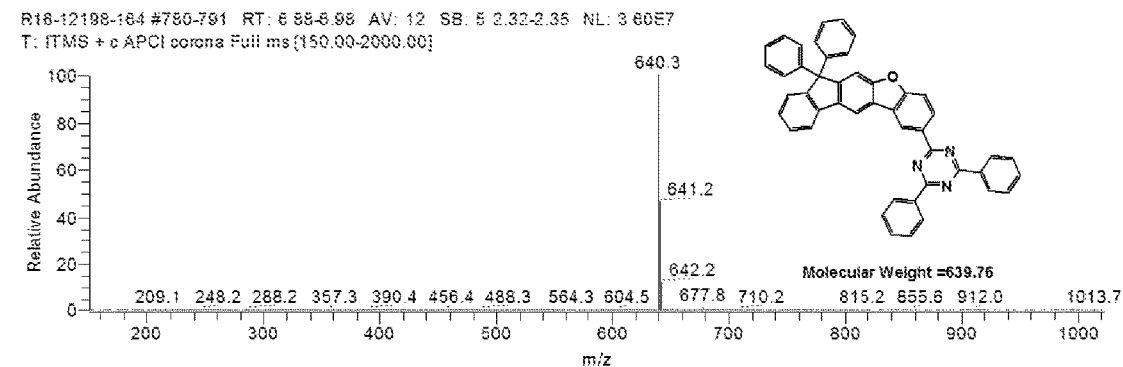
[Figure 8]
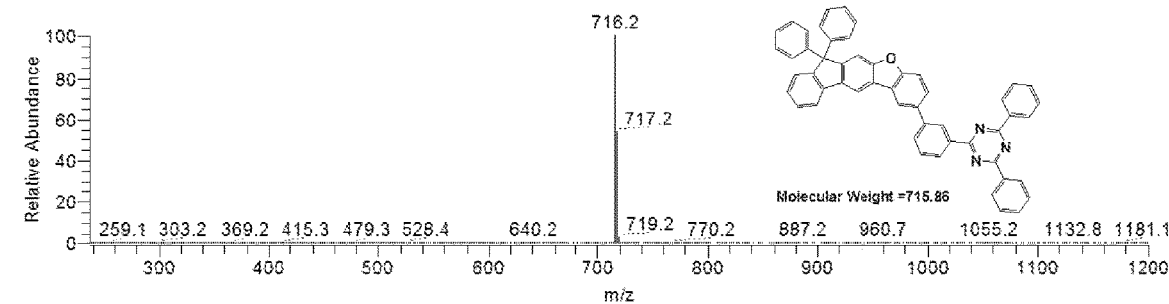

[Figure 9]
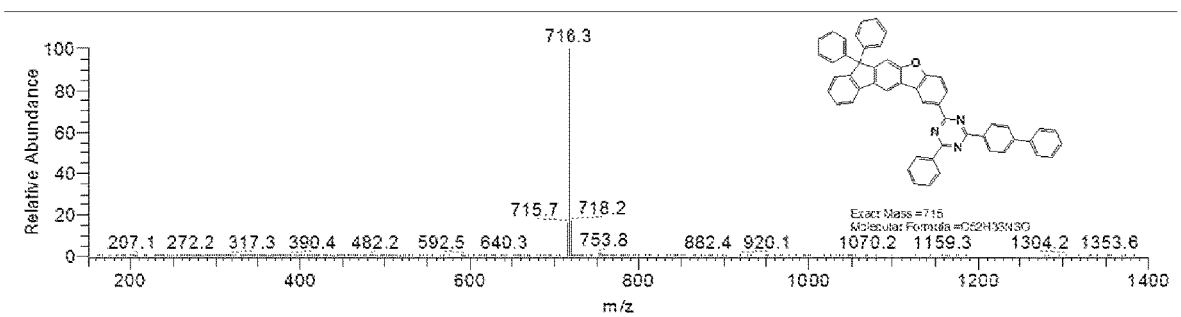

HETEROCYCLIC COMPOUND AND ORGANIC LIGHT EMITTING DIODE CONTAINING SAME

CROSS-REFERENCE TO RELATED APPLICATIONS

The present application is a national phase entry under 35 U.S.C. § 371 of International Application No. PCT/KR2017/001977 filed Feb. 23, 2017, which claims priority form Korean Patent Application No. 10-2016-0021349 filed in the Korean Intellectual Property Office on Feb. 23, 2016, the entire contents of which are incorporated herein by reference.

TECHNICAL FIELD

The present specification relates to a hetero-cyclic compound and an organic light emitting device including the same.

BACKGROUND ART

In general, an organic light emitting phenomenon refers to a phenomenon in which electric energy is converted into light energy by using an organic material. Ar1 organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document (Patent Document 1) US Patent Publication No. 2004-0251816

DETAILED DESCRIPTION OF THE INVENTION

Technical Problem

The present specification provides a hetero-cyclic compound and an organic light emitting device including the same.

Technical Solution

An exemplary embodiment of the present specification provides a hetero-cyclic compound represented by the following Chemical Formula 1.

[Chemical Formula 1]

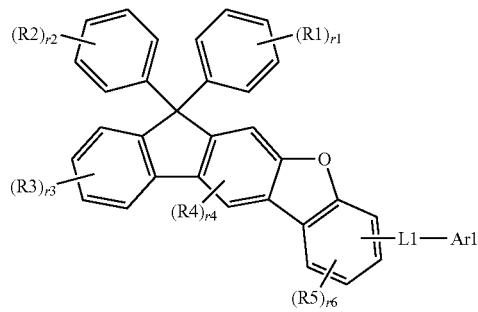

In Chemical Formula 1,

R1 to R5 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, L1 is a direct bond; a substituted or unsubstituted arylene group; or a substituted or unsubstituted heteroarylene group, Ar1 is a substituted or unsubstituted amine group; a substituted or unsubstituted phosphine oxide group; a substituted or unsubstituted aryl group; or a substituted or unsubstituted heteroaryl group, r1 and r2 are each an integer from 1 to 5, r3 is an integer from 1 to 4, r4 is 1 or 2, r5 is an integer from 1 to 3, and when r1 to r5 are each present in a plural number, a plurality of structures in the parenthesis is the same as or different from each other.

Further, an exemplary embodiment of the present specification provides an organic light emitting device including: a first electrode; a second electrode disposed to face the first electrode; and an organic material layer having one or more layers disposed between the first electrode and the second electrode, in which one or more layers of the organic material layer include the hetero-cyclic compound represented by Chemical Formula 1.

Advantageous Effects

The hetero-cyclic compound according to an exemplary embodiment of the present specification may be used as a material for an organic material layer of an organic light emitting device, and it is possible to improve efficiency, achieve low driving voltage, and/or improve service life characteristics in the organic light emitting device by using the same.

BRIEF DESCRIPTION OF DRAWINGS

FIG. 1 illustrates an organic light emitting device 10 according to an exemplary embodiment of the present specification.

FIG. 2 illustrates an organic light emitting device 11 according to another exemplary embodiment of the present specification.

FIG. 3 is a synthesis confirmation material of a precursor of Compound C according to still another exemplary embodiment of the present specification.

FIG. 4 is a synthesis confirmation material of a precursor of Compound B according to yet another exemplary embodiment of the present specification.

FIG. 5 is a synthesis confirmation material of Compound C according to still yet another exemplary embodiment of the present specification.

FIG. 6 is a synthesis confirmation material of Compound C-1 according to a further exemplary embodiment of the present specification.

FIG. 7 is a synthesis confirmation material of a compound according to another further exemplary embodiment of the present specification.

FIG. 8 is a synthesis confirmation material of a compound according to still another further exemplary embodiment of the present specification.

FIG. 9 is a synthesis confirmation material of a compound according to yet another further exemplary embodiment of the present specification.

EXPLANATION OF REFERENCE NUMERALS AND SYMBOLS 10, 11: Organic light emitting device
20: Substrate
30: First electrode
40: Light emitting layer
50: Second electrode
60: Hole injection layer
70: Hole transporting layer
80: Electron transporting layer
90: Electron injection layer

BEST MODE

Hereinafter, the present specification will be described in more detail.

The present specification provides the hetero-cyclic compound represented by Chemical Formula 1.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with the another member, but also a case where still another member is present between the two members.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a nitrile group; a nitro group; an imide group; an amide group; a carbonyl group; an ester group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heterocyclic group or being substituted with a substituent to which two or more substituents are linked among the substituents exemplified above, or having no substituent. For example, "the substituent to which two or more substituents are linked" may be a biphenyl group. That is, the biphenyl group may also be an aryl group, and may be interpreted as a substituent to which two phenyl groups are linked.

In the present specification,

means a moiety bonded to another substituent or a bonding portion. In the present specification, a halogen group may be fluorine, chlorine, bromine, or iodine.

In the present specification, the number of carbon atoms of an imide group is not particularly limited, but is preferably 1 to 30. Specifically, the imide group may be a compound having the following structures, but is not limited thereto.

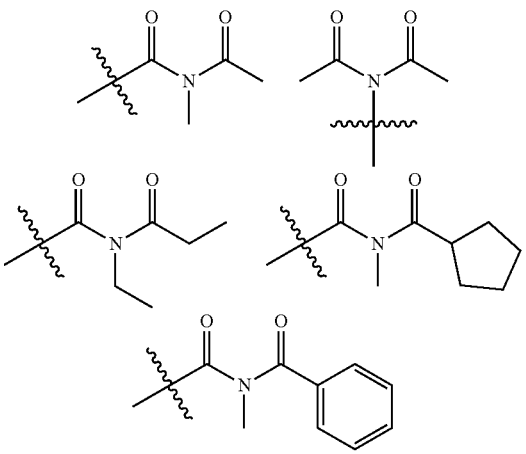

In the present specification, for an amide group, the nitrogen of the amide group may be substituted with hydrogen, a straight, branched, or cyclic alkyl group having 1 to 30 carbon atoms, or an aryl group having 6 to 30 carbon atoms. Specifically, the amide group may be a compound having the following structural formulae, but is not limited thereto.

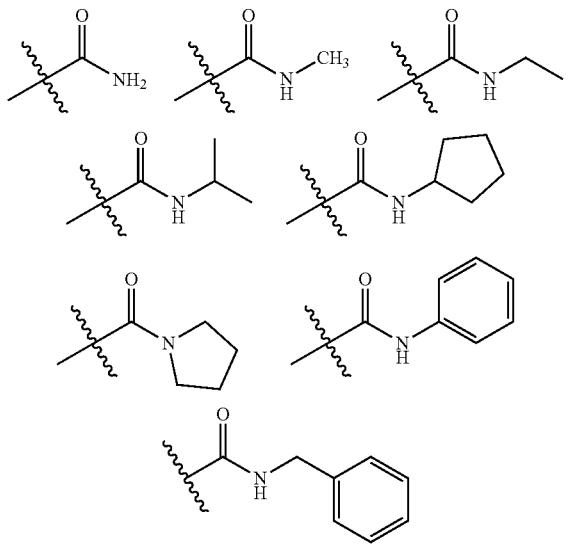

In the present specification, the number of carbon atoms of a carbonyl group is not particularly limited, but is preferably 1 to 30. Specifically, the carbonyl group may be a compound having the following structures, but is not limited thereto.

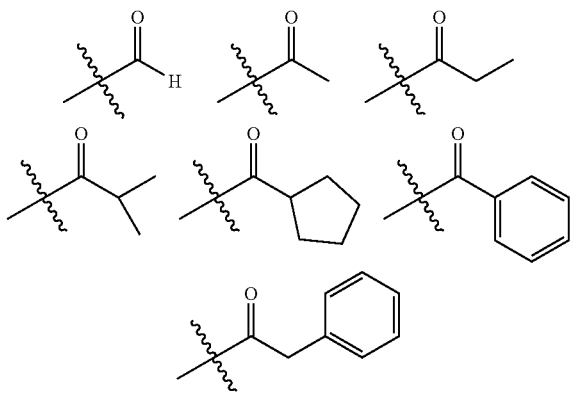

In the present specification, for an ester group, the oxygen of the ester group may be substituted with a straight, branched, or cyclic alkyl group having 1 to 25 carbon atoms, or an aryl group having 6 to 30 carbon atoms. Specifically, the ester group may be a compound having the following structural formulae, but is not limited thereto.

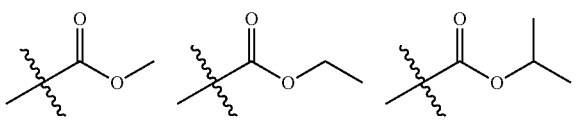

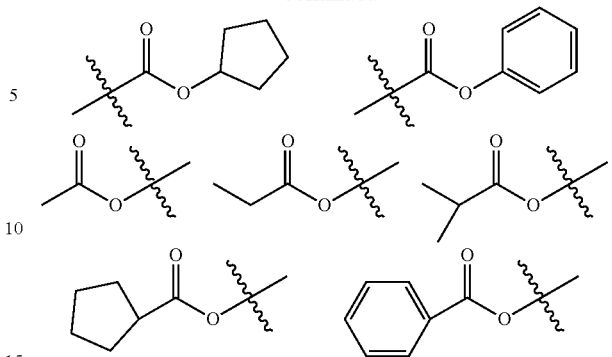

In the present specification, the alkyl group may be straight or branched, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but has preferably 3 to 30 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight, branched, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, an amine group may be selected from the group consisting of —$NH_2$; an alkylamine group; an N-alkylarylamine group; an arylamine group; an N-arylheteroarylamine group; an N-alkylheteroarylamine group; and a heteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group, an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenyl terphenylamine group; an N-phenanthrenylfluorenylamine group; an N-biphenylfluorenylamine group, and the like, but are not limited thereto.

In the present specification, an N-alkylarylamine group means an amine group in which an alkyl group and an aryl group are substituted with N of the amine group. In the present specification, an N-arylheteroarylamine group means an amine group in which an aryl group and a heteroaryl group are substituted with N of the amine group.

In the present specification, an N-alkylheteroarylamine group means an amine group in which an alkyl group and a heteroaryl group are substituted with N of the amine group.

In the present specification, the alkyl group in the alkylamine group, the N-arylalkylamine group, the alkylthioxy group, the alkylsulfoxy group, and the N-alkylheteroarylamine group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but the examples are not limited thereto.

In the present specification, the alkenyl group may be straight or branched, and the number of carbon atoms thereof is not particularly limited, but is preferably 2 to 30. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be —BR$_{100}$R$_{101}$, and R$_{100}$ and R$_{101}$ are the same as or different from each other, and may be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted straight or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present specification, specific examples of a phosphine oxide group include a diphenylphosphine oxide group, dinaphthylphosphine oxide group, and the like, but are not limited thereto.

In the present specification, an aryl group is not particularly limited, but has preferably 6 to 30 carbon atoms, and the aryl group may be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a triphenyl group, a pyrenyl group, a phenalenyl group, a perylenyl group, a chrysenyl group, a fluorenyl group, and the like, but are not limited thereto.

In the present specification, the fluorenyl group may be substituted, and adjacent substituents may be bonded to each other to form a ring.

When the fluorenyl group is substituted, the fluorenyl group may be

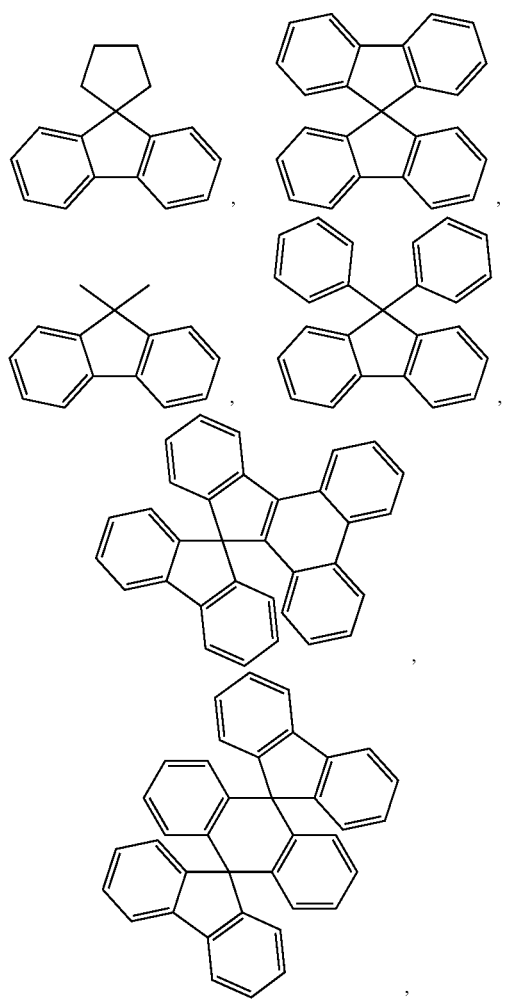

and the like. However, the fluorenyl group is not limited thereto.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the aryl group in the aryloxy group, the arylthioxy group, the arylsulfoxy group, the N-arylalkylamine group, the N-arylheteroarylamine group, and the arylphosphine group is the same as the above-described examples of the aryl group. Specifically, examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but the examples are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group. For example, the aryl group in the arylamine group may be selected from the above-described examples of the aryl group.

In the present specification, a heteroaryl group includes one or more atoms other than carbon, that is, one or more heteroatoms, and specifically, the heteroatom may include one or more atoms selected from the group consisting of O, N, Se, and S, and the like. The number of carbon atoms thereof is not particularly limited, but is preferably 2 to 30, and the heteroaryl group may be monocyclic or polycyclic. Examples of a hetero-cyclic group include a thiophene group, a furanyl group, a pyrrole group, an imidazolyl group, a triazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group (phenanthroline), an isoxazolyl group, a thiadiazolyl group, a phenothiazinyl group, a dibenzofuranyl group, and the like, but are not limited thereto.

In the present specification, examples of a heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include a monocyclic heteroaryl group, a polycyclic heteroaryl group, or both a monocyclic heteroaryl group and a polycyclic heteroaryl group. For example, the heteroaryl group in the heteroarylamine group may be selected from the above-described examples of the heteroaryl group.

In the present specification, examples of the heteroaryl group in the N-arylheteroarylamine group and the N-alkylheteroarylamine group are the same as the above-described examples of the heteroaryl group.

In the present specification, an arylene group means a group having two bonding positions in an aryl group, that is, a divalent group. The above-described description on the aryl group may be applied to the arylene group, except for a divalent arylene group.

In the present specification, a heteroarylene group means a group having two bonding positions in a heteroaryl group, that is, a divalent group. The above-described description on the heteroaryl group may be applied to the heteroarylene group, except for a divalent heteroarylene group.

According to an exemplary embodiment of the present specification, Chemical Formula 1 is represented by any one of the following Chemical Formulae 2 to 5.

[Chemical Formula 2]

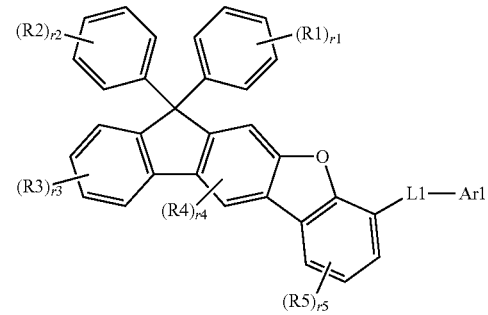

[Chemical Formula 3]

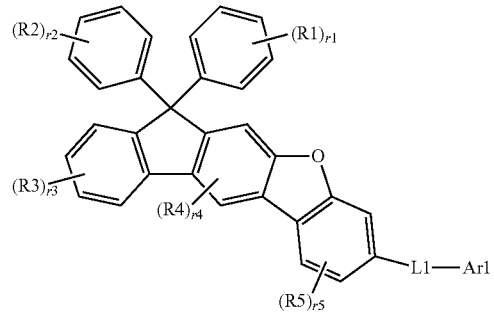

[Chemical Formula 4]

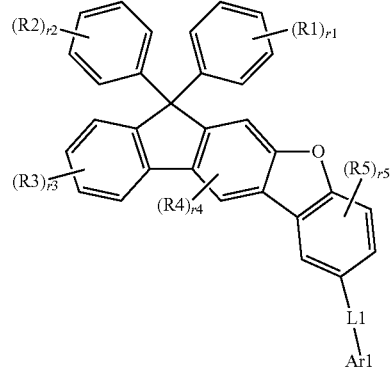

-continued

[Chemical Formula 5]

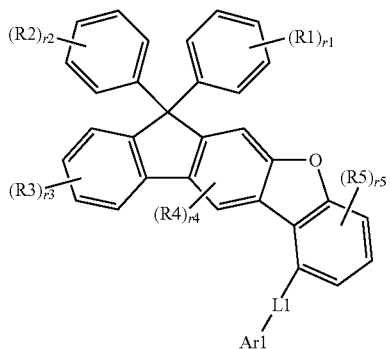

[Chemical Formula 8]

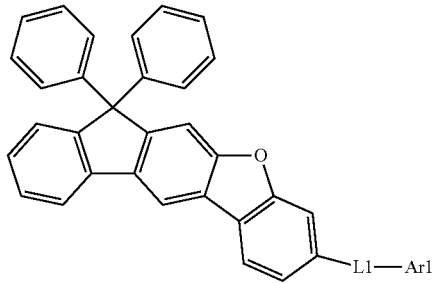

[Chemical Formula 9]

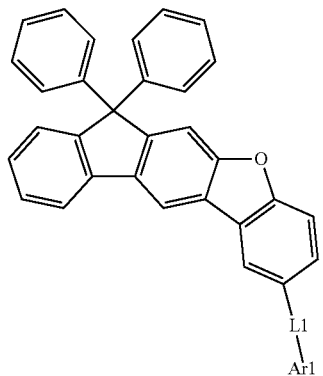

In Chemical Formulae 2 to 5, the definitions of R1 to R5, r1 to r5, L1, and Ar1 are the same as those in Chemical Formula 1.

According to an exemplary embodiment of the present specification, Chemical Formula 1 is represented by the following Chemical Formula 6.

[Chemical Formula 6]

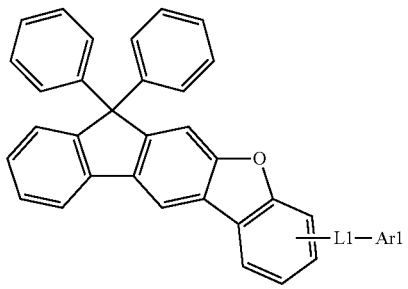

[Chemical Formula 10]

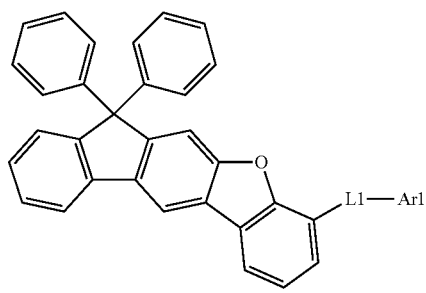

In Chemical Formula 6, the definitions of L1 and Ar1 are the same as those in Chemical Formula 1.

According to an exemplary embodiment of the present specification, Chemical Formula 1 is represented by any one of the following Chemical Formulae 7 to 10.

[Chemical Formula 7]

In Chemical Formulae 7 to 10, the definitions of L1 and Ar1 are the same as those in Chemical Formula 1.

According to an exemplary embodiment of the present specification, in Chemical Formula 1, L1 is a direct bond; an arylene group; or a heteroarylene group.

According to an exemplary embodiment of the present specification, in Chemical Formula 1, L1 is a direct bond.

According to an exemplary embodiment of the present specification, in Chemical Formula 1, L1 is a monocyclic arylene group.

According to an exemplary embodiment of the present specification, in Chemical Formula 1, L1 is a monocyclic arylene group having 6 to 20 carbon atoms.

According to an exemplary embodiment of the present specification, in Chemical Formula 1, L1 is a substituted or unsubstituted phenylene group.

According to an exemplary embodiment of the present specification, in Chemical Formula 1, L1 is a phenylene group.

According to an exemplary embodiment of the present specification, in Chemical Formula 1, L1 is a polycyclic arylene group having 10 to 20 carbon atoms.

According to an exemplary embodiment of the present invention, in Chemical Formula 1, L1 is a substituted or unsubstituted phenylene group; a substituted or unsubstituted biphenylylene group; a substituted or unsubstituted naphthylene group; a substituted or unsubstituted terphenylene group; a substituted or unsubstituted quarterphenylene group; a substituted or unsubstituted anthracenylene group; a substituted or unsubstituted fluorenylene group; a substituted or unsubstituted phenanthrenylene group; a substituted or unsubstituted pyrenylene group; or a substituted or unsubstituted triphenylenylene group.

According to an exemplary embodiment of the present invention, in Chemical Formula 1, L1 is a biphenylylene group; a naphthylene group; a terphenylene group; a quarterphenylene group; an anthracenylene group; a fluorenylene group; a phenanthrenylene group; a pyrenylene group; or a triphenylenylene group.

According to an exemplary embodiment of the present specification, in Chemical Formula 1, L1 is a monocyclic or polycyclic heteroarylene group.

According to an exemplary embodiment of the present specification, in Chemical Formula 1, L1 is a monocyclic or polycyclic N-containing heteroarylene group.

According to an exemplary embodiment of the present specification, in Chemical Formula 1, L1 is a polycyclic N-containing heteroarylene group.

According to an exemplary embodiment of the present specification, in Chemical Formula 1, L1 is a polycyclic N-containing heteroarylene group having 6 to 20 carbon atoms.

According to an exemplary embodiment of the present specification, in Chemical Formula 1, L1 is an unsubstituted carbazolylene group.

According to an exemplary embodiment of the present specification, in Chemical Formula 1, L1 is a direct bond; a phenylene group; a naphthylene group; an anthracenylene group; a fluorenylene group; a phenanthrenylene group; or a carbazolylene group.

According to an exemplary embodiment of the present specification, in Chemical Formula 1, L1 is a direct bond; a phenylene group; an anthracenylene group; a fluorenylene group; a phenanthrenylene group; or a carbazolylene group.

According to an exemplary embodiment of the present specification, in Chemical Formula 1, L1 may be any one of the following structures, but is not limited thereto.

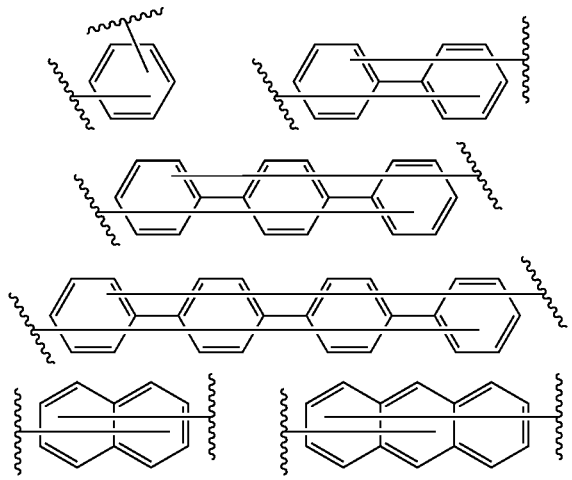

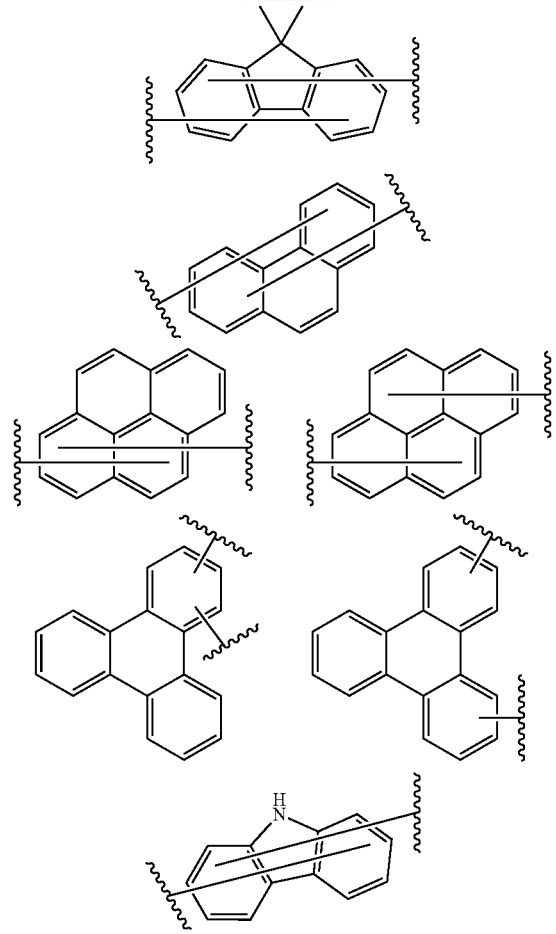

According to an exemplary embodiment of the present specification, in Chemical Formula 1, L1 is a direct bond; a phenylene group; an anthracenylene group; or a carbazolylene group.

According to an exemplary embodiment of the present specification, in Chemical Formula 1, L1 is a direct bond; a phenylene group; or a carbazolylene group.

According to an exemplary embodiment of the present specification, in Chemical Formula 1, Ar1 is selected from the group consisting of a substituted or unsubstituted diarylamine group; a substituted or unsubstituted diheteroarylamine group; a substituted or unsubstituted silyl group; a substituted or unsubstituted phosphine oxide group; a substituted or unsubstituted aryl group; and a substituted or unsubstituted heteroaryl group.

According to an exemplary embodiment of the present specification, in Chemical Formula 1, Ar1 is selected from the group consisting of a substituted or unsubstituted phenyl group; a substituted or unsubstituted biphenyl group; a substituted or unsubstituted phenanthrenyl group; a substituted or unsubstituted naphthyl group; a substituted or unsubstituted terphenyl group; a substituted or unsubstituted fluorenyl group; a substituted or unsubstituted anthracenyl group; a substituted or unsubstituted chrysenyl group; a substituted or unsubstituted quarterphenyl group; a substituted or unsubstituted spirobifluorenyl group; a substituted or unsubstituted pyrenyl group; a substituted or unsubstituted triphenylenyl group; a substituted or unsubstituted perylenyl group; a substituted or unsubstituted triazinyl group; a substituted or unsubstituted pyrimidyl group; a substituted or unsubstituted pyridyl group; a substituted or unsubstituted quinolinyl group; a substituted or unsubstituted quinazolinyl group; a substituted or unsubstituted benzoquinolinyl group; a substituted or unsubstituted phenanthrolinyl group; a substituted or unsubstituted quinoxalinyl group; a substituted or unsubstituted dibenzofuranyl group; a substituted or unsubstituted dibenzothiophene group; a substituted or unsubstituted benzonaphthofuranyl group; a substituted or unsubstituted benzonaphthothiophene group; a substituted or unsubstituted dimethylphosphine oxide group; a substituted or unsubstituted diphenylphosphine oxide group; a substituted or unsubstituted dinaphthylphosphine oxide group; a substituted or unsubstituted benzoxazolyl group; a substituted or unsubstituted benzothiazolyl group; a substituted or unsubstituted benzimidazolyl group; a substituted or unsubstituted triphenylsilyl group; a substituted or unsubstituted phenothiazinyl group; a substituted or unsubstituted phenoxazinyl group; a substituted or unsubstituted thiophene group; a substituted or unsubstituted diphenylamine group; a substituted or unsubstituted N-phenylnaphthylamine group; a substituted or unsubstituted N-phenylbiphenylamine group; a substituted or unsubstituted N-phenylphenanthrenylamine group; a substituted or unsubstituted N-biphenylnaphthylamine group; a substituted or unsubstituted dibiphenylamine group; a substituted or unsubstituted N-biphenylphenanthrenylamine group; a substituted or unsubstituted dinaphthylamine group; a substituted or unsubstituted N-quarterphenylfluorenylamine group; a substituted or unsubstituted N-terphenylfluorenylamine group; a substituted or unsubstituted N-biphenylterphenylamine group; a substituted or unsubstituted N-biphenylfluorenylamine group; a substituted or unsubstituted N-phenylfluorenylamine group; a substituted or unsubstituted N-naphthylfluorenylamine group; a substituted or unsubstituted N-phenanthrenylfluorenylamine group; a substituted or unsubstituted difluorenylamine group; a substituted or unsubstituted N-phenylterphenylamine group; a substituted or unsubstituted N-phenylcarbazolylamine group; a substituted or unsubstituted N-biphenylcarbazolylamine group; a substituted or unsubstituted N-phenylbenzocarbazolylamine group; a substituted or unsubstituted N-biphenylbenzocarbazolylamine group; a substituted or unsubstituted N-fluorenylcarbazolylamine group; a substituted or unsubstituted benzocarbazolyl group; a substituted or unsubstituted dibenzocarbazolyl group; a substituted or unsubstituted carbazolyl group; and a structure represented by the following Chemical Formula a, and ---- means a moiety bonded to Chemical Formula 1 via L1.

[Chemical Formula a]

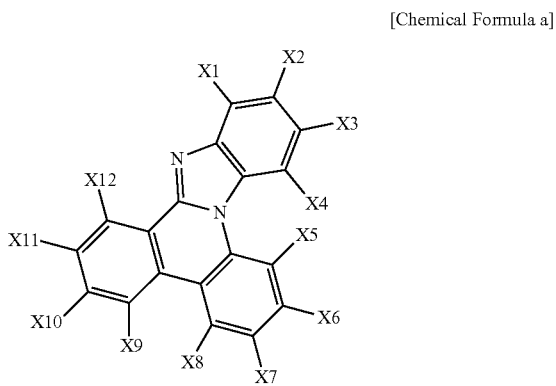

In Chemical Formula a, any one of X1 to X12 is a moiety bonded to Chemical Formula 1 via L1, and the others are the same as or different from each other, and are each independently hydrogen; a substituted or unsubstituted alkyl group; a substituted or unsubstituted aryl group; or a substituted or unsubstituted heteroaryl group, or adjacent groups are linked to each other to form a substituted or unsubstituted ring.

According to an exemplary embodiment of the present specification, in Chemical Formula a, any one of X1 to X12 is a moiety bonded to Chemical Formula 1 via L1, and the others are hydrogen.

According to an exemplary embodiment of the present specification, in Chemical Formula a, X11 and X12 are linked to each other to form a substituted or unsubstituted monocyclic or polycyclic hydrocarbon ring having 6 to 20 carbon atoms.

According to an exemplary embodiment of the present specification, in Chemical Formula a, X11 and X12 are linked to each other to form a substituted or unsubstituted monocyclic or polycyclic hydrocarbon ring having 6 to 10 carbon atoms.

According to an exemplary embodiment of the present specification, in Chemical Formula a, X11 and X12 are linked to each other to form a substituted or unsubstituted benzene ring.

According to an exemplary embodiment of the present specification, in Chemical Formula a, X11 and X12 are linked to each other to form a benzene ring.

According to an exemplary embodiment of the present specification, in Chemical Formula 1, Ar1 is a substituted or unsubstituted amine group; a substituted or unsubstituted phosphine oxide group; a substituted or unsubstituted aryl group; or a substituted or unsubstituted heteroaryl group.

According to an exemplary embodiment of the present specification, in Chemical Formula 1, Ar1 is selected from the group consisting of a phenyl group; a biphenyl group; a phenanthrenyl group; a naphthyl group; a terphenyl group; a fluorenyl group; an anthracenyl group; a chrysenyl group; a quarterphenyl group; a spirobifluorenyl group; a pyrenyl group; a triphenylenyl group; a perylenyl group; a triazinyl group; a pyrimidyl group; a pyridyl group; a quinolinyl group; a quinazolinyl group; a benzoquinolinyl group; a phenanthrolinyl group; a quinoxalinyl group; a dibenzofuranyl group; a dibenzothiophene group; benzonaphthofuranyl group; a benzonaphthothiophene group; a dimethylphosphine oxide group; diphenylphosphine oxide group; dinaphthylphosphine oxide group; a benzoxazolyl group; a benzothiazolyl group; a benzimidazolyl group; a triphenylsilyl group; a phenothiazinyl group; a phenoxazinyl group; a thiophene group; a diphenylamine group; an N-phenylnaphthylamine group; an N-phenylbiphenylamine group; an N-phenylphenanthrenylamine group; an N-biphenylnaphthylamine group; a dibiphenylamine group; an N-biphenylphenanthrenylamine group; a dinaphthylamine group; an N-quarterphenylfluorenylamine group; an N-terphenylfluorenylamine group; an N-biphenylterphenylamine group; an N-biphenylfluorenylamine group; a substituted or unsubstituted N-phenylfluorenylamine group; an N-naphthylfluorenylamine group; an N-phenanthrenylfluorenylamine group; a difluorenylamine group; an N-phenylterphenylamine group; an N-phenylcarbazolylamine group; an N-biphenylcarbazolylamine group; an N-phenylbenzocarbazolylamine group; an N-biphenylbenzocarbazolylamine group; an N-fluorenylcarbazolylamine group; a benzocarbazolyl group; a dibenzocarbazolyl group; a carbazolyl group;

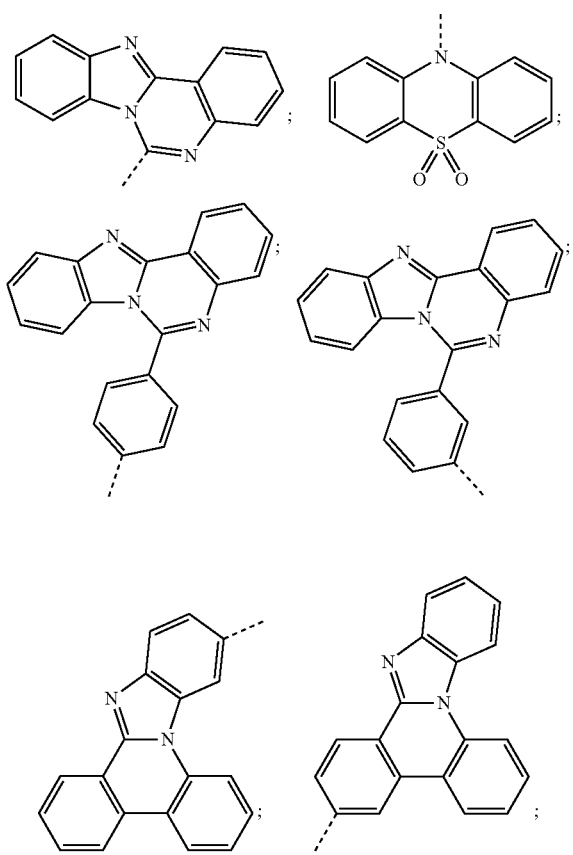

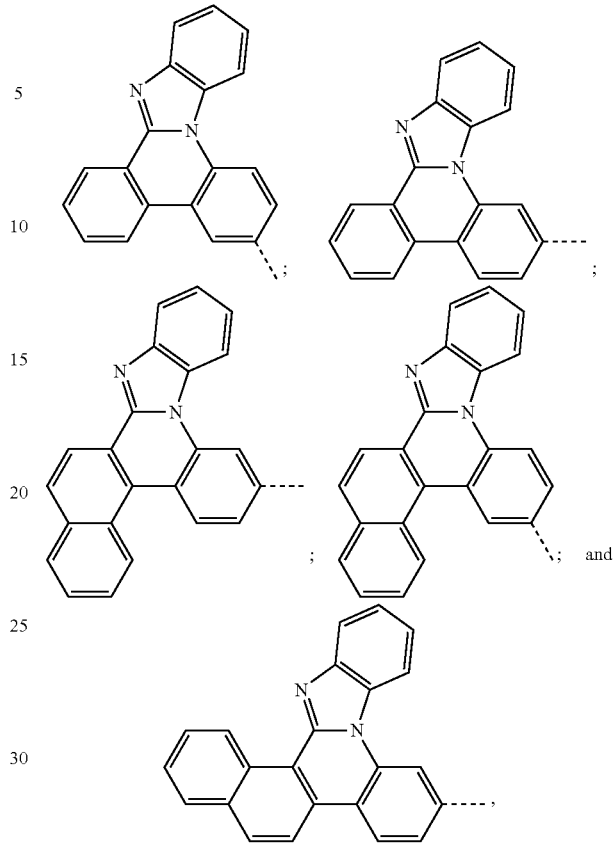

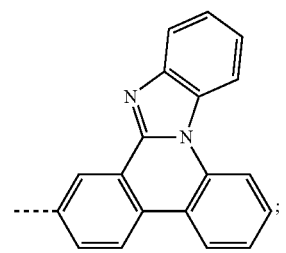

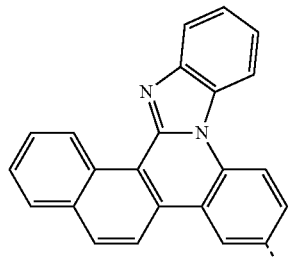

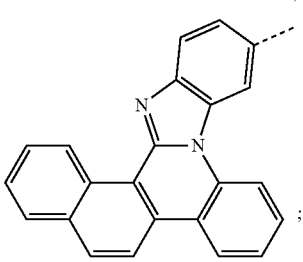

and

Ar1 may be unsubstituted or substituted with one or more selected from the group consisting of deuterium; a fluorine group; a nitrile group; a methyl group; a t-butyl group; a phenyl group; a biphenyl group; a naphthyl group; a fluorenyl group; a phenanthrenyl group; a carbazolyl group; a benzocarbazolyl group; a pyridyl group; a triazinyl group; a triphenylenyl group; a pyrimidyl group; a quinolinyl group; a dibenzofuranyl group; a dibenzothiophene group; a benzimidazolyl group; a benzothiazolyl group; a benzoxazolyl group; a thiophene group; a dimethylphosphine oxide group; a diphenylphosphine oxide group; a dinaphthylphosphine oxide group; a trimethylsilyl group; a triphenylsilyl group; a diphenylamine group; a dibiphenylamine group; an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-phenanthrenylfluorenylamine group; an N-biphenylfluorenylamine group; and

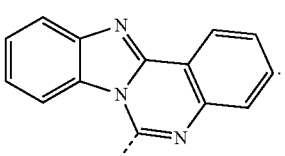

---- means a moiety bonded to Chemical Formula 1 via L1.

According to an exemplary embodiment of the present specification, in Chemical Formula 1, Ar1 is represented by any one of the following Structural Formulae [A-1] to [A-5].
[A-1]
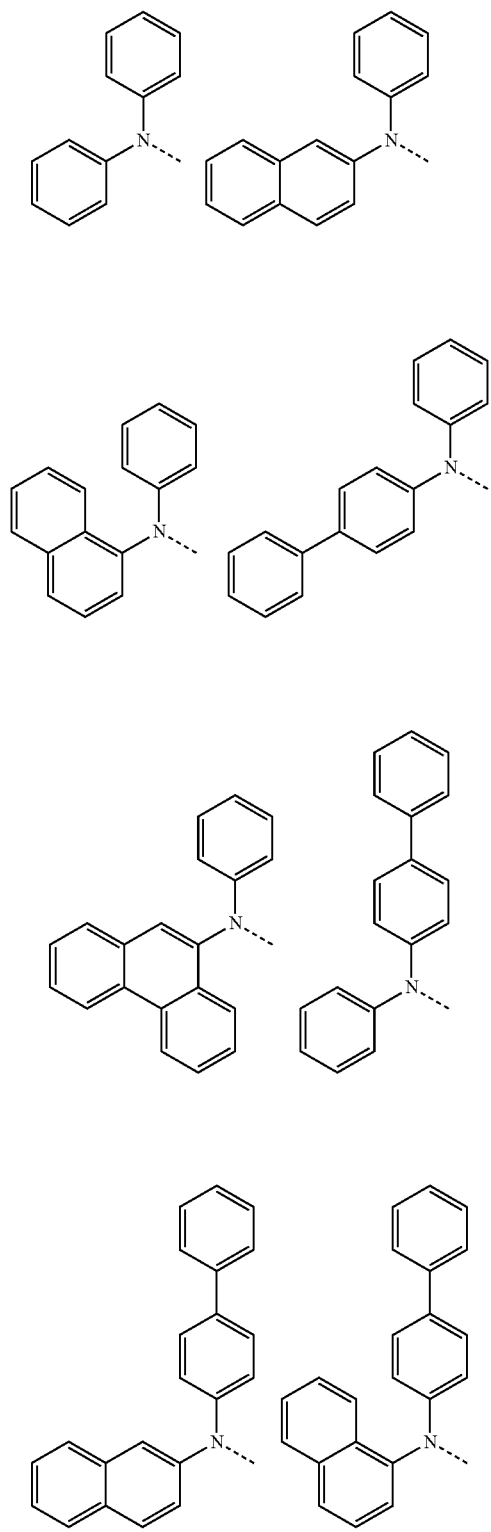
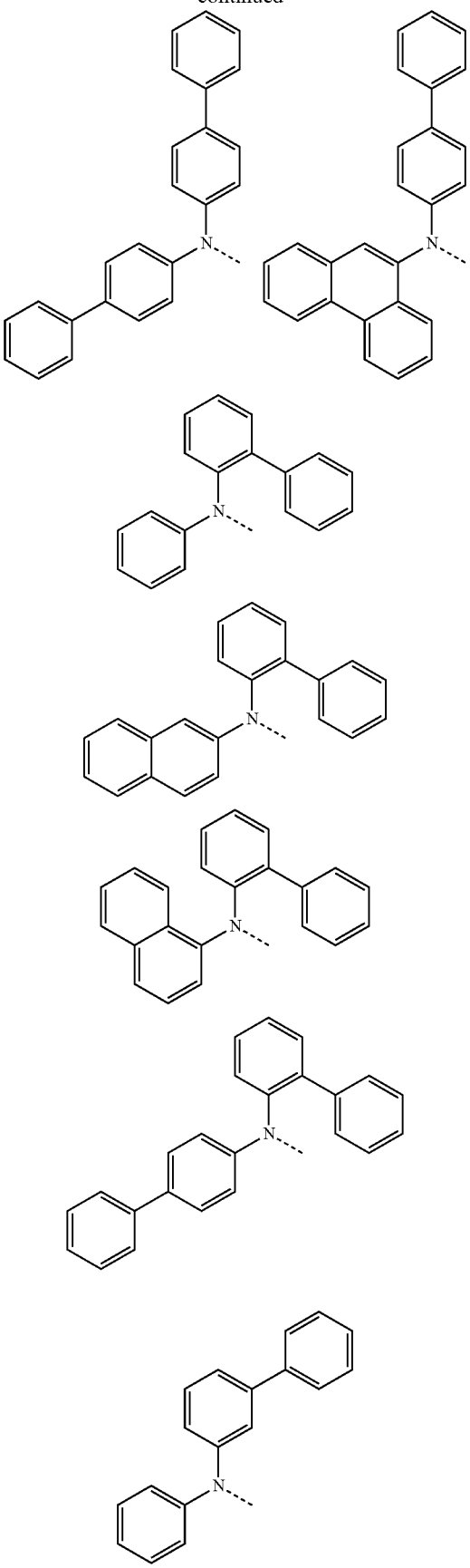

-continued
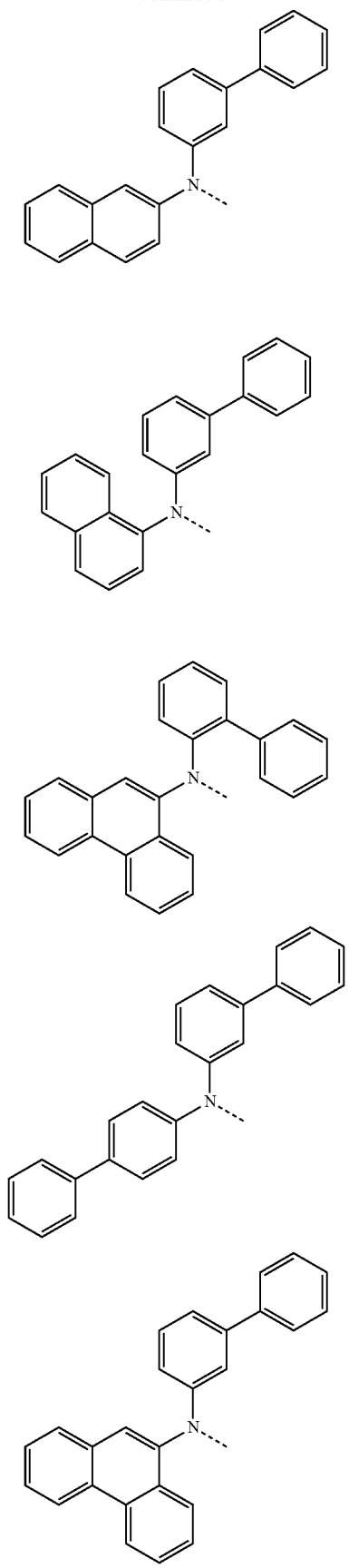
-continued
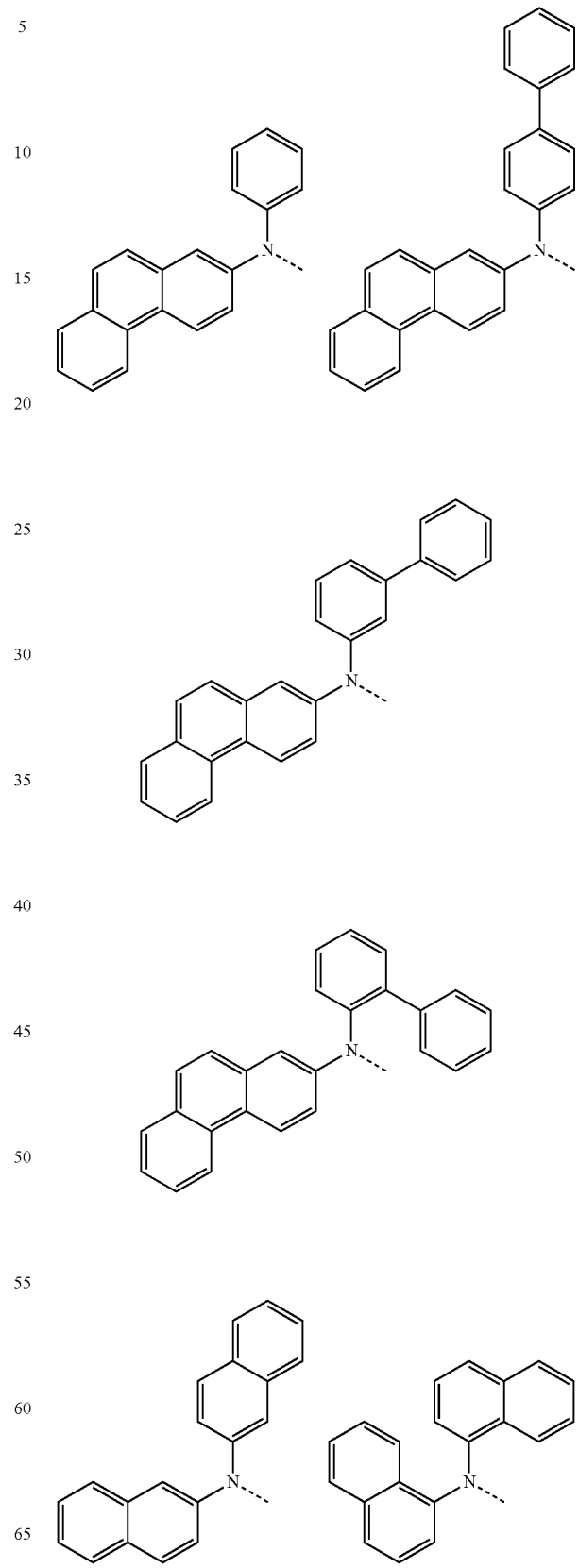

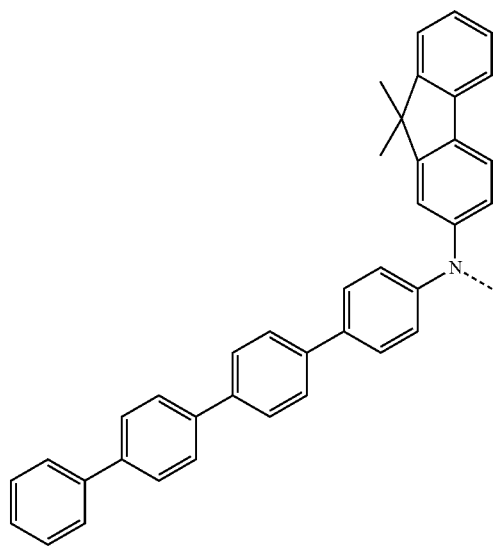
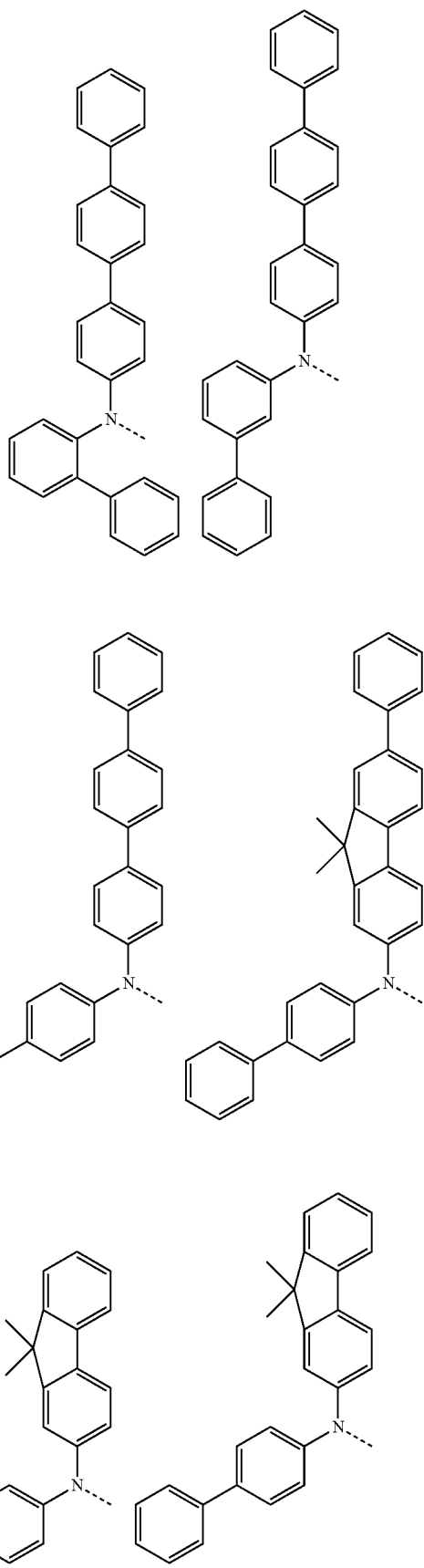

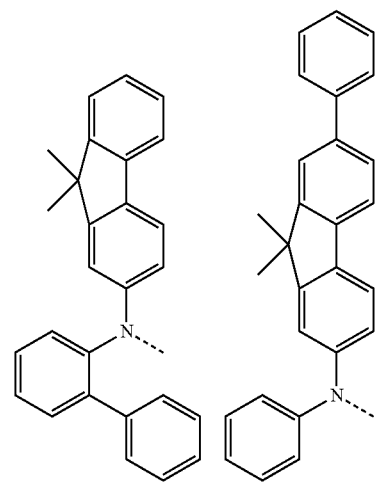
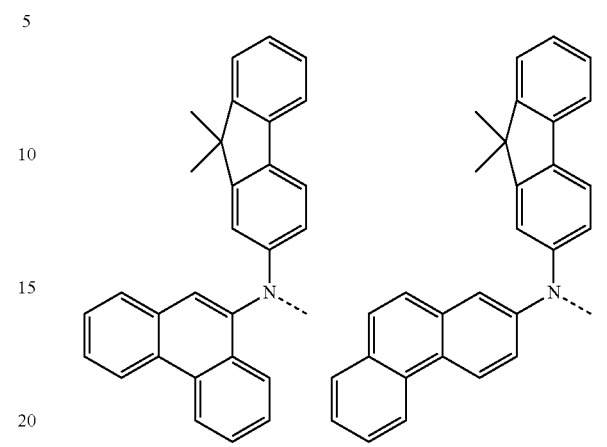
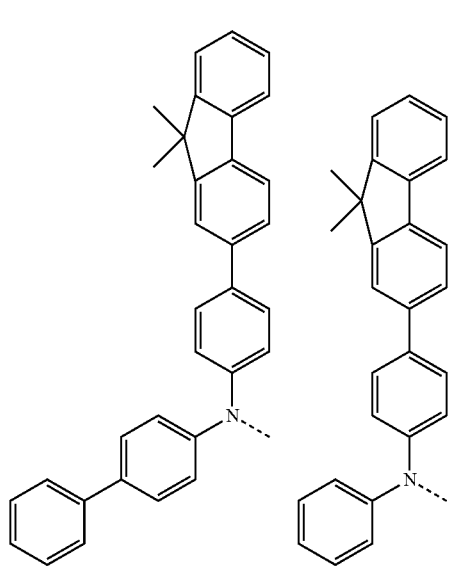
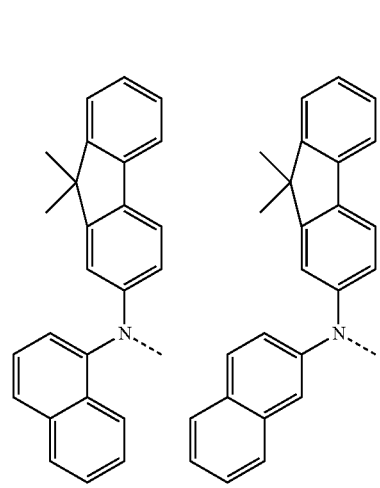
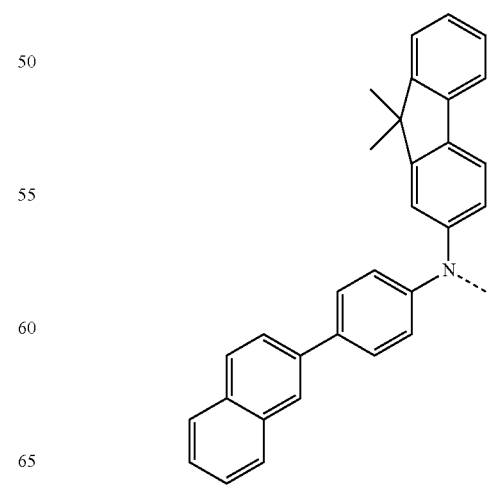

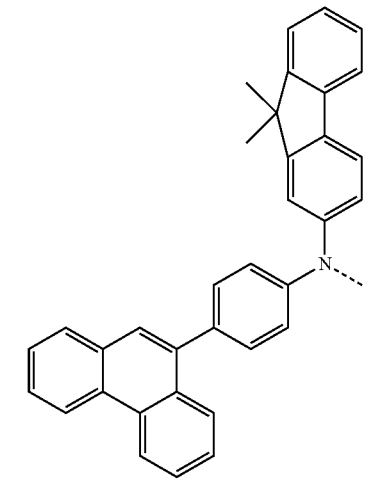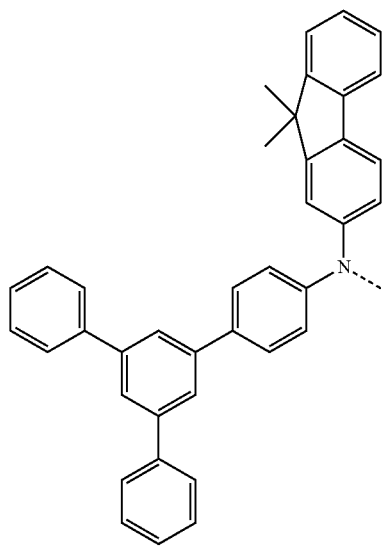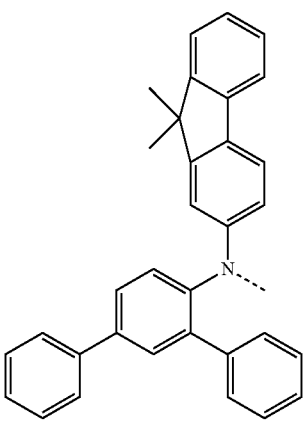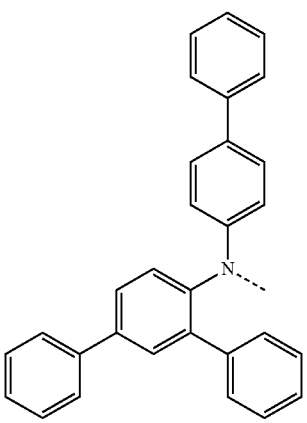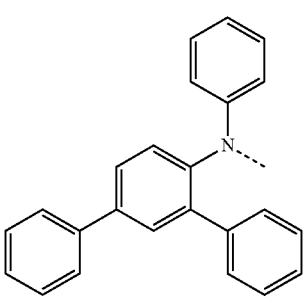

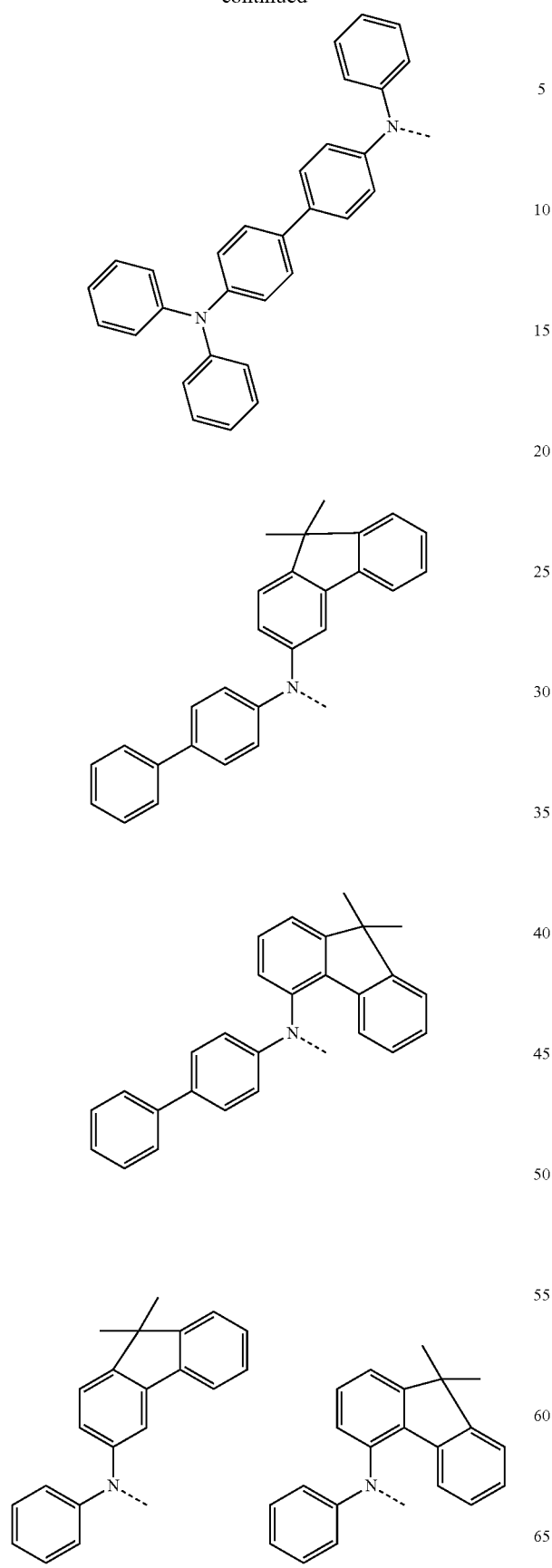
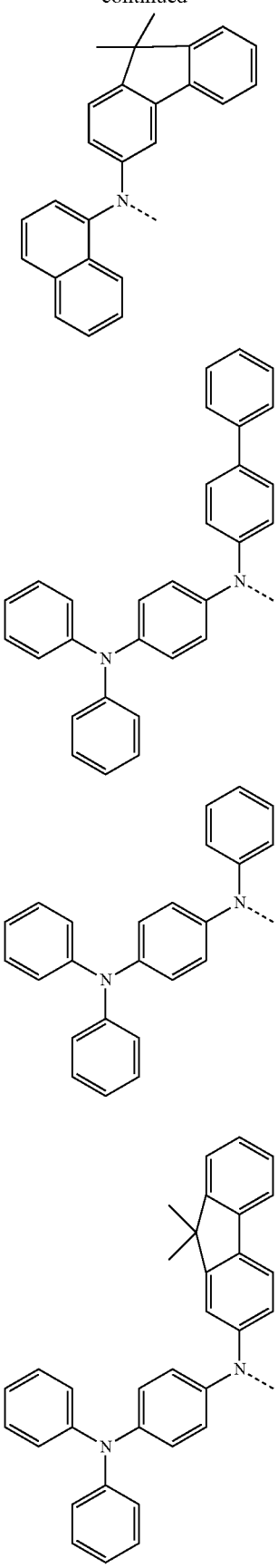

31
-continued
32
-continued
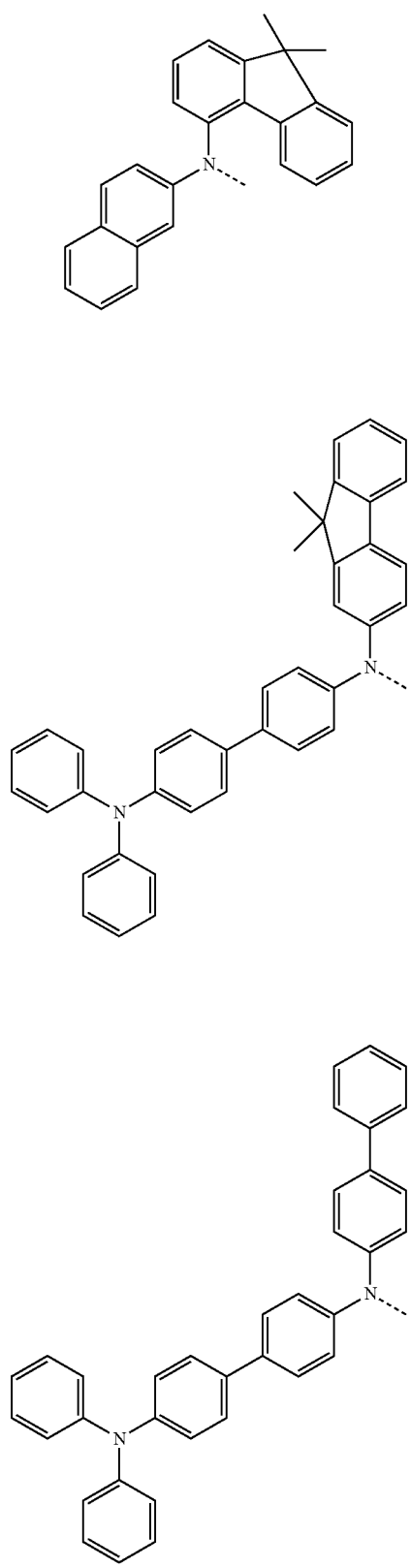
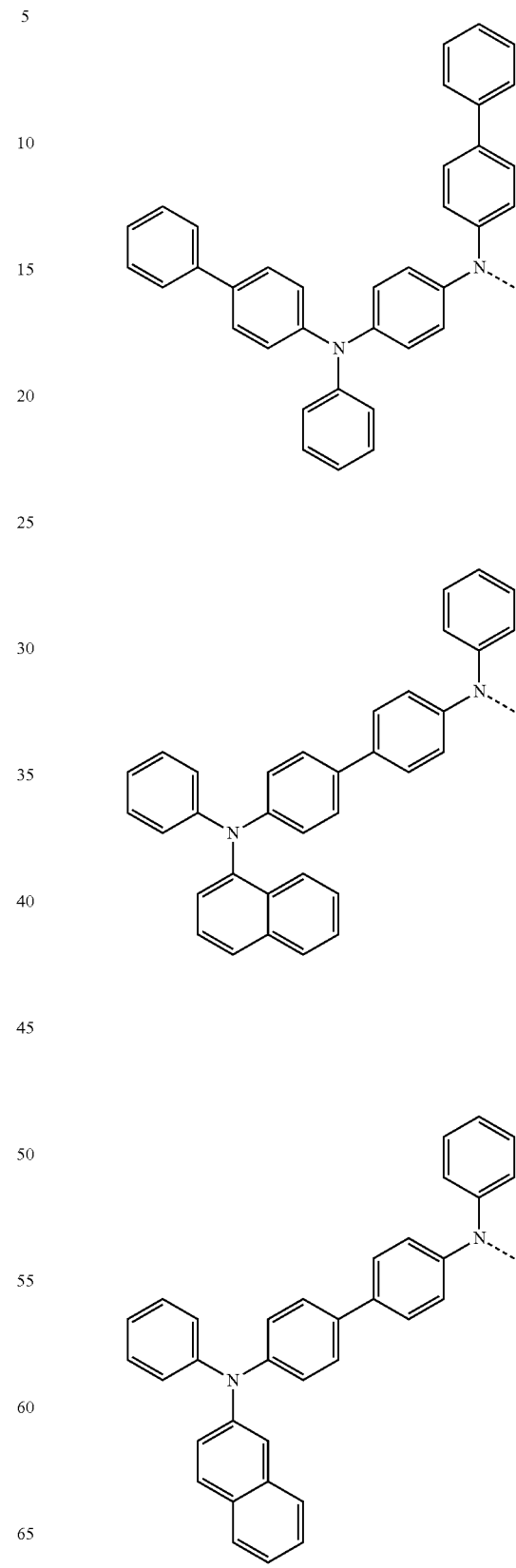

-continued
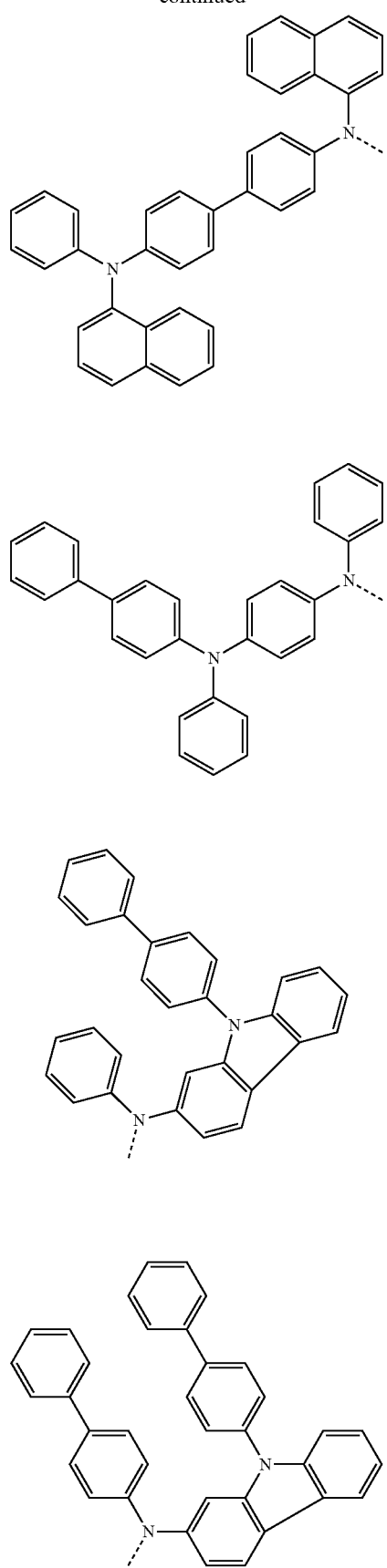
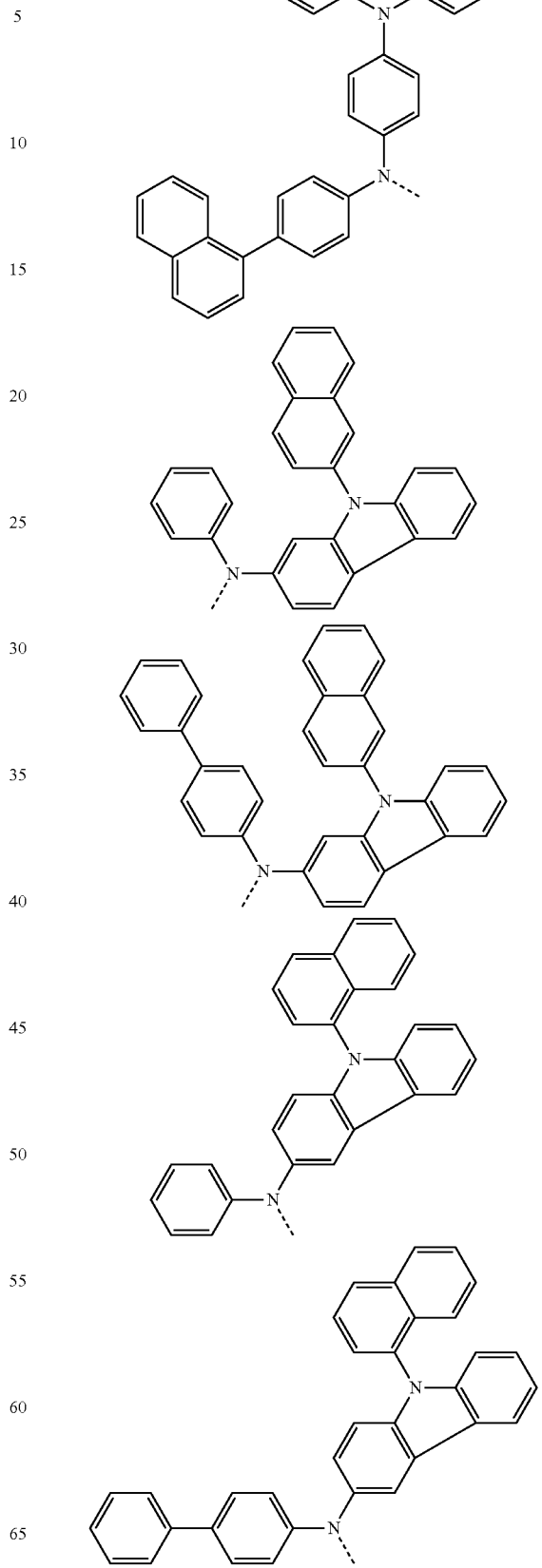

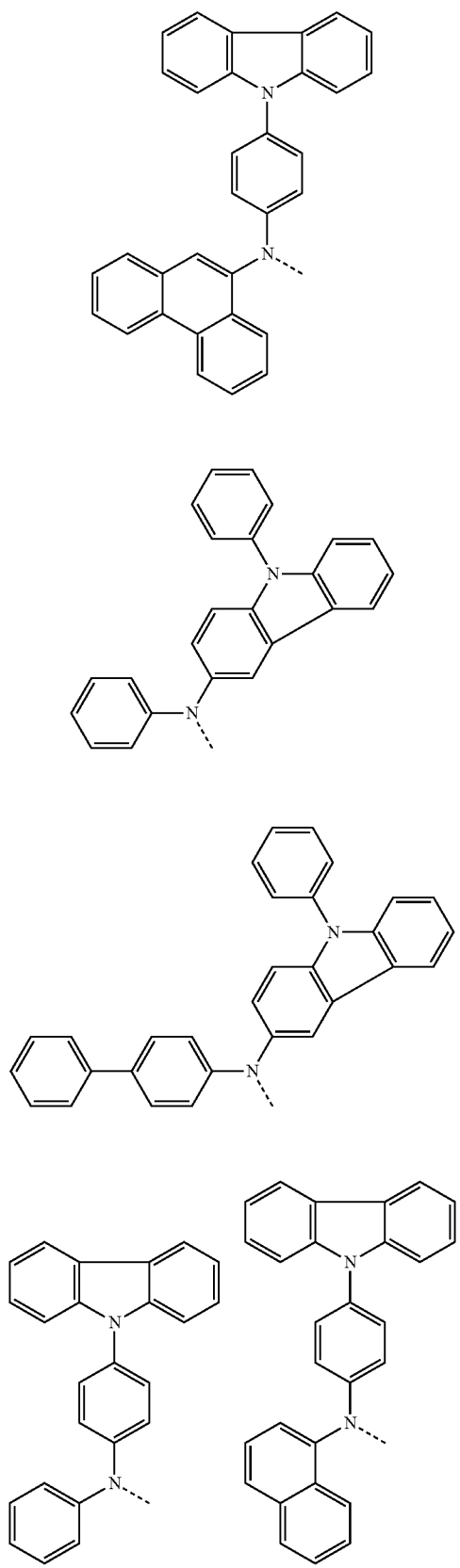

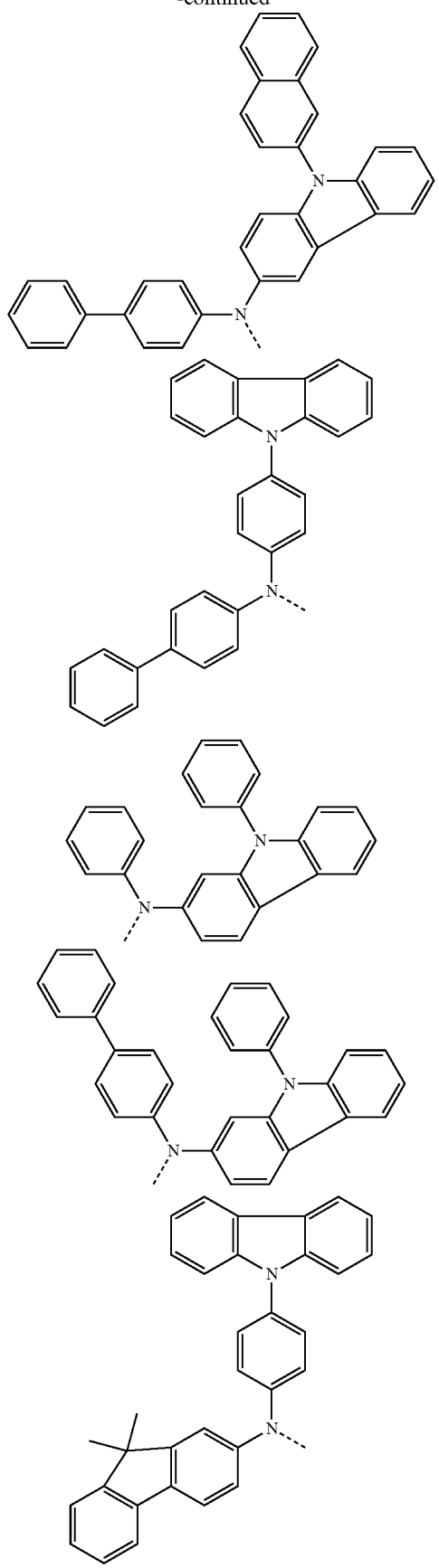
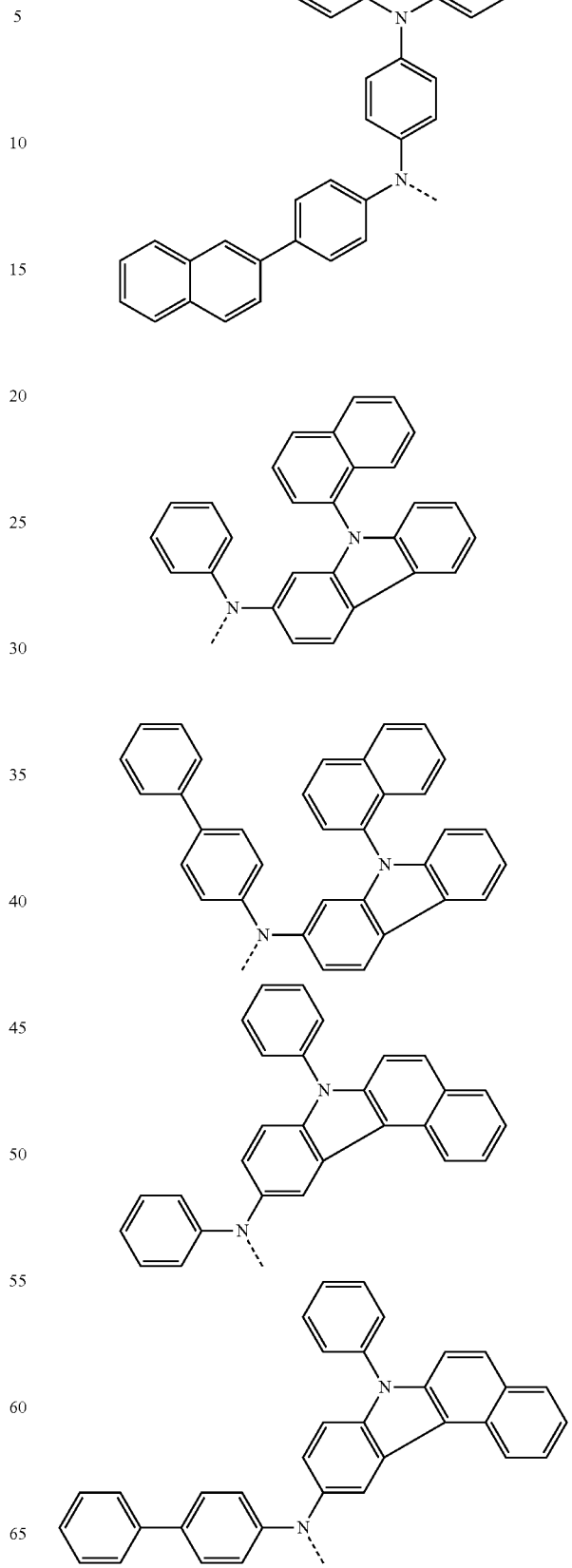

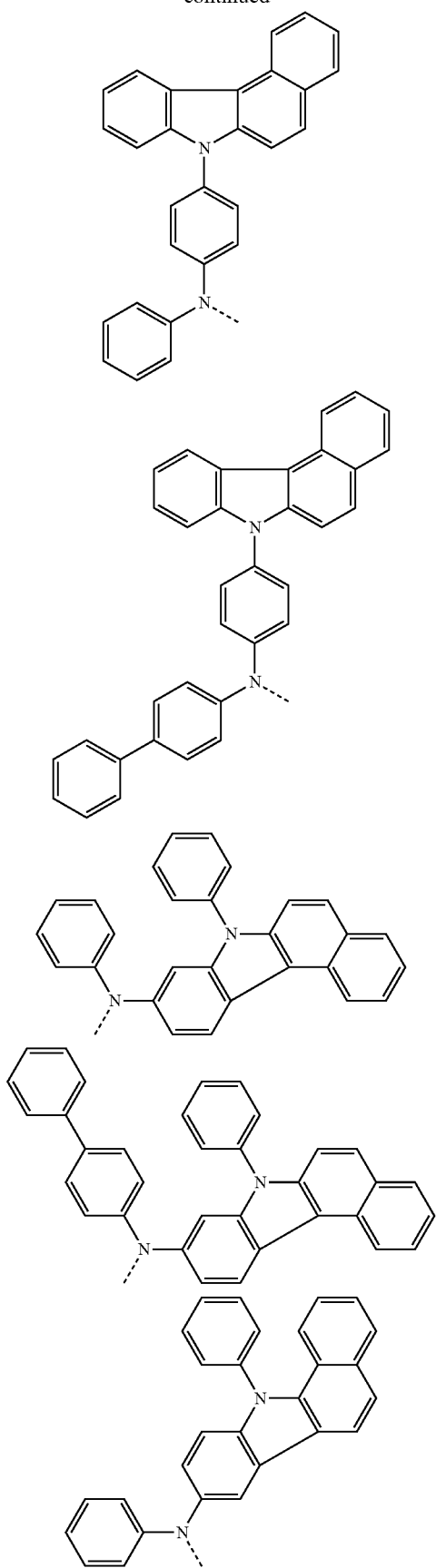
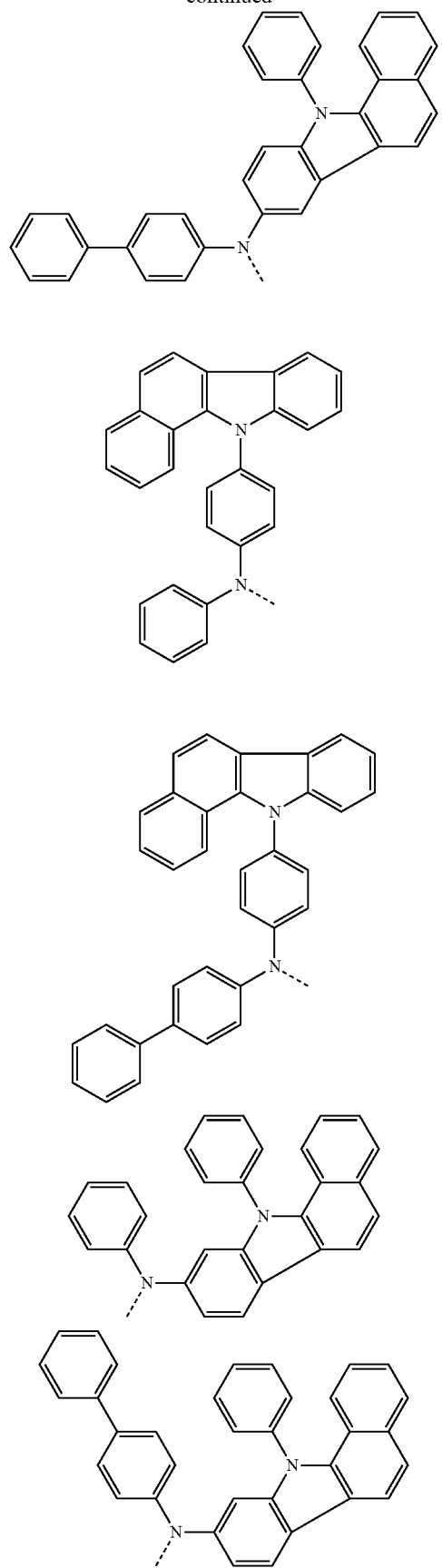

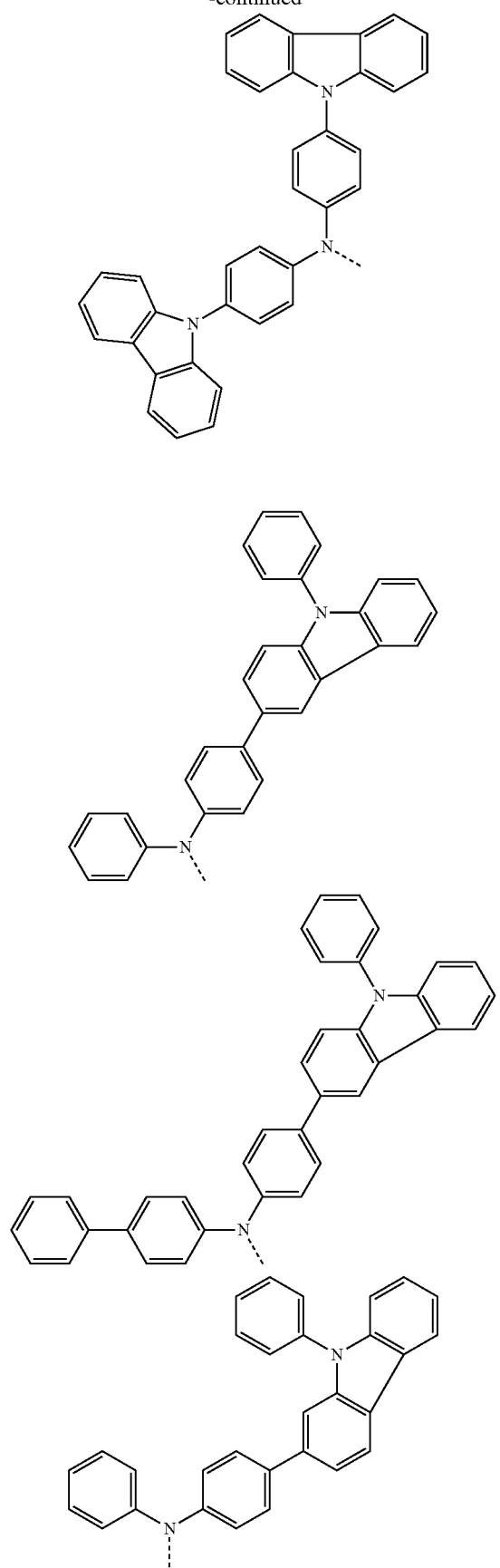
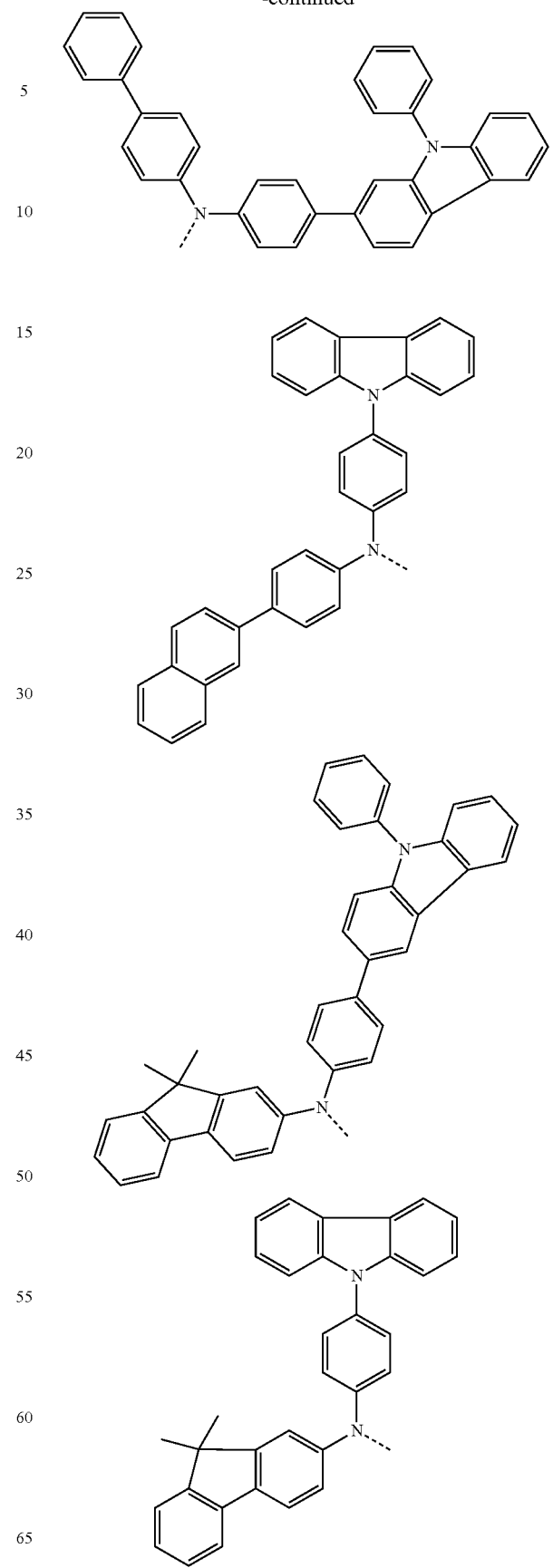

43
-continued
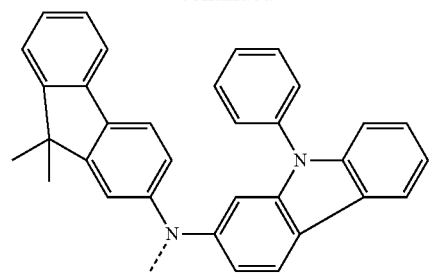
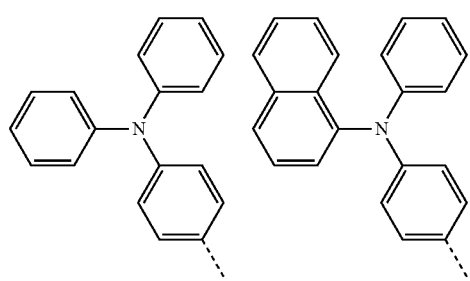
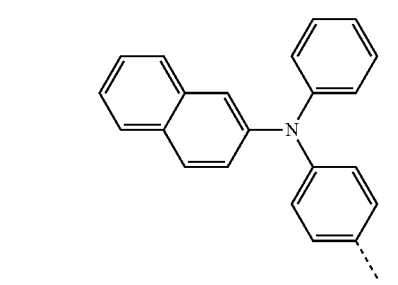
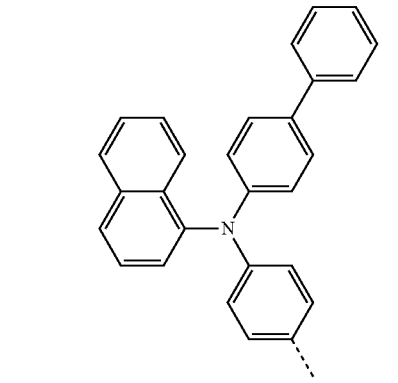
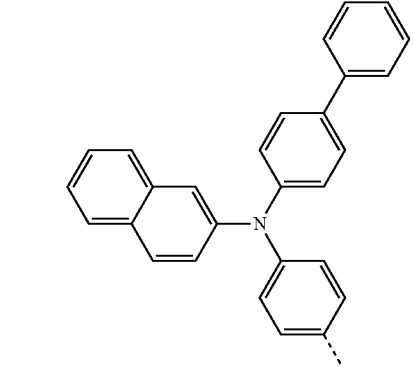
44
-continued
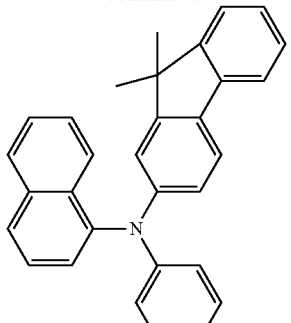
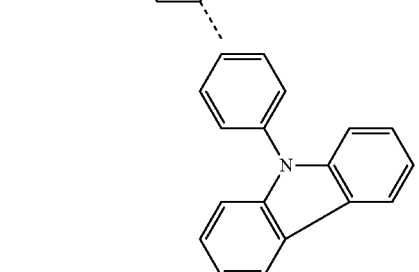
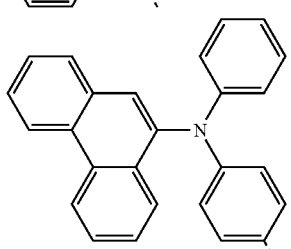
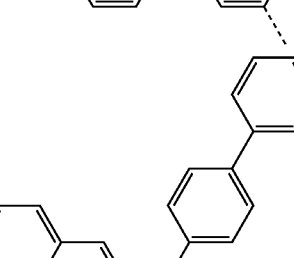
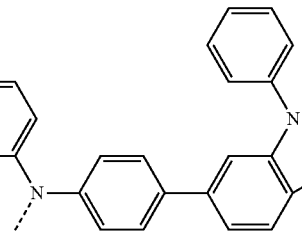

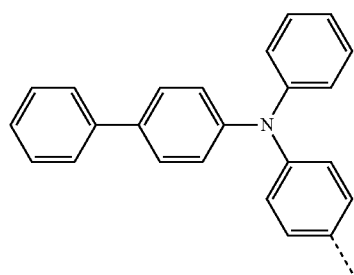
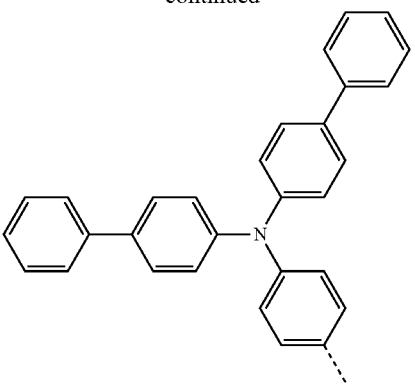
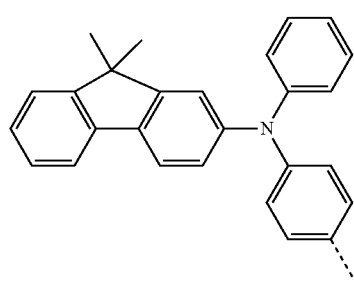
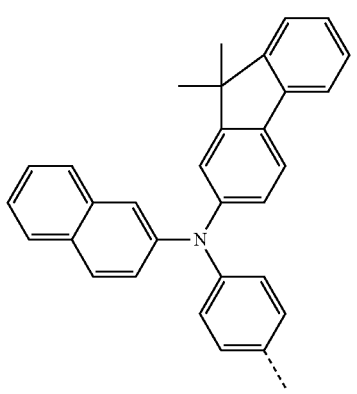
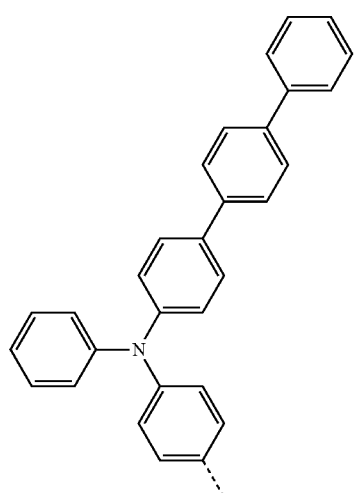
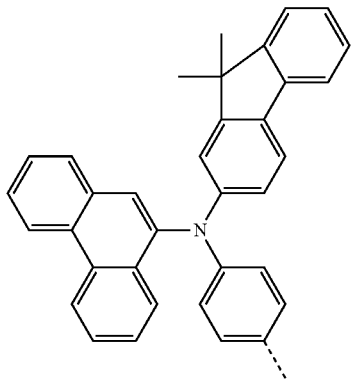
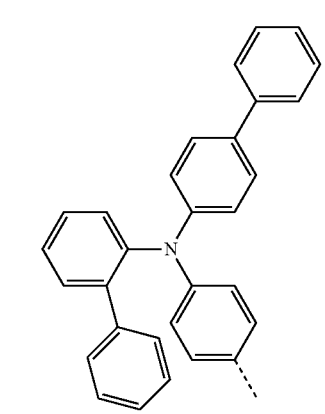
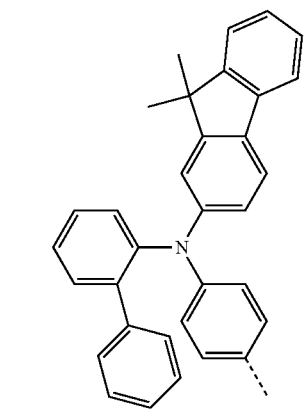

-continued
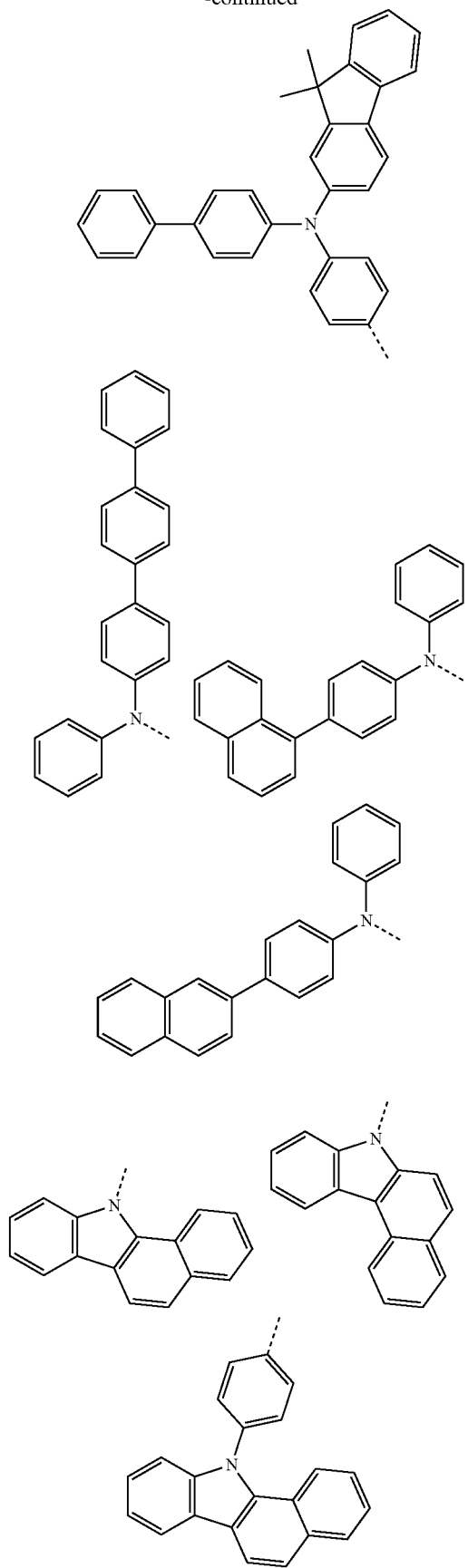
[A-2]
-continued
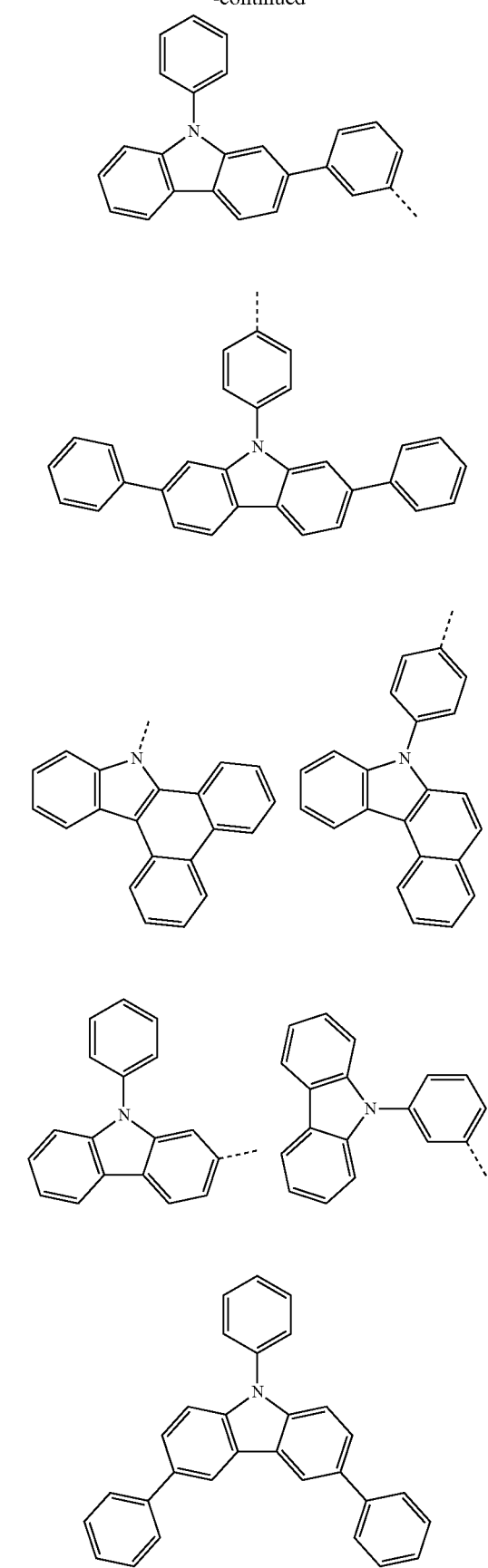

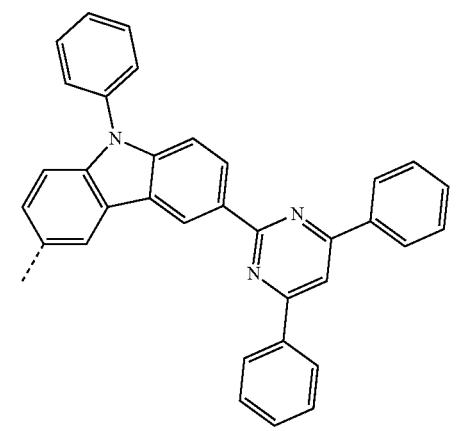
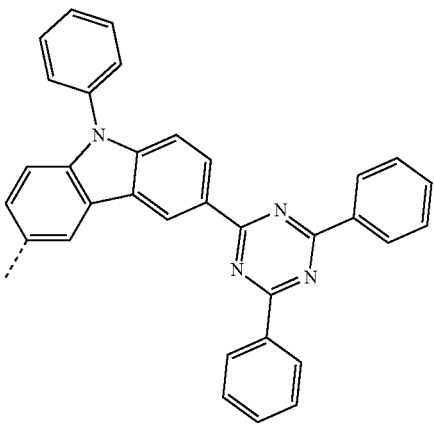
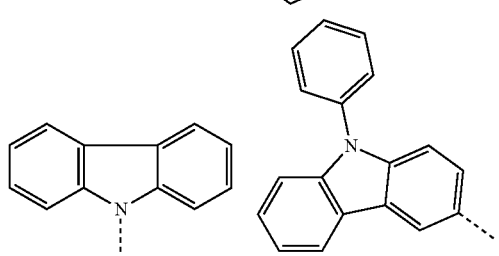
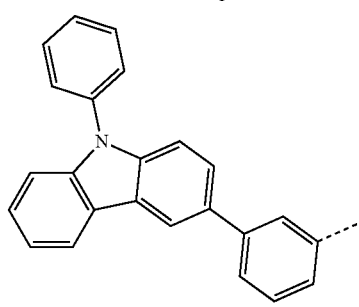
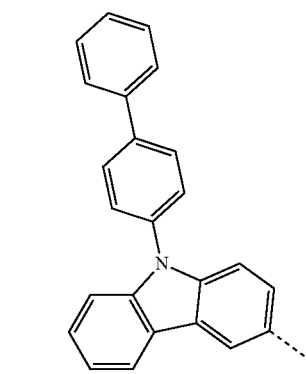
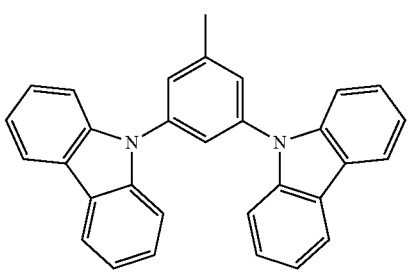
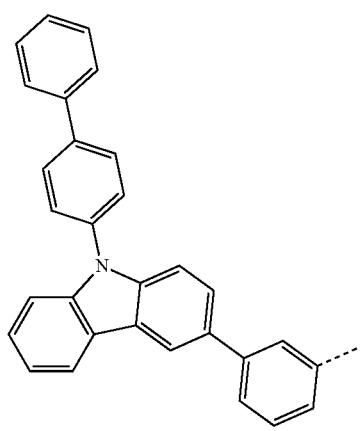
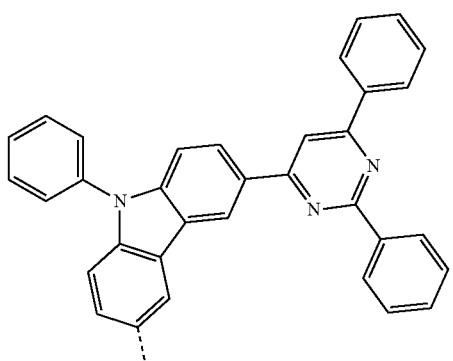
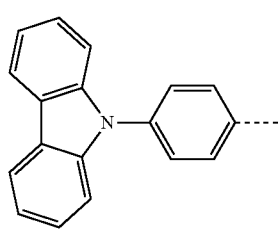
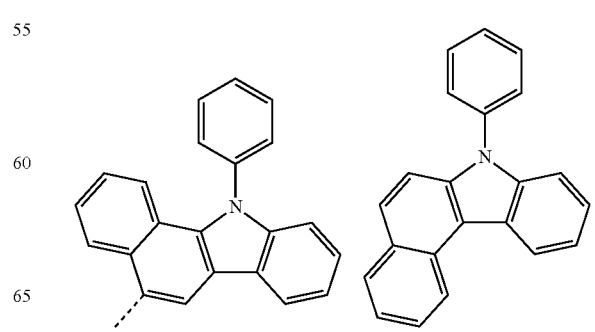

[A-3]
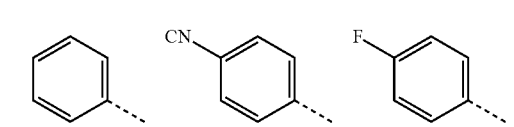
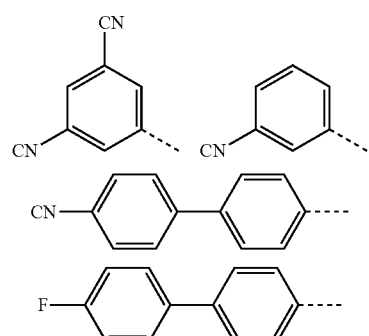
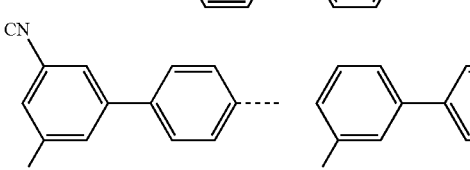
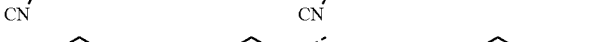
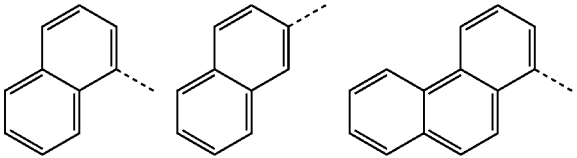
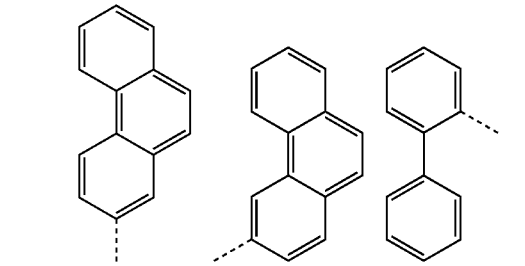
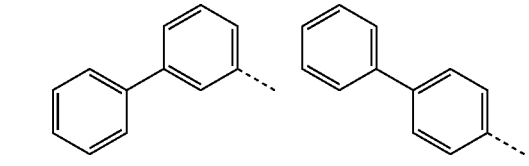
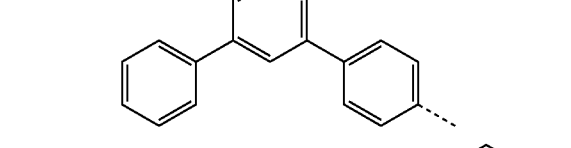
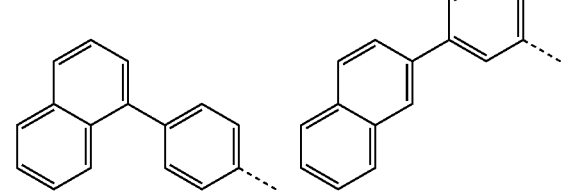
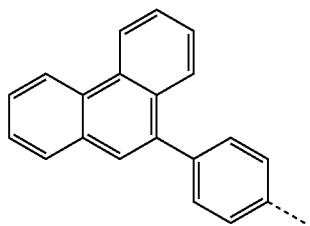
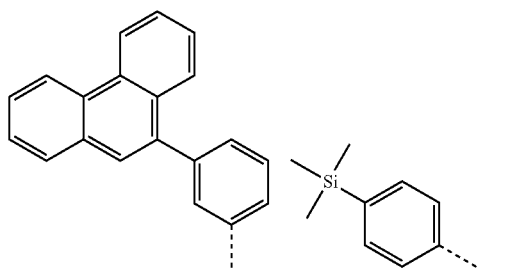
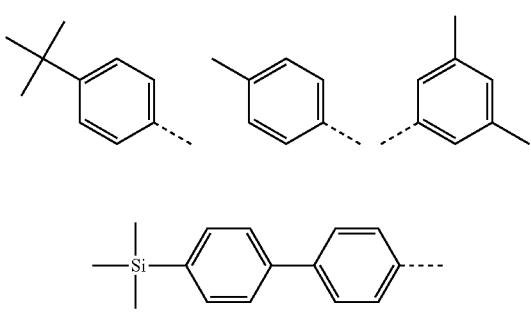
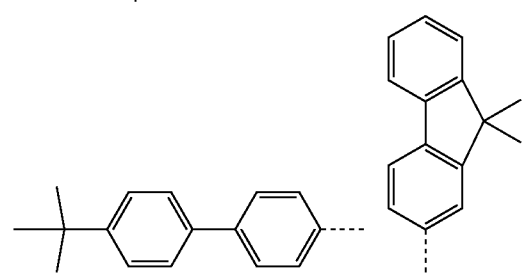
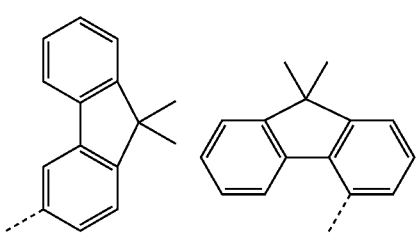
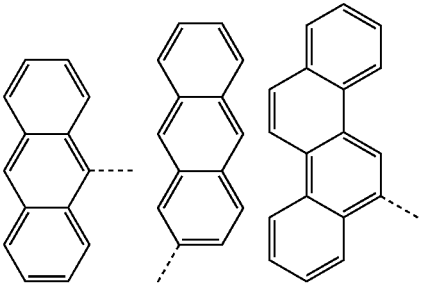

-continued
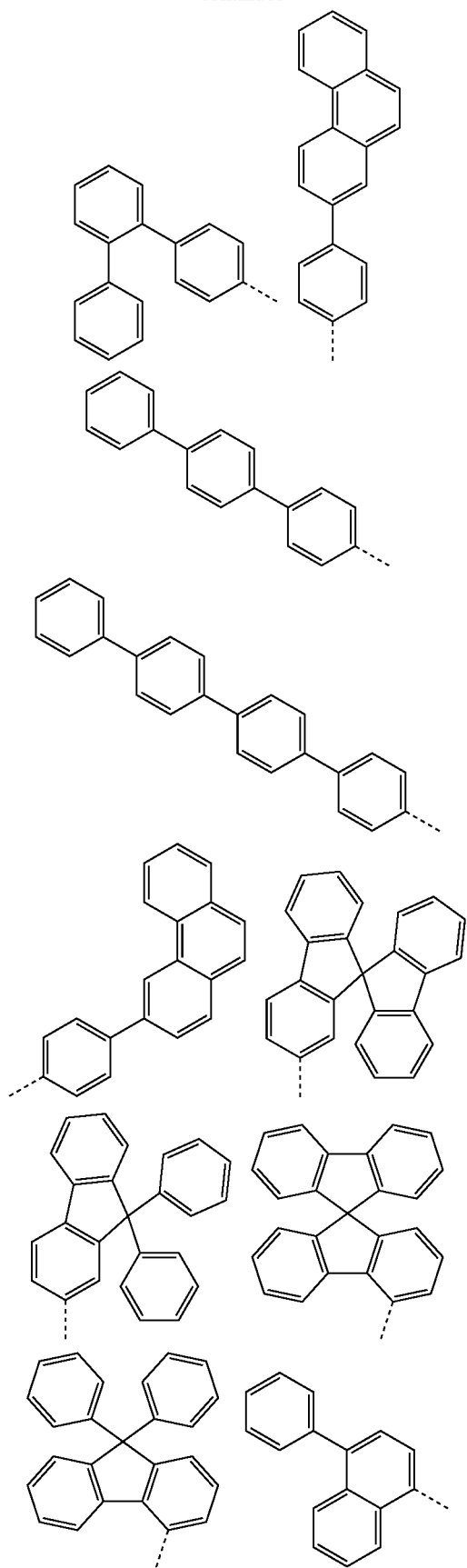
-continued
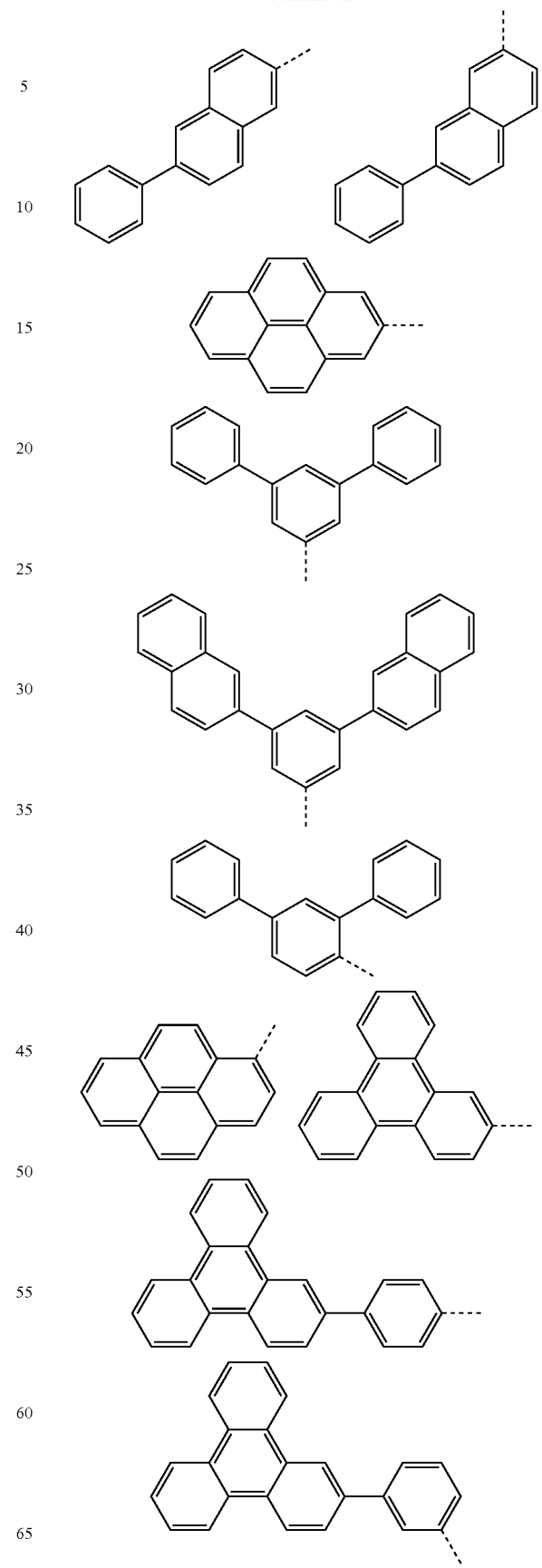

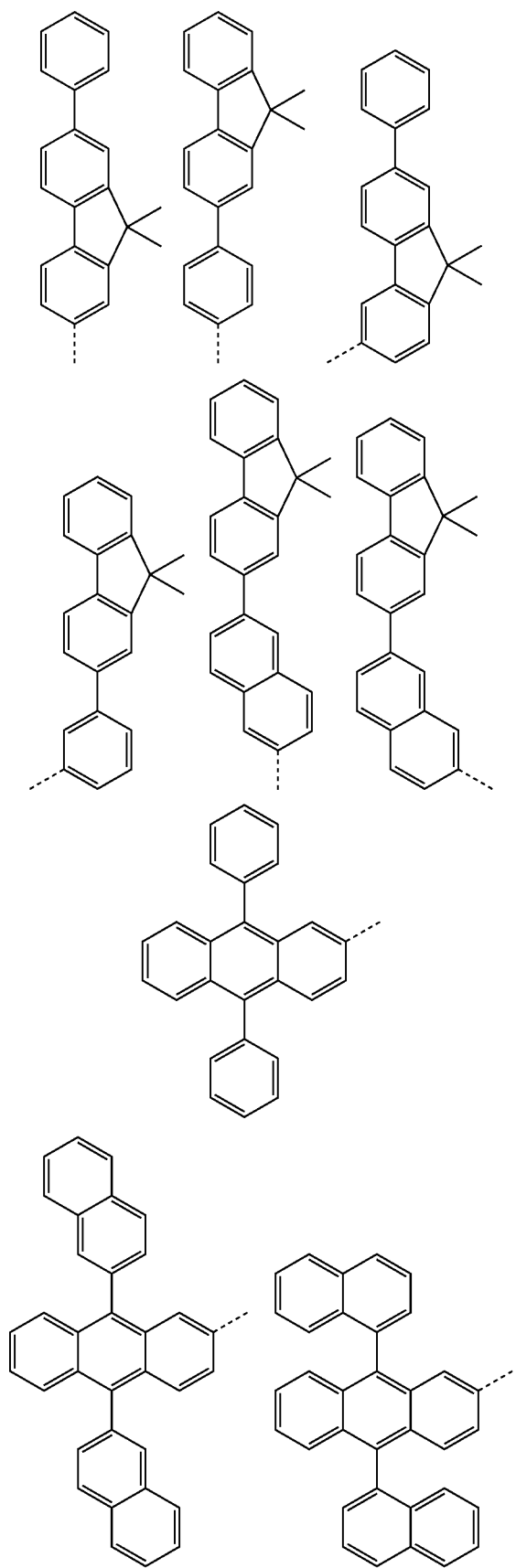
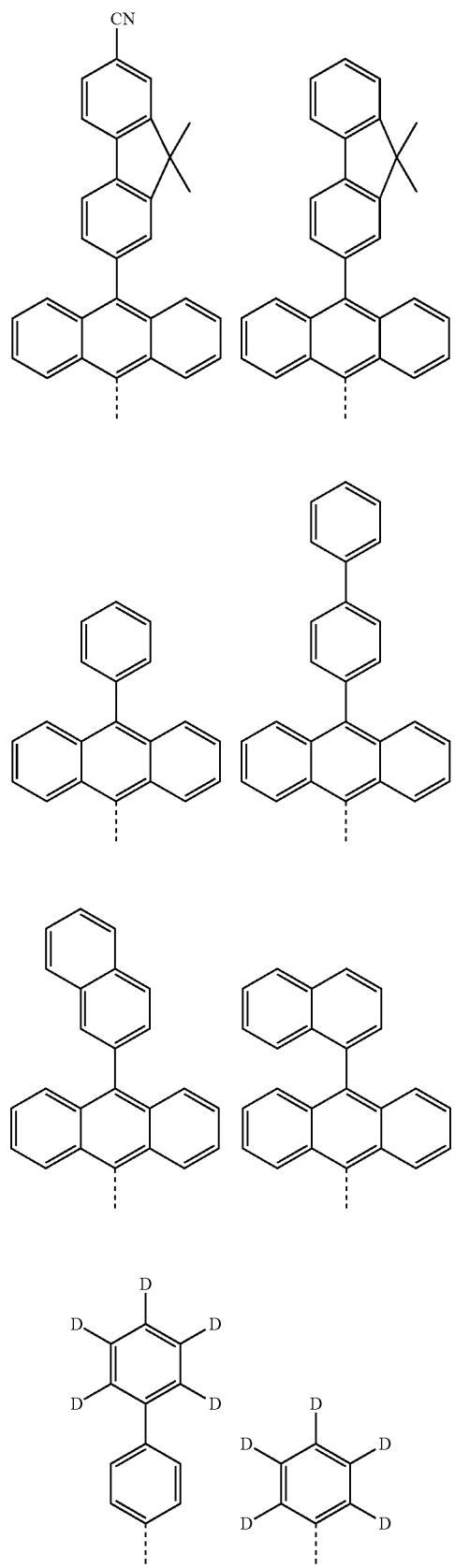

-continued
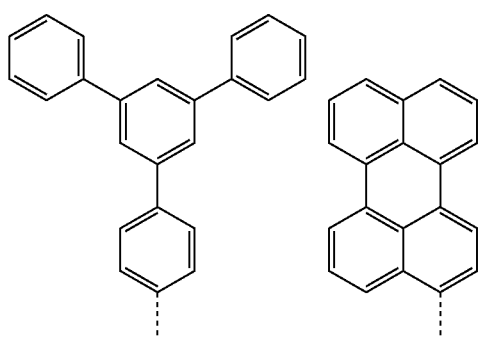
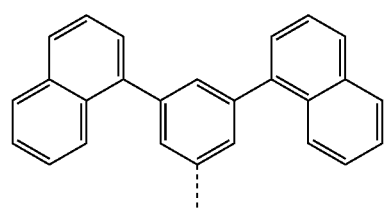
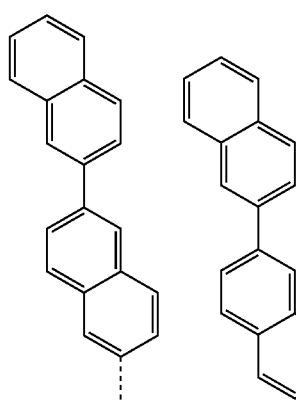
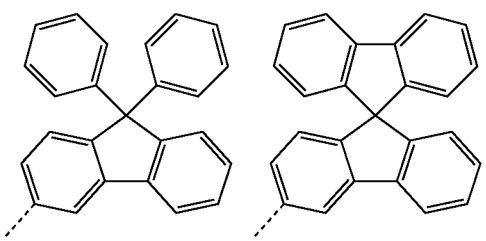
[A-4]
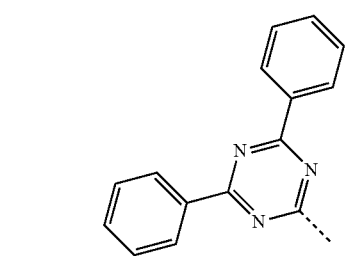
-continued
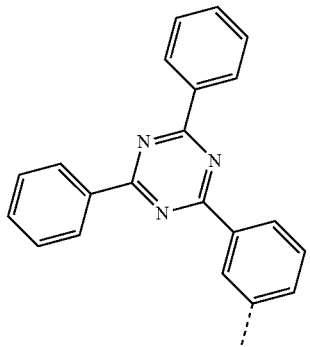
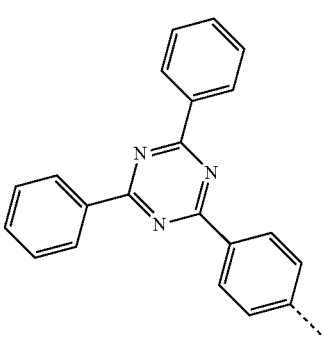
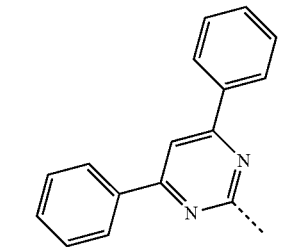
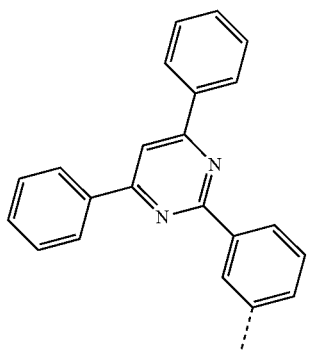
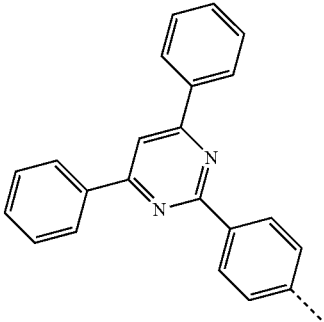

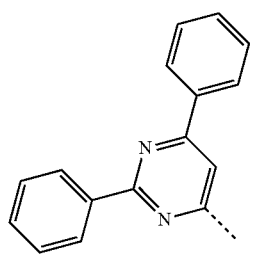
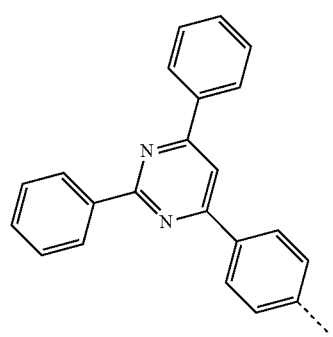
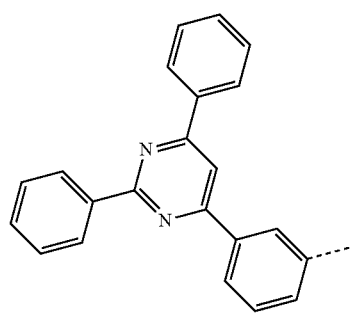
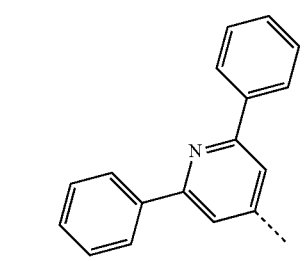
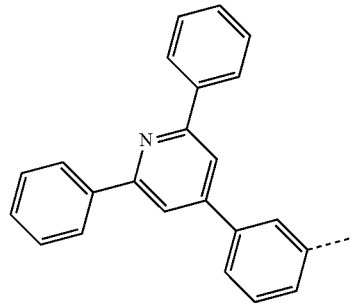
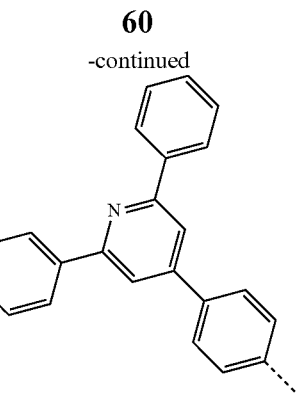
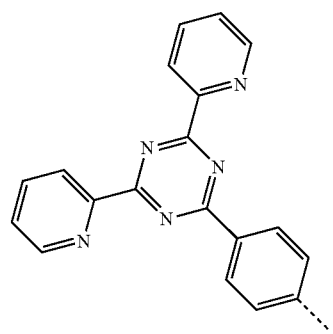
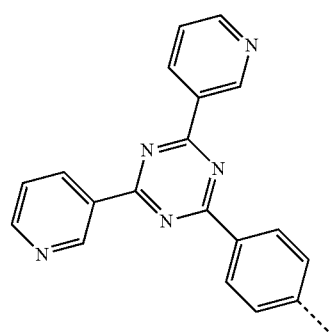
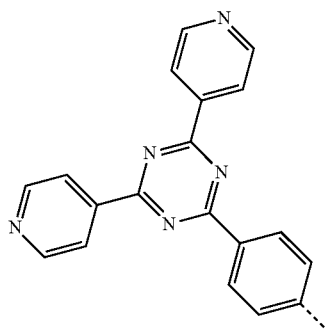
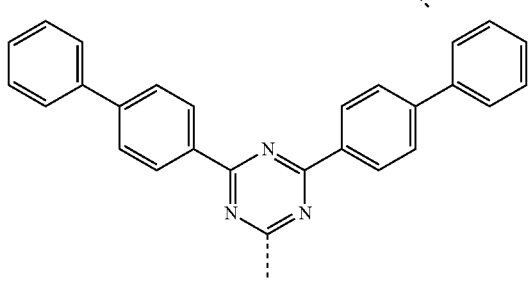

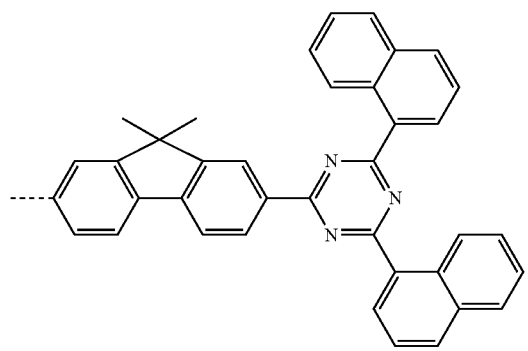
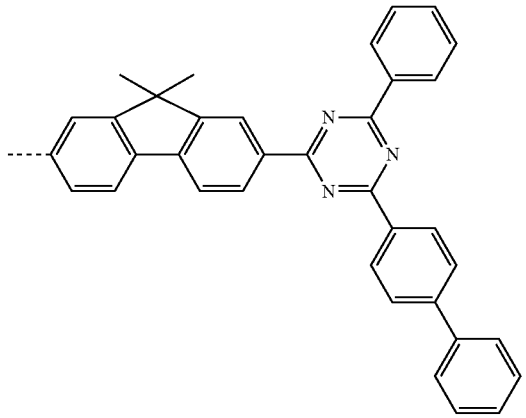
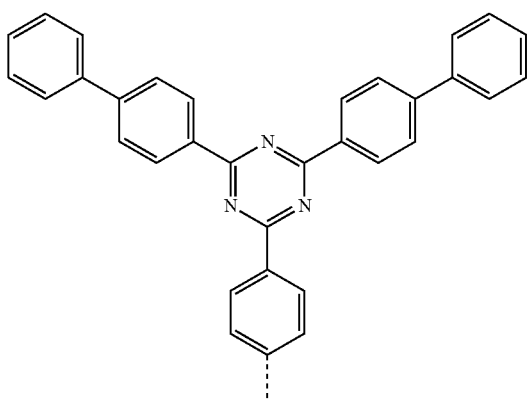
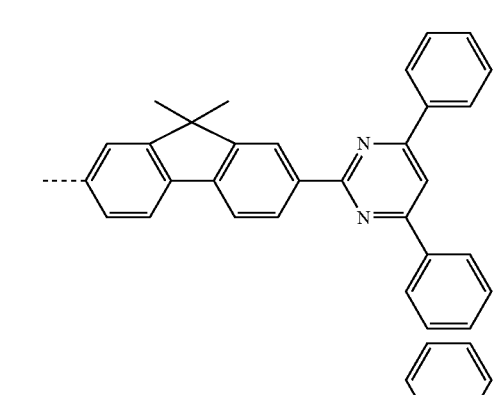
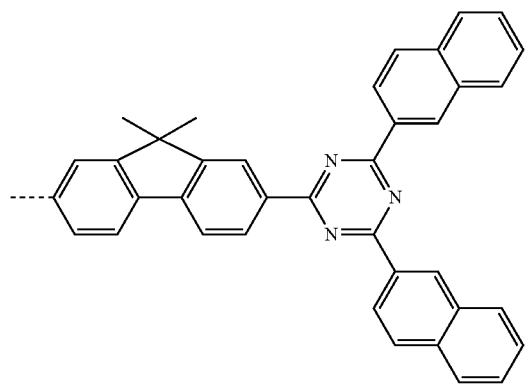
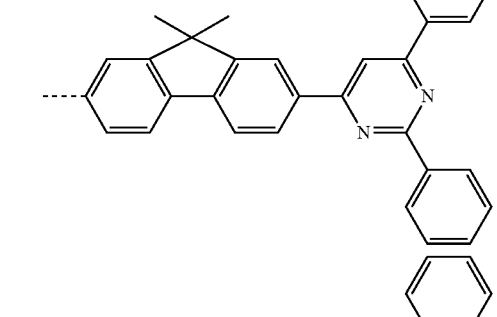
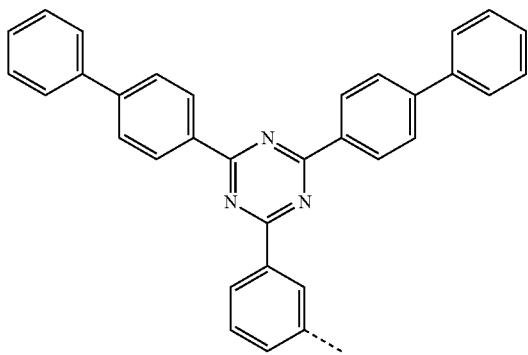
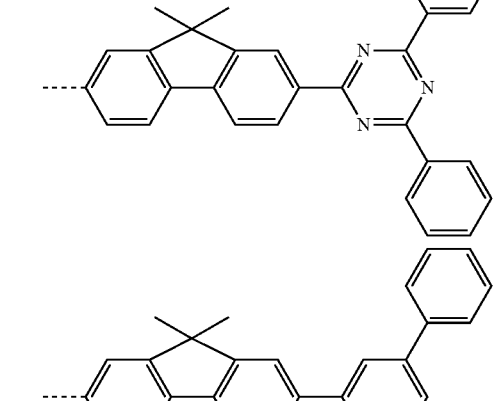
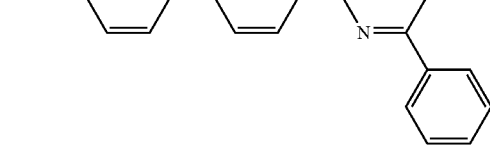

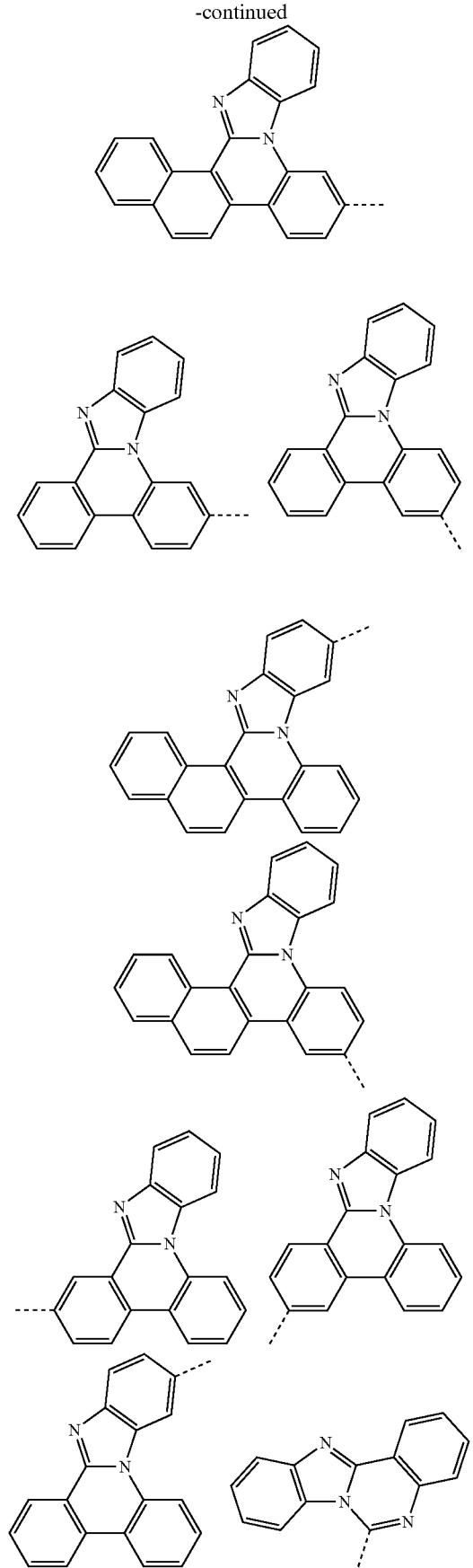
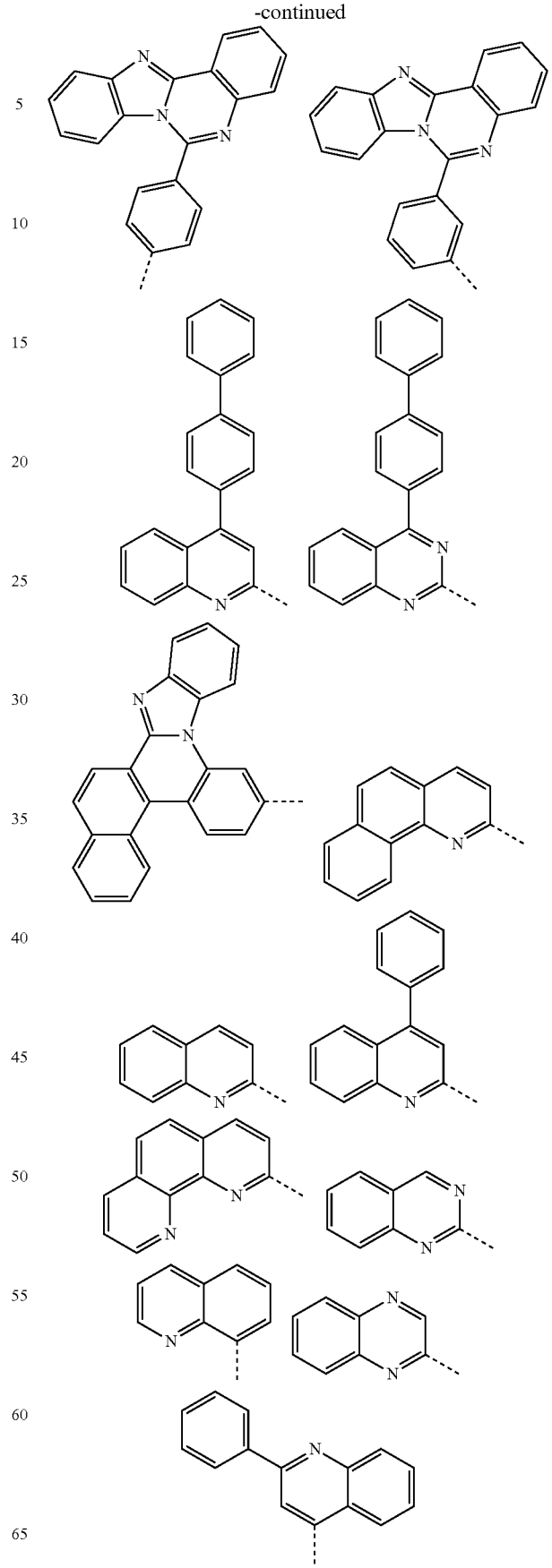

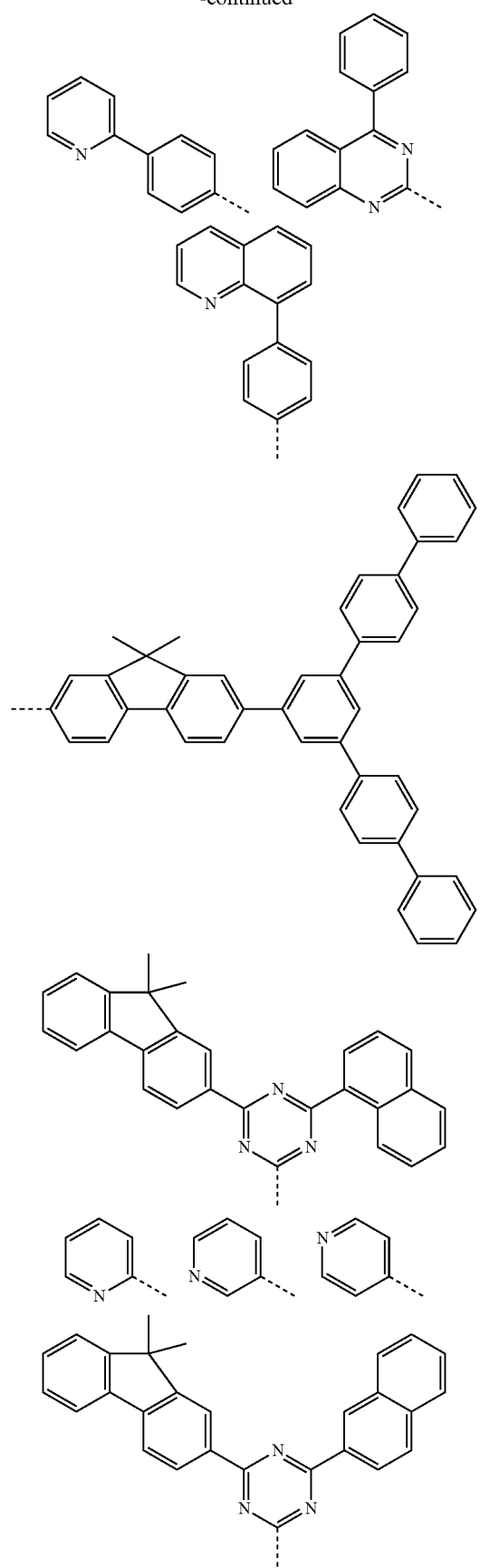
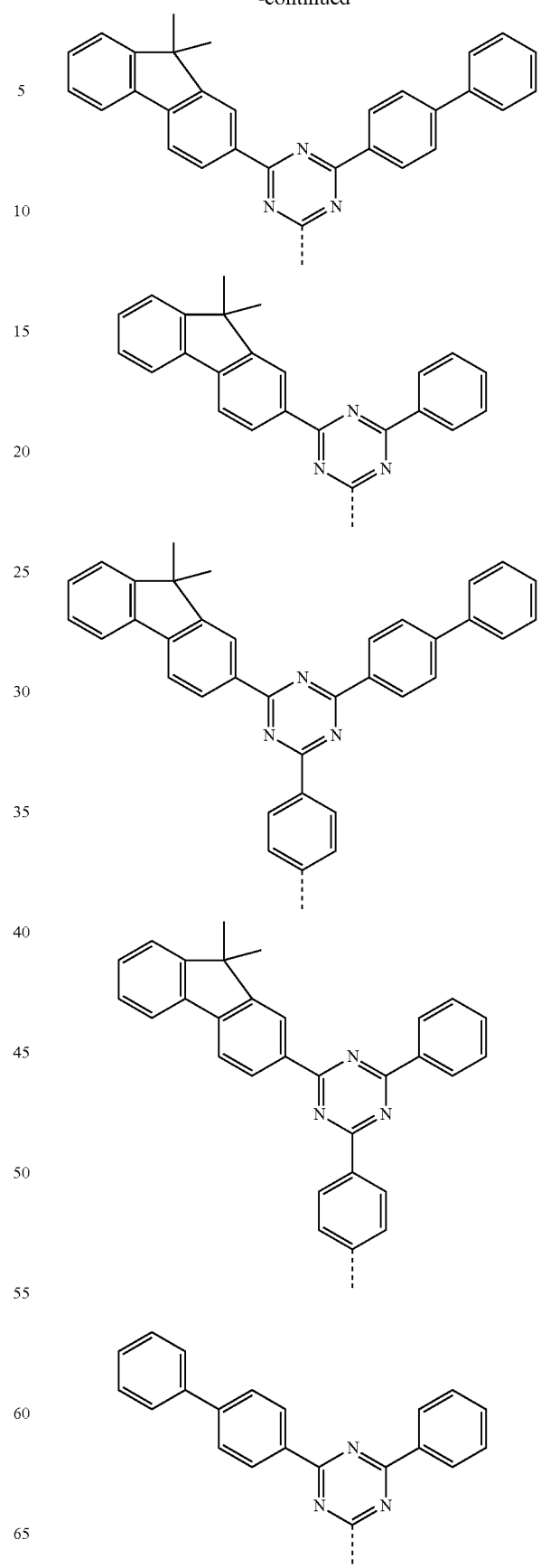

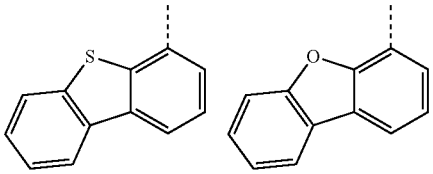
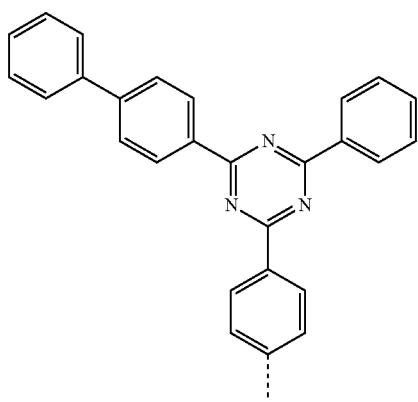
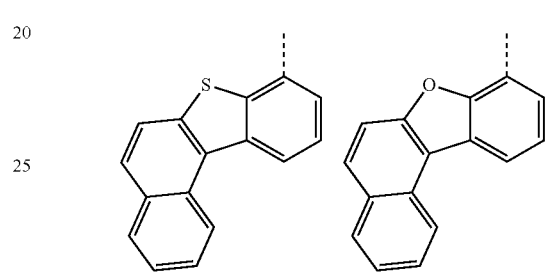
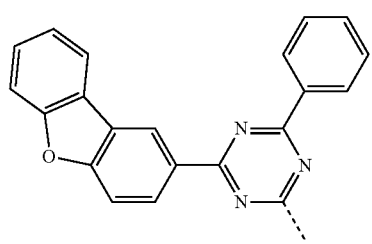
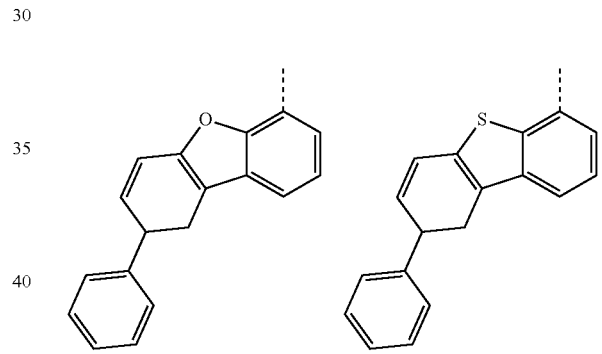
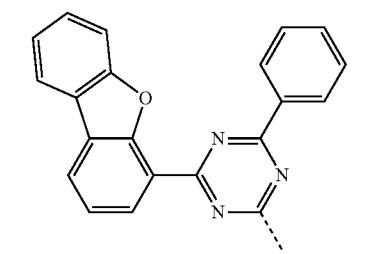
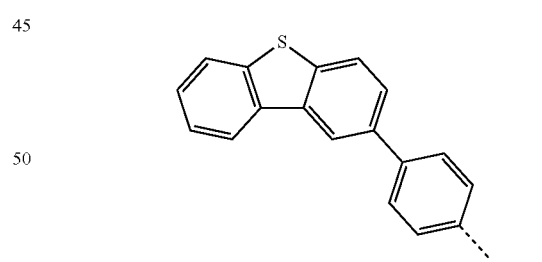
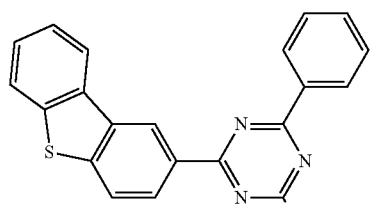
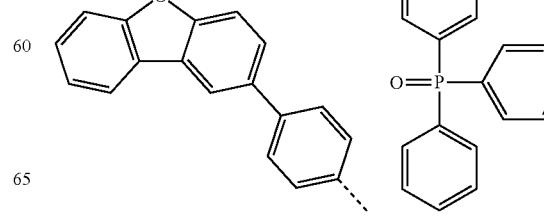
[A-5]
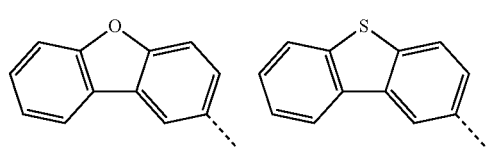

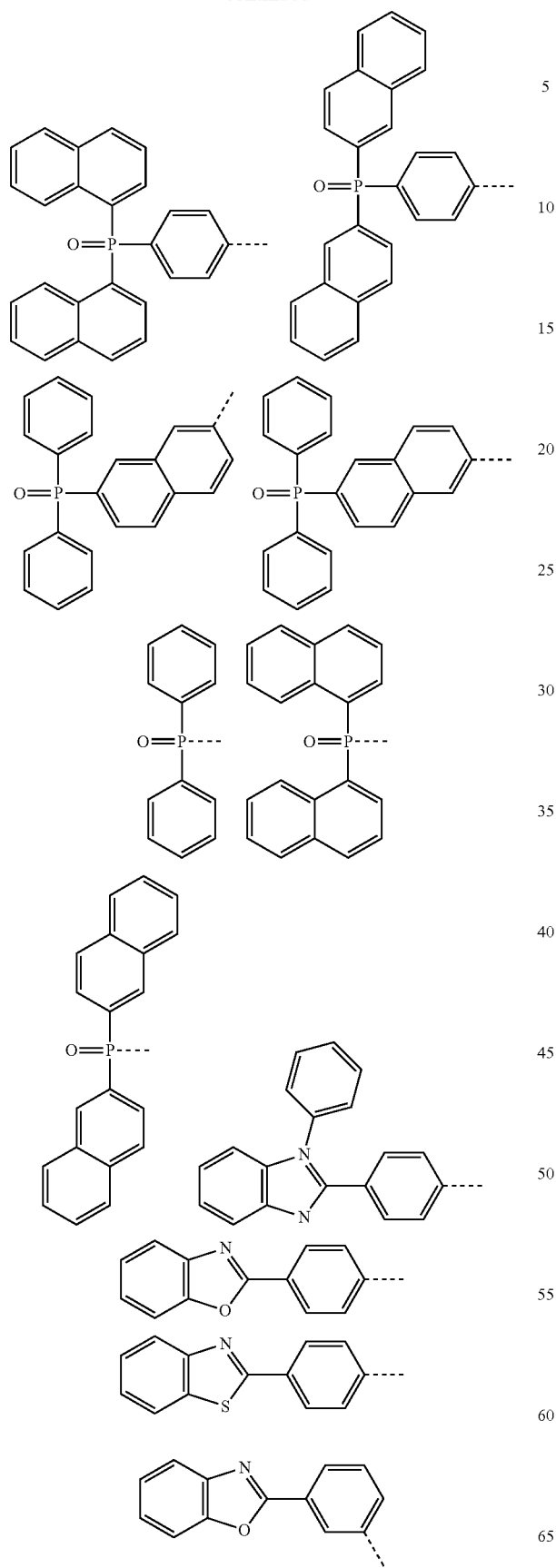
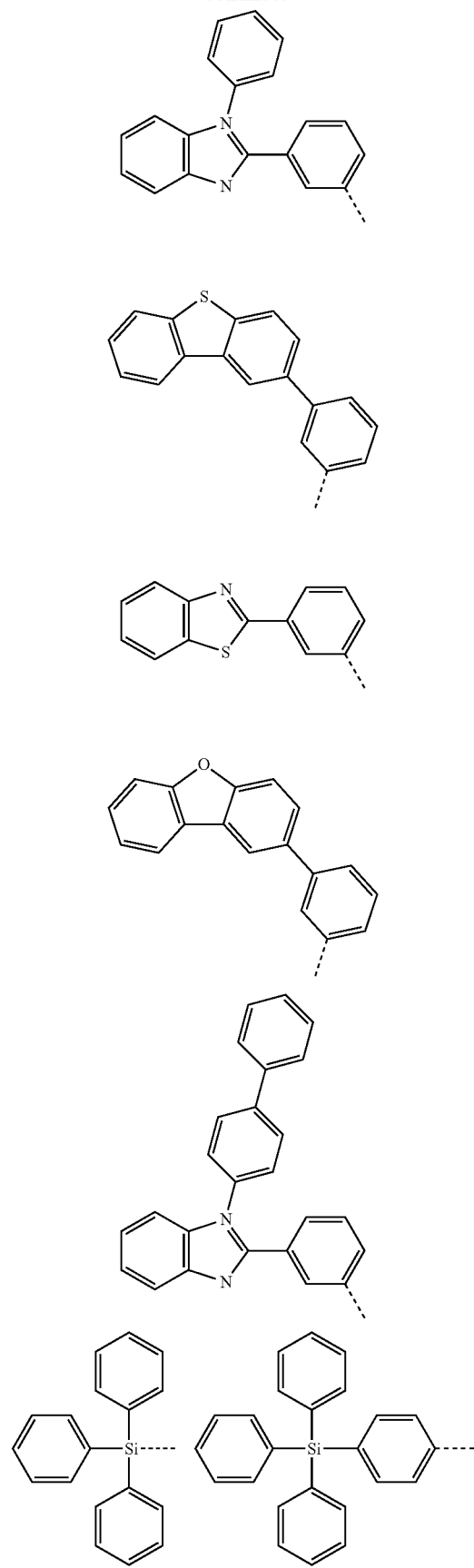

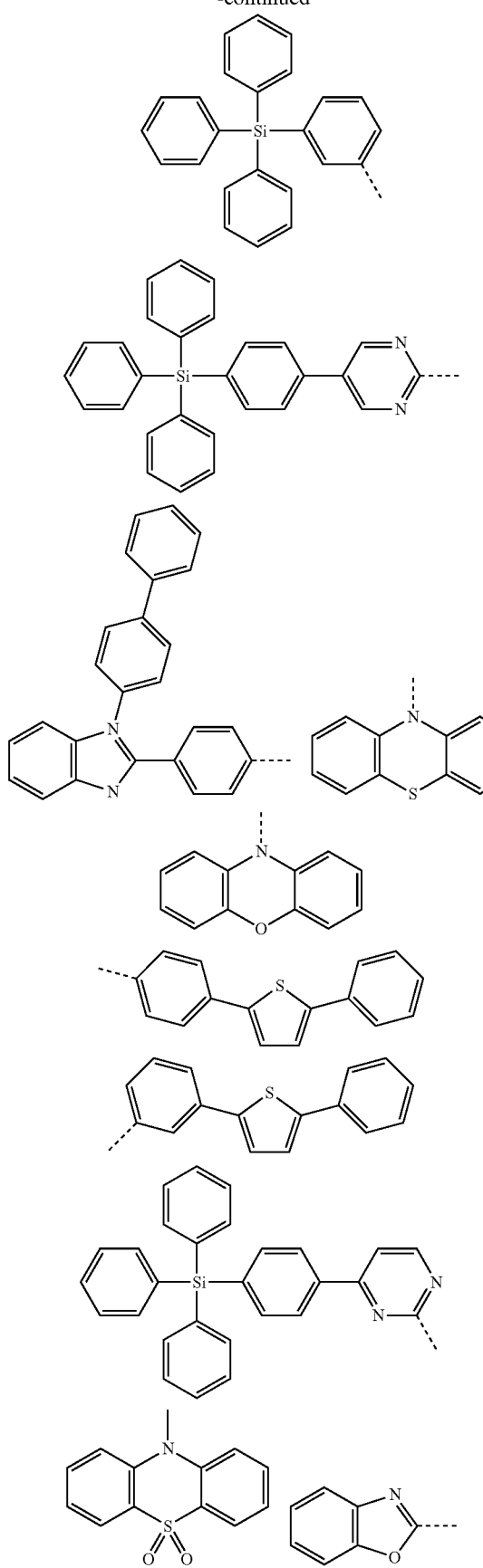
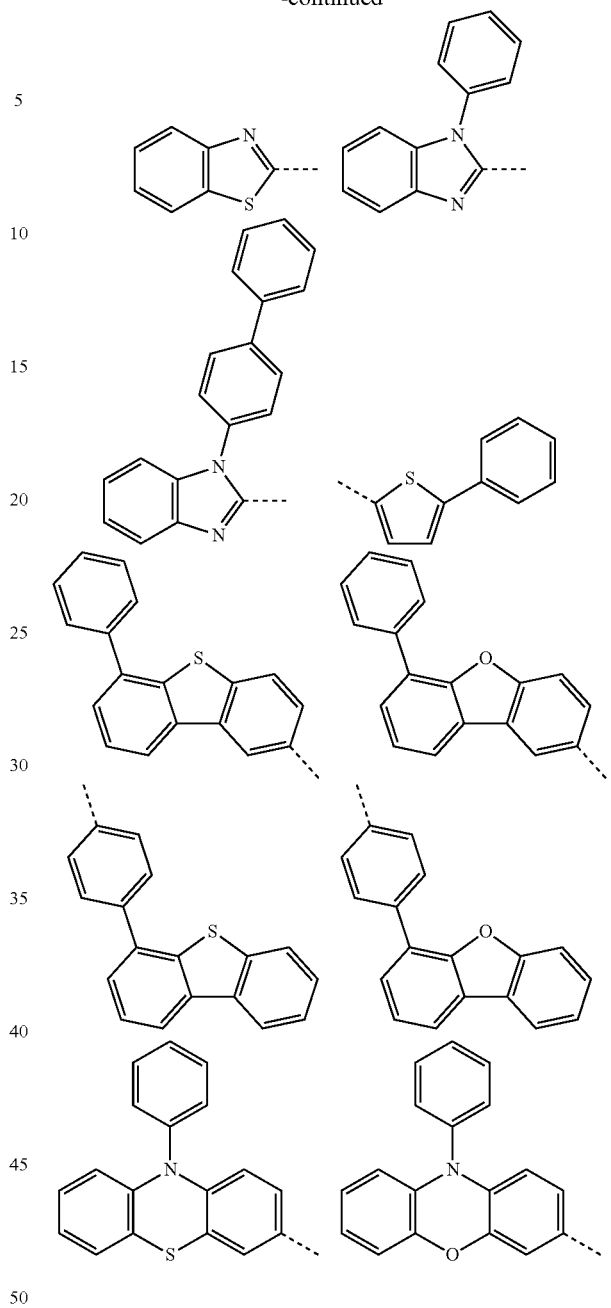

In the structural formulae, ---- means a moiety bonded to Chemical Formula 1 via L1.

According to an exemplary embodiment of the present specification, in Chemical Formula 1, Ar1 is an arylamine group which is unsubstituted or substituted with an alkyl group or a heteroaryl group; an N-arylheteroarylamine group which is unsubstituted or substituted with an aryl group; a phosphine oxide group which is substituted with an aryl group; an aryl group which is unsubstituted or substituted with an alkyl group or an aryl group; or a heteroaryl group which is unsubstituted or substituted with an aryl group.

According to an exemplary embodiment of the present specification, in Chemical Formula 1, Ar1 is an N-fluorenylphenylamine group which is substituted with an alkyl group; an N-fluorenylbiphenylamine group which is substituted with an alkyl group; an N-phenylbiphenylamine group which is unsubstituted or substituted with a heteroaryl group; a diphenylamine group which is unsubstituted or substituted with a heteroaryl group; a dibiphenylamine group; an N-phenyldibenzofuranylamine group; an N-biphenyldibenzofuranylamine group; an N-phenyldibenzothiopheneamine group; an N-biphenyldibenzothiopheneamine group; an N-biphenylcarbazolylamine group which is unsubstituted or substituted with an aryl group; a phosphine oxide group which is substituted with an aryl group; a phenyl group; a biphenyl group; a naphthyl group; a terphenyl group; a fluorenyl group which is substituted with an alkyl group; a triphenylenyl group; a pyridyl group which is unsubstituted or substituted with an aryl group; a pyridmidyl group which is unsubstituted or substituted with an aryl group; a triazinyl group which is unsubstituted or substituted with an aryl group; a dibenzofuranyl group; a dibenzothiophene group; a quinazolyl group which is unsubstituted or substituted with an aryl group; a quinolyl group; a benzocarbazolyl group; a carbazolyl group which is unsubstituted or substituted with an aryl group; or a benzimidazolyl group which is unsubstituted or substituted with an aryl group.

According to an exemplary embodiment of the present specification, in Chemical Formula 1, Ar1 is an N-fluorenylphenylamine group which is substituted with a methyl group; an N-fluorenylbiphenylamine group which is substituted with a methyl group; an N-phenylbiphenylamine group which is unsubstituted or substituted with dibenzofuranyl group or a dibenzothiophene group; a diphenylamine group which is unsubstituted or substituted with dibenzofuranyl group or a dibenzothiophene group; a dibiphenylamine group; an N-phenyldibenzofuranylamine group; an N-biphenyldibenzofuranylamine group; an N-phenyldibenzothiopheneamine group; an N-biphenyldibenzothiopheneamine group; an N-biphenylcarbazolylamine group which is unsubstituted or substituted with a phenyl group or a biphenyl group; a phosphine oxide group which is substituted with a phenyl group; a phenyl group; a biphenyl group; a naphthyl group; a terphenyl group; a fluorenyl group which is substituted with a methyl group; a triphenylenyl group; a pyridyl group which is unsubstituted or substituted with a phenyl group; a pyridmidyl group which is unsubstituted or substituted with a phenyl group; a triazinyl group which is unsubstituted or substituted with one or more selected from the group consisting of a phenyl group, a biphenyl group, and a naphthyl group; a dibenzofuranyl group; a dibenzothiophene group; a quinazolyl group which is unsubstituted or substituted with a phenyl group, a biphenyl group, or a naphthyl group; a quinolyl group; a benzocarbazolyl group; a carbazolyl group which is unsubstituted or substituted with a phenyl group, a biphenyl group, or a naphthyl group; or a benzimidazolyl group which is unsubstituted or substituted with a phenyl group.

According to an exemplary embodiment of the present specification, in Chemical Formula 1, Ar1 is a substituted or unsubstituted amine group.

According to an exemplary embodiment of the present specification, in Chemical Formula 1, the amine group in Ar1 is unsubstituted or substituted with an aryl group or a heteroaryl group.

According to an exemplary embodiment of the present specification, in Chemical Formula 1, the amine group in Ar1 is unsubstituted or substituted with a substituted or unsubstituted aryl group having 6 to 20 carbon atoms or a substituted or unsubstituted heteroaryl group having 6 to 20 carbon atoms.

According to an exemplary embodiment of the present specification, in Chemical Formula 1, the amine group in Ar1 is a naphthobenzothiophene group which is unsubstituted or substituted with a phenyl group, a biphenyl group, a dimethylfluorene group, a dibenzofuran group, a dibenzothiophene group, an N-phenyl carbazole group, an N-biphenyl-carbazole group, a naphthobenzofuran group which is unsubstituted or substituted with a phenyl group, or a phenyl group.

According to an exemplary embodiment of the present specification, in Chemical Formula 1, Ar1 is a phosphine oxide group which is unsubstituted or substituted with an aryl group.

According to an exemplary embodiment of the present specification, in Chemical Formula 1, Ar1 is a phosphine oxide group which is substituted with a phenyl group or a naphthylene group.

According to an exemplary embodiment of the present specification, in Chemical Formula 1, Ar1 is a substituted or unsubstituted aryl group.

According to an exemplary embodiment of the present specification, in Chemical Formula 1, Ar1 is a monocyclic aryl group having 6 to 20 carbon atoms.

According to an exemplary embodiment of the present specification, in Chemical Formula 1, Ar1 is a phenyl group.

According to an exemplary embodiment of the present specification, in Chemical Formula 1, Ar1 is a substituted or unsubstituted polycyclic aryl group having 10 to 20 carbon atoms.

According to an exemplary embodiment of the present specification, in Chemical Formula 1, Ar1 is a polycyclic aryl group having 10 to 20 carbon atoms, which is unsubstituted or substituted with an alkyl group.

According to an exemplary embodiment of the present specification, in Chemical Formula 1, Ar1 is a polycyclic aryl group having 10 to 20 carbon atoms, which is unsubstituted or substituted with an alkyl group having 1 to 10 carbon atoms.

According to an exemplary embodiment of the present specification, in Chemical Formula 1, Ar1 is a fluorene group which is unsubstituted or substituted with a methyl group; a naphthyl group; or a triphenylene group.

According to an exemplary embodiment of the present specification, in Chemical Formula 1, Ar1 is a heteroaryl group.

According to an exemplary embodiment of the present specification, in Chemical Formula 1, Ar1 is a substituted or unsubstituted heteroaryl group including N.

According to an exemplary embodiment of the present specification, in Chemical Formula 1, Ar1 is a substituted or unsubstituted monocyclic heteroaryl group including N.

According to an exemplary embodiment of the present specification, in Chemical Formula 1, Ar1 is a pyridine group, a pyrimidine group, or a triazine group.

According to an exemplary embodiment of the present specification, in Chemical Formula 1, the pyridine group, the pyrimidine group, or the triazine group in Ar1 is unsubstituted or substituted with an aryl group.

According to an exemplary embodiment of the present specification, in Chemical Formula 1, the pyridine group, the pyrimidine group, or the triazine group in Ar1 is unsubstituted or substituted with an aryl group having 6 to 20 carbon atoms.

According to an exemplary embodiment of the present specification, in Chemical Formula 1, the pyridine group, the pyrimidine group, or the triazine group in Ar1 is unsubstituted or substituted with a phenyl group, a biphenyl group, or a naphthyl group.

According to an exemplary embodiment of the present specification, in Chemical Formula 1, Ar1 is a substituted or unsubstituted polycyclic heteroaryl group including N.

According to an exemplary embodiment of the present specification, in Chemical Formula 1, Ar1 is a quinoline group, a quinazoline group, a carbazole group, or a benzocarbazole group.

According to an exemplary embodiment of the present specification, in Chemical Formula 1, Ar1 is a substituted or unsubstituted polycyclic heteroaryl group including O or S.

According to an exemplary embodiment of the present specification, in Chemical Formula 1, Ar1 is a dibenzofuran group or a dibenzothiophene group.

According to an exemplary embodiment of the present specification, in Chemical Formula 1, Ar1 is a substituted or unsubstituted amine group; a substituted or unsubstituted phosphine oxide group; or a substituted or unsubstituted N-containing hetero ring.

According to an exemplary embodiment of the present specification, in Chemical Formula 1, Ar1 is a phosphine oxide group which is unsubstituted or substituted with an alkyl group or an aryl group; a triazinyl group which is unsubstituted or substituted with an aryl group; a quinazolinyl group which is unsubstituted or substituted with an aryl group; a carbazolyl group which is unsubstituted or substituted with a triazine group which is unsubstituted or substituted with an aryl group, or an aryl group; a pyridyl group which is unsubstituted or substituted with an aryl group; or a pyrimidyl group which is unsubstituted or substituted with an aryl group.

According to an exemplary embodiment of the present specification, in Chemical Formula 1, Ar1 is an amine group, and the amine group is substituted with an aryl group which is unsubstituted or substituted with an alkyl group, or a heteroaryl group including N, O, or S.

According to an exemplary embodiment of the present specification, Chemical Formula 1 is any one selected from the following compounds.

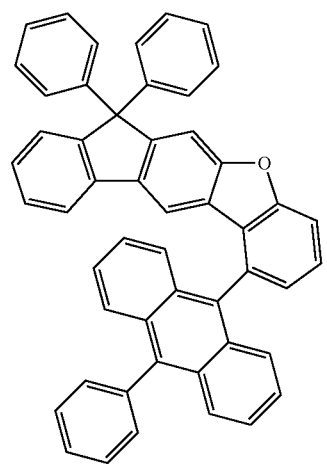

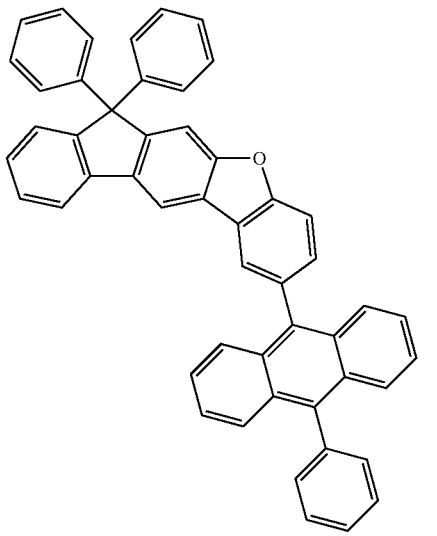

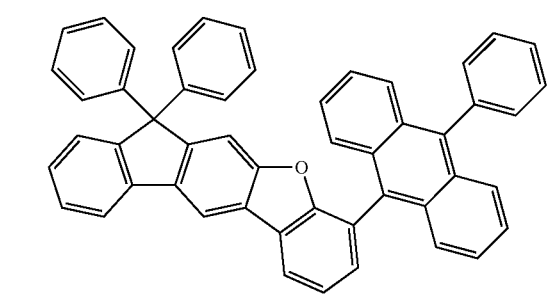

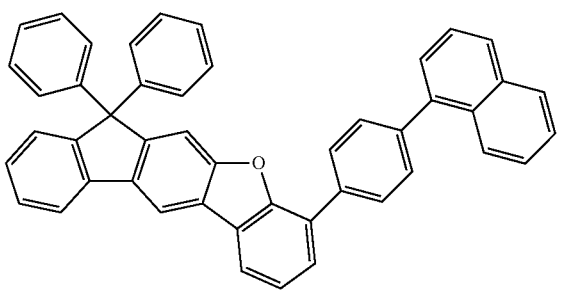

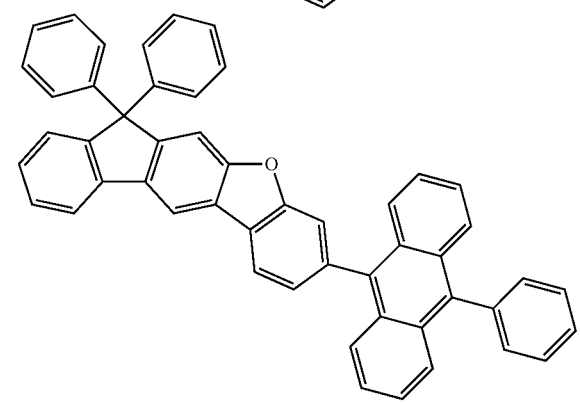

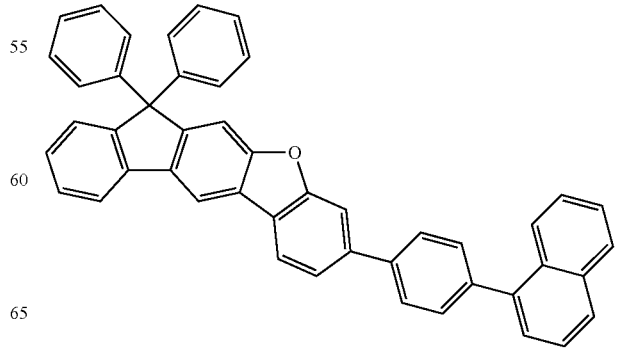

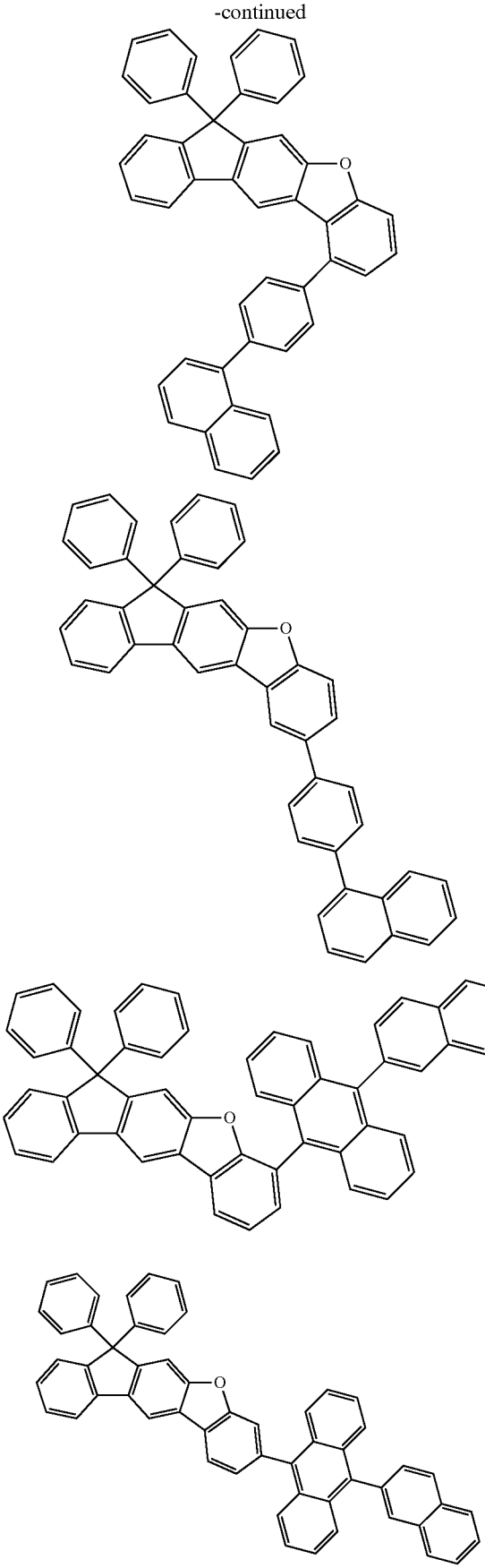
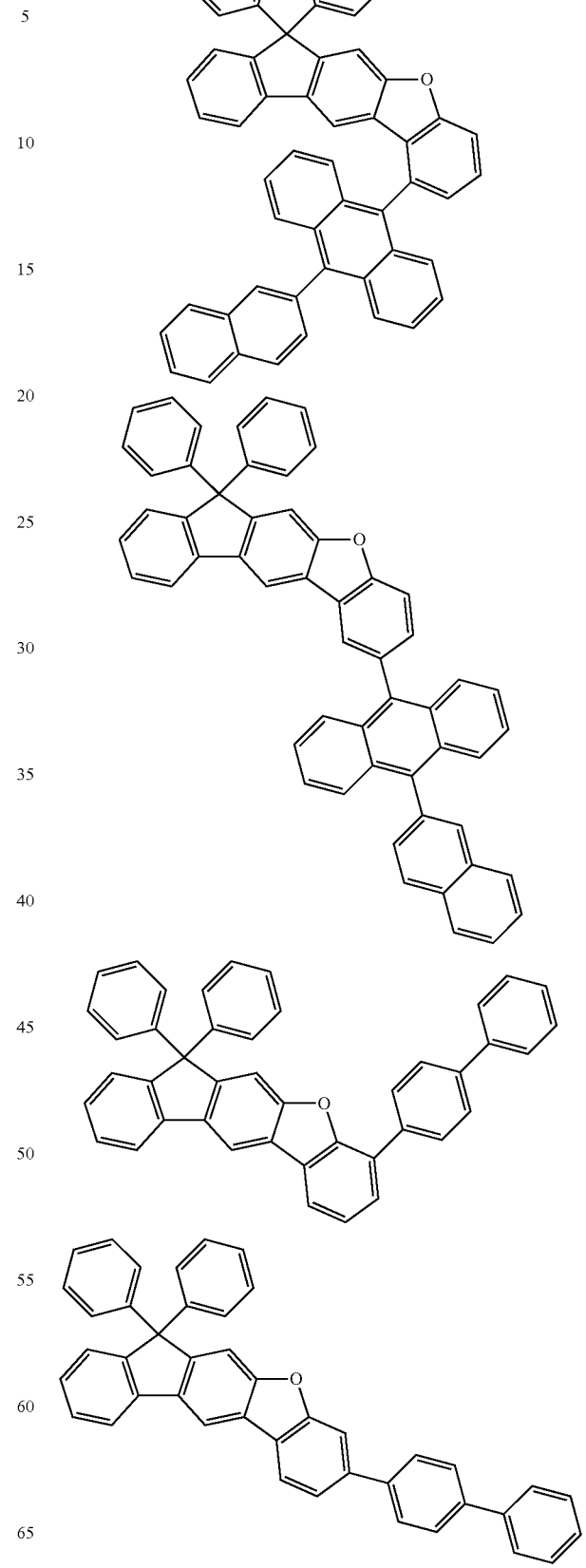

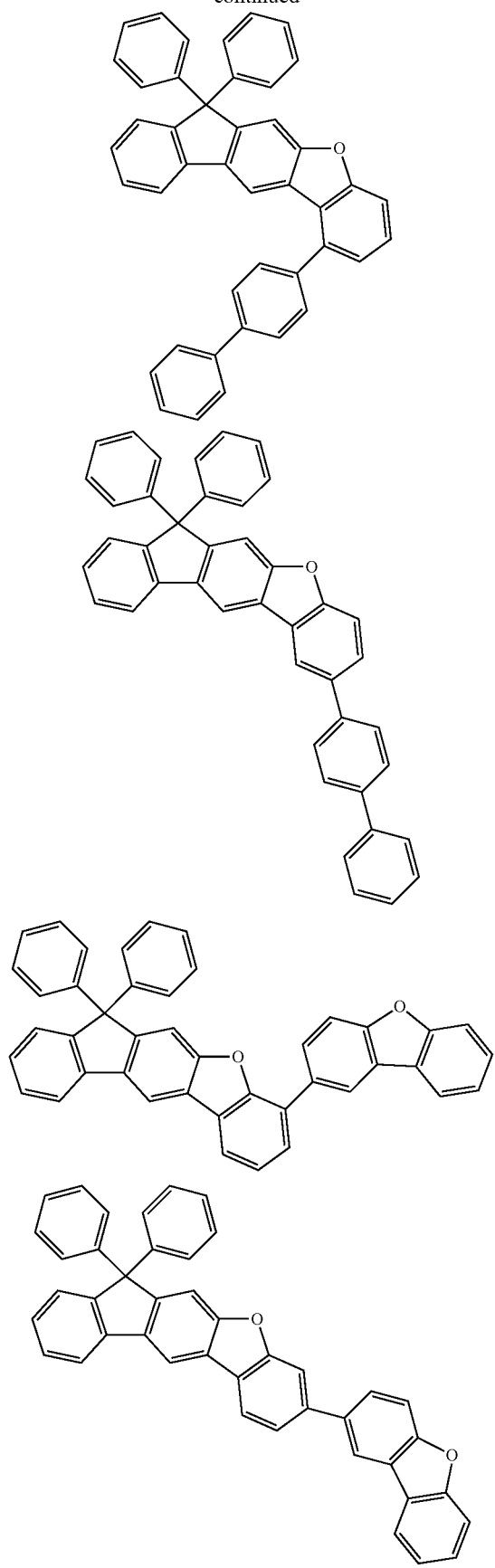
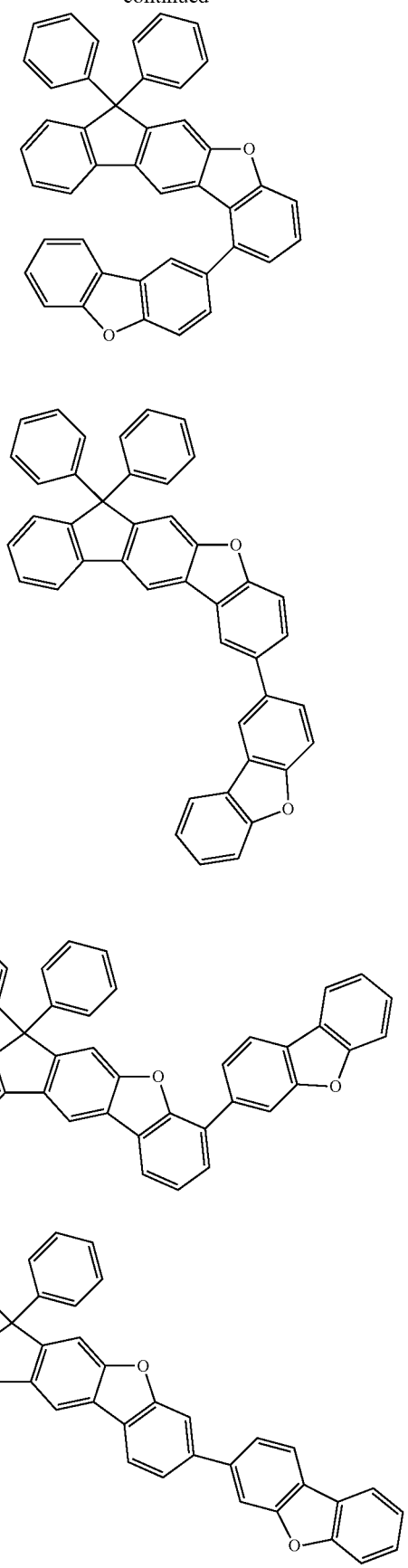

81
-continued
82
-continued
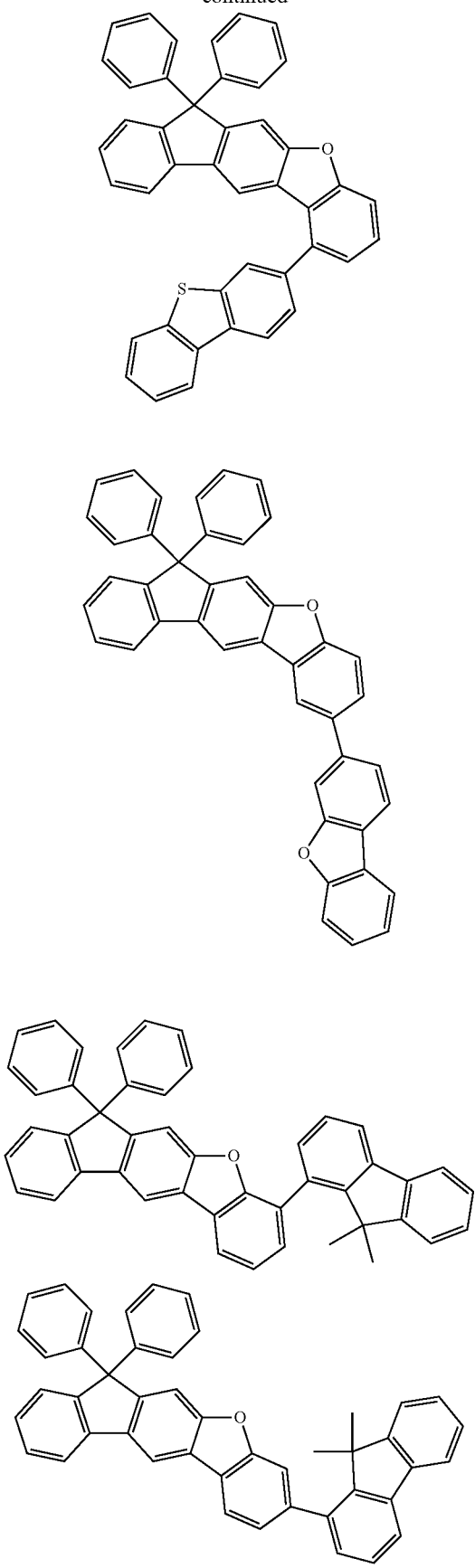
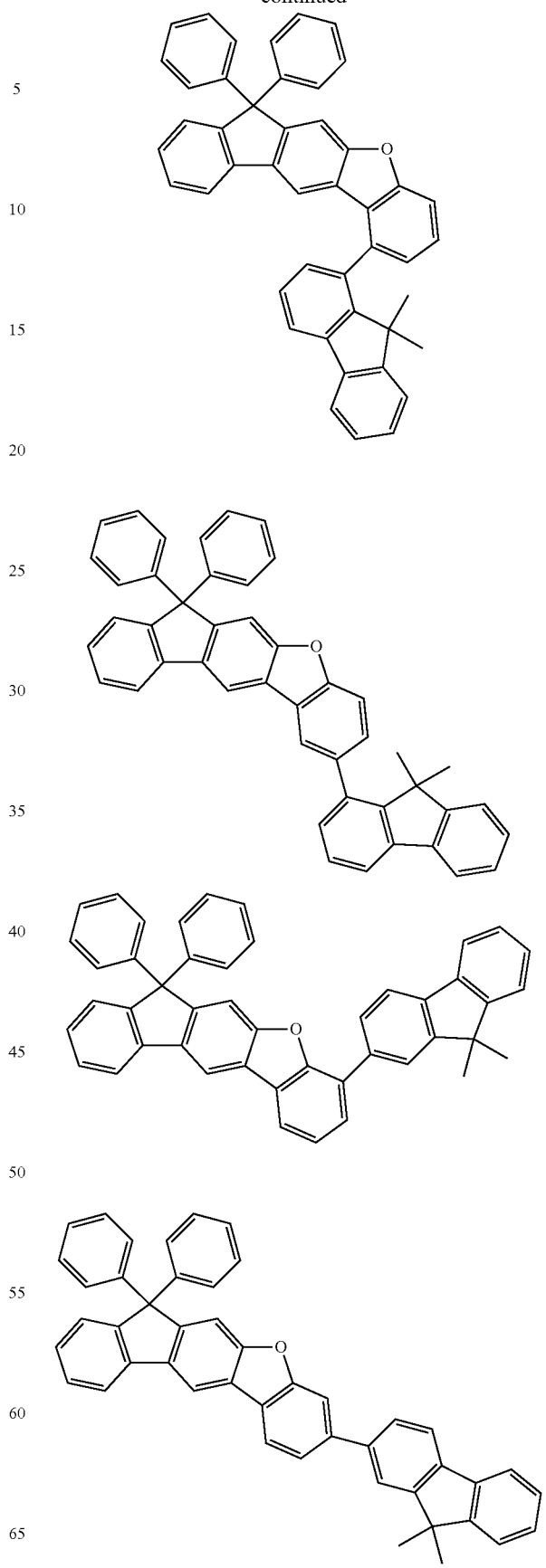

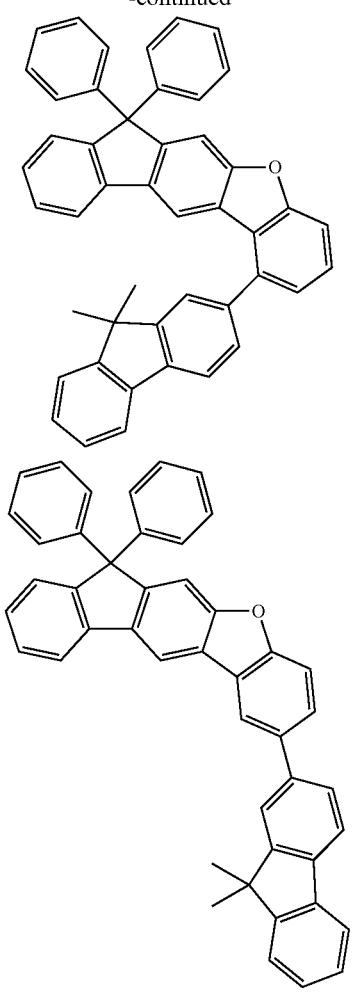
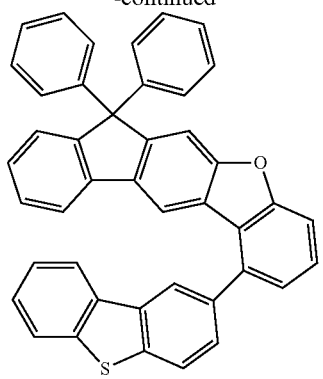
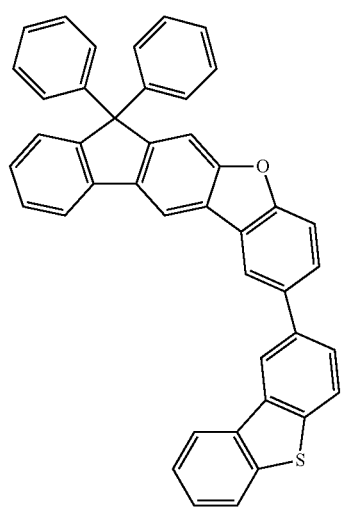
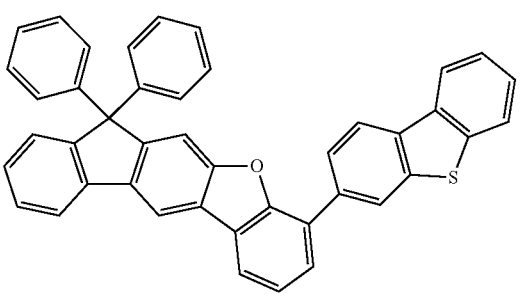
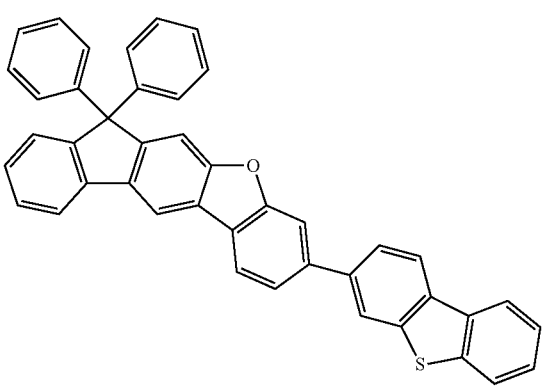

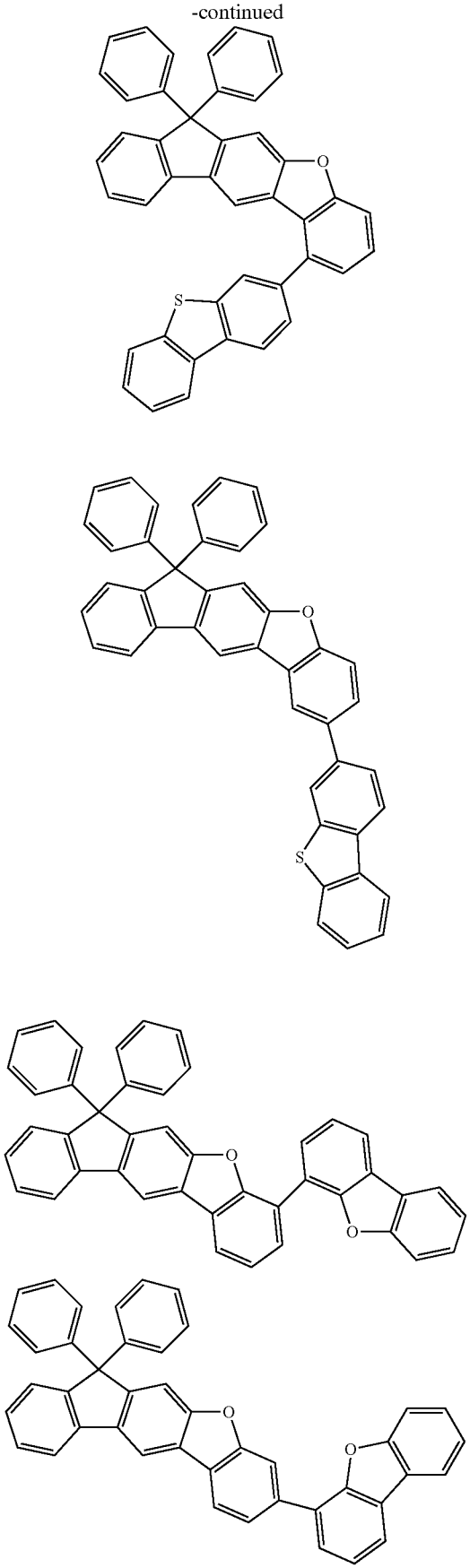

87
-continued

88
-continued

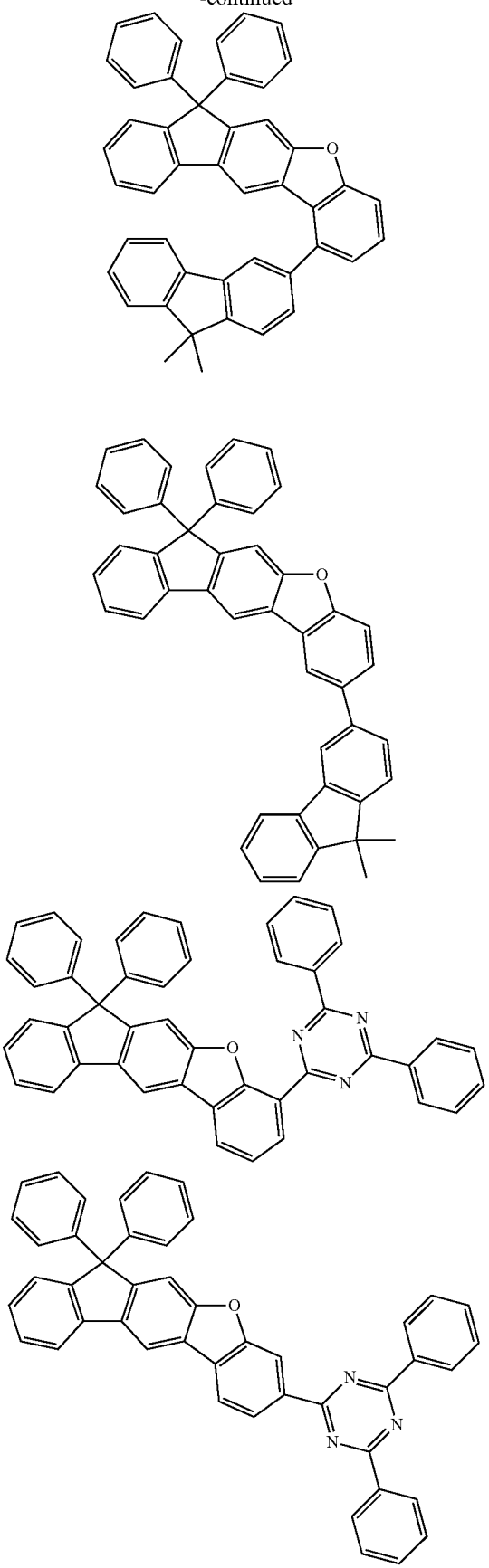

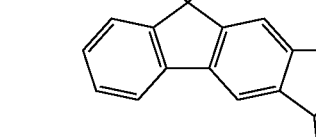
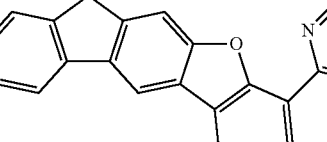
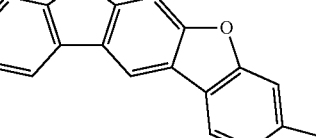

91
-continued
92
-continued
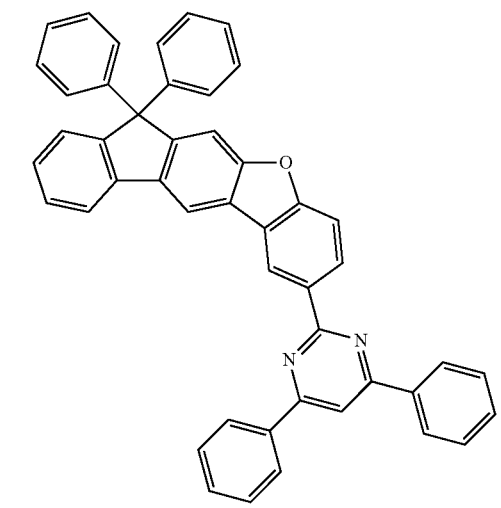
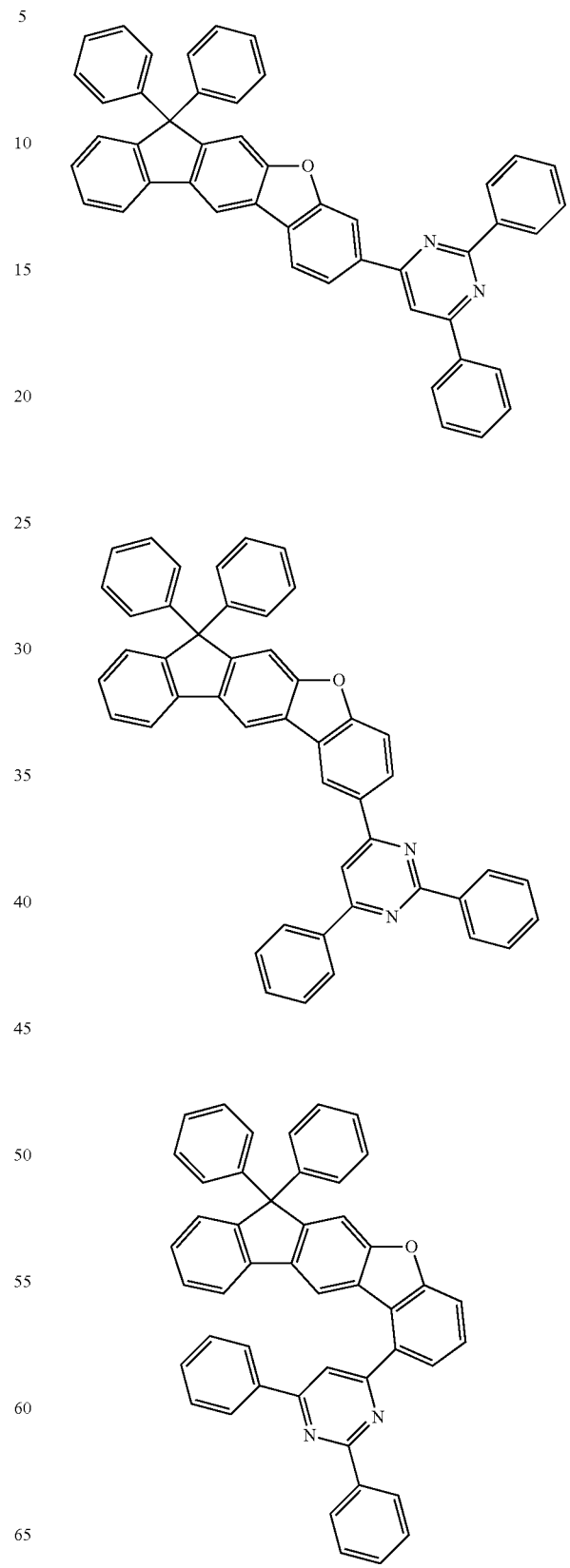

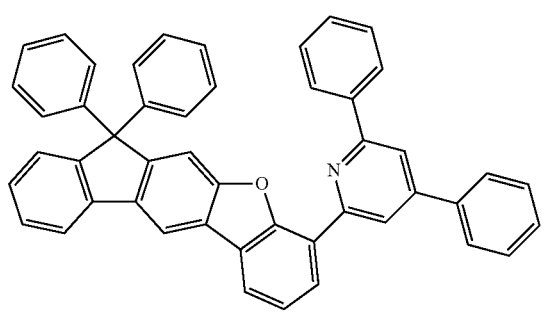
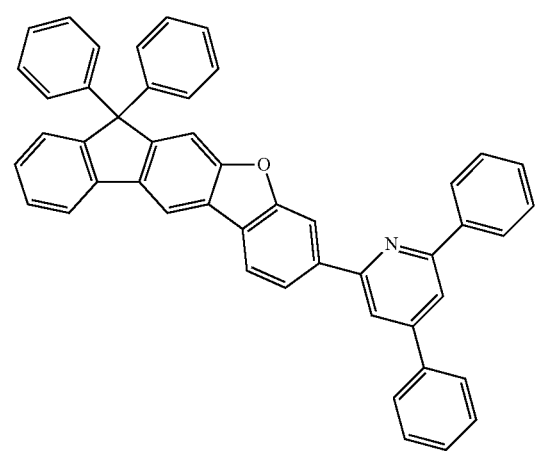
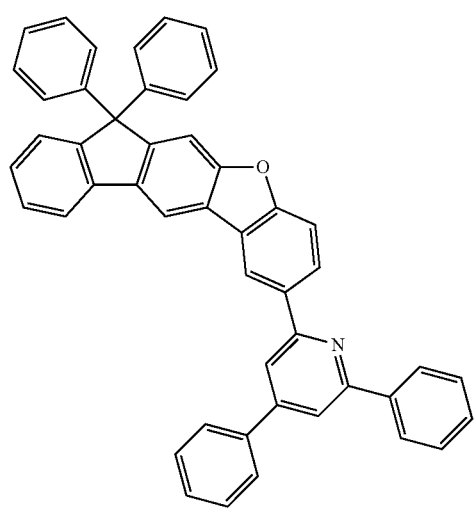
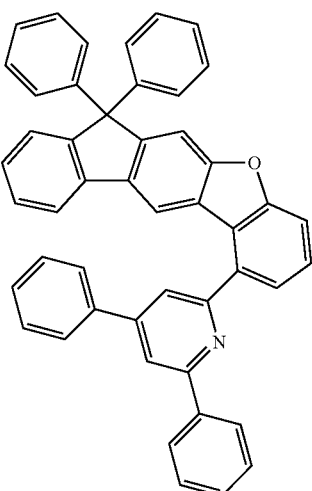
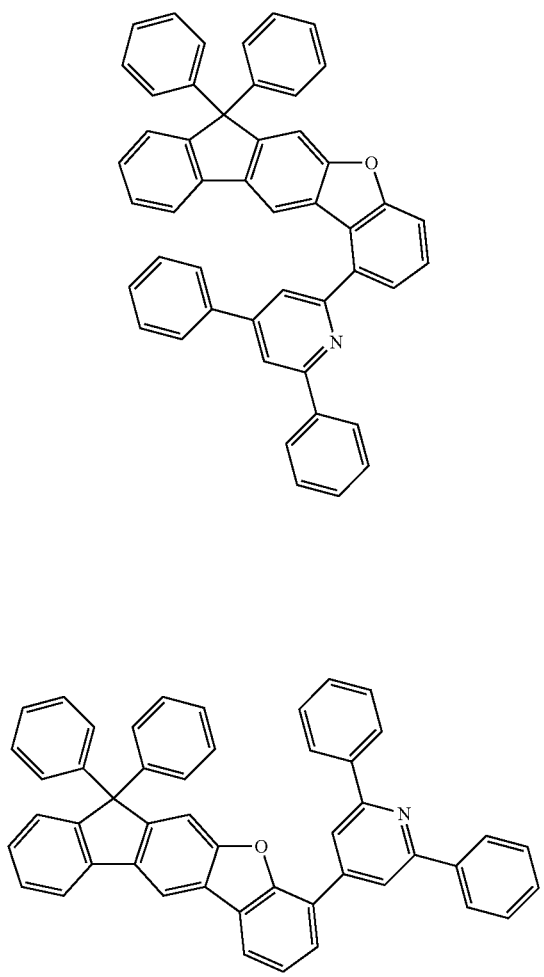
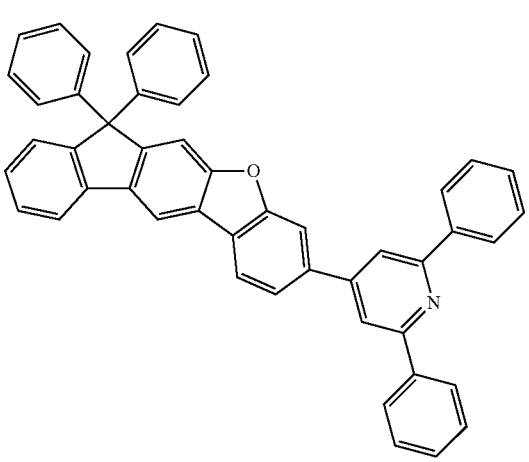

-continued
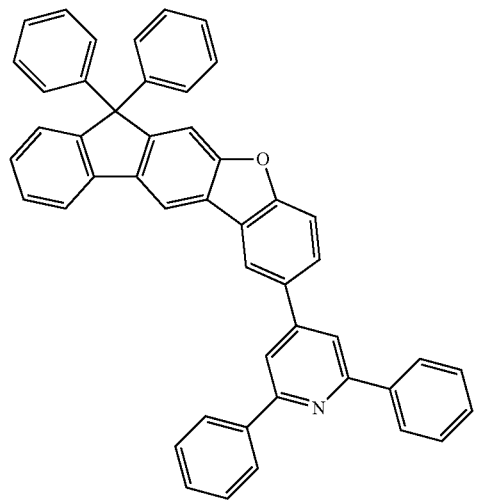
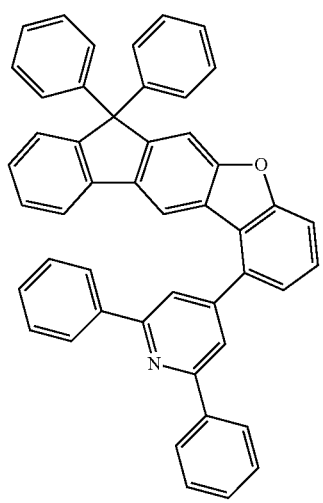
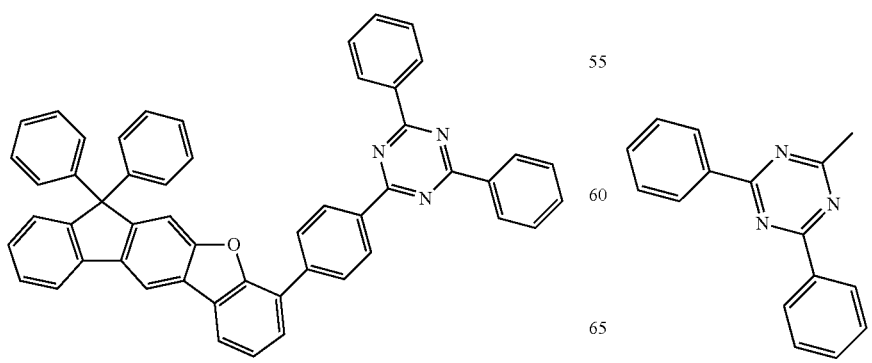
-continued
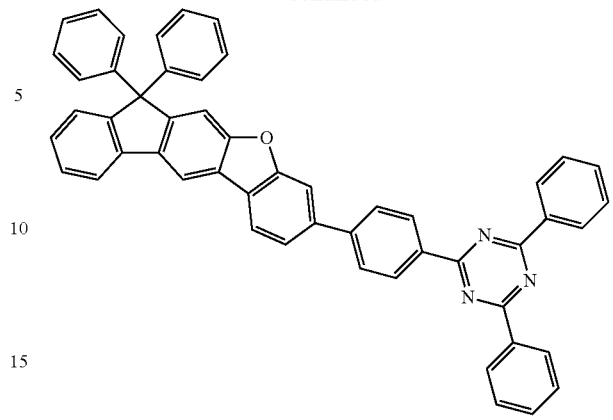
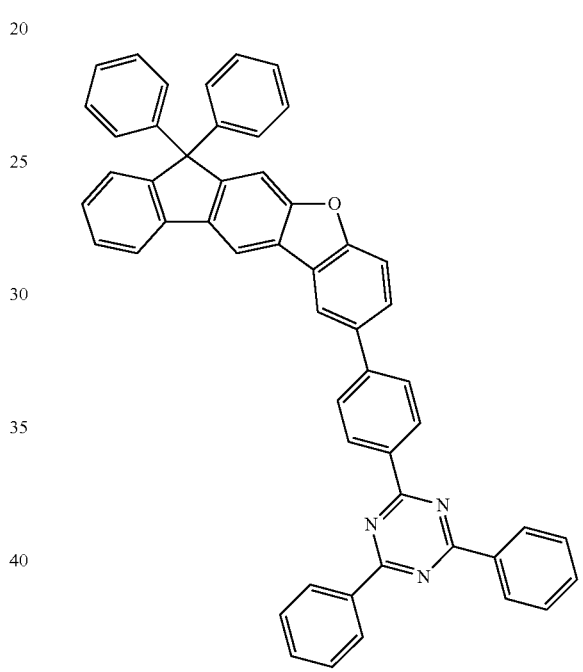
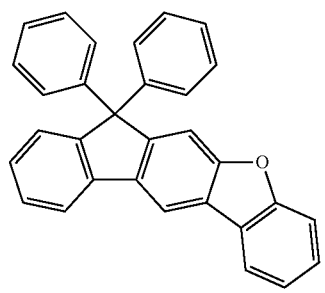

97
-continued
98
-continued
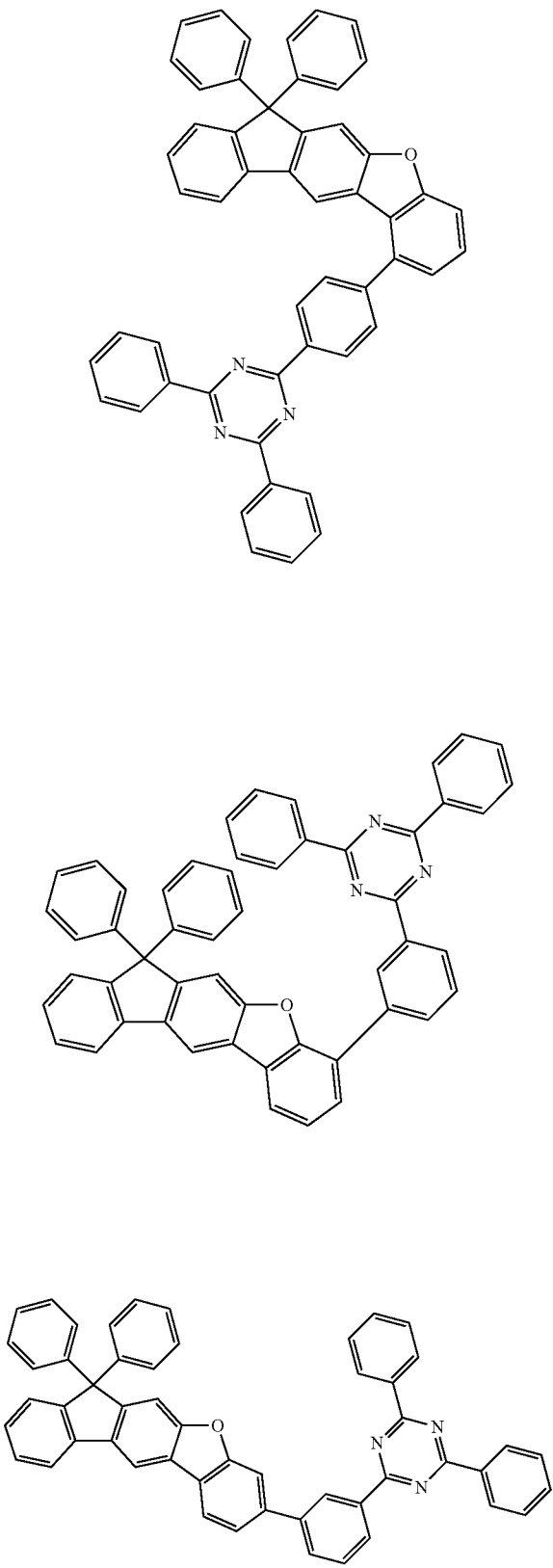
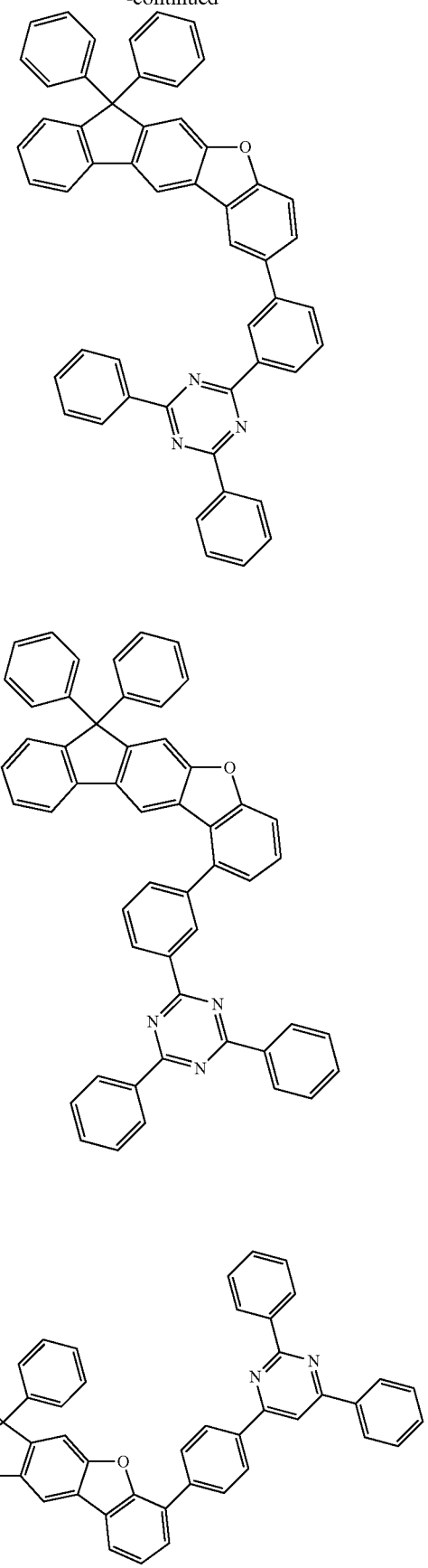

99
-continued
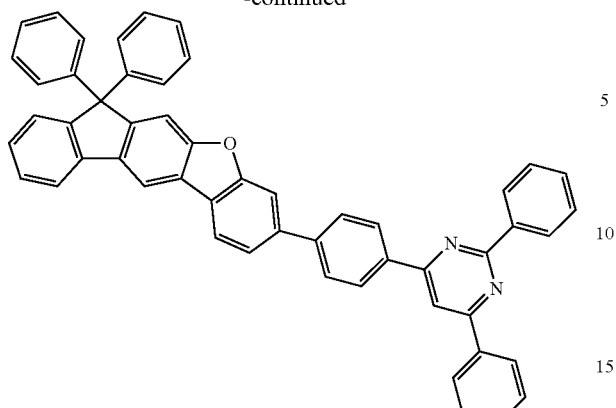
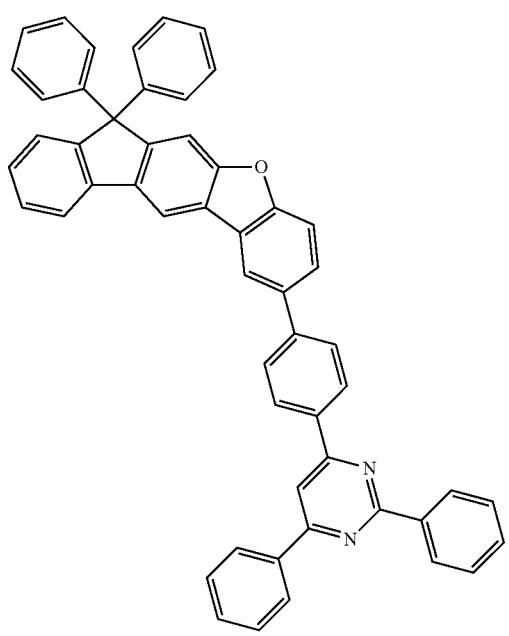
100
-continued
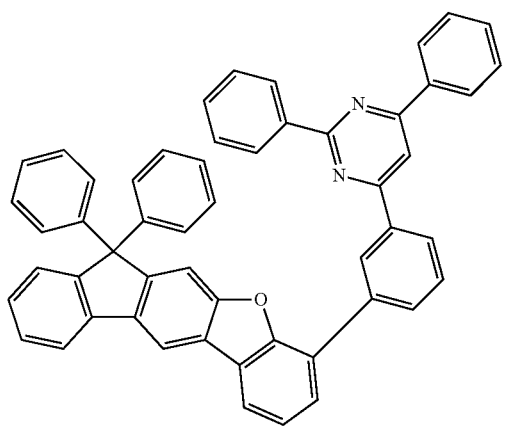
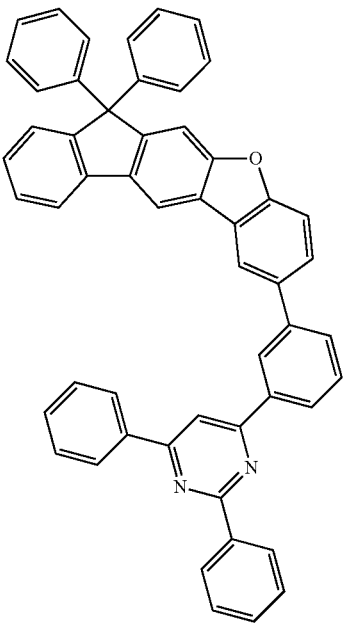

101
-continued
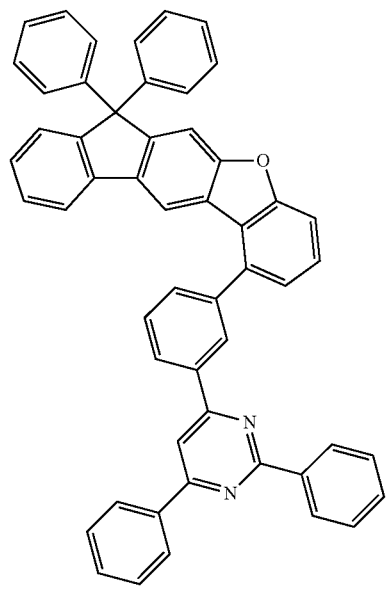
102
-continued
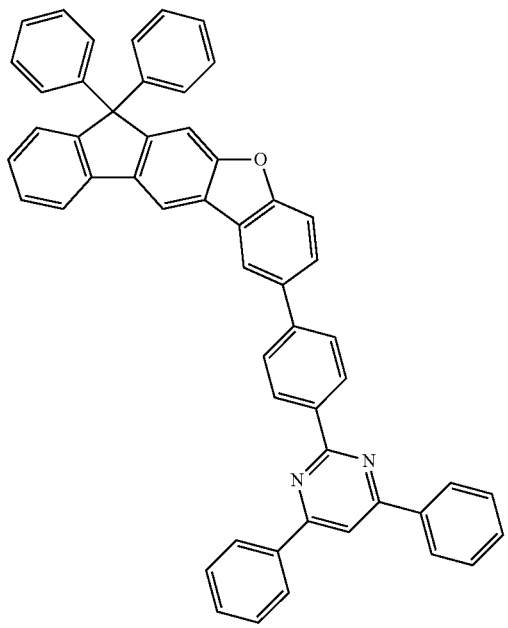
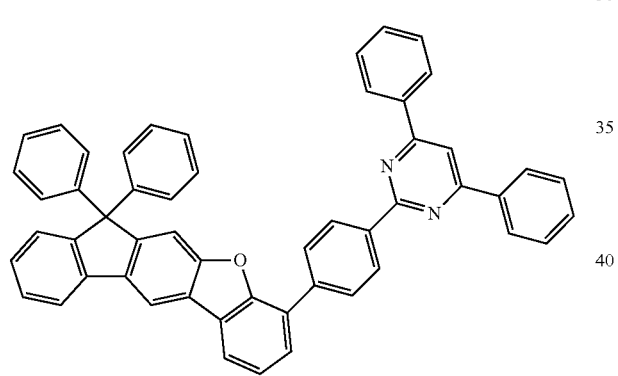
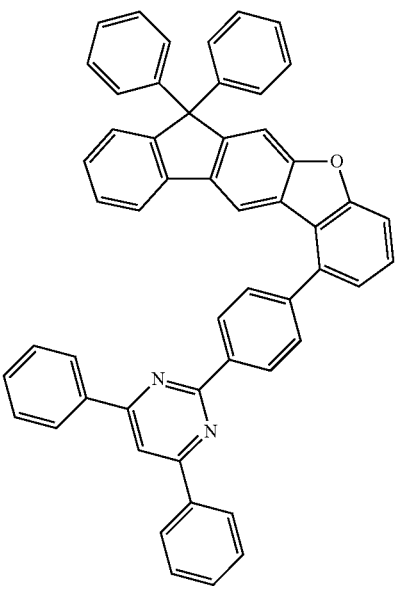 [SMILES: c1ccc(-c2cc(-c3ccc(-c4cccc5oc6cc7c(cc6c45)-c4ccccc4C7(c4ccccc4)c4ccccc4)cc3)nc(-c3ccccc3)n2)cc1]
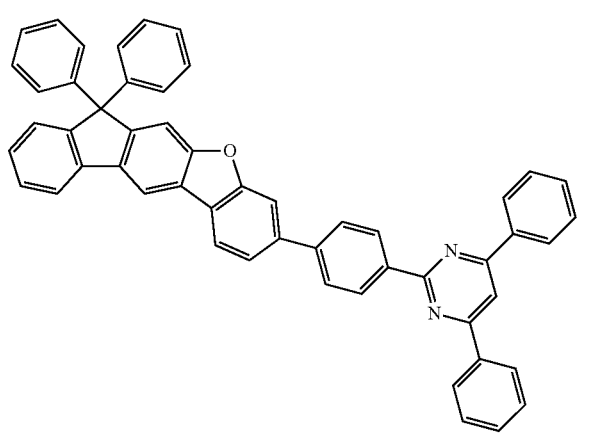
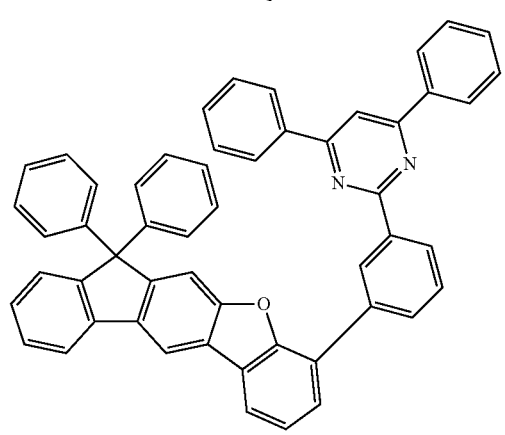

103
-continued
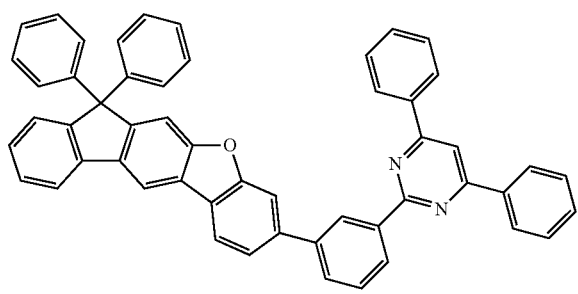
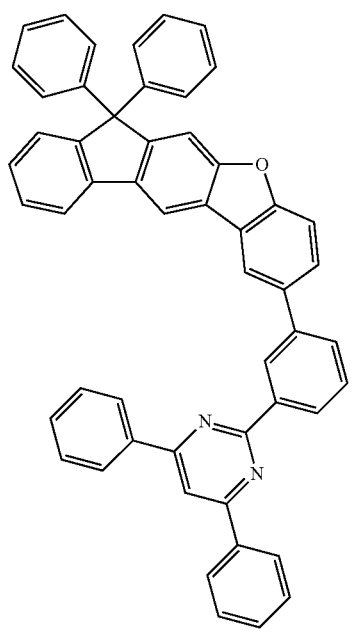
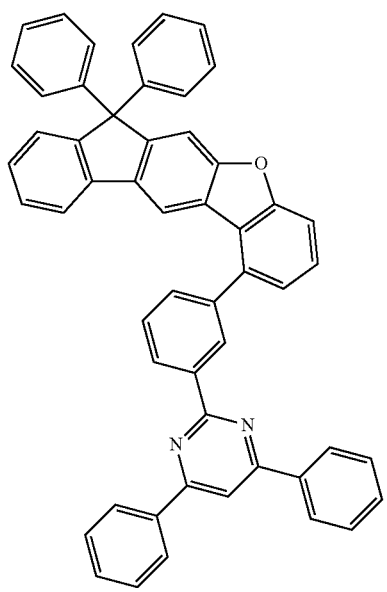 [SMILES: c1ccc(-c2cc(-c3ccccc3)nc(-c3cccc(-c4cccc5oc6cc7c(cc6c45)-c4ccccc4C7(c4ccccc4)c4ccccc4)c3)n2)cc1]
104
-continued
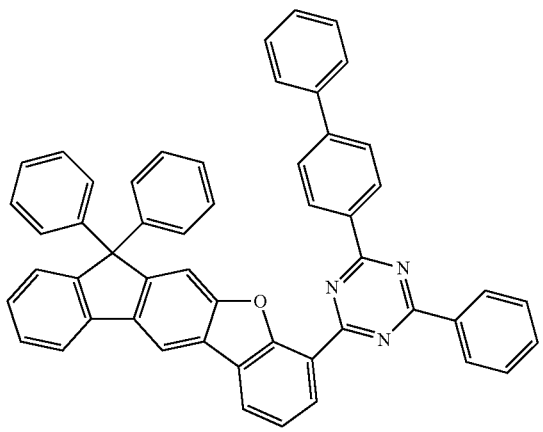
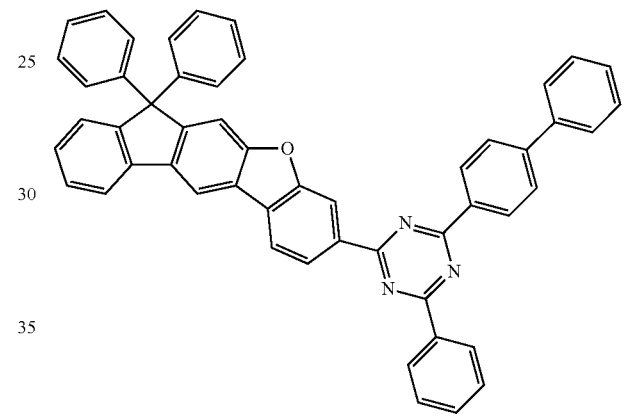
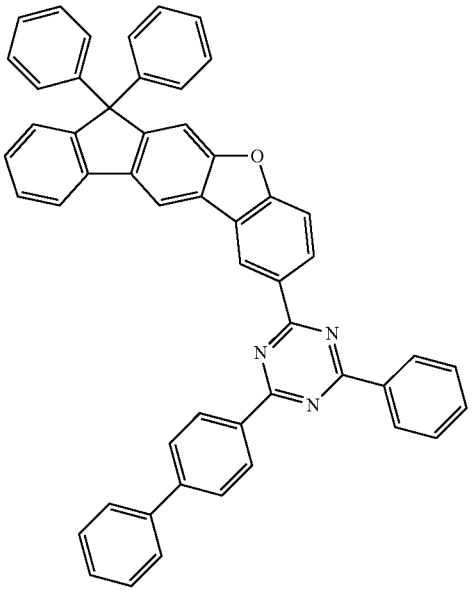

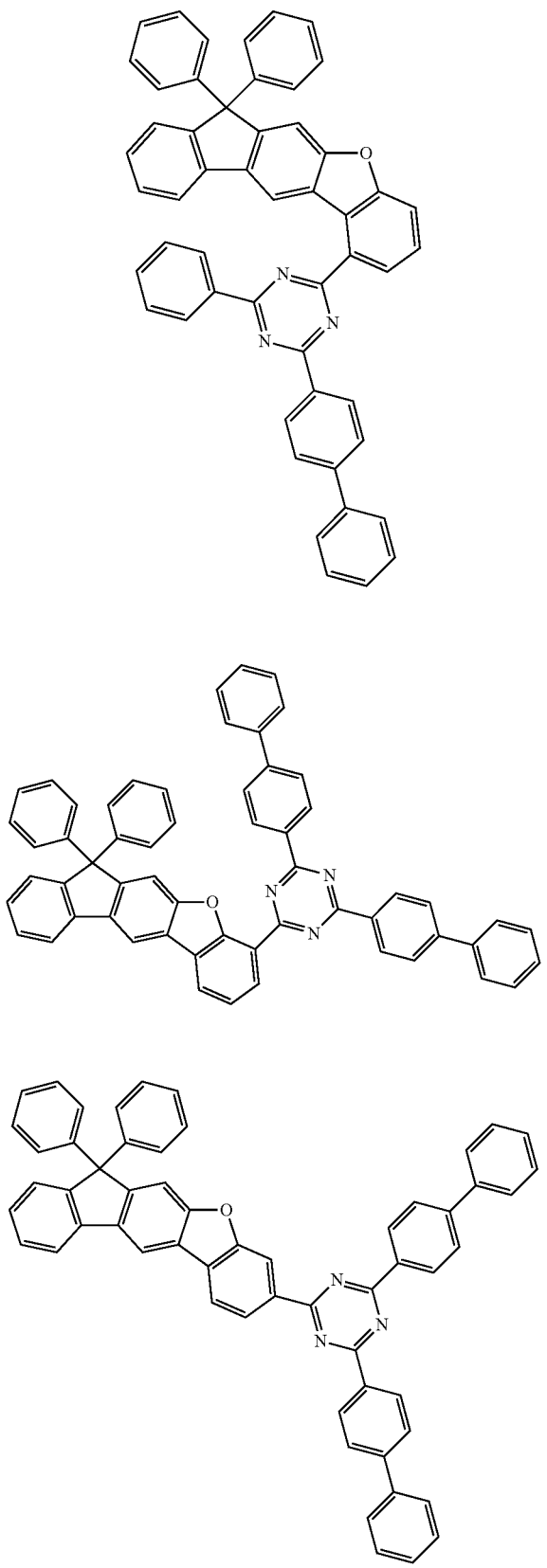
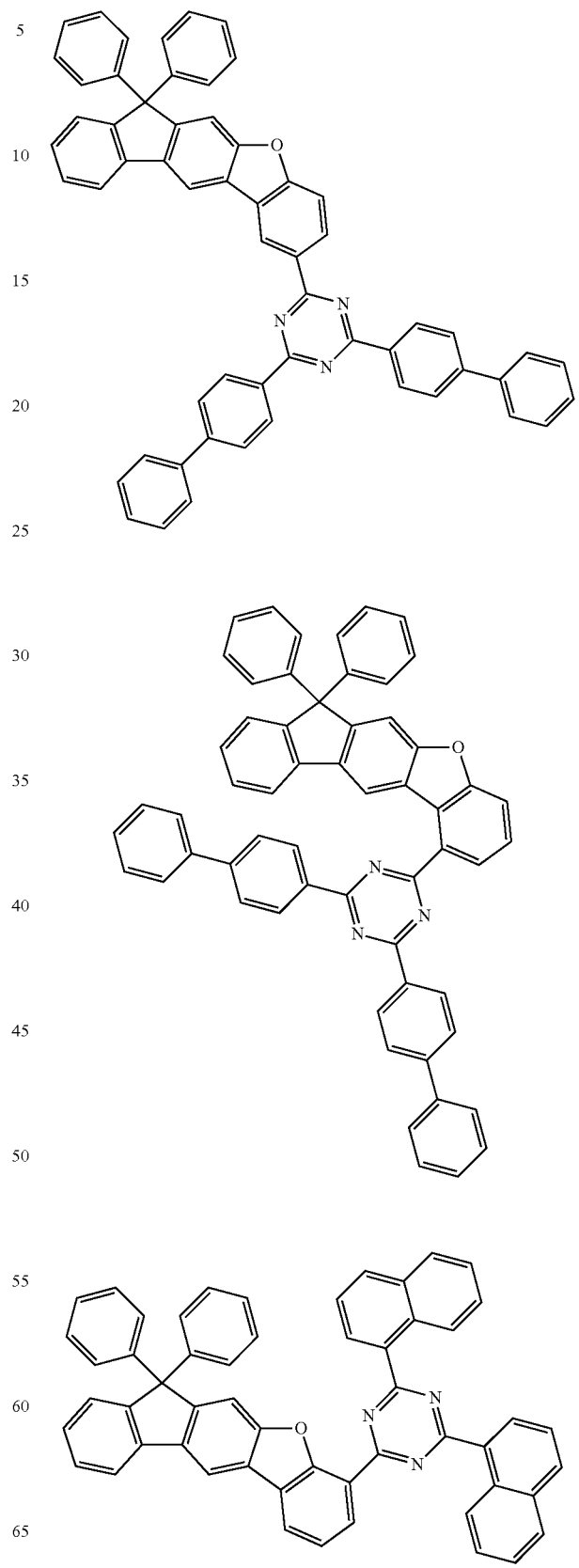

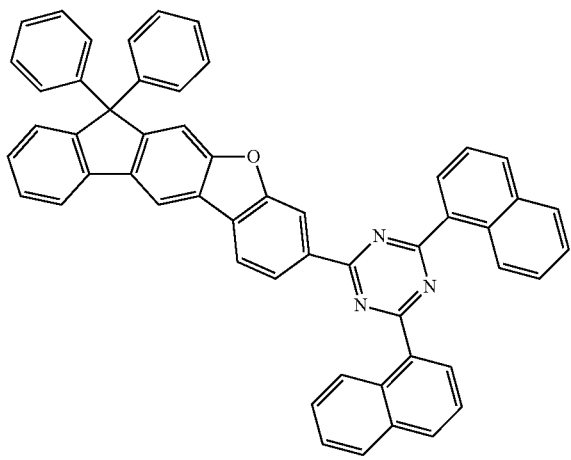
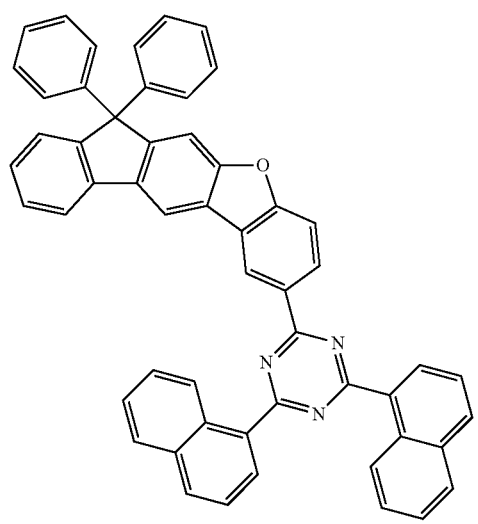
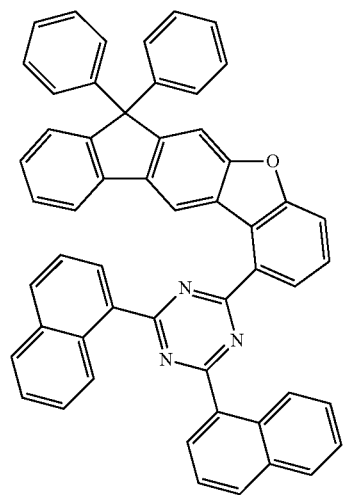
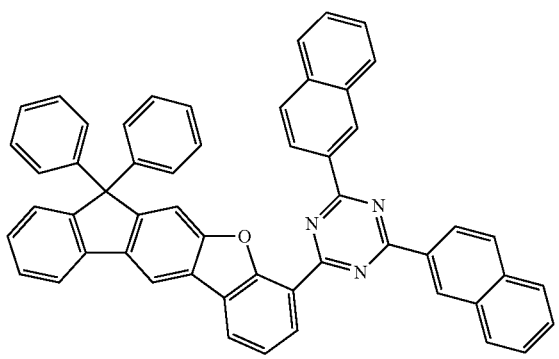
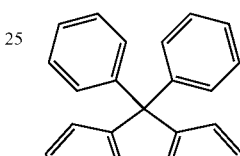
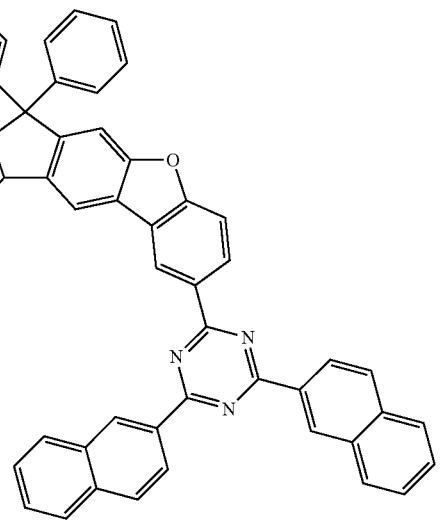

109
-continued
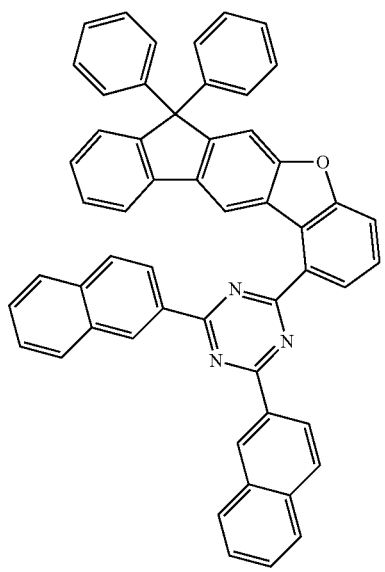 [SMILES: c1ccc(C2(c3ccccc3)c3ccccc3-c3cc4c(cc32)oc2cccc(-c3nc(-c5ccc6ccccc6c5)nc(-c5ccc6ccccc6c5)n3)c24)cc1]
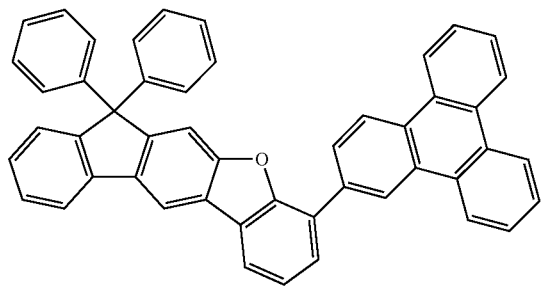
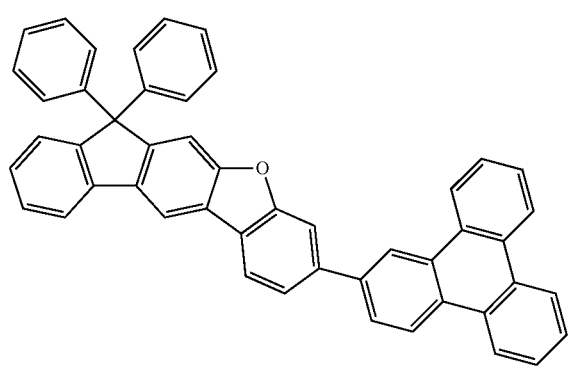
110
-continued
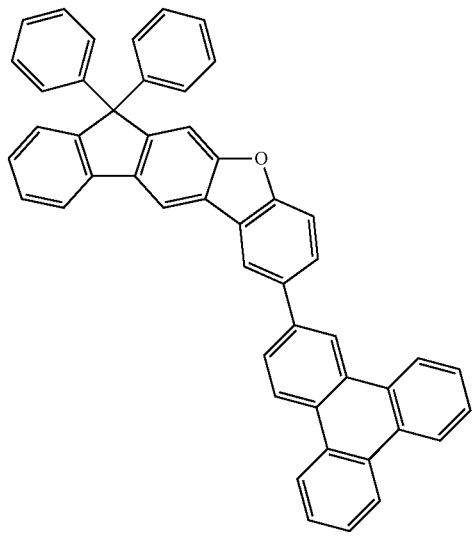
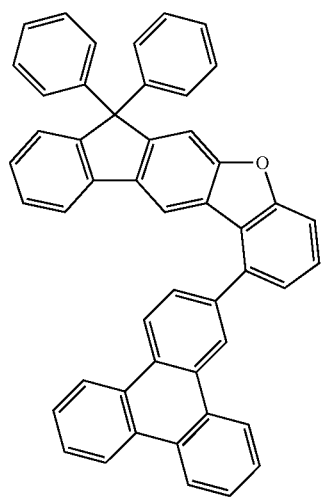
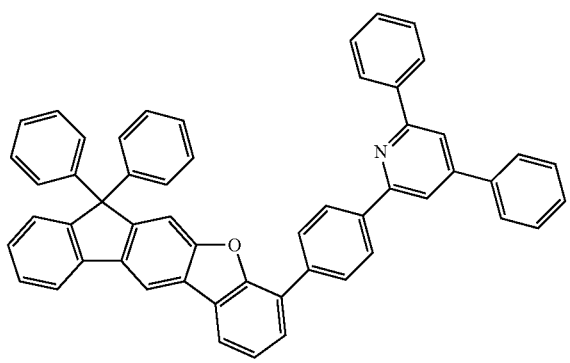

111
-continued
112
-continued
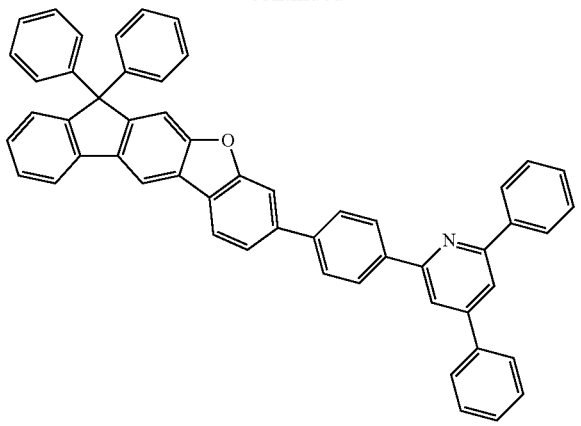
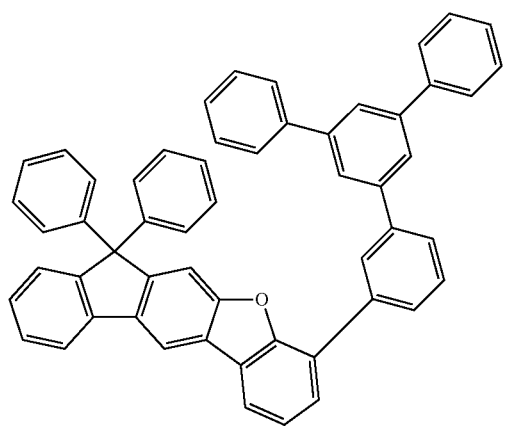
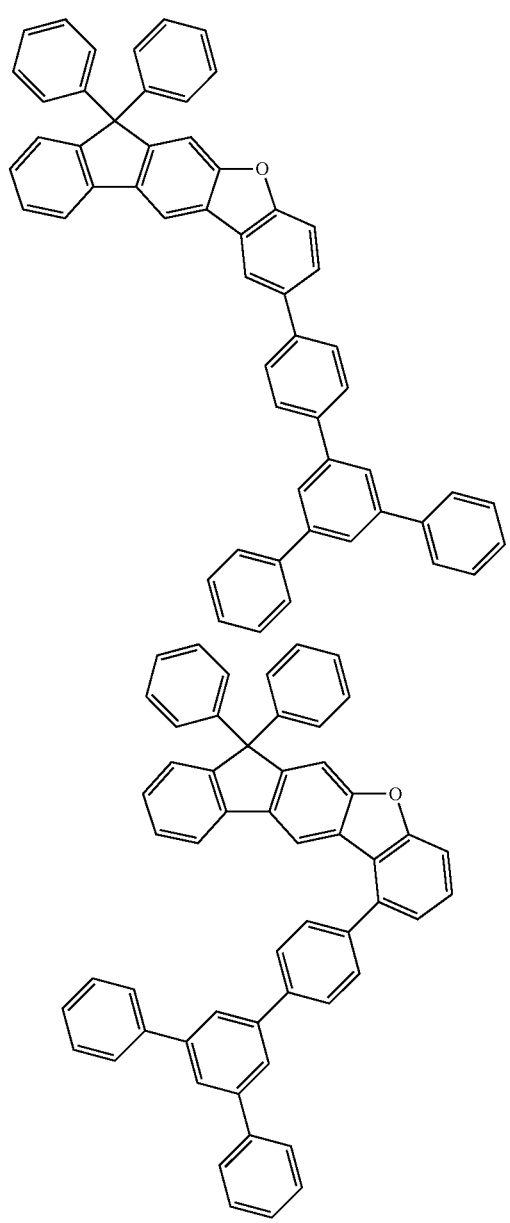
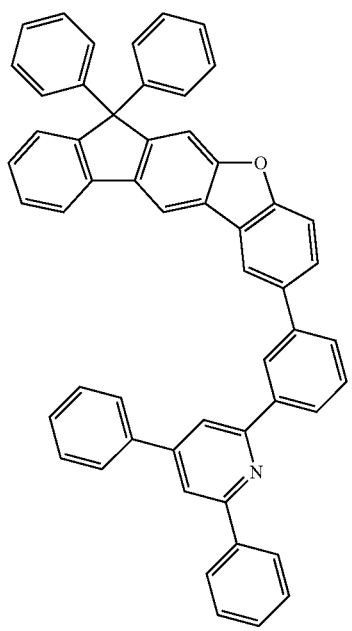

113
-continued
114
-continued
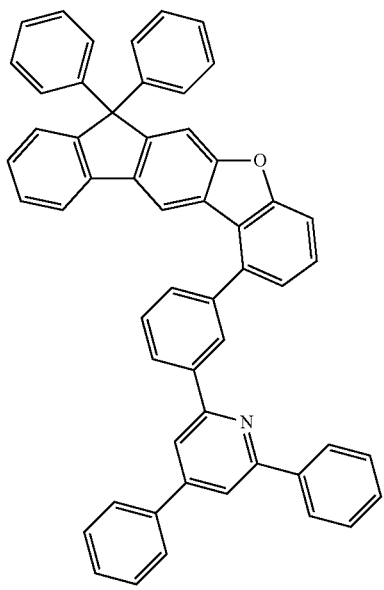 [SMILES: c1ccc(-c2cc(-c3ccccc3)nc(-c3cccc(-c4cccc5oc6cc7c(cc6c45)-c4ccccc4C7(c4ccccc4)c4ccccc4)c3)c2)cc1]
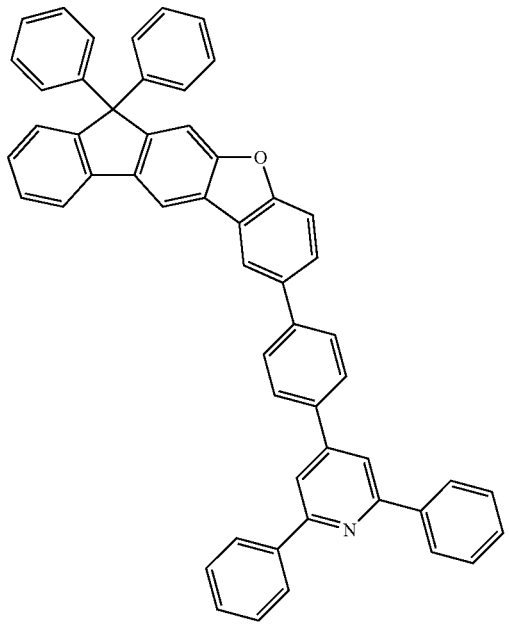
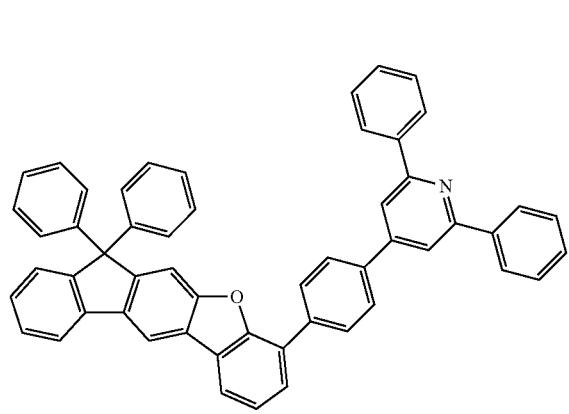
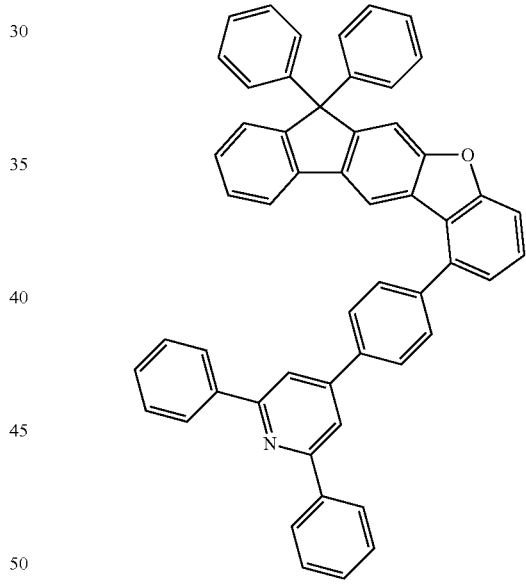
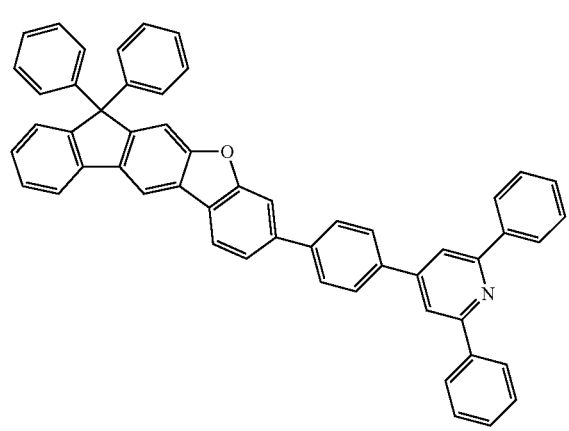
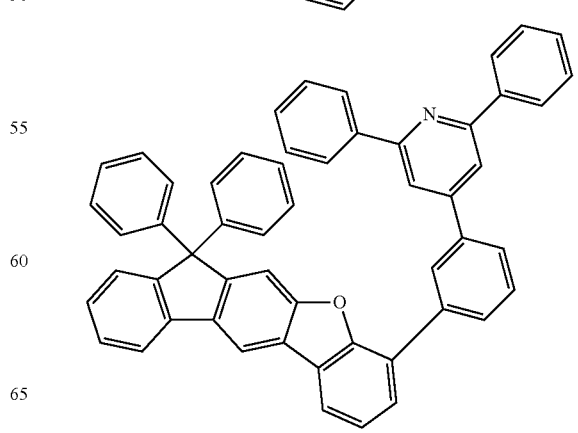

115
-continued
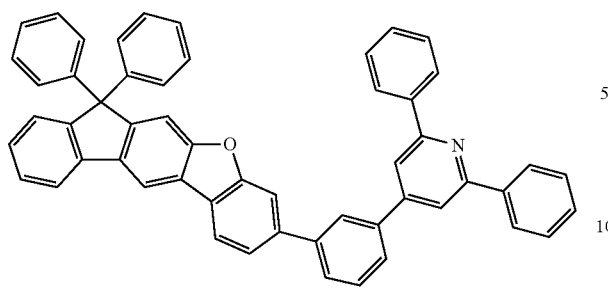
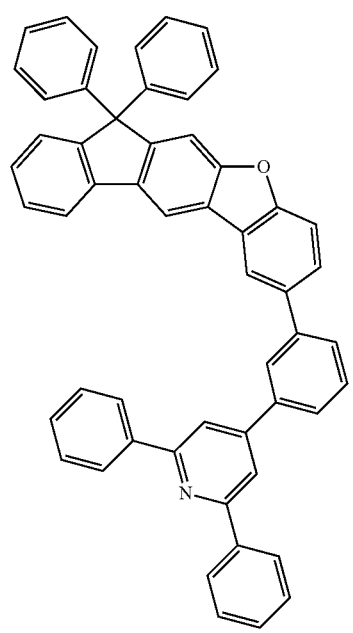
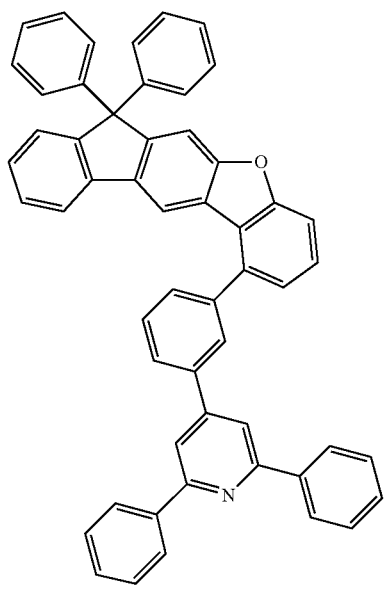 [SMILES: c1ccc(-c2cc(-c3cccc(-c4cccc5oc6cc7c(cc6c45)-c4ccccc4C7(c4ccccc4)c4ccccc4)c3)cc(-c3ccccc3)n2)cc1]
116
-continued
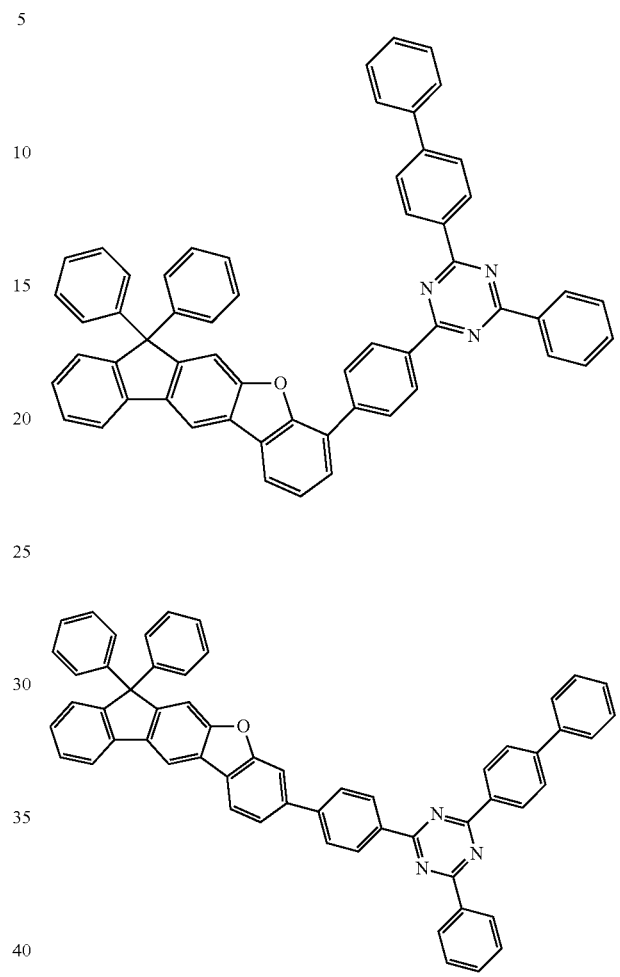
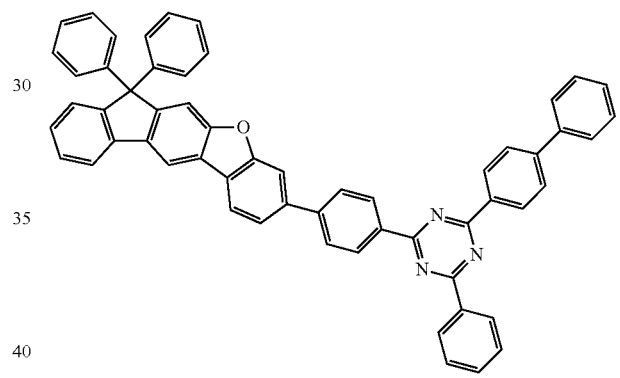
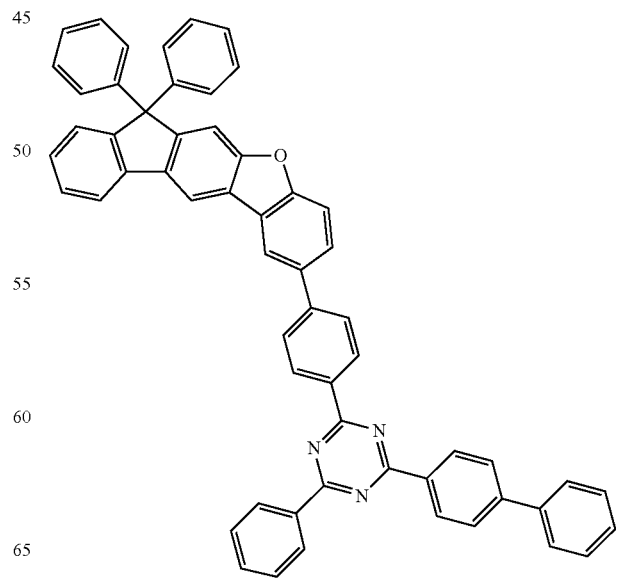

| 117 | 118 |
|---|---|
| -continued | -continued |
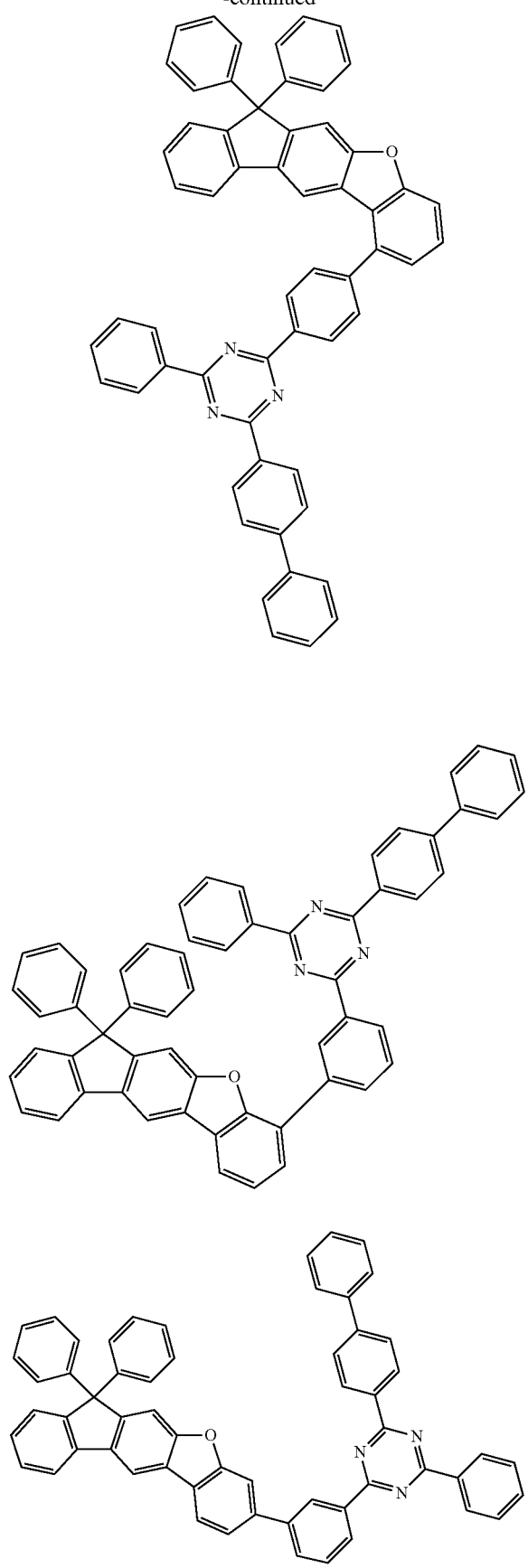
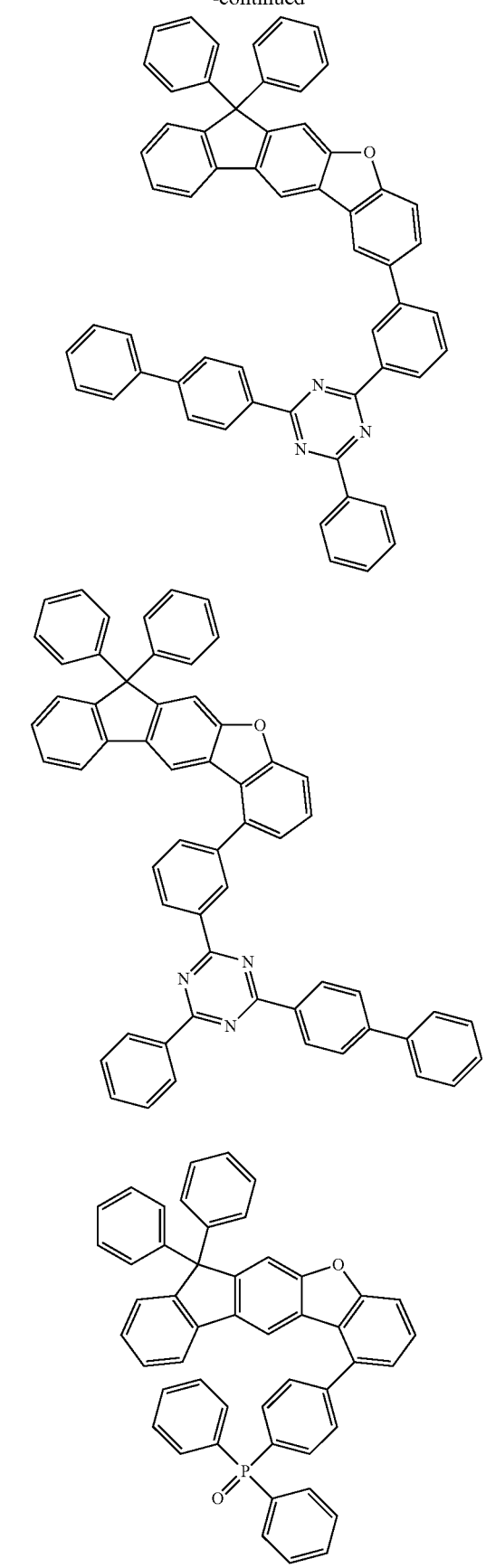

119
-continued
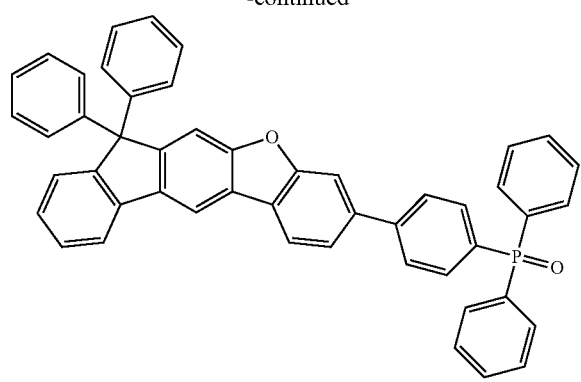
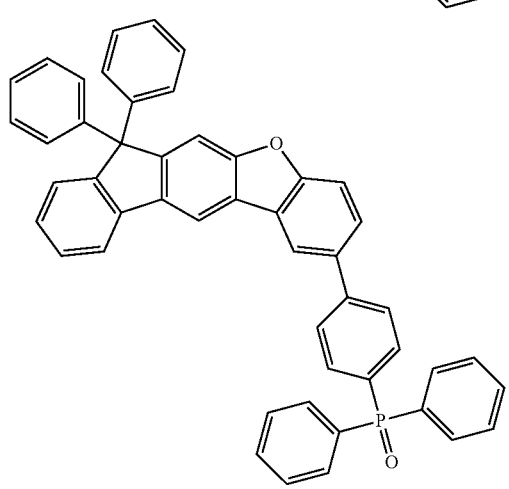
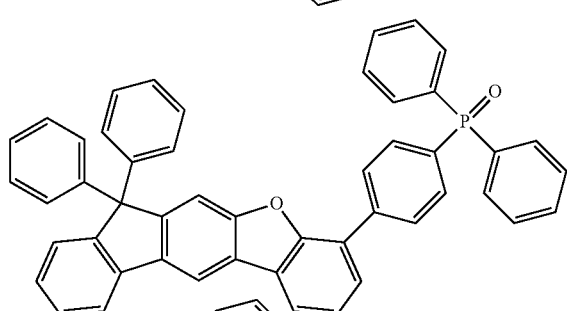
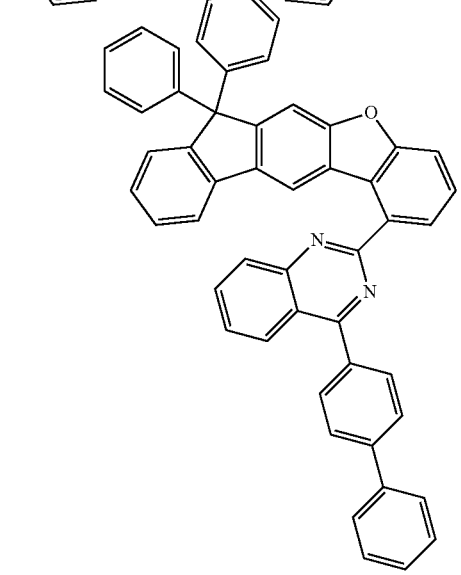
120
-continued
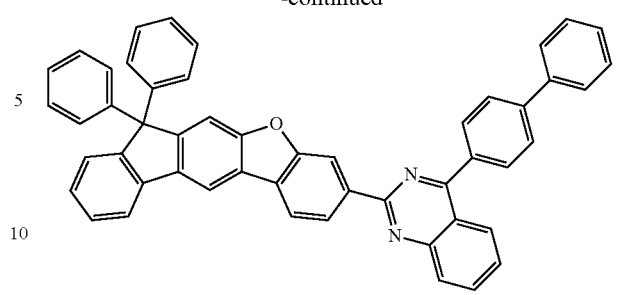
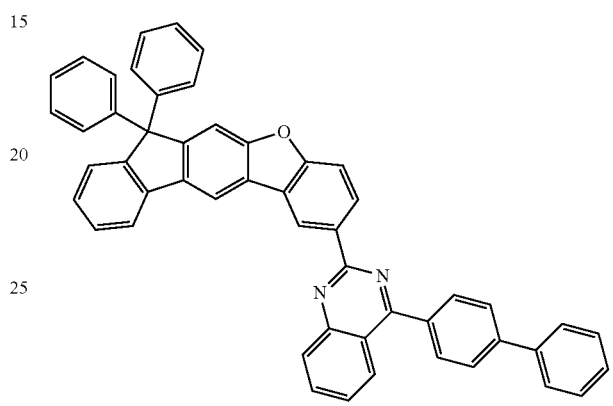
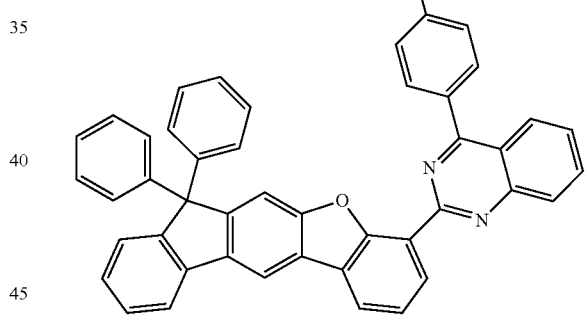
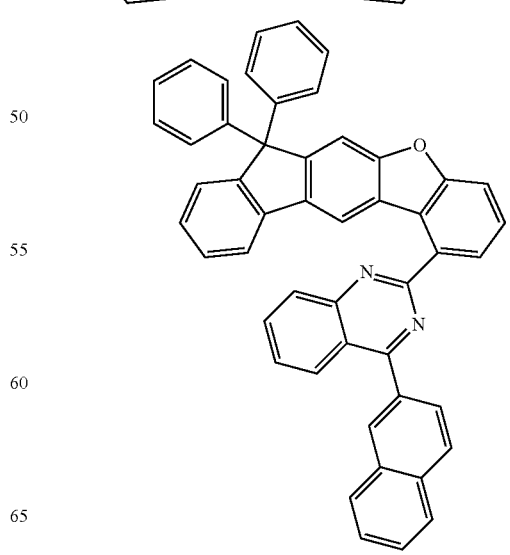

121
-continued
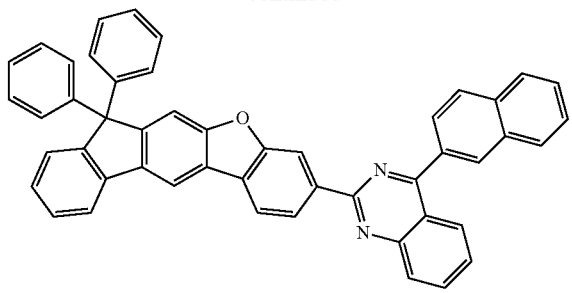
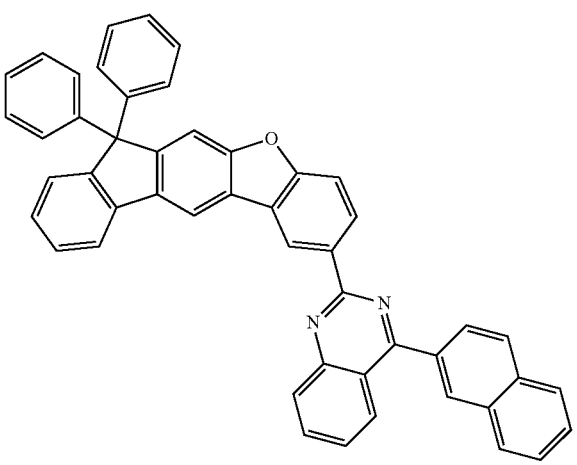
122
-continued
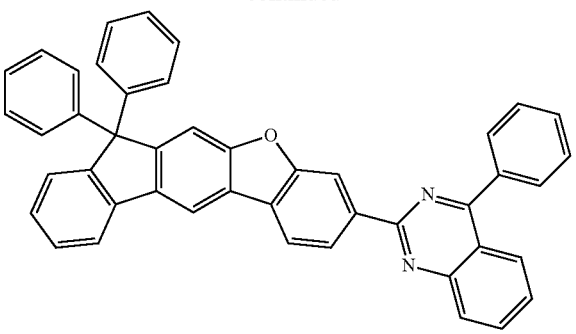
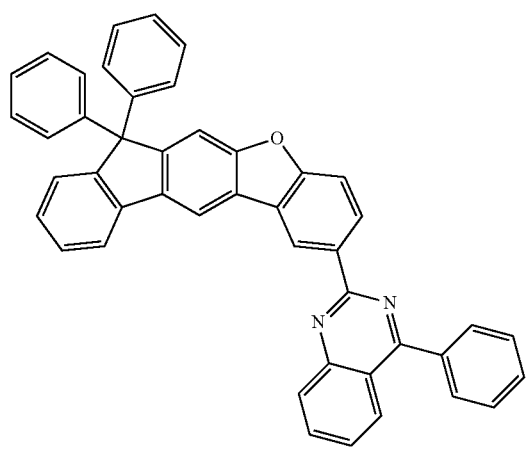
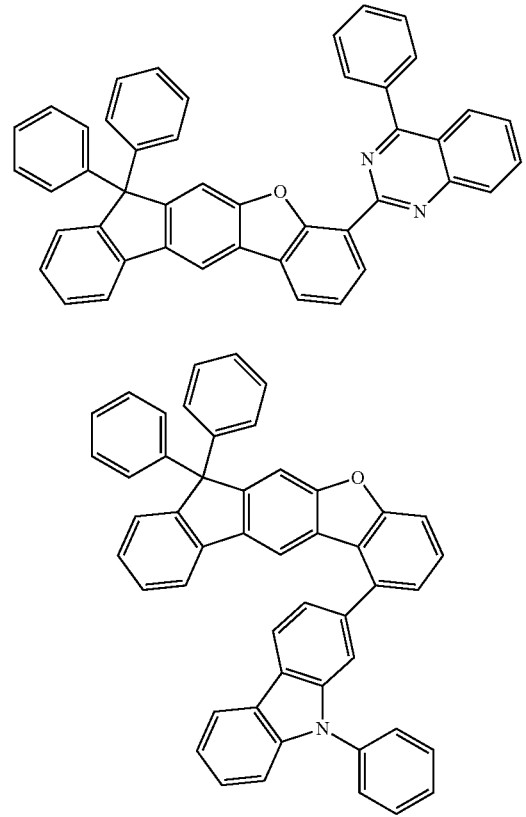

123
-continued
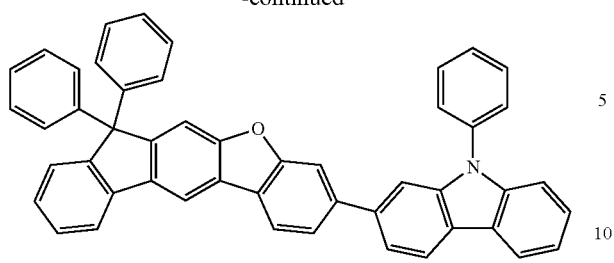
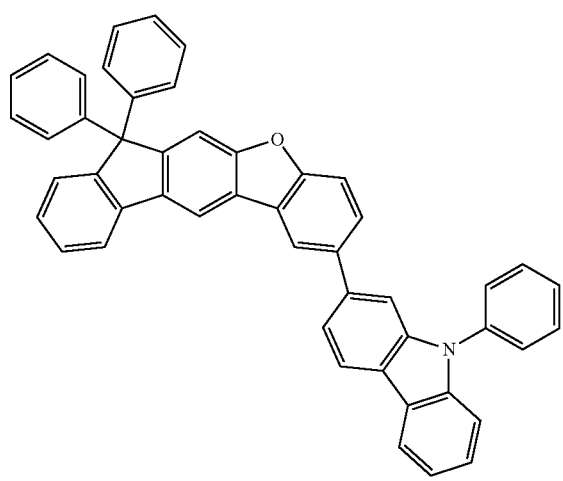
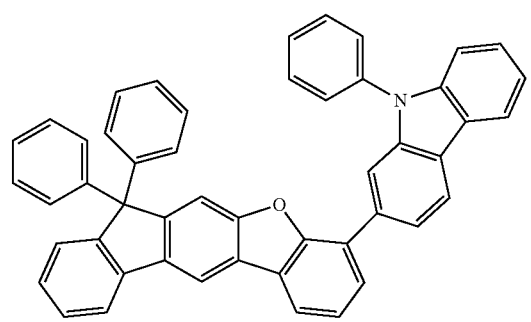
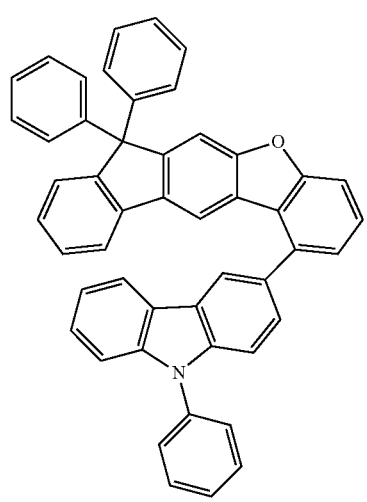
124
-continued
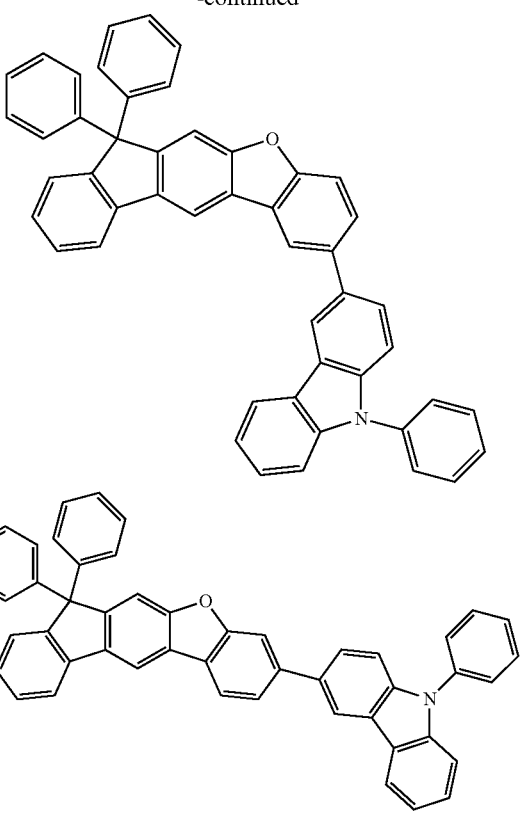
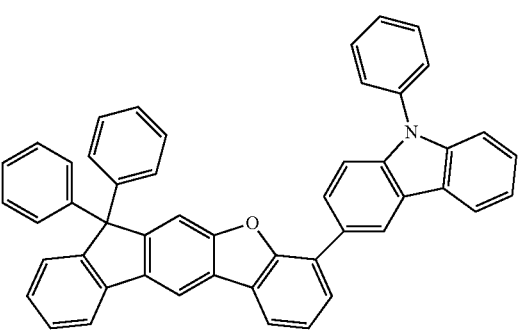
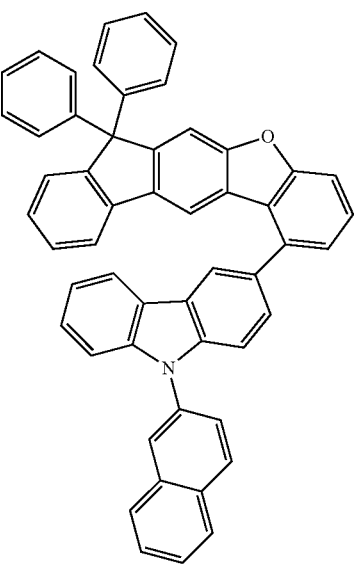

125
-continued
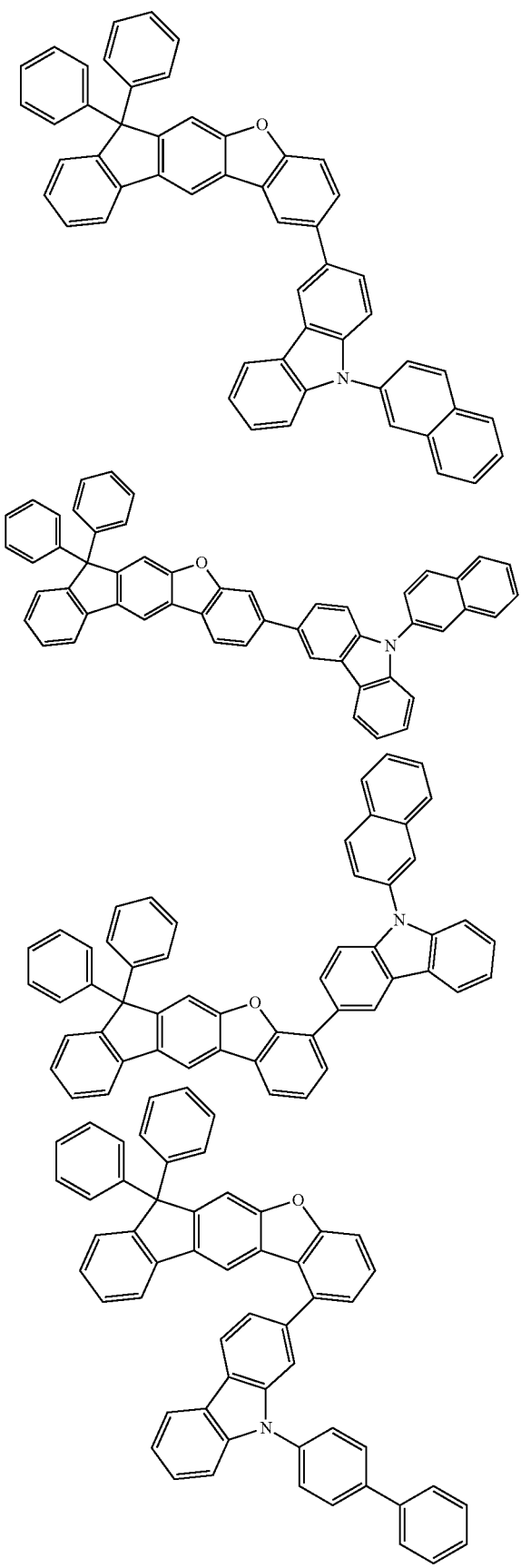
126
-continued
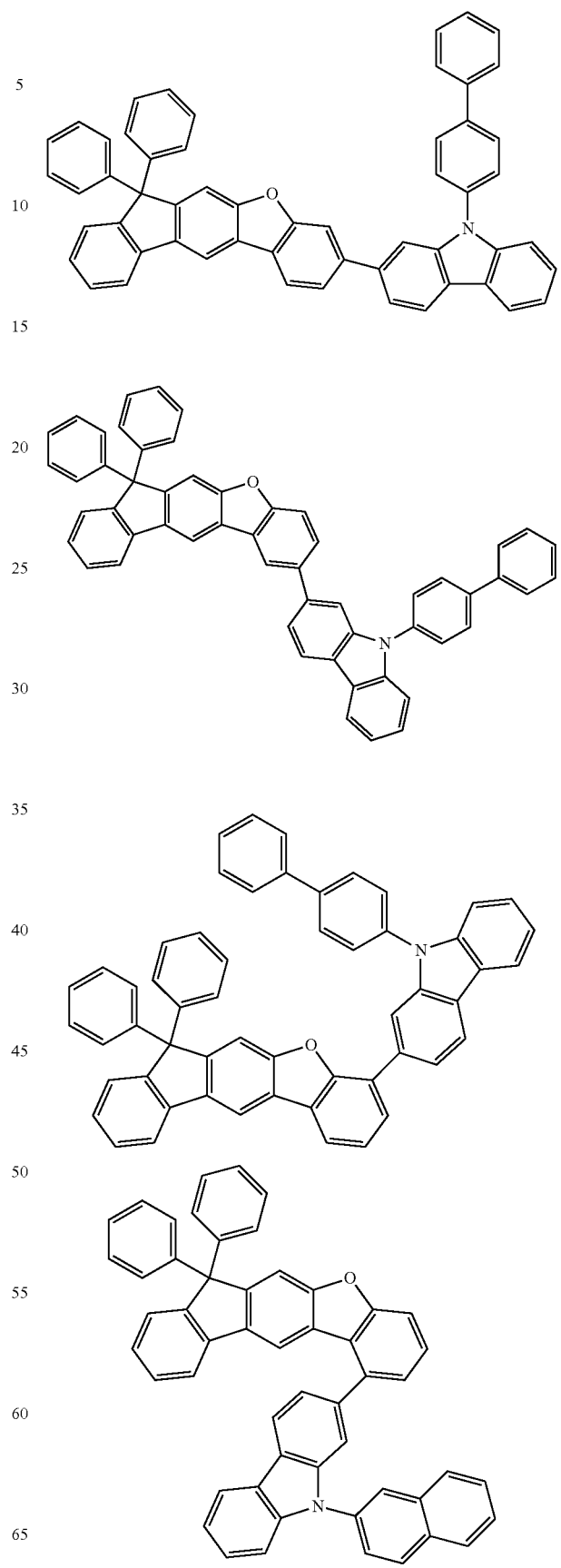

127
-continued
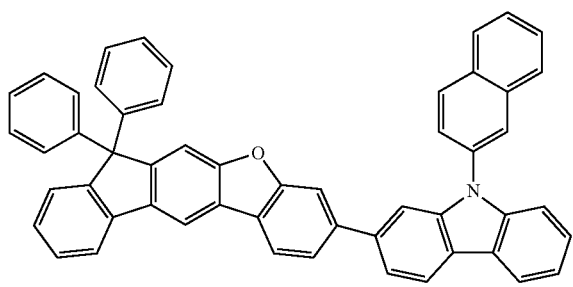
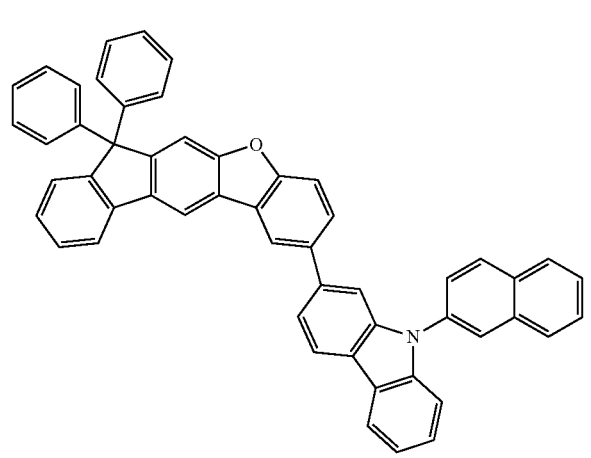
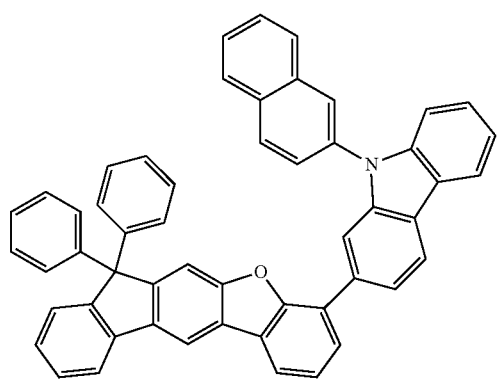
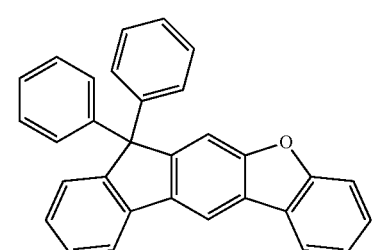
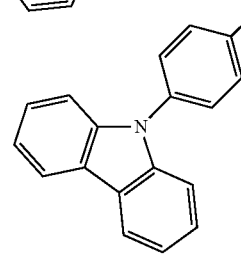
128
-continued
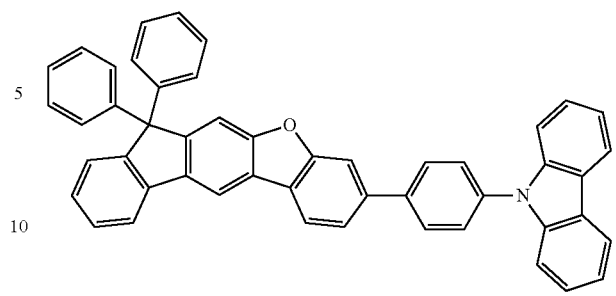
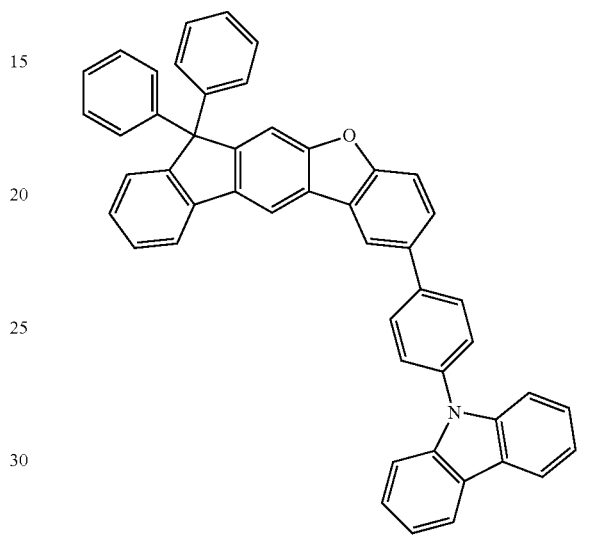
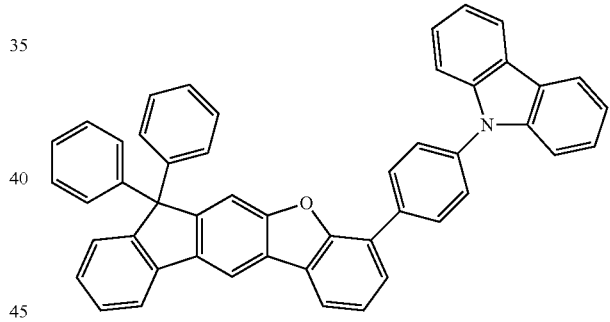
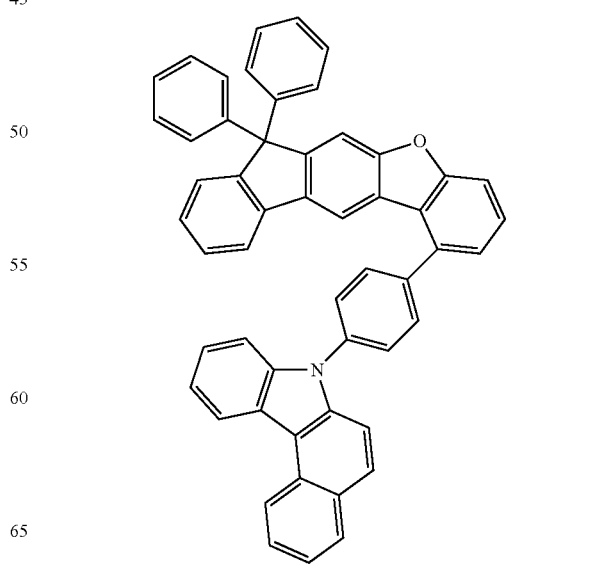

129
-continued
130
-continued
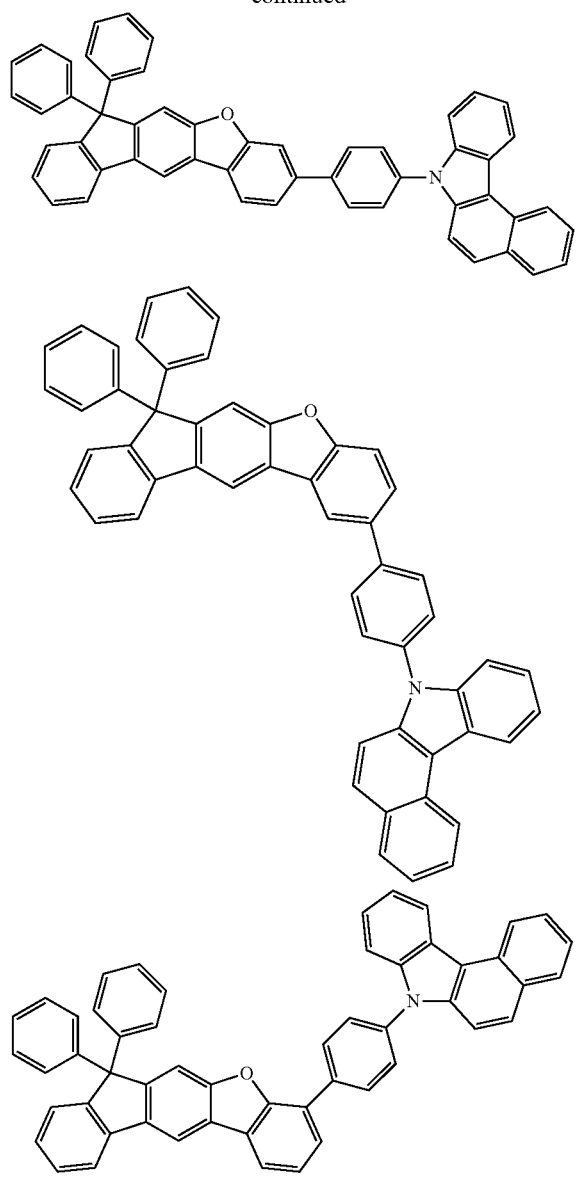
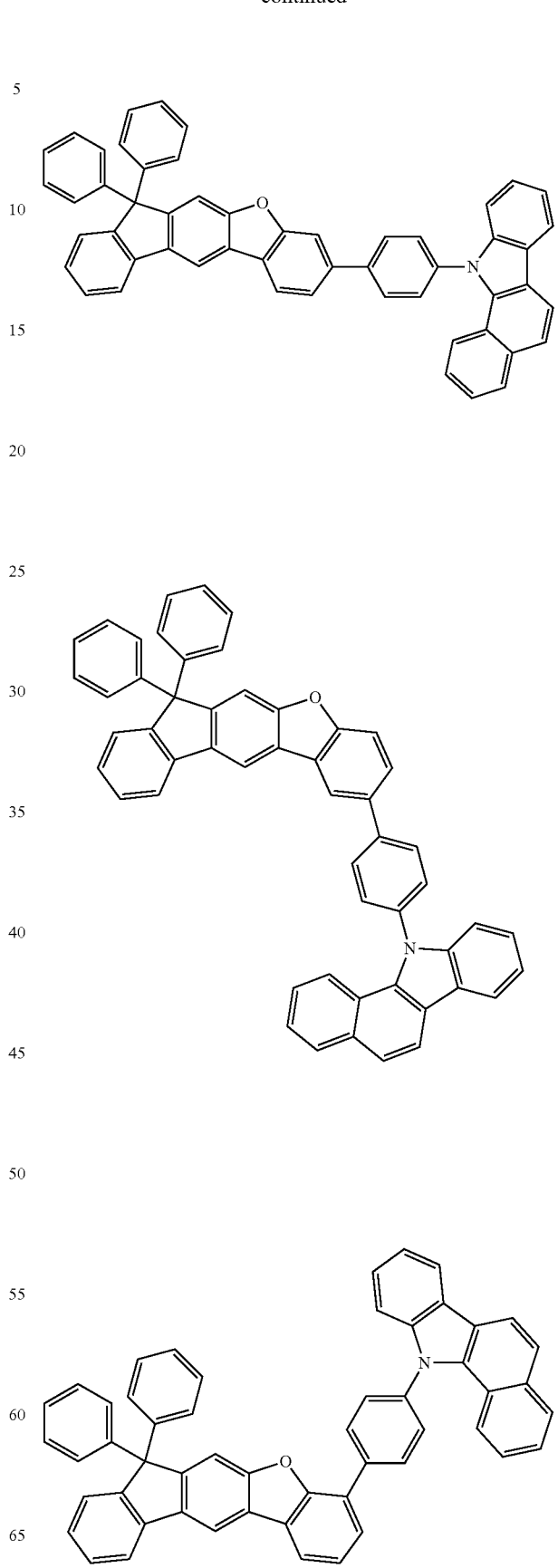

131
-continued
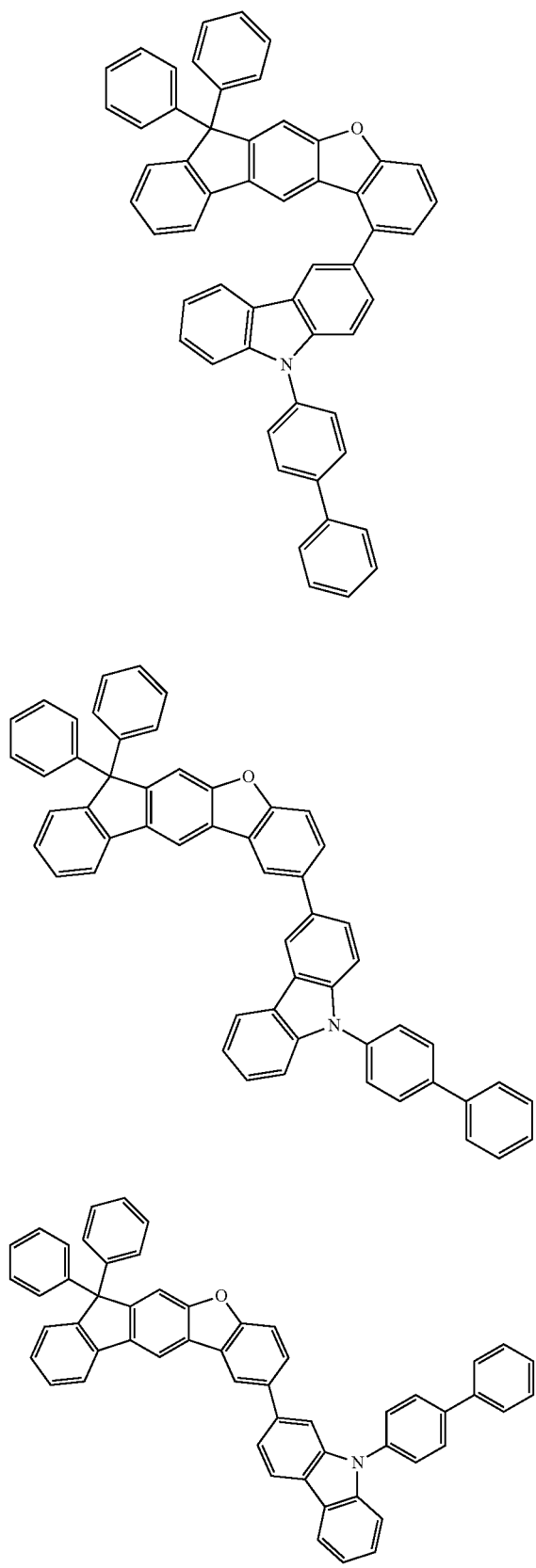
132
-continued
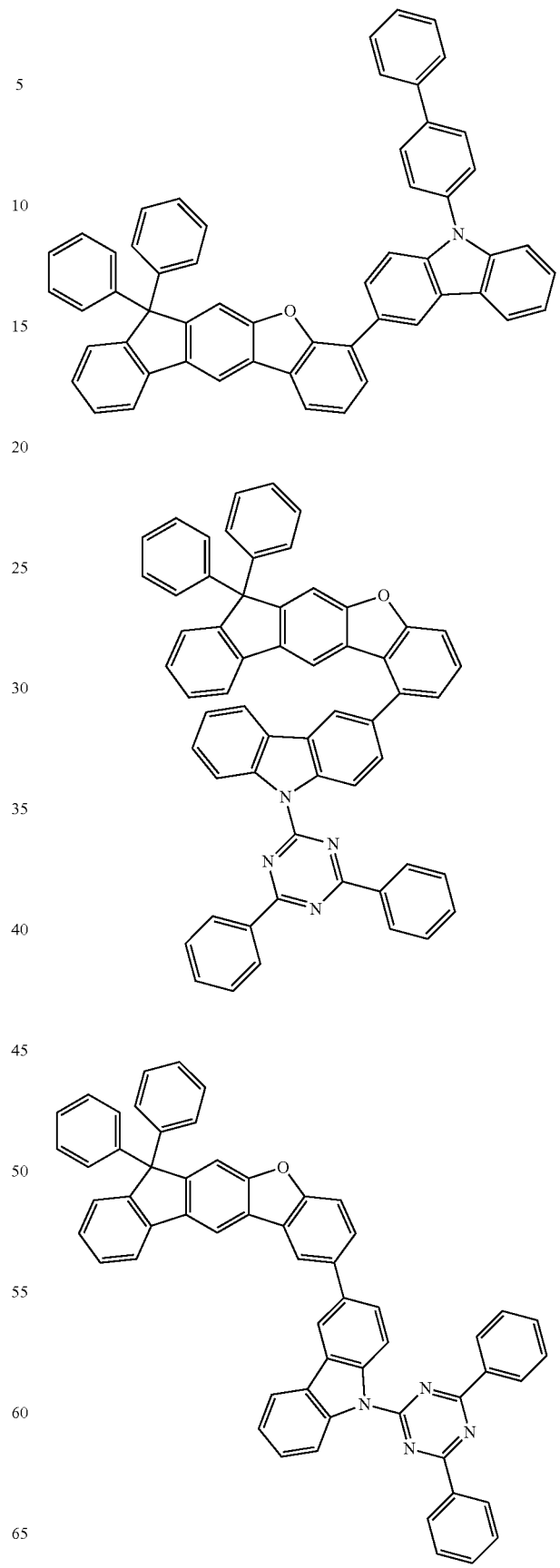

133
-continued
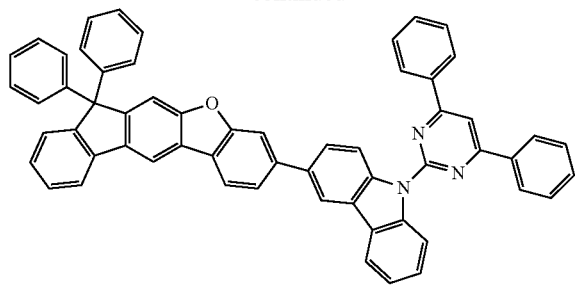
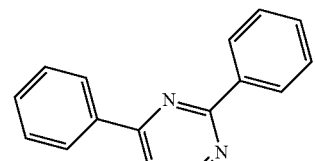
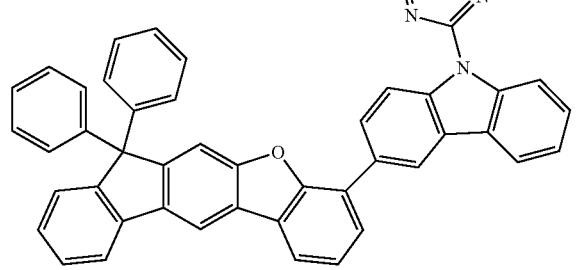
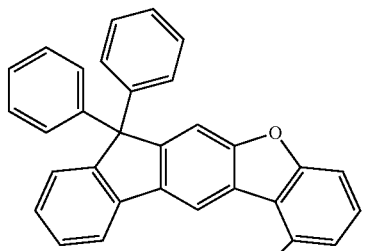
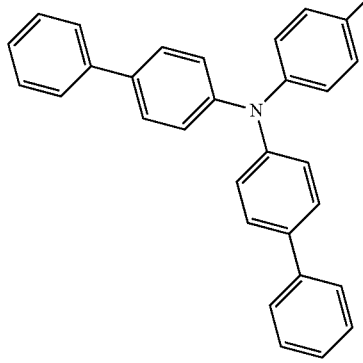
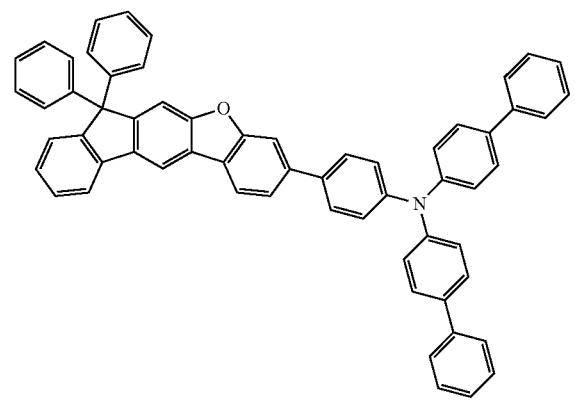
134
-continued
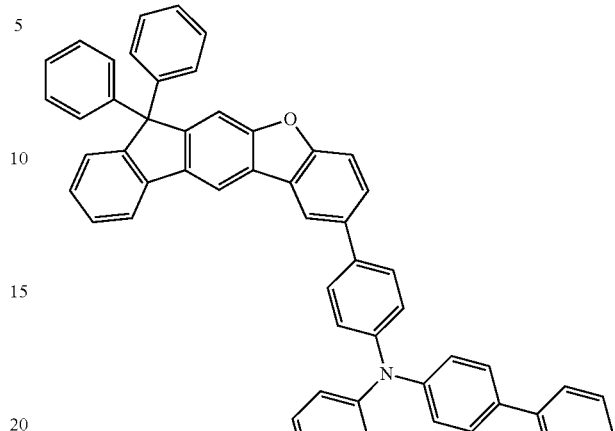
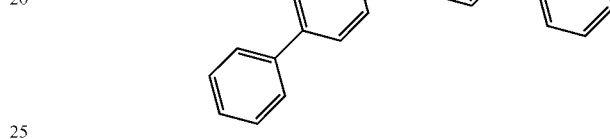
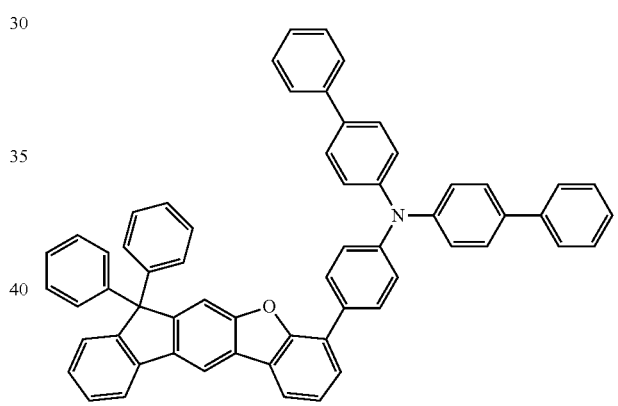
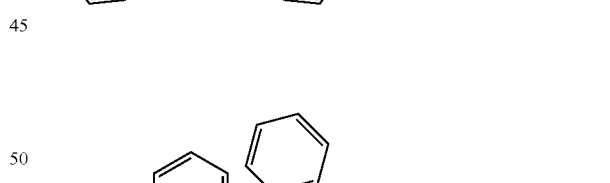
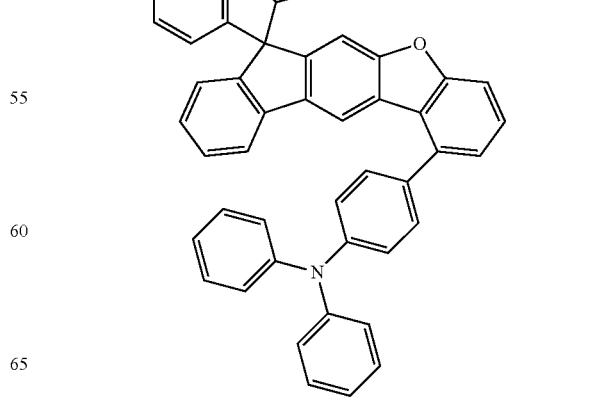

135
-continued
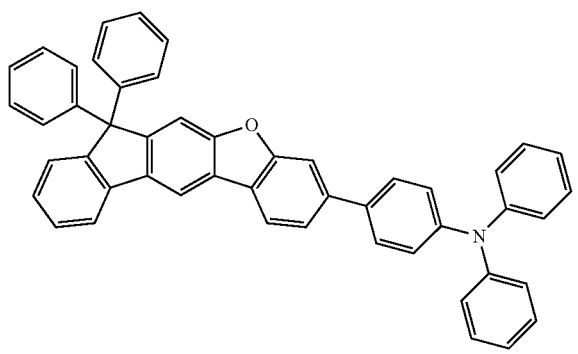
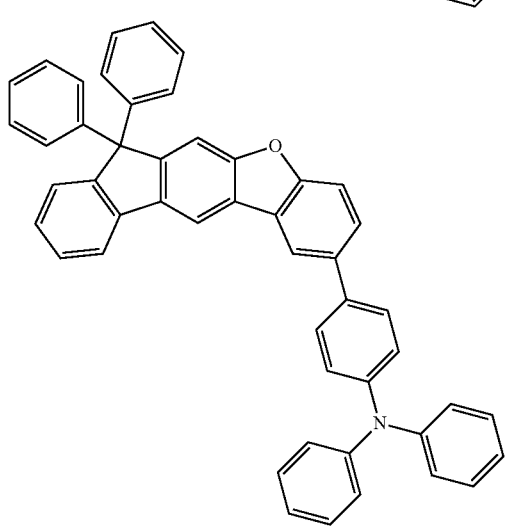
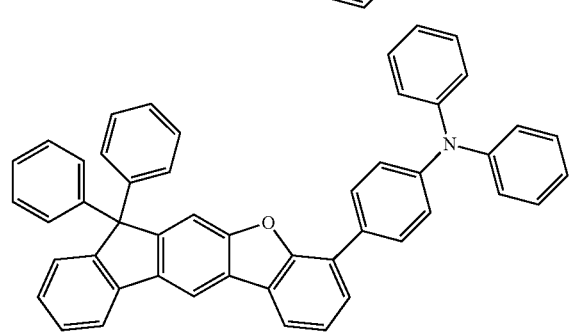
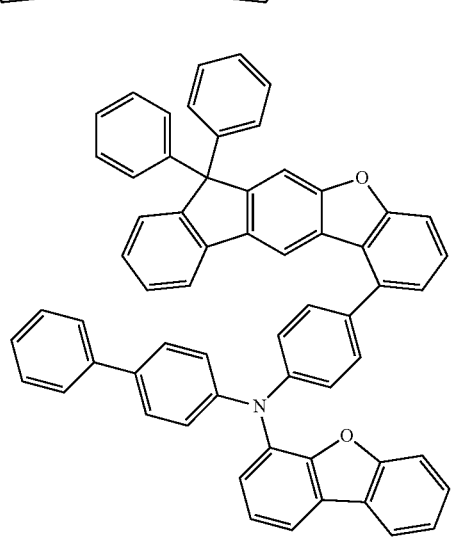
136
-continued
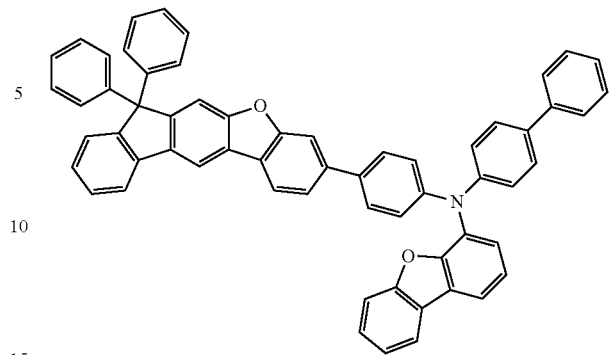
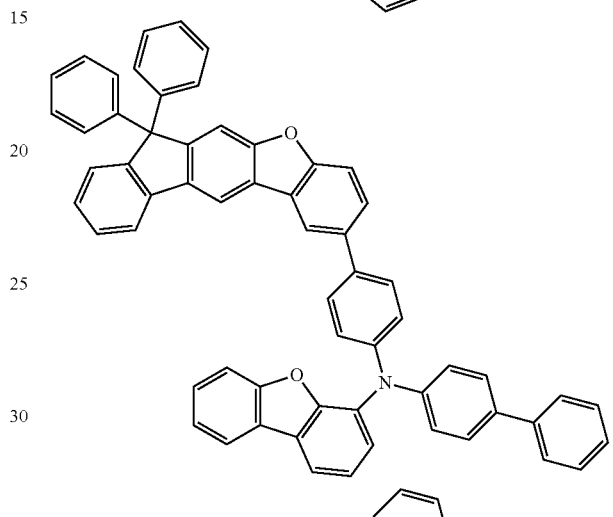
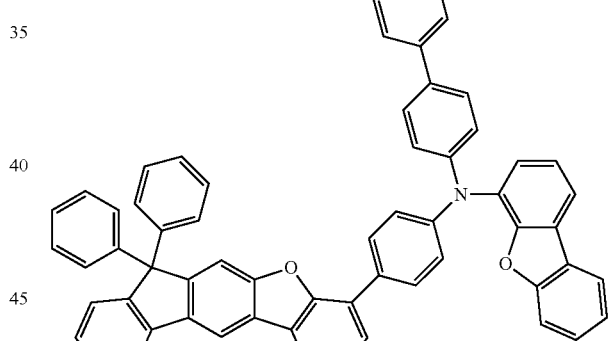
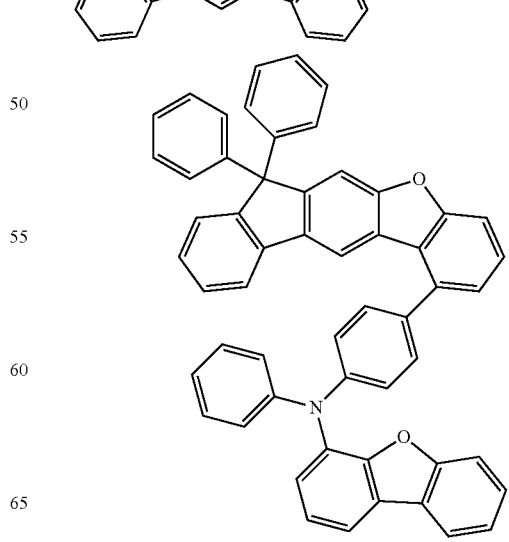

137
-continued
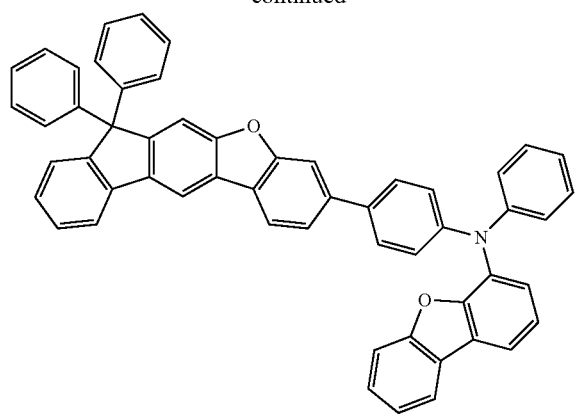
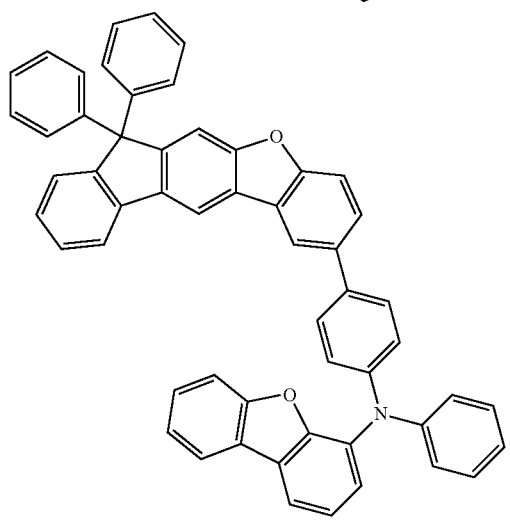
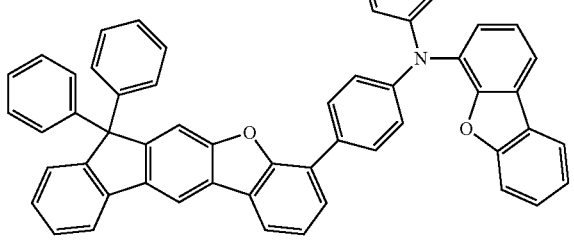
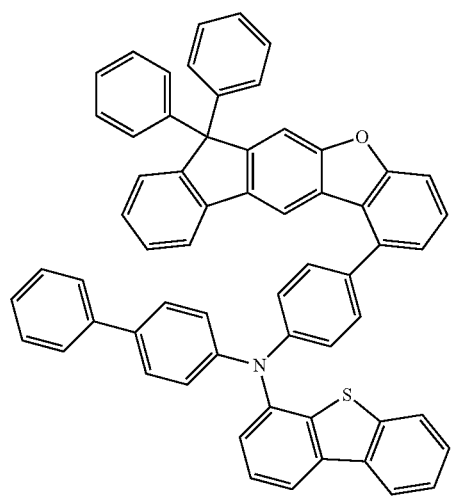
138
-continued
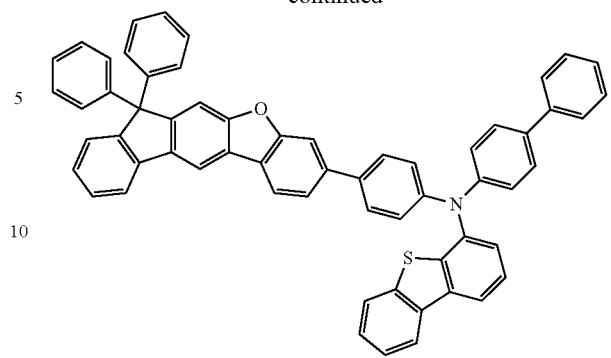
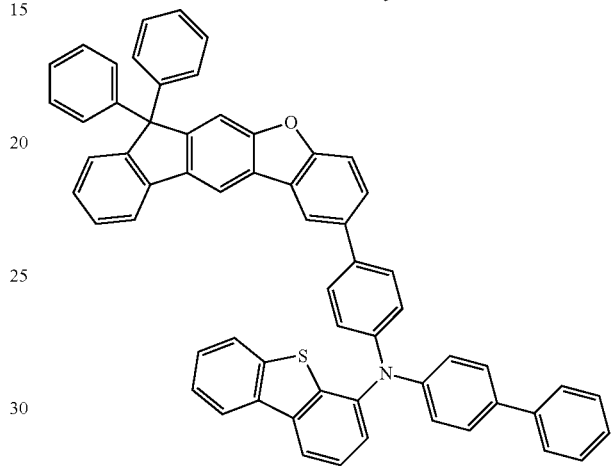
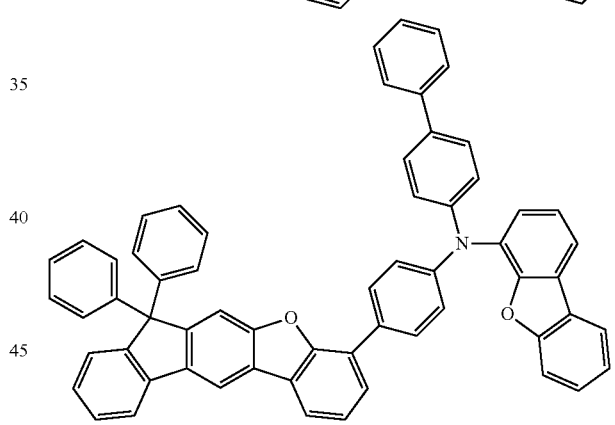
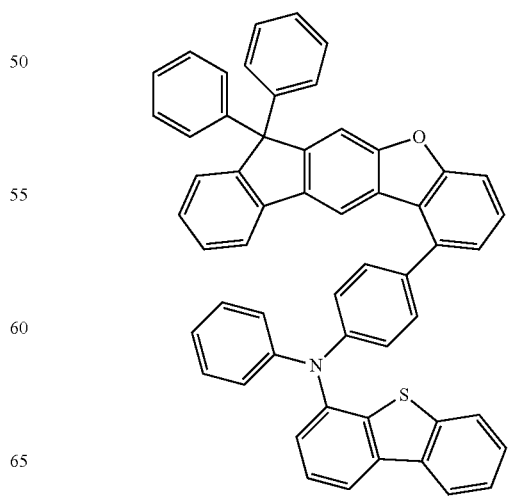

139
-continued
140
-continued
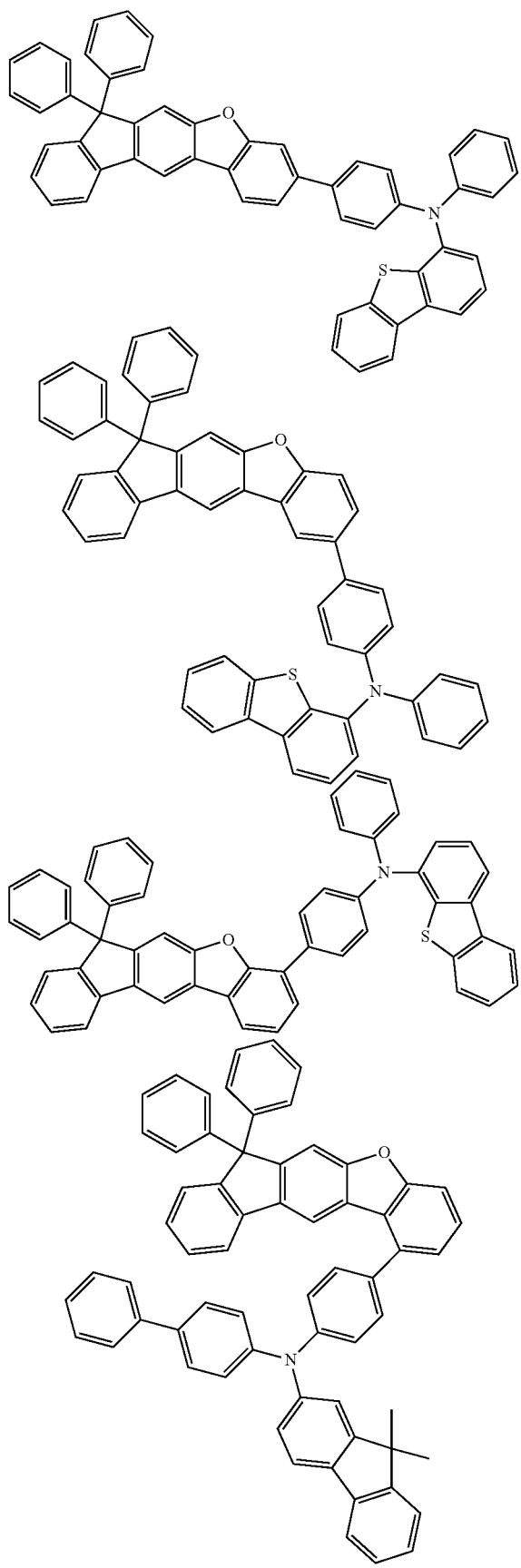
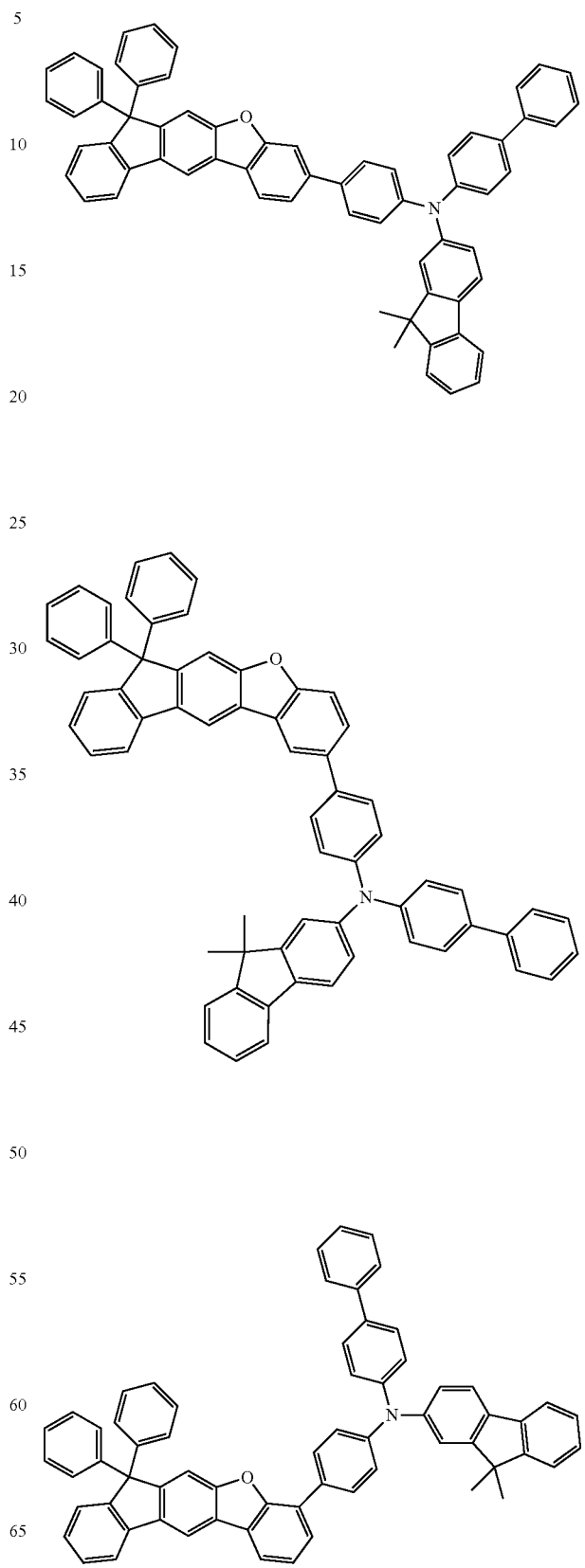

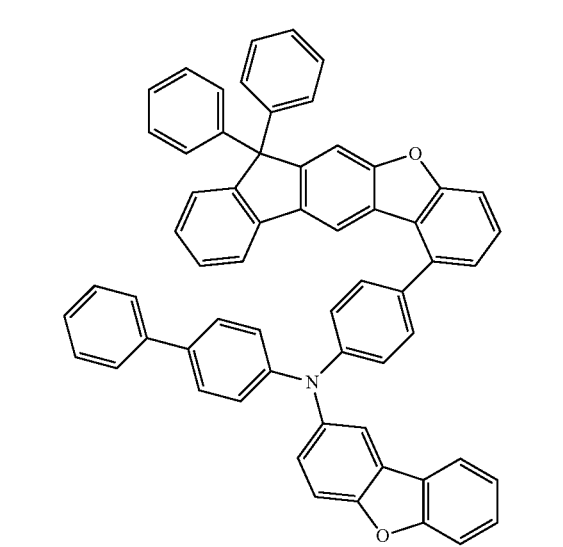
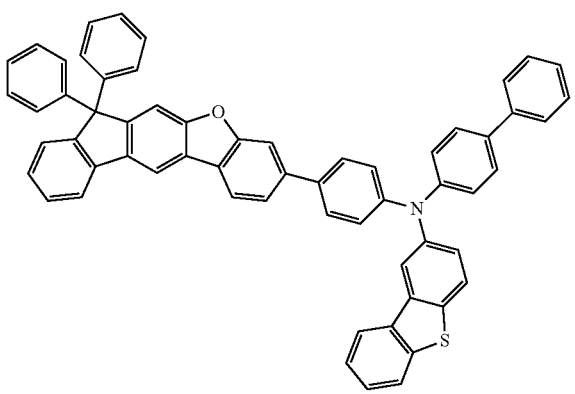
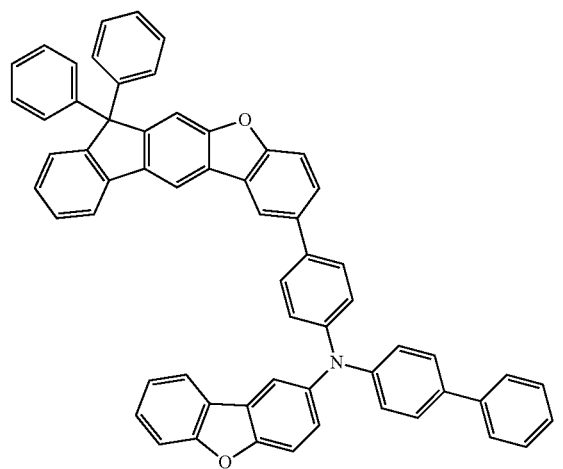
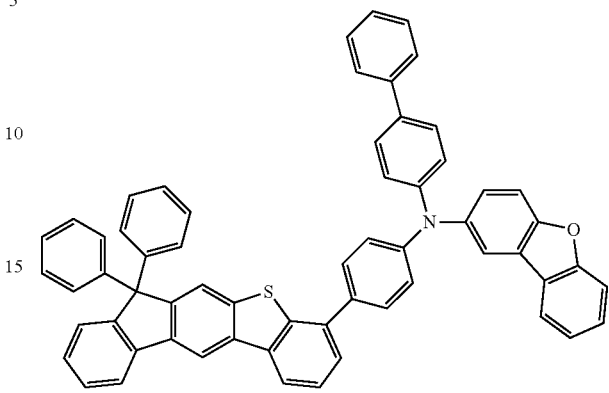
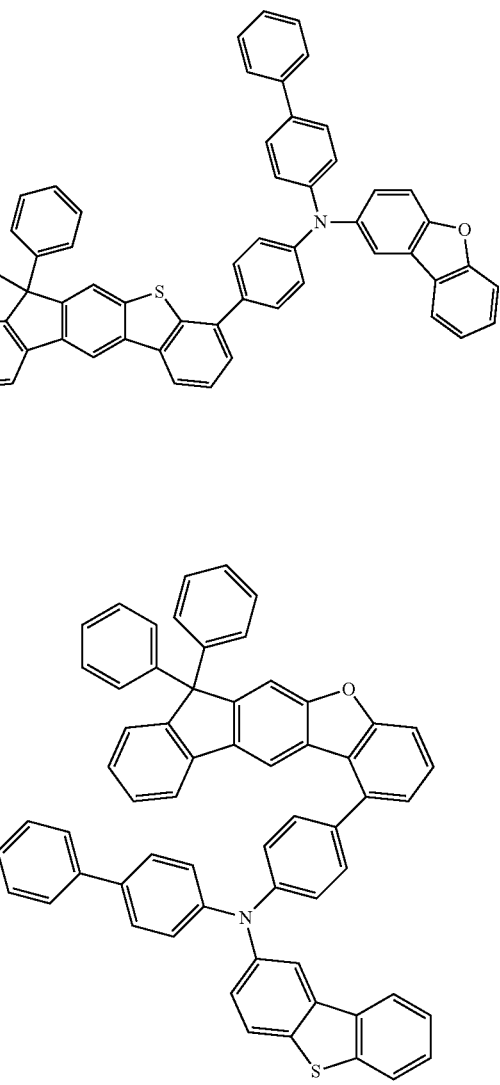

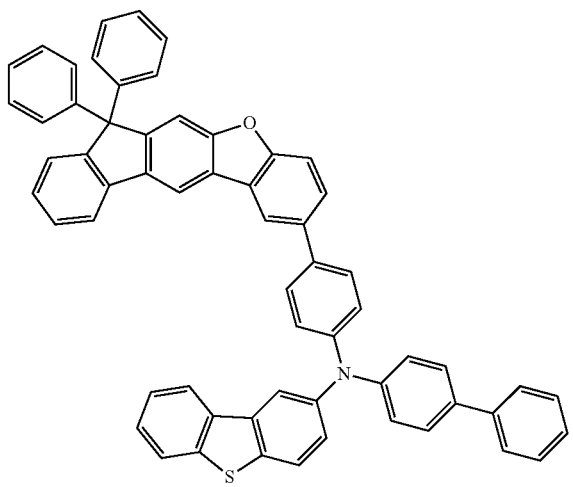
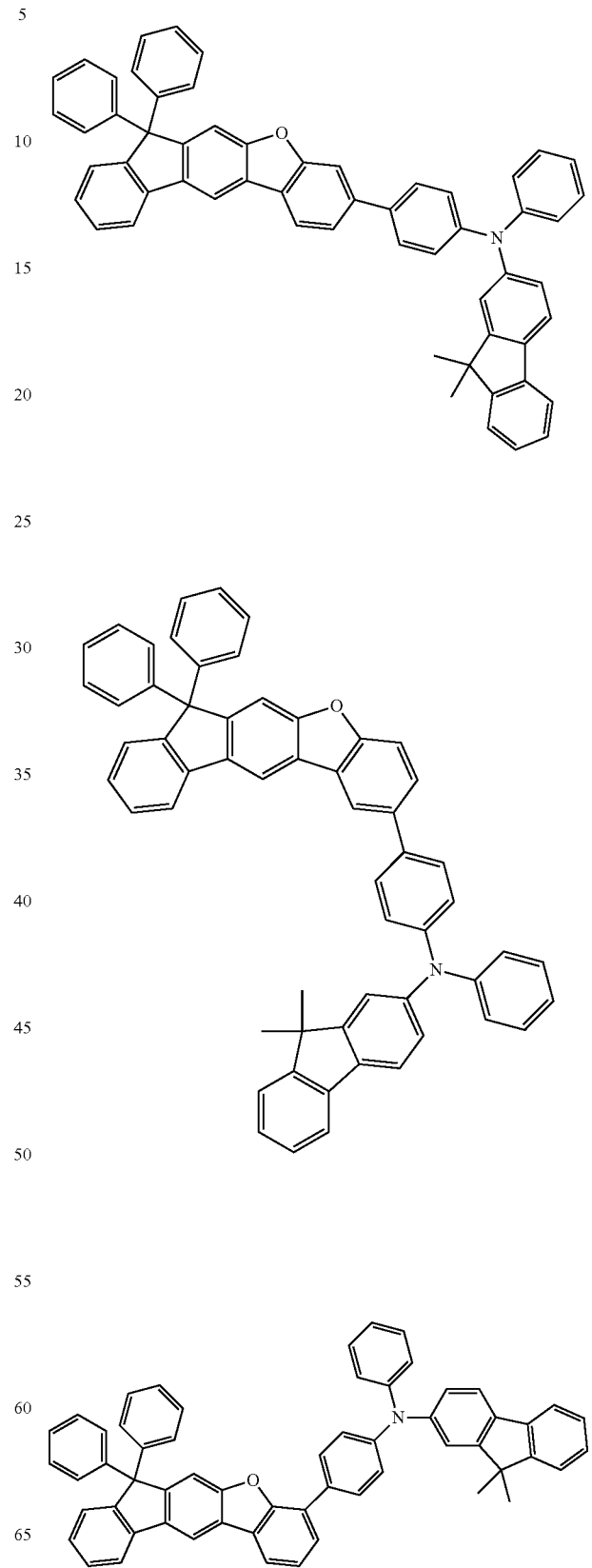

145
-continued
146
-continued
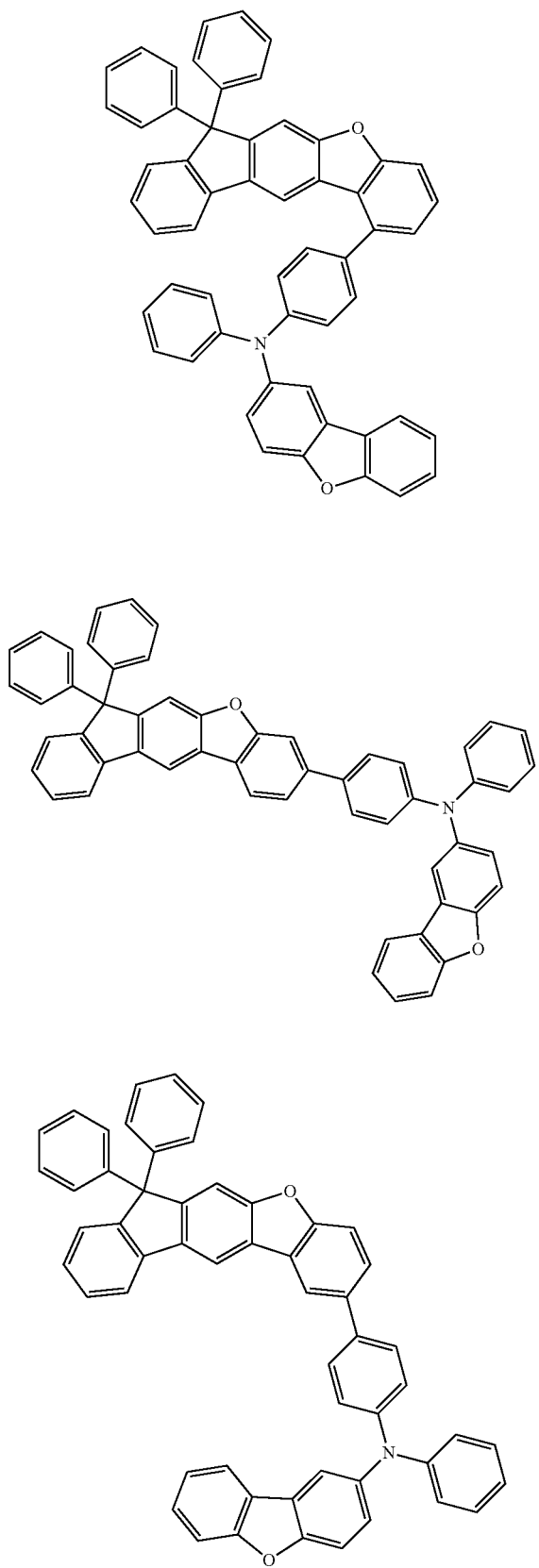
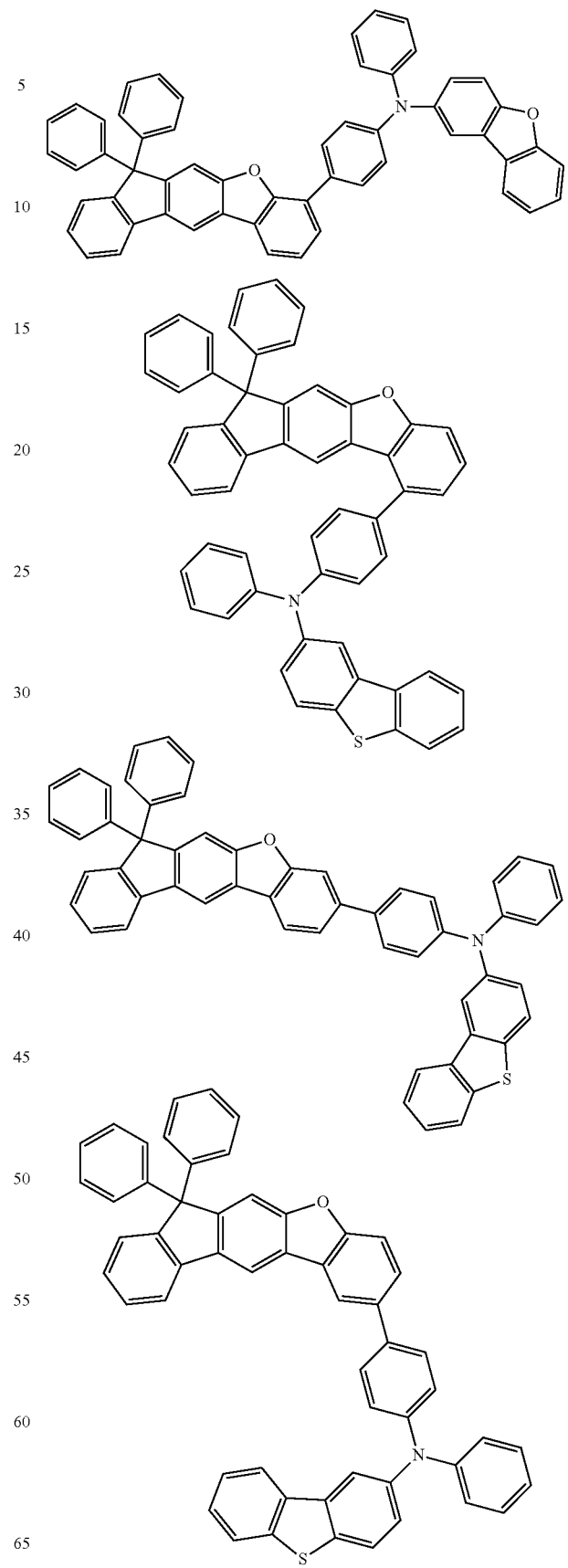

147
-continued
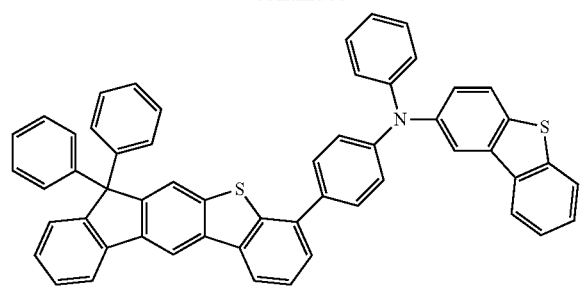
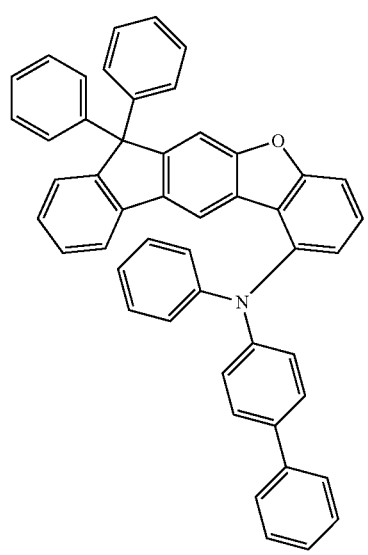
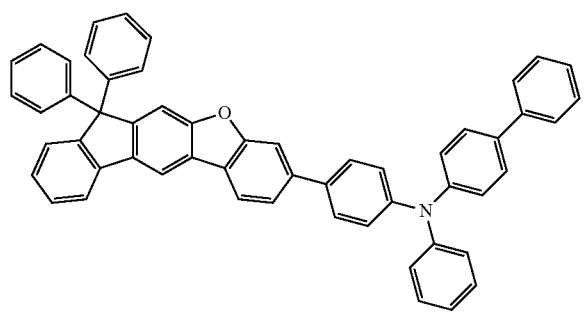
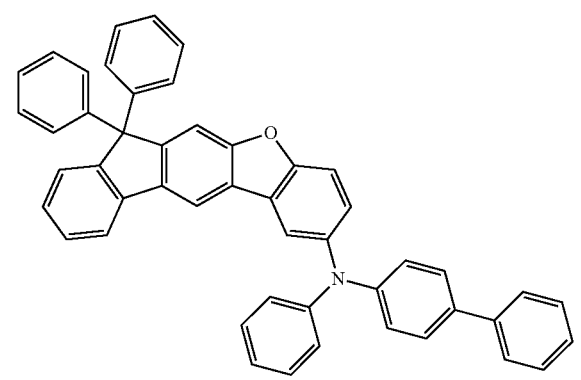
148
-continued
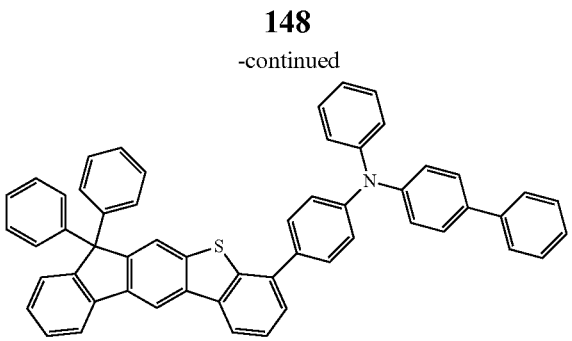
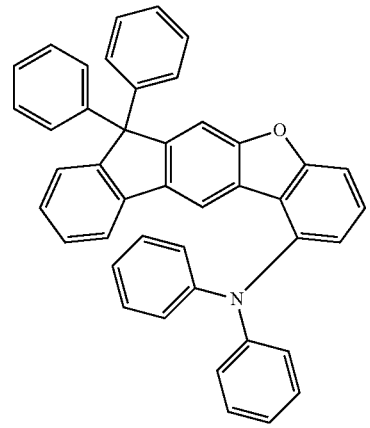
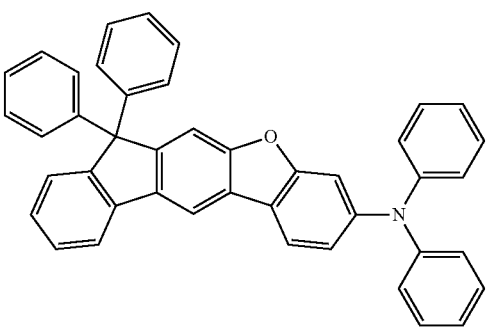
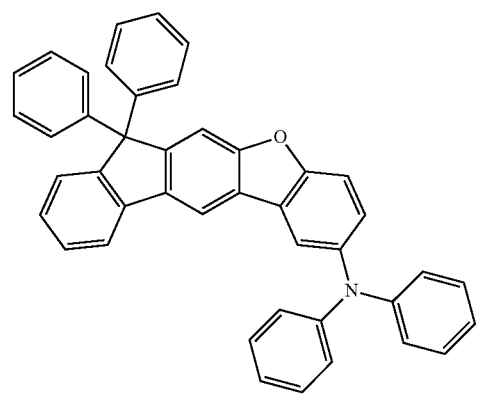
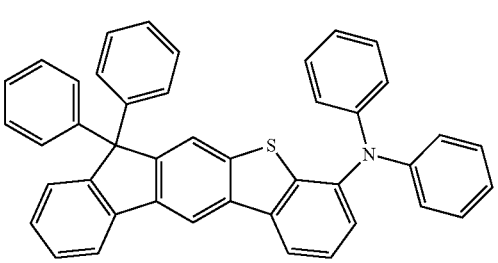

149
-continued
150
-continued
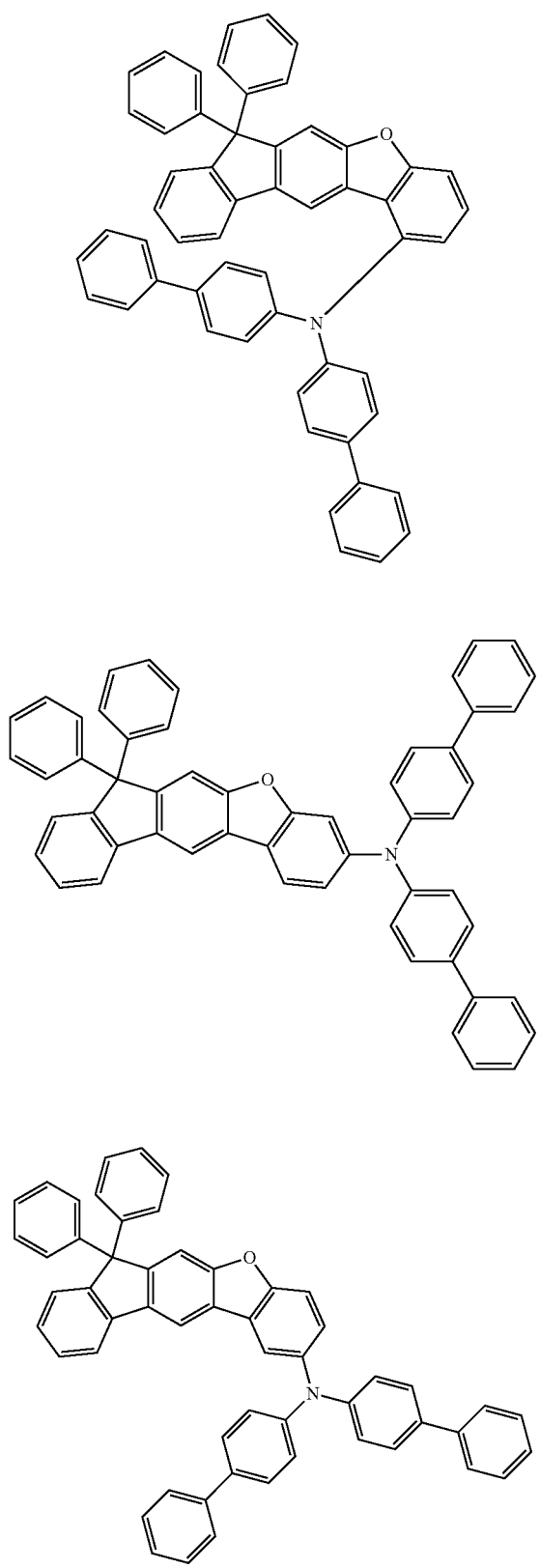
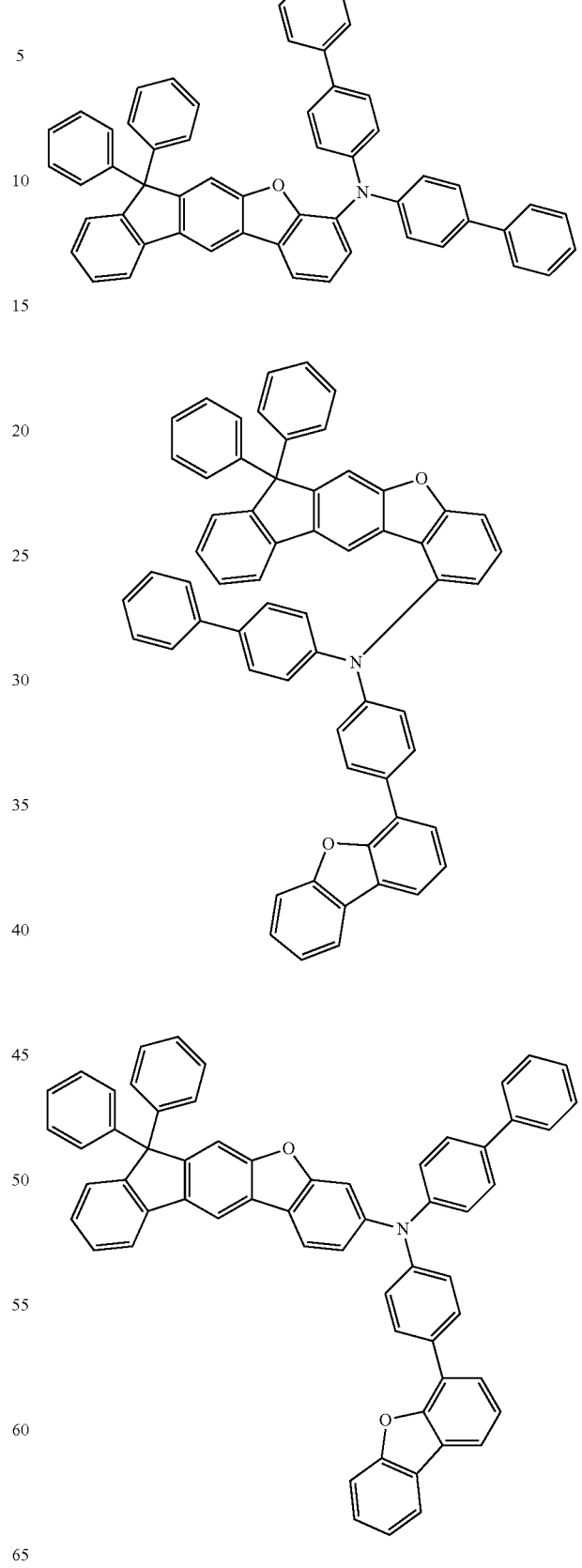

151
-continued
152
-continued
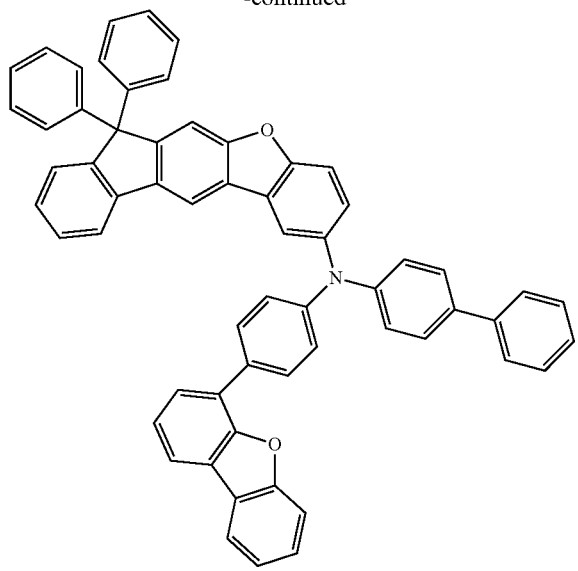
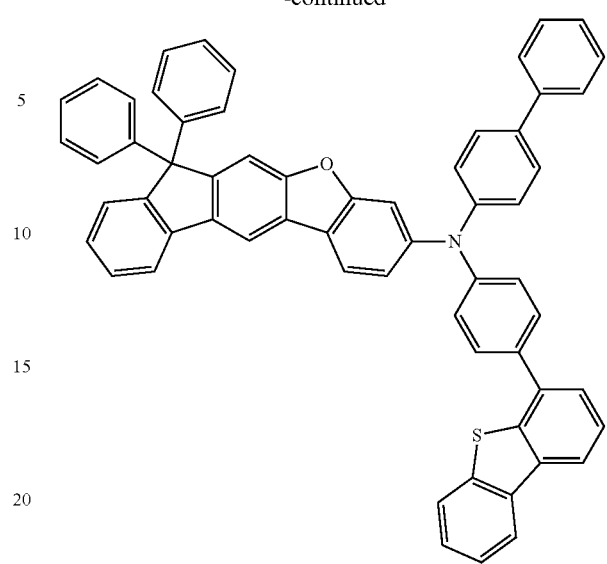
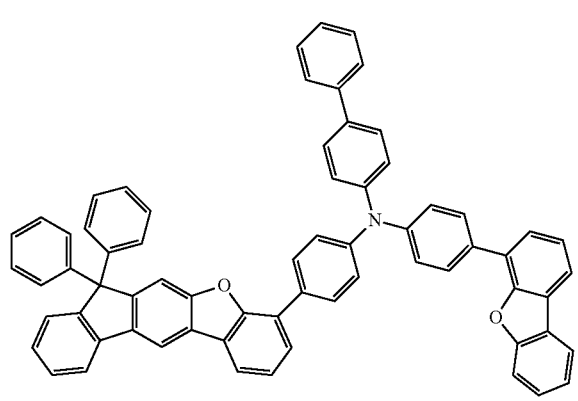 [SMILES: c1ccc(-c2ccc(N(c3ccc(-c4cccc5c4oc4ccccc45)cc3)c3ccc(-c4cccc5c4oc4cc6c(cc45)-c4ccccc4C6(c4ccccc4)c4ccccc4)cc3)cc2)cc1]
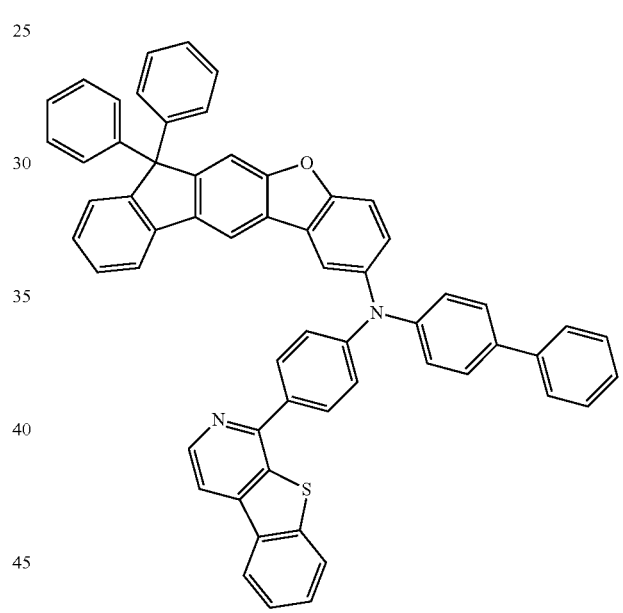
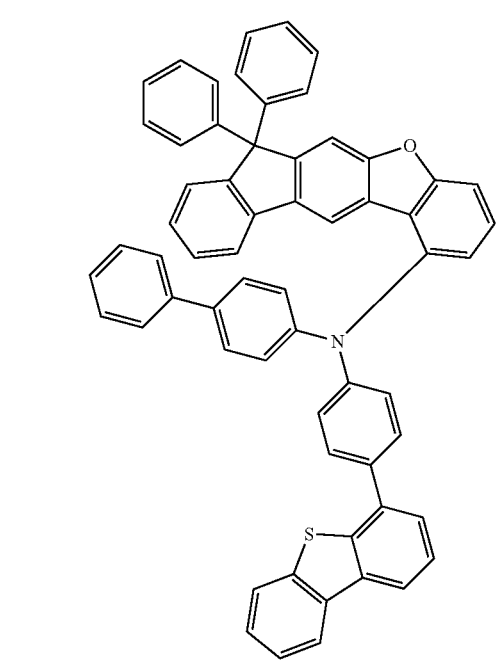
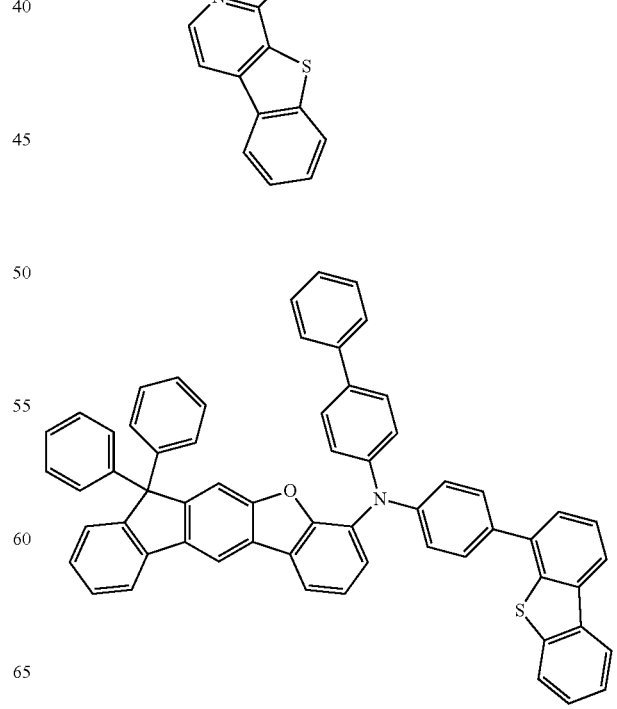

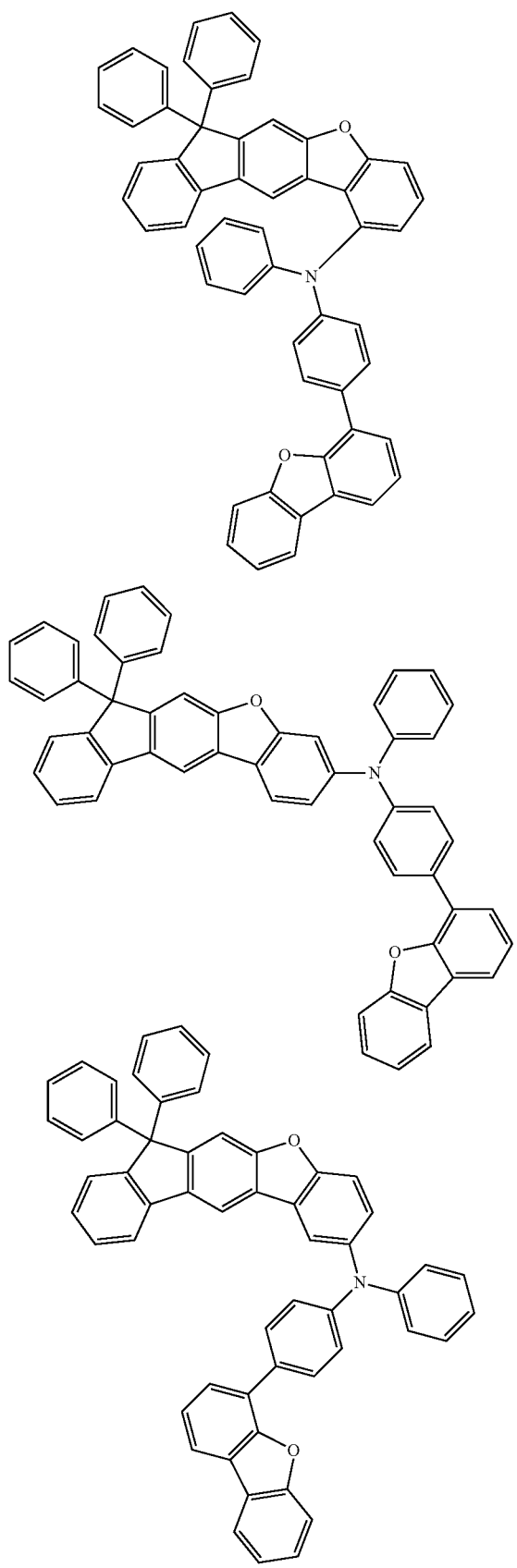
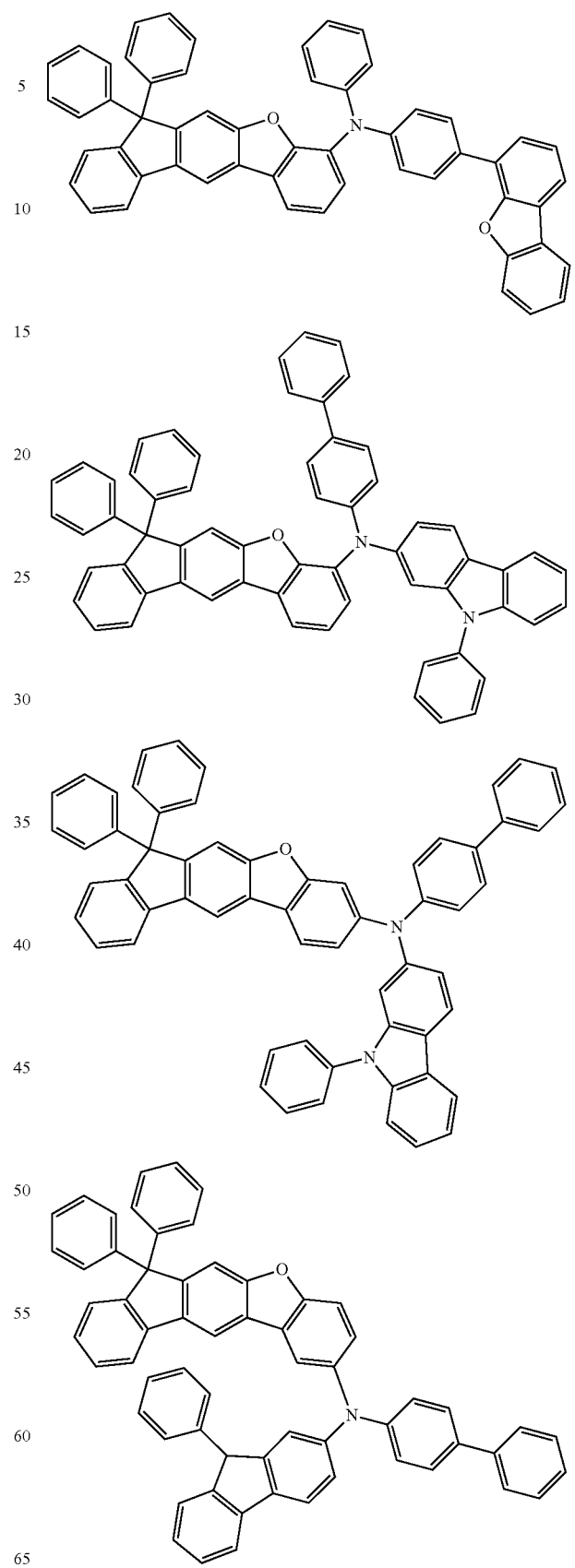

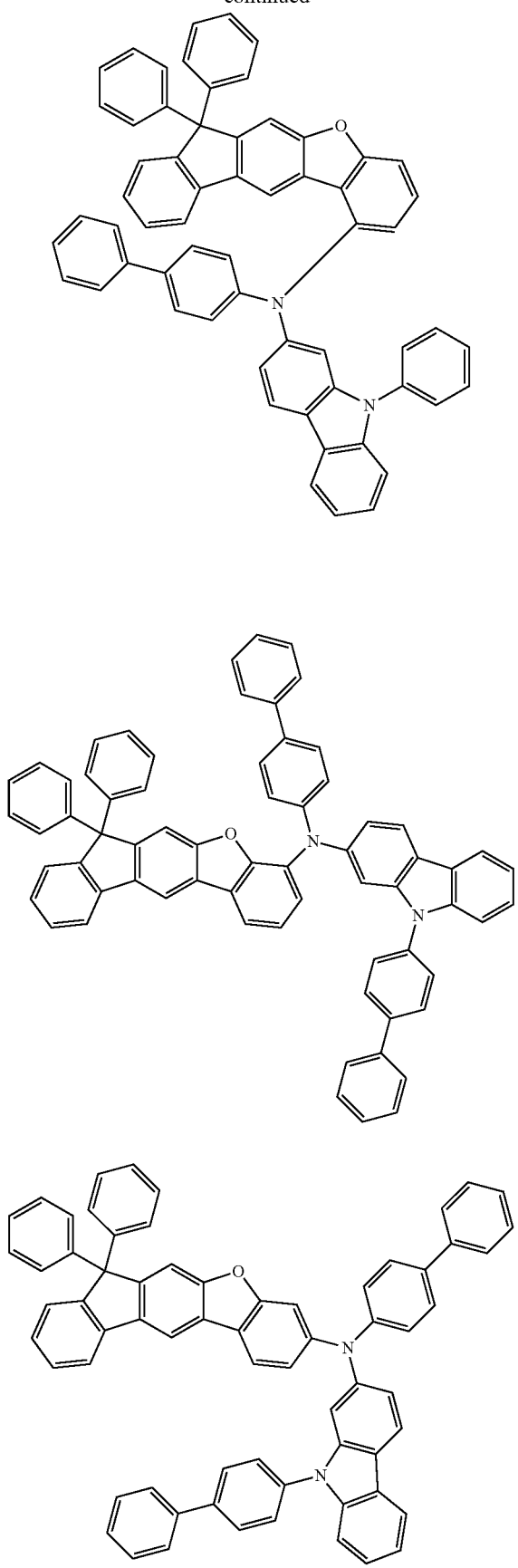
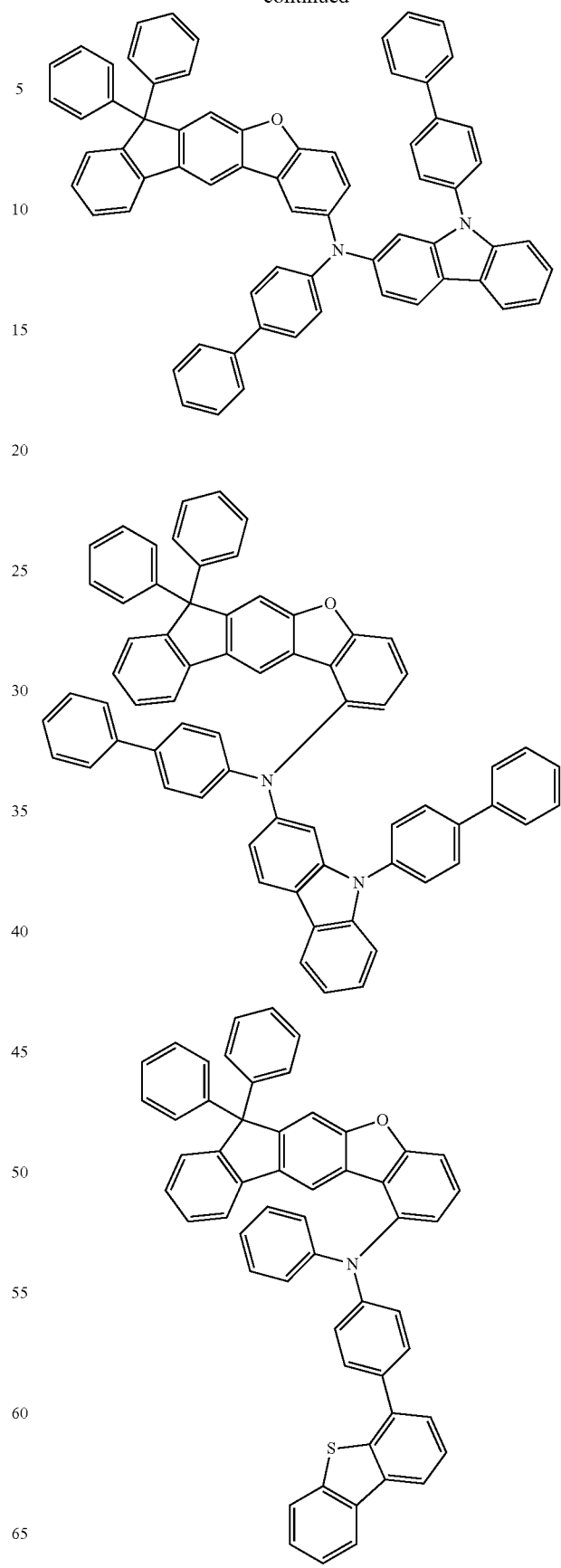

157
-continued
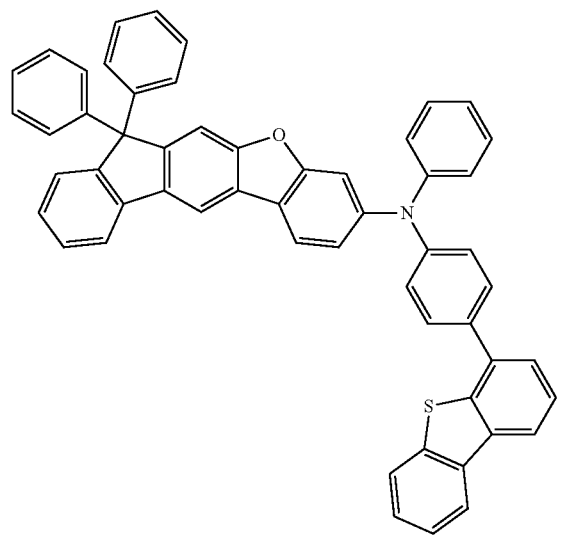
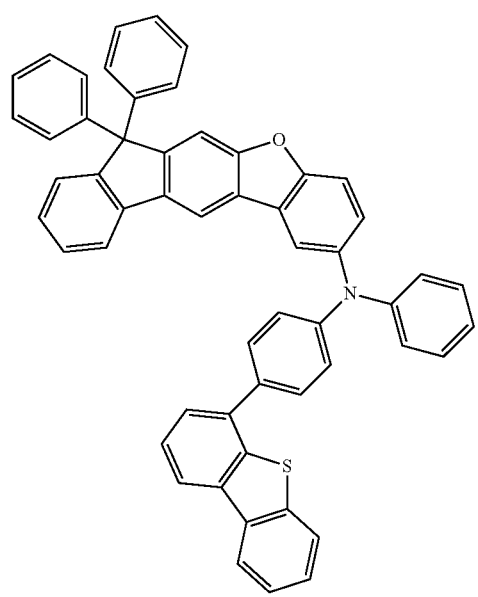
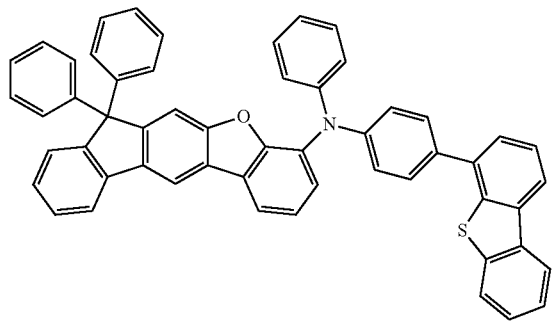 [SMILES: c1ccc(N(c2ccc(-c3cccc4c3oc3ccccc34)cc2)c2cccc3c2oc2cc4c(cc23)-c2ccccc2C4(c2ccccc2)c2ccccc2)cc1]
158
-continued
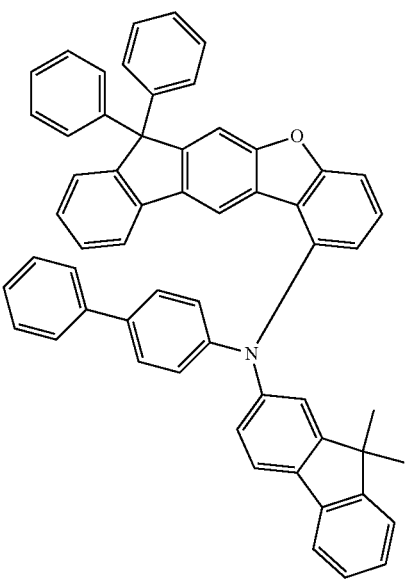
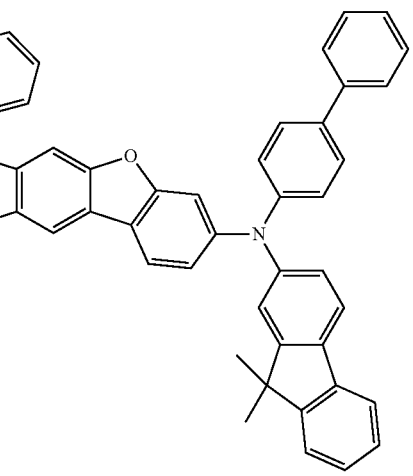
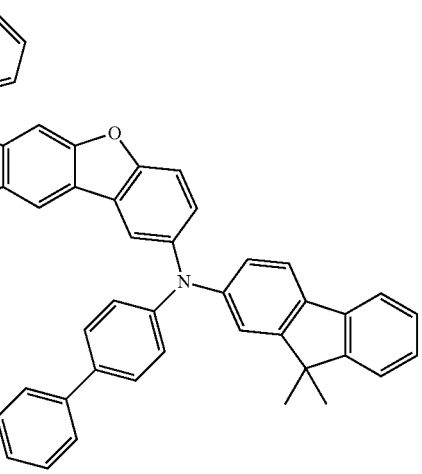

-continued
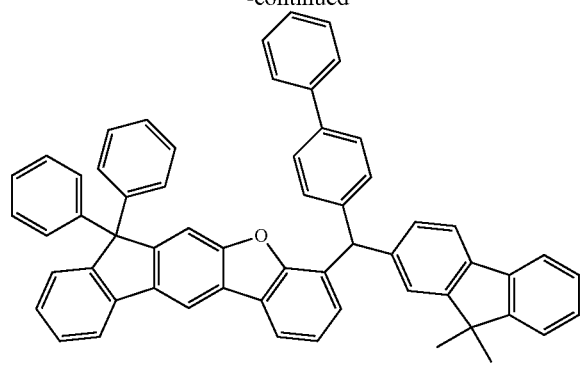
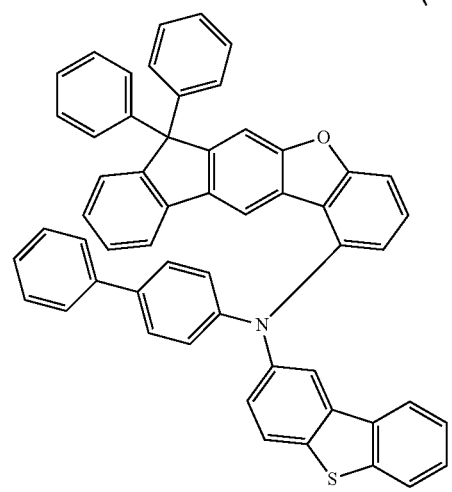
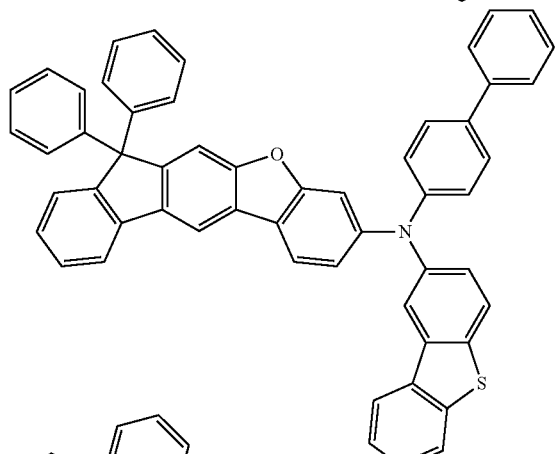
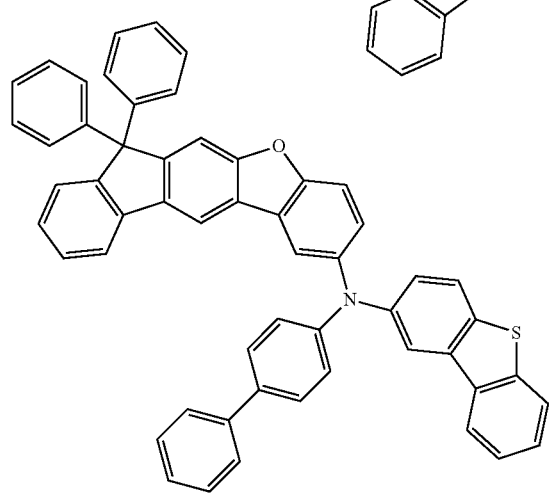
-continued
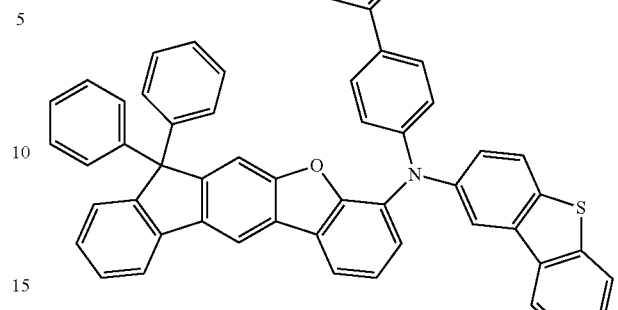
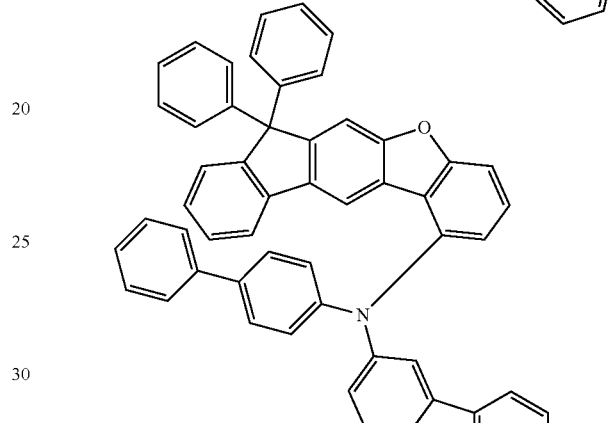
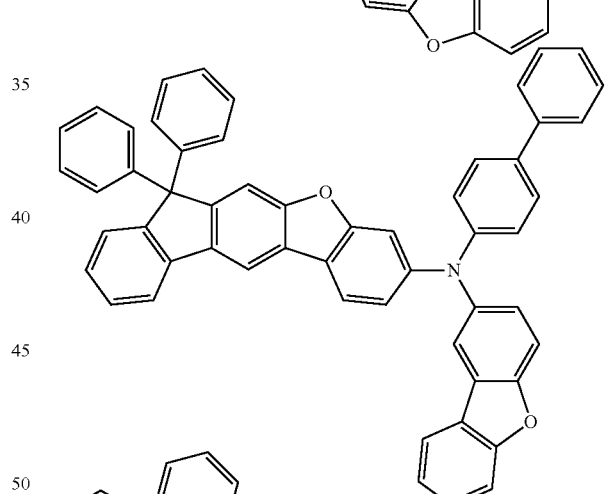
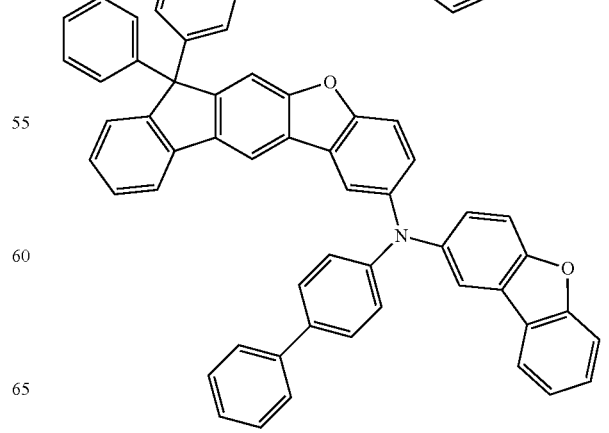

-continued
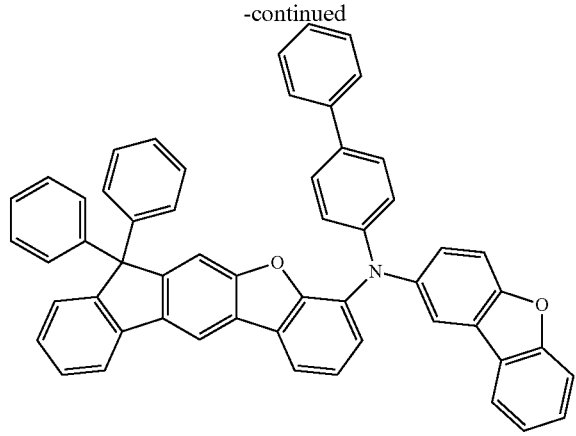
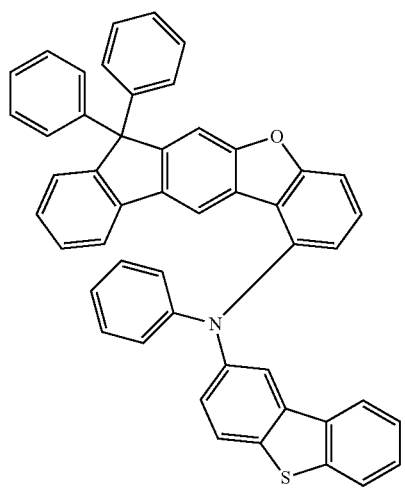
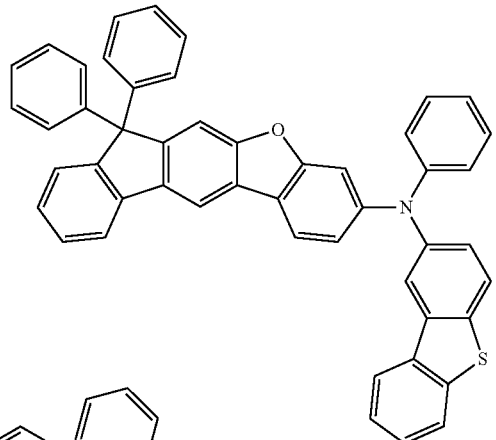
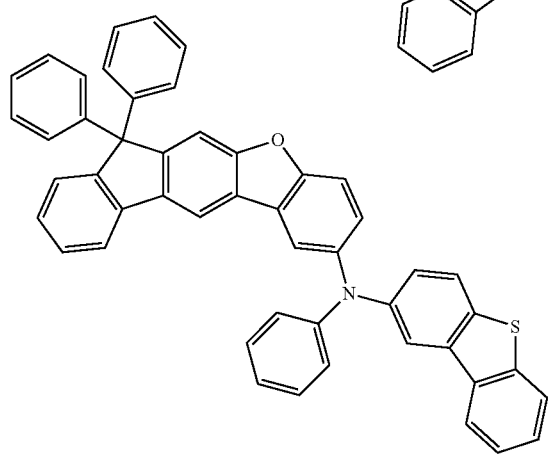
-continued
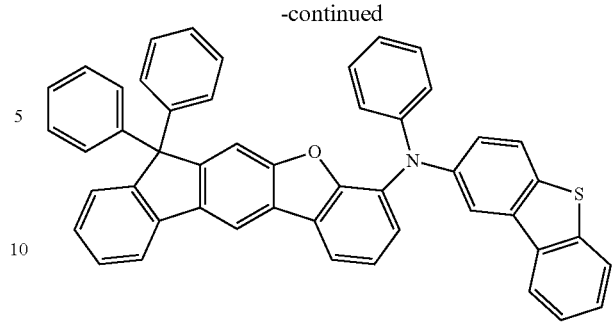
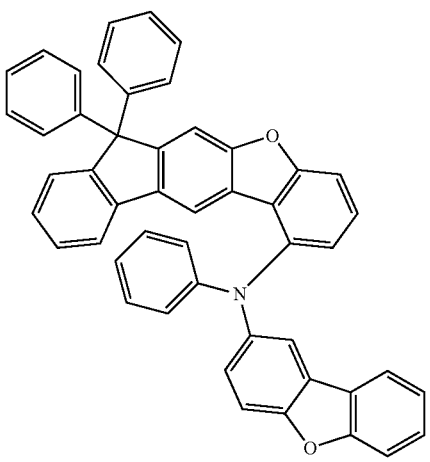
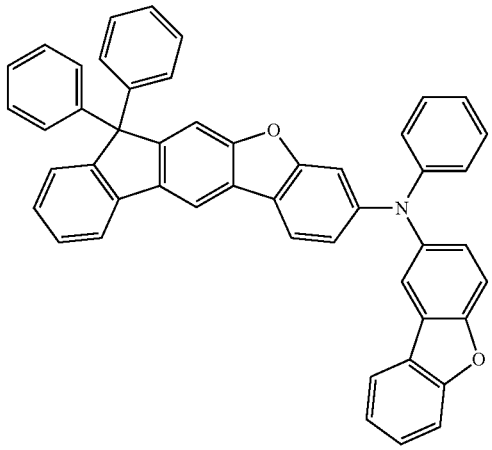
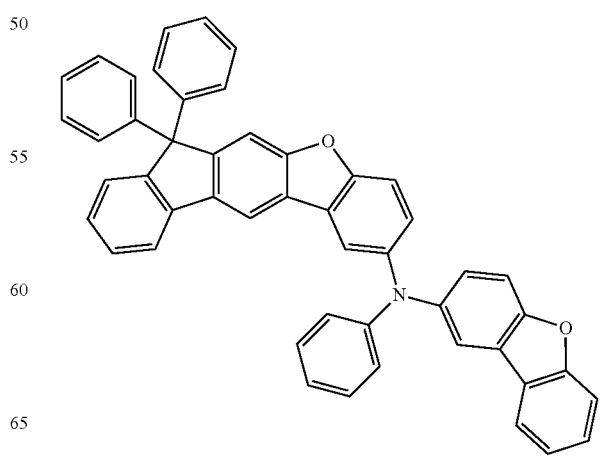

163
-continued
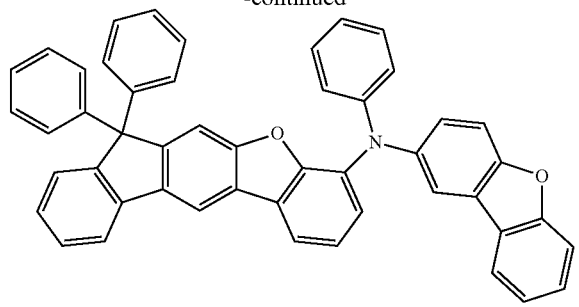
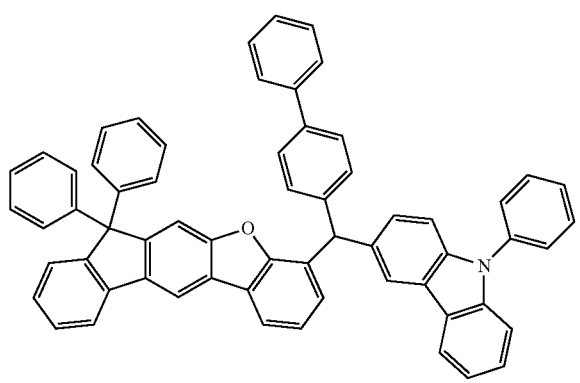
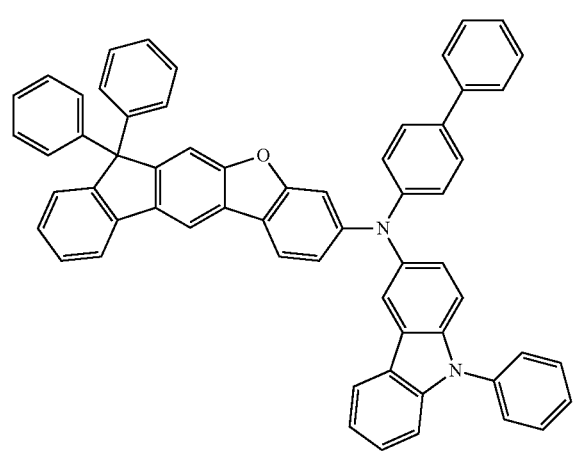
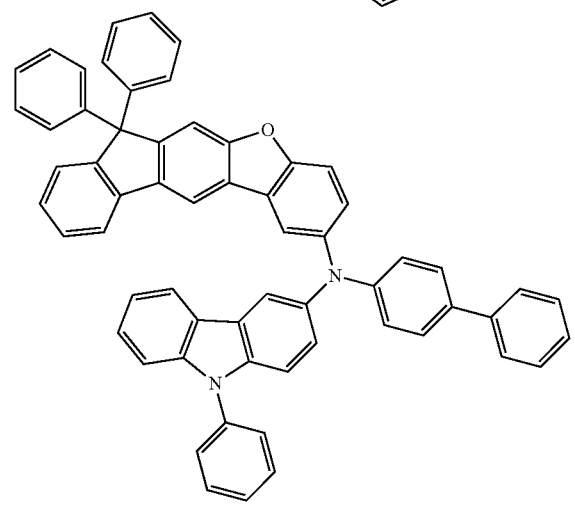
164
-continued
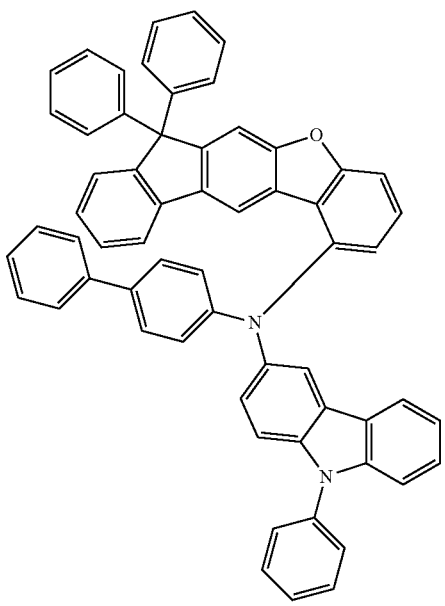 [SMILES: c1ccc(-c2ccc(N(c3ccc4c(c3)c3ccccc3n4-c3ccccc3)c3cccc4oc5cc6c(cc5c34)-c3ccccc3C6(c3ccccc3)c3ccccc3)cc2)cc1]
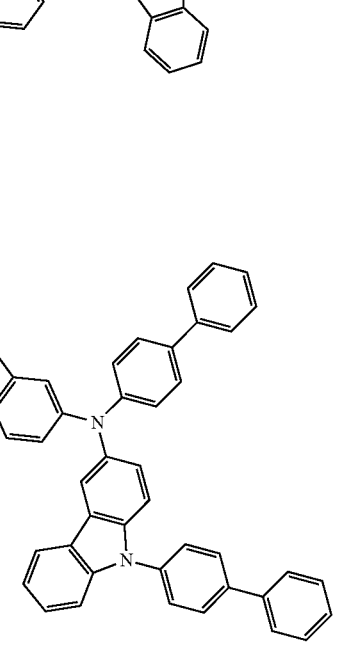

165
-continued

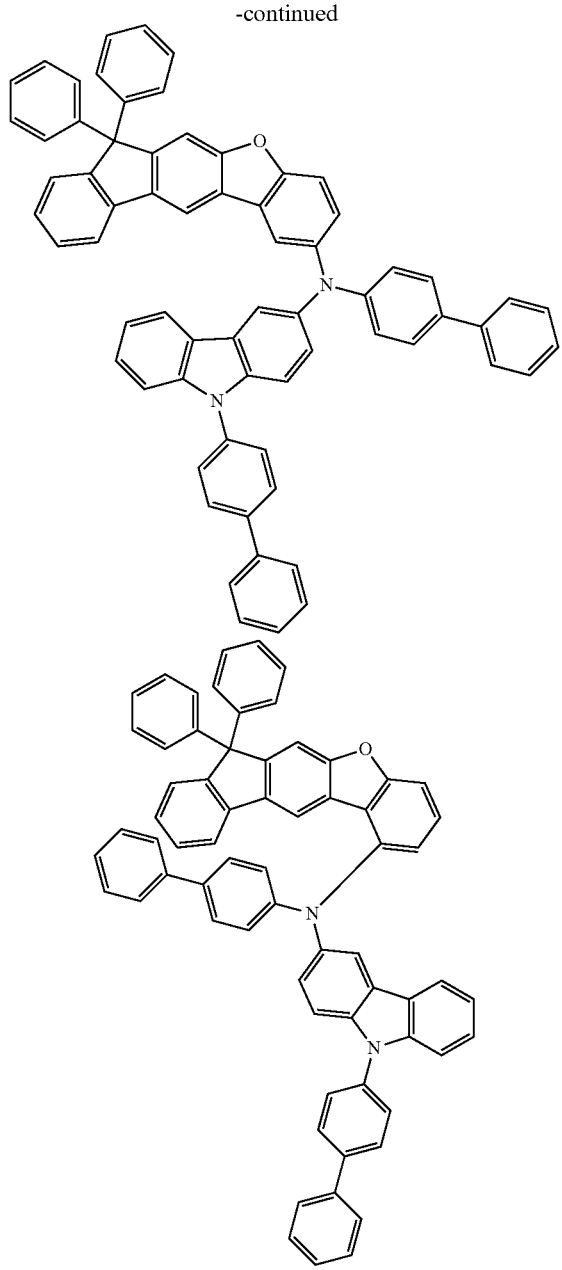

According to an exemplary embodiment of the present specification, a core structure of the hetero-cyclic compound represented by Chemical Formula 1 may be prepared by the following General Formula 1, but the preparation method thereof is not limited thereto.

[General Formula 1]

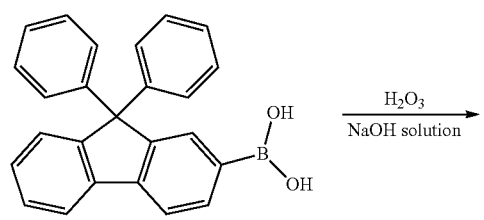

166
-continued

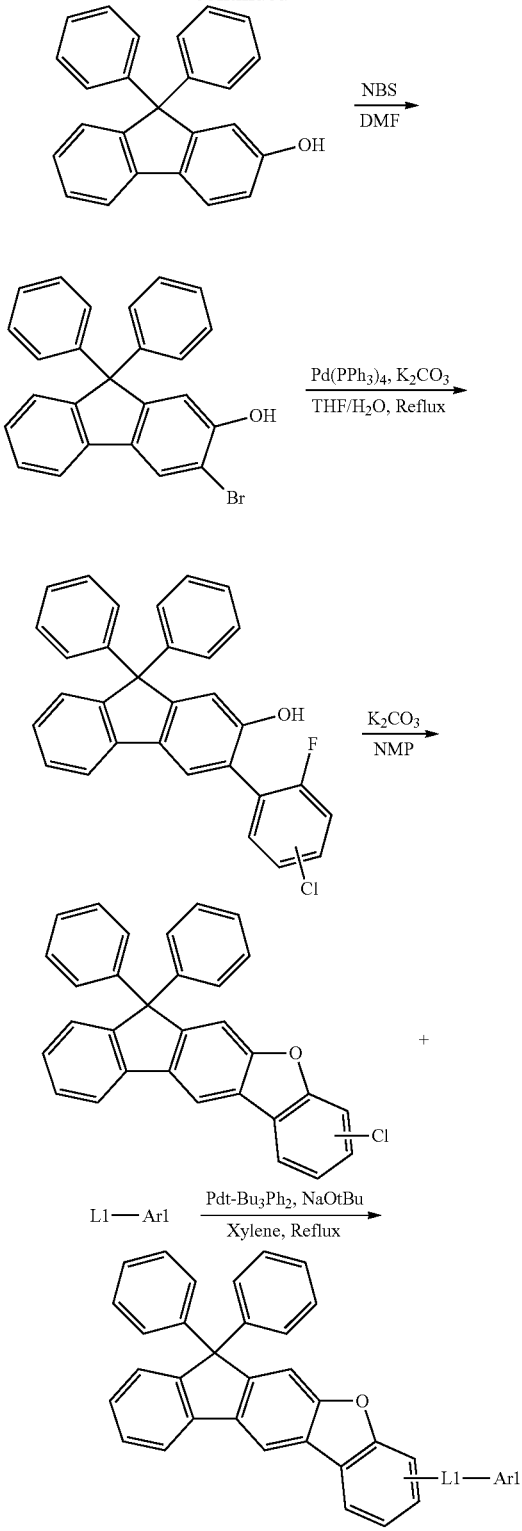

In General Formula 1, the definitions of L1 and Ar1 are the same as those in Chemical Formula 1.

When the core structure of the hetero-cyclic compound represented by Chemical Formula 1 is substituted with a methyl group instead of a phenyl group, the core structure may be prepared by the following General Formula 2.

[General Formula 2]

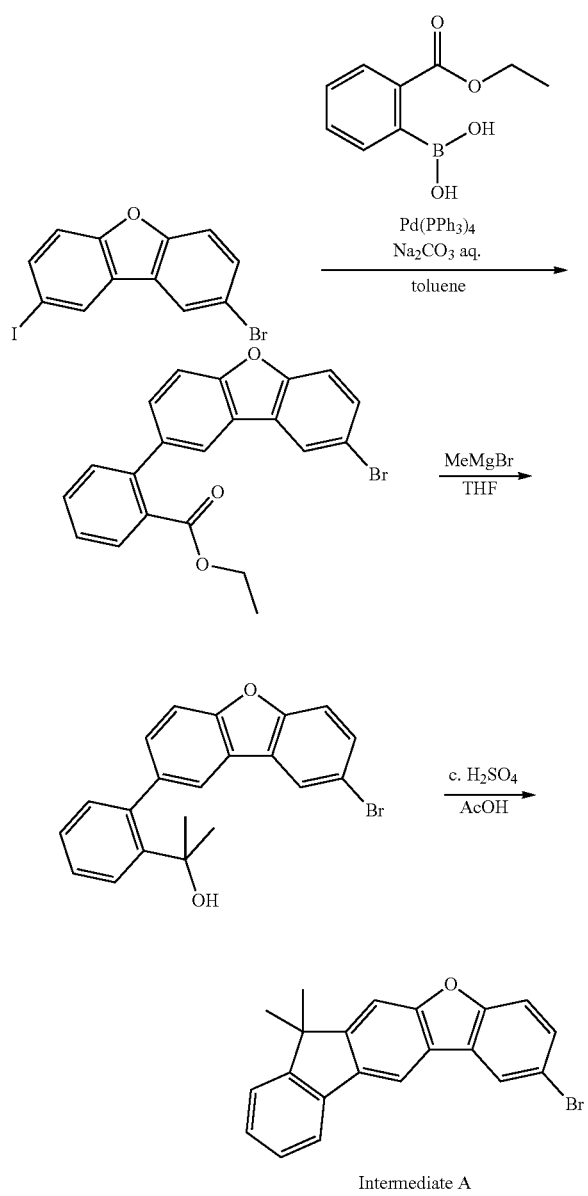

Intermediate A

According to the substituent at a No. 9 position of a fluorene mother nucleus of the core of the hetero-cyclic compound represented by Chemical Formula 1, the electric charge mobility of the core is affected, and as a result, characteristics are changed into an OLED material. Referring to a device example, since the LUMO values of 9,9-diphenylfluorene derivatives are relatively larger than the LUMO value of a 9,9-dimethylfluorene derivative (~0.1 eV), there is no barrier with a light emitting layer, and as a result, electrons are easily injected, thereby exhibiting a result that a driving voltage is also decreased and efficiency characteristics are improved. When a device has these characteristics, the service life thereof is normally decreased, but 9,9-diphenylfluorene is slower than 9,9-dimethylfluorene in terms of mobility, and as a result, it is thought that 9,9-diphenylfluorene exhibits an advantage in terms of service life as compared to 9,9-dimethylfluorene. When used as an electron transporting layer, 9,9-dimethylfluorene derivatives are a type of injecting electrons into a light emitting layer too rapidly, and 9,9-diphenylfluorene derivatives having a relatively slow mobility have a long service life. When another matter is guessed, in terms of purity and color of a compound which most greatly affects a service life of an organic light emitting device, 9,9-dimethylfluorene-type cores exhibit a slightly yellow color and are difficult to purify due to high solubility, and impurities from which a methyl group is detached are always present and are difficult to remove. In contrast, diphenylfluorene-type cores also have a white color and are easily purified due to low solubility, and may be made more cleanly.

The following FIGS. 3 to 8 are NMR results supporting that the hetero-cyclic compound represented by Chemical Formula 1 of the present specification is prepared by General Formula 1. In General Formula 1, a person with ordinary skill in the art may prepare all the compounds of the present invention by changing the position and type of substituent.

An exemplary embodiment of the present specification provides an organic light emitting device including: a first electrode; a second electrode disposed to face the first electrode; and an organic material layer having one or more layers disposed between the first electrode and the second electrode, in which one or more layers of the organic material layer include the above-described hetero-cyclic compound.

According to an exemplary embodiment of the present specification, the organic material layer of the organic light emitting device of the present specification may be composed of a mono layer structure, but may be composed of a multi-layer structure in which two or more organic material layers are stacked. For example, the organic light emitting device of the present invention may have a structure including a hole injection layer, a hole transporting layer, an electron blocking layer, a light emitting layer, a hole blocking layer, an electron transporting layer, an electron injection layer, and the like as organic material layers. However, the structure of the organic light emitting device is not limited thereto, and may include fewer or more organic layers.

According to an exemplary embodiment of the present specification, the organic material layer of the organic light emitting device of the present specification may have a structure including an electron transporting layer or a light emitting layer.

According to an exemplary embodiment of the present specification, the organic material layer of the organic light emitting device of the present specification may have a structure including an electron blocking layer or a hole transporting layer.

For example, the structure of the organic light emitting device of the present specification may have a structure as illustrated in FIGS. 1 and 2, but is not limited thereto.

FIG. 1 exemplifies the structure of an organic light emitting device 10 in which a first electrode 30, a light emitting layer 40, and a second electrode 50 are sequentially stacked on a substrate 20. FIG. 1 is an exemplified structure of the organic light emitting device according to an exemplary embodiment of the present specification, and may further include other organic material layers.

FIG. 2 exemplifies the structure of an organic light emitting device in which a first electrode 30, a hole injection layer 60, a hole transporting layer 70, a light emitting layer 40, an electron transporting layer 80, an electron injection layer 90, and a second electrode 50 are sequentially stacked on a substrate 20. FIG. 2 is an exemplified structure according to another exemplary embodiment of the present specification, and may further include other organic material layers.

According to an exemplary embodiment of the present specification, the organic material layer includes a hole transporting layer, and the hole transporting layer includes the hetero-cyclic compound represented by Chemical Formula 1.

According to an exemplary embodiment of the present specification, the organic material layer includes an electron blocking layer, and the electron blocking layer includes the hetero-cyclic compound represented by Chemical Formula 1.

According to an exemplary embodiment of the present specification, the organic material layer includes an electron transporting layer, and the electron transporting layer includes the hetero-cyclic compound represented by Chemical Formula 1.

According to an exemplary embodiment of the present specification, the organic material layer includes a light emitting layer, and the light emitting layer includes the hetero-cyclic compound represented by Chemical Formula 1.

According to an exemplary embodiment of the present specification, the organic material layer includes a light emitting layer, and the light emitting layer includes the hetero-cyclic compound represented by Chemical Formula 1 as a host of the light emitting layer.

According to an exemplary embodiment of the present specification, the organic material layer of the organic light emitting device of the present specification includes an electron transporting layer or a light emitting layer, and the electron transporting layer or the light emitting layer may have a structure in which the substituent Ar1 of Chemical Formula 1 is a phosphine oxide group which is unsubstituted or substituted with an alkyl group or an aryl group; a triazinyl group which is unsubstituted or substituted with an aryl group; a quinazolinyl group which is unsubstituted or substituted with an aryl group; a carbazolyl group which is unsubstituted or substituted with a triazine group which is unsubstituted or substituted with an aryl group, or an aryl group; a pyridyl group which is unsubstituted or substituted with an aryl group; or a pyrimidyl group which is unsubstituted or substituted with an aryl group.

According to an exemplary embodiment of the present specification, the organic material layer of the organic light emitting device of the present specification includes an electron blocking layer or a hole transporting layer, and the electron blocking layer or the hole transporting layer may have a structure in which the substituent Ar1 of Chemical Formula 1 is an amine group which is unsubstituted or substituted with an aryl group which is unsubstituted or substituted with an alkyl group.

In an exemplary embodiment of the present specification, the organic material layer may include the hetero-cyclic compound represented by Chemical Formula 1 as a host, and may include another organic compound, a metal or a metal compound as a dopant.

The dopant may be one or more selected from the following exemplified compounds, but is not limited thereto.

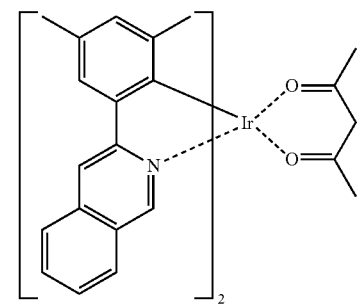

Dp-1

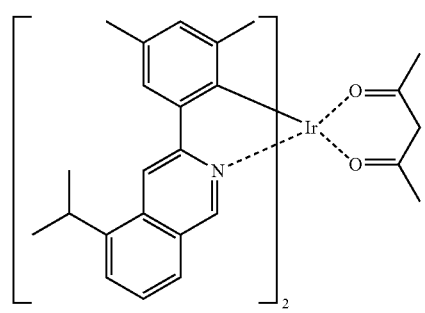

Dp-2

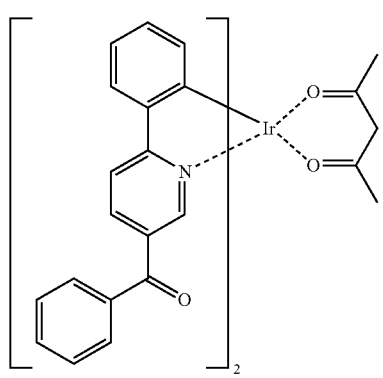

Dp-3

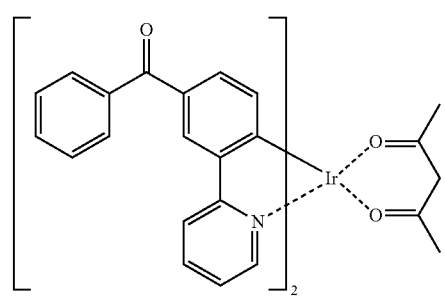

Dp-4

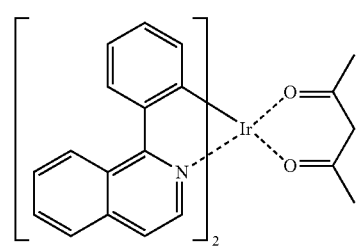

Dp-5

Dp-6
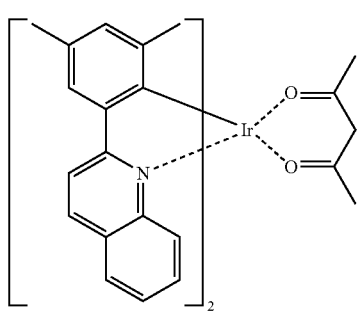
Dp-7
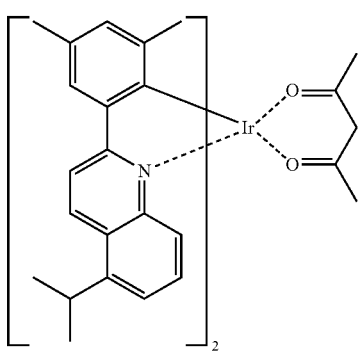
Dp-8
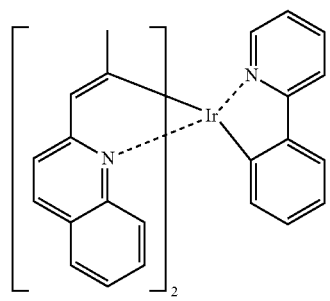
Dp-9
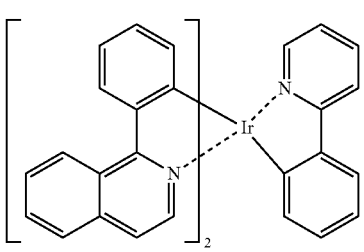
Dp-10
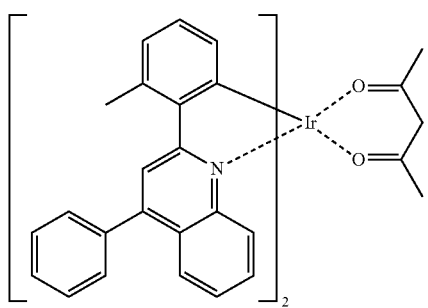
Dp-11
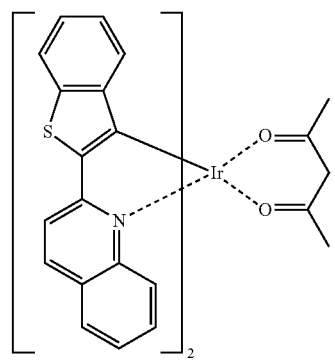
Dp-12
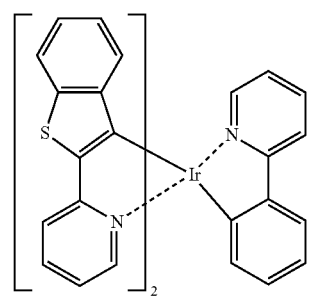
Dp-13
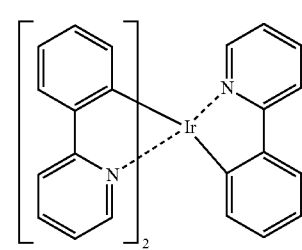
Dp-14
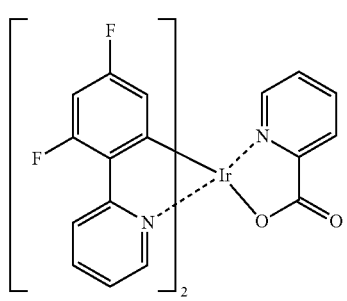
Dp-15
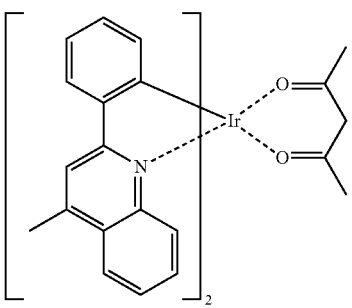

-continued
Dp-16
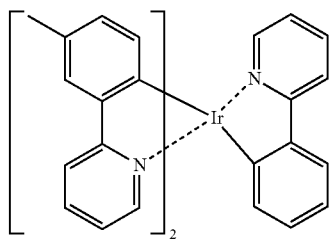
Dp-17
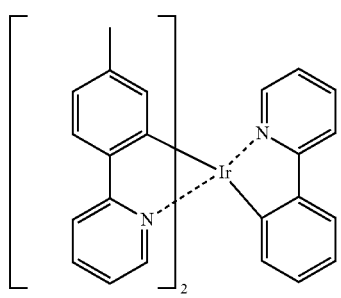
Dp-18
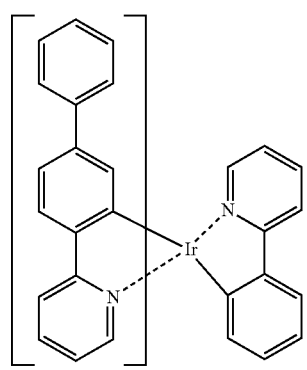
Dp-19
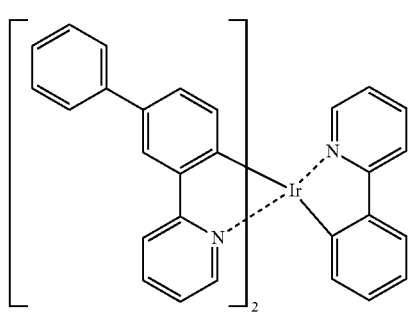
Dp-20
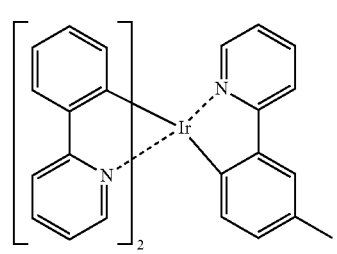
-continued
Dp-21
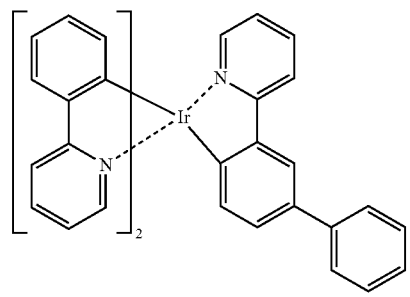
Dp-22
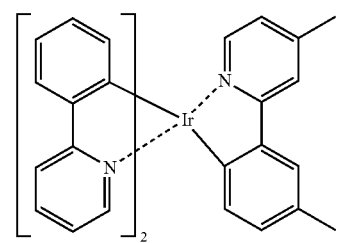
Dp-23
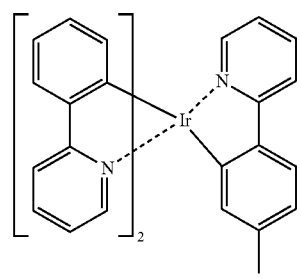
Dp-24
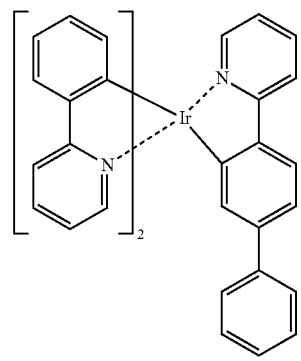
Dp-25
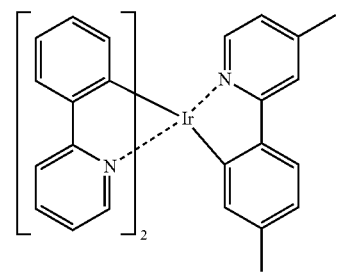

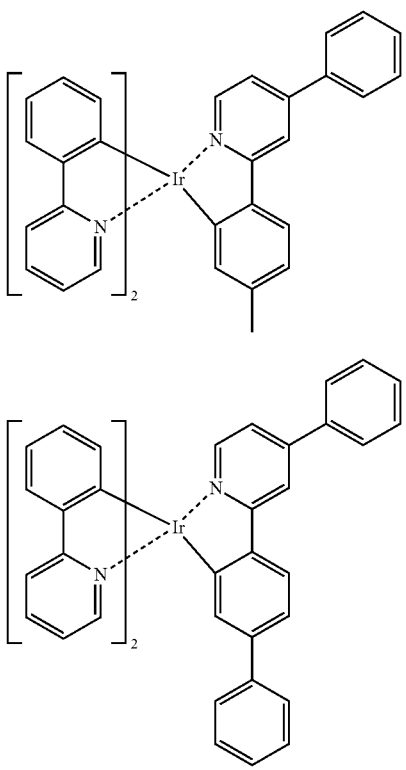

Dp-26

Dp-27

According to an exemplary embodiment of the present specification, the organic material layer may further include one or more layers selected from the group consisting of a hole injection layer, a hole transporting layer, a light emitting layer, an electron transporting layer, and an electron injection layer.

The organic light emitting device of the present specification may be manufactured by the materials and methods known in the art, except that one or more layers of the organic material layer include the hetero-cyclic compound of the present specification, that is, the hetero-cyclic compound represented by Chemical Formula 1.

When the organic light emitting device includes a plurality of organic material layers, the organic material layers may be formed of the same material or different materials.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a first electrode, forming an organic material layer including a hole injection layer, a hole transporting layer, a light emitting layer, and an electron transporting layer thereon, and then depositing a material, which may be used as a second electrode, thereon, by using a physical vapor deposition (PVD) method such as sputtering or e-beam evaporation. In addition to the method described above, an organic light emitting device may be made by sequentially depositing a second electrode material, an organic material layer, and a first electrode material on a substrate. Further, the hetero-cyclic compound represented by Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

According to an exemplary embodiment of the present specification, the first electrode is a positive electrode, and the second electrode is a negative electrode.

According to another exemplary embodiment of the present specification, the first electrode is a negative electrode, and the second electrode is a positive electrode.

As the positive electrode material, materials having a high work function are usually preferred so as to facilitate the injection of holes into an organic material layer. Specific examples of the positive electrode material which may be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or SnO$_2$:Sb; a conductive polymer such as poly(3-methylthiophene), poly[3,4-(ethylene-1,2-dioxy)thiophene] (PEDOT), polypyrrole, and polyaniline; and the like, but are not limited thereto.

As the negative electrode material, materials having a low work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or LiO$_2$/Al and Mg/Ag, and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transporting layer is a layer which accepts holes from a hole injection layer and transports the holes to a light emitting layer, and a hole transporting material is suitably a material having high hole mobility which may accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The electron blocking layer is a layer which may improve the service life and efficiency of the device by preventing electrons injected from an electron injection layer from passing through a light emitting layer and entering a hole injection layer, and may be formed at an appropriate portion between the light emitting layer and the hole injection layer using publicly-known materials, if necessary.

A light emitting material for the light emitting layer is a material which may emit light in a visible light region by accepting and combining holes and electrons from a hole transporting layer and an electron transporting layer, respectively, and is preferably a material having high quantum efficiency for fluorescence or phosphorescence. Specific examples thereof include: an 8-hydroxy-quinoline aluminum complex ($Alq_3$); carbazole-based compounds; dimerized styryl compounds; BAlq; 10-hydroxybenzoquinoline-metal compounds; benzoxazole-based, benzothiazole-based and benzimidazole-based compounds; poly(p-phenylenevinylene) (PPV)-based polymers; spiro compounds; polyfluorene, lubrene, and the like, but are not limited thereto.

The light emitting layer may include a host material and a dopant material. Examples of the host material include a fused aromatic ring derivative, or a hetero ring-containing compound, and the like. Specifically, examples of the fused aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto. The hole blocking layer is a layer which may improve the service life and efficiency of the device by preventing holes injected from a hole injection layer from passing through a light emitting layer and entering an electron injection layer, and may be formed at an appropriate portion between the light emitting layer and the electron injection layer using publicly-known materials, if necessary.

The electron transporting layer is a layer which accepts electrons from an electron injection layer and transports the electrons to a light emitting layer, and an electron transporting material is suitably a material having high electron mobility which may proficiently accept electrons from a negative electrode and transfer the electrons to a light emitting layer. Specific examples thereof include: Al complexes of 8-hydroxyquinoline; complexes including $Alq_3$; organic radical compounds; hydroxyflavone-metal complexes, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto. Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The organic light emitting device according to the present specification may be a top emission type, a bottom emission type, or a dual emission type according to the materials to be used.

According to an exemplary embodiment of the present specification, the hetero-cyclic compound represented by Chemical Formula 1 may be included in an organic solar cell or an organic transistor in addition to the organic light emitting device.

Hereinafter, the present specification will be described in detail with reference to Examples for specifically describing the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

By the following Reaction Formula 1, Compounds A, B, C, D, A-1, B-1, C-1, and D-1 were prepared.

[Reaction Formula 1]
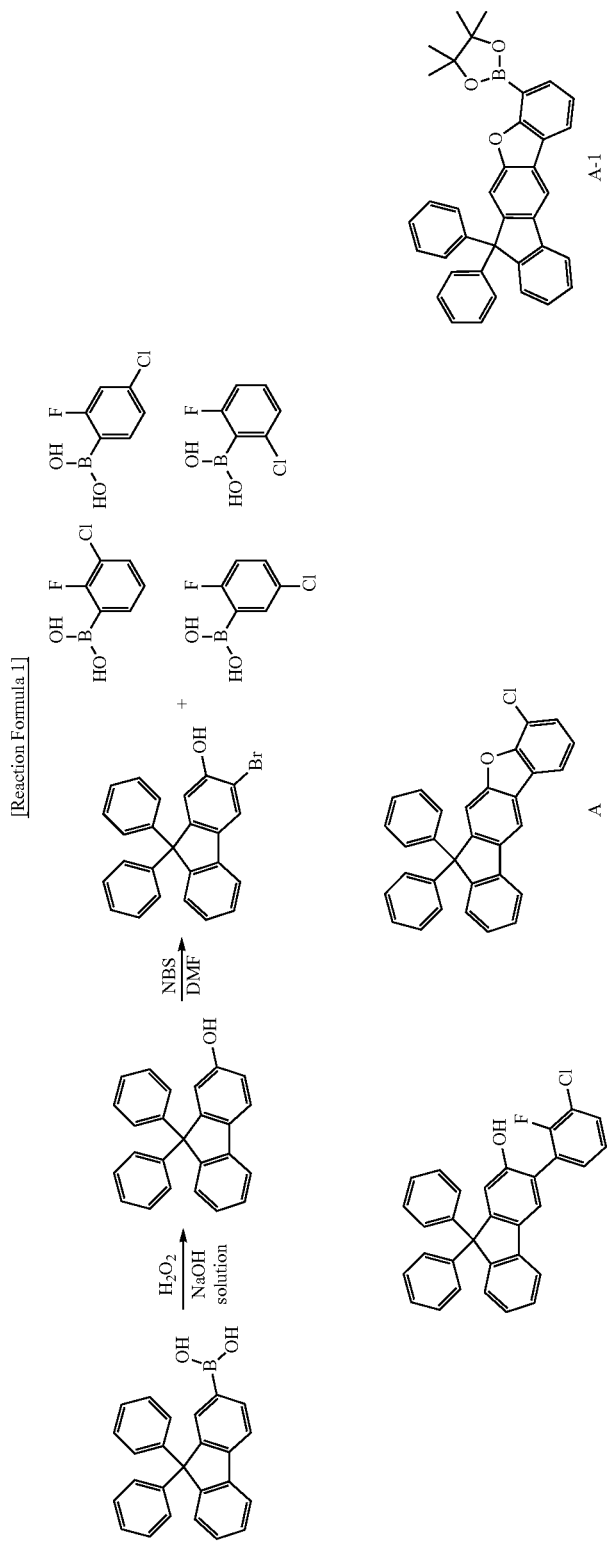

-continued
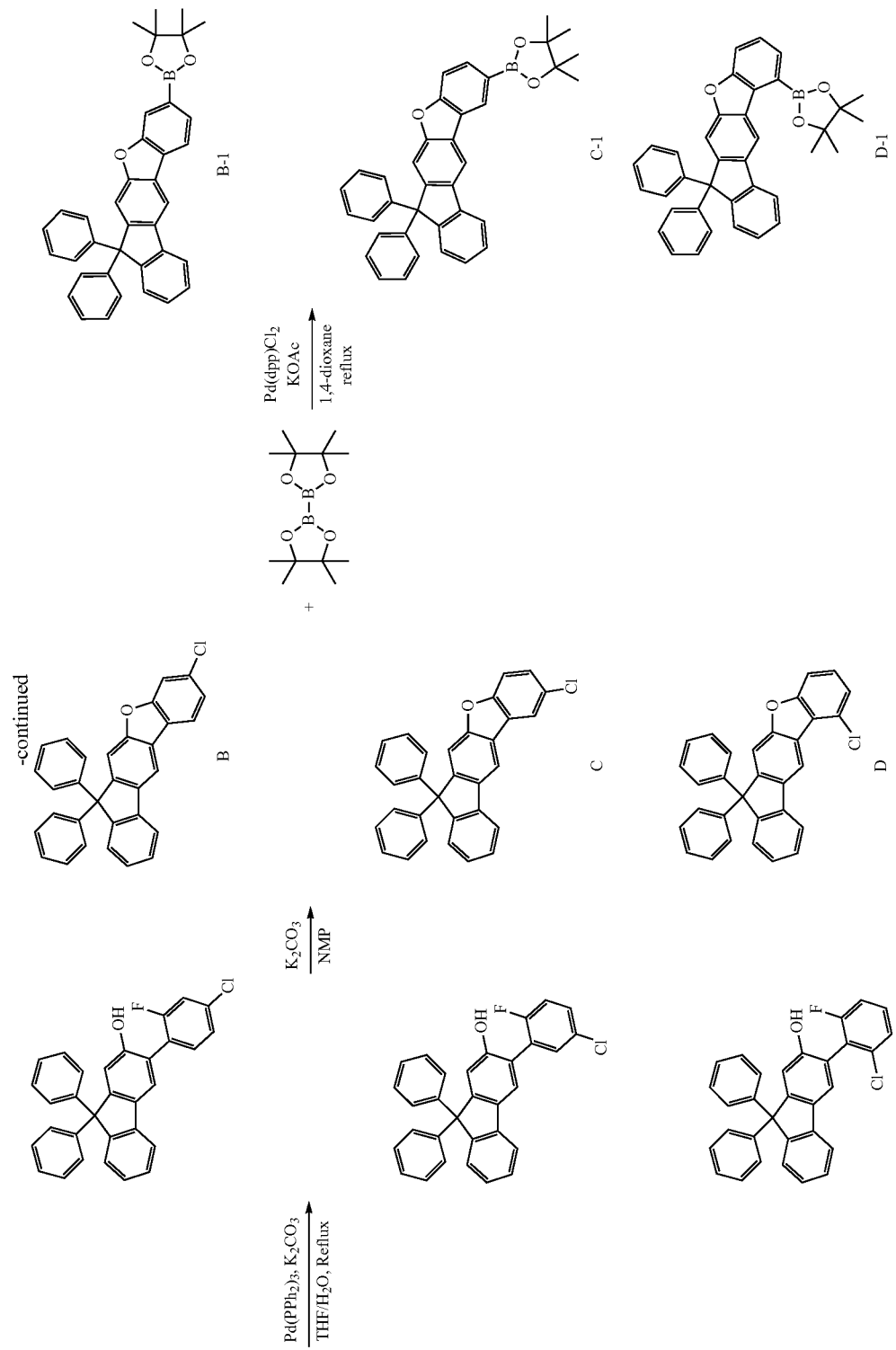

PREPARATION EXAMPLE 1

Preparation of Compound 1

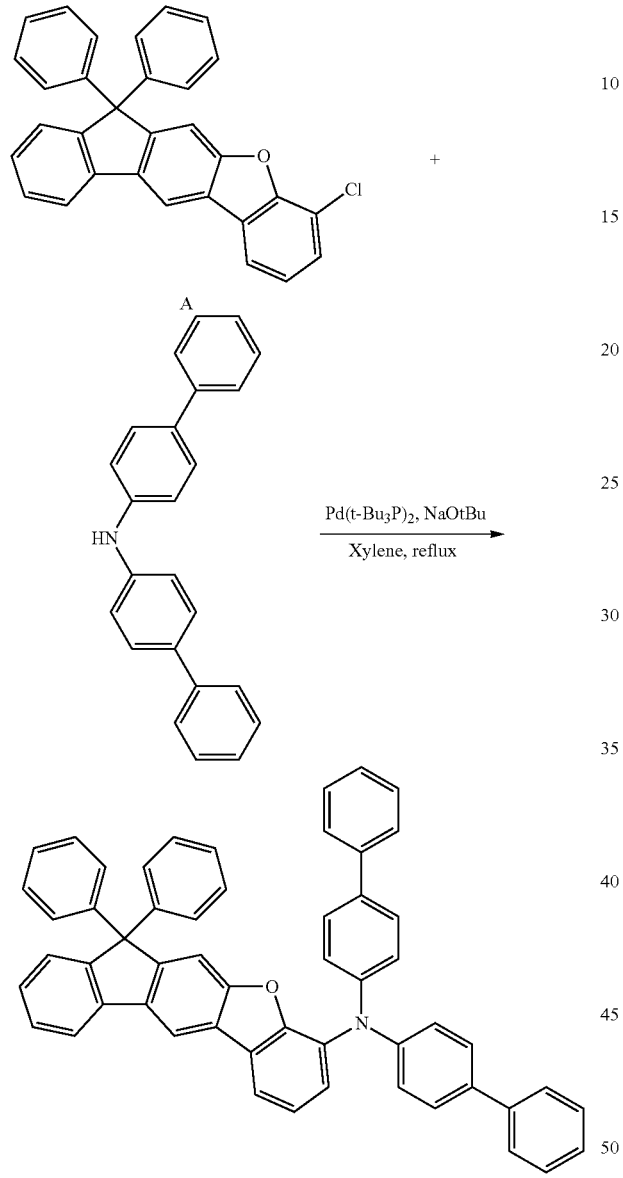

[Compound 1]

PREPARATION EXAMPLE 2

Preparation of Compound 2

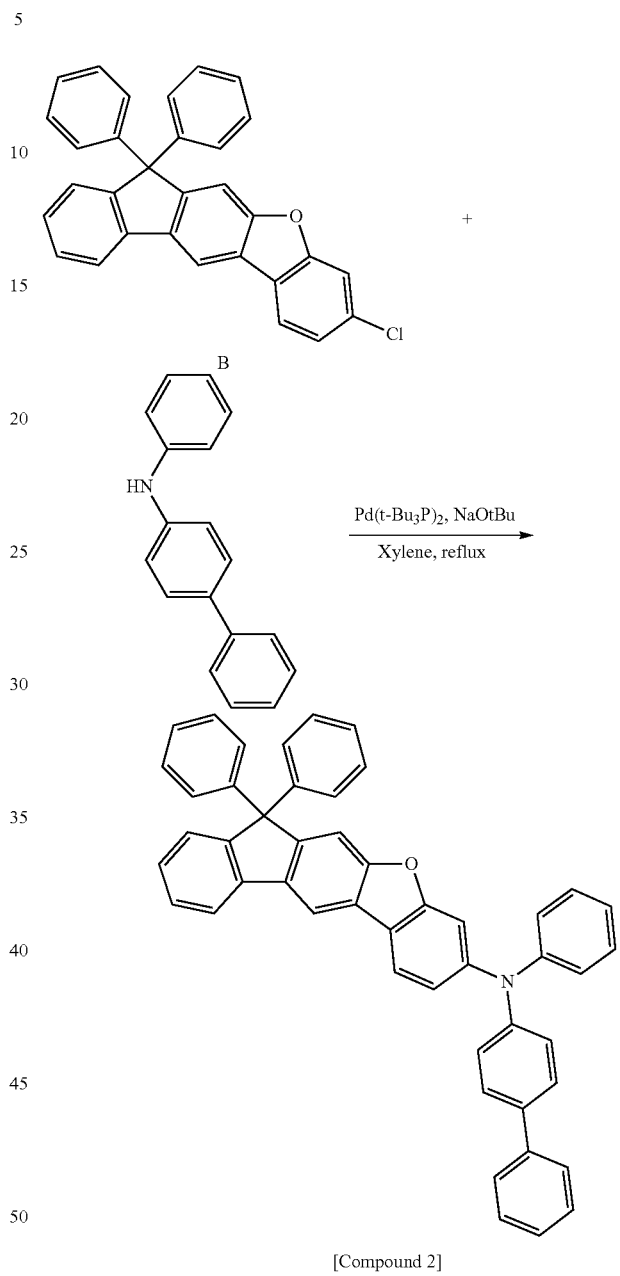

[Compound 2]

Compound A (10 g, 22.62 mmol) and di([1,1'-biphenyl]-4-yl)amine (7.63 g, 23.76 mmol) were completely dissolved in 210 ml of xylene in a 500-ml round bottom flask under a nitrogen atmosphere, and then sodium tert-butoxide (2.61 g, 27.15 mmol) was added thereto, bis(tri-tert-butylphosphine) palladium(0) (0.12 g, 0.23 mmol) was put thereinto, and then the resulting mixture was heated and stirred for 3 hours. The temperature was lowered to room temperature, the resulting mixture was filtered to remove the salt, and then xylene was concentrated under reduced pressure, and the residue was recrystallized with 250 ml of ethyl acetate to prepare Compound 1 (13.87 g, yield: 84%).

MS[M+H]$^+$=728

Compound B (10 g, 22.62 mmol) and N-phenyl-[1,1'-biphenyl]-4-amine (5.82 g, 23.76 mmol) were completely dissolved in 170 ml of xylene in a 500-ml round bottom flask under a nitrogen atmosphere, and then sodium tert-butoxide (2.61 g, 27.15 mmol) was added thereto, bis(tri-tert-butylphosphine) palladium(0) (0.12 g, 0.23 mmol) was put thereinto, and then the resulting mixture was heated and stirred for 2 hours. The temperature was lowered to room temperature, the resulting mixture was filtered to remove the salt, and then xylene was concentrated under reduced pressure, and the residue was recrystallized with 200 ml of ethyl acetate to prepare Compound 2 (13.87 g, yield: 84%).

MS[M+H]$^+$=652

185
PREPARATION EXAMPLE 3
Preparation of Compound 3

186
PREPARATION EXAMPLE 4
Preparation of Compound 4

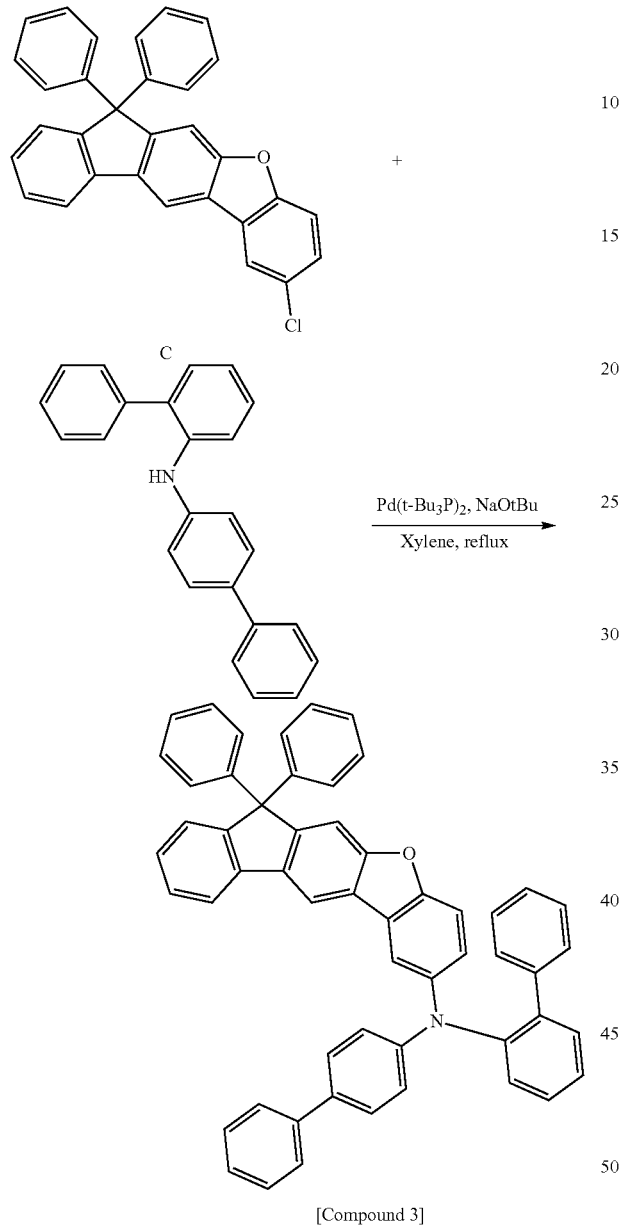

[Compound 3]

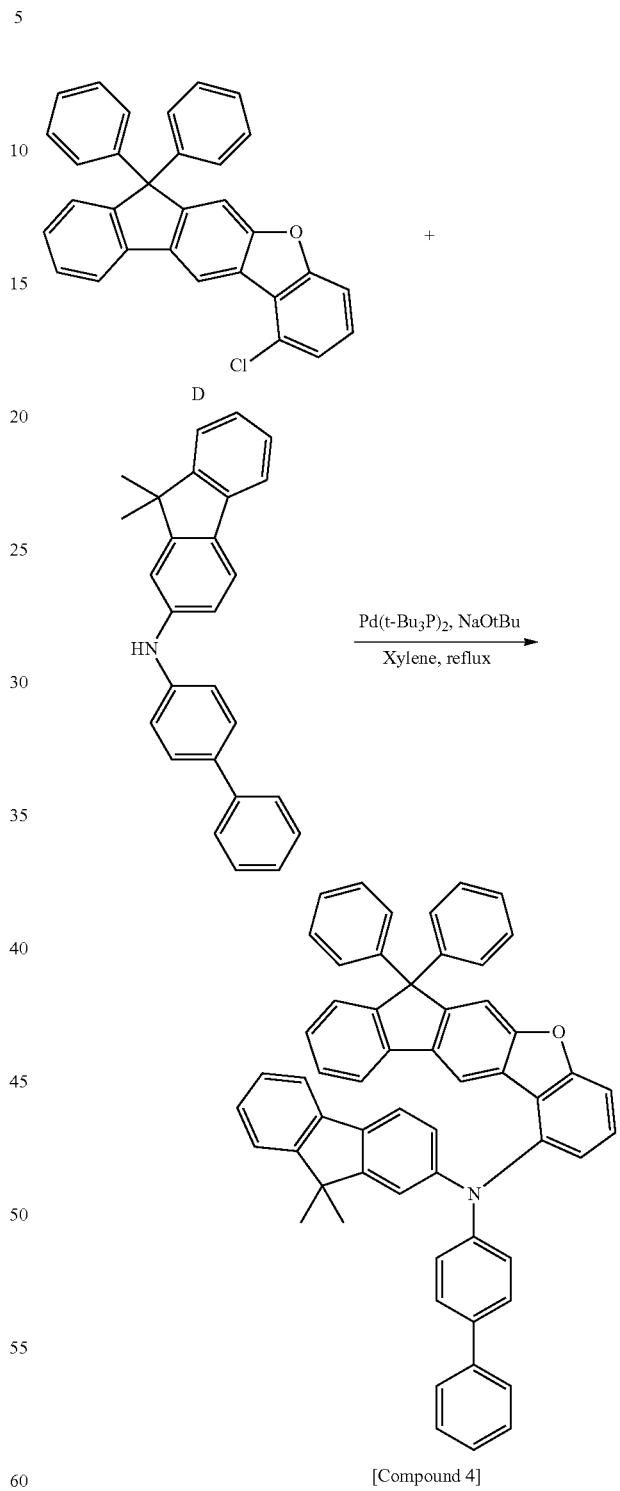

[Compound 4]

Compound C (10 g, 22.62 mmol) and N-([1,1'-biphenyl]-4-yl)-[1,1'-biphenyl]-2-amine (7.63 g, 23.76 mmol) were completely dissolved in 210 ml of xylene in a 500-ml round bottom flask under a nitrogen atmosphere, and then sodium tert-butoxide (2.61 g, 27.15 mmol) was added thereto, bis(tri-tert-butylphosphine) palladium(0) (0.12 g, 0.23 mmol) was put thereinto, and then the resulting mixture was heated and stirred for 5 hours. The temperature was lowered to room temperature, the resulting mixture was filtered to remove the salt, and then xylene was concentrated under reduced pressure, and the residue was recrystallized with 220 ml of ethyl acetate to prepare Compound 3 (11.23 g, yield: 68%).

MS[M+H]$^+$=728

Compound D (10 g, 22.62 mmol) and N-([1,1'-biphenyl]-4-yl)-9,9-dimethyl-9H-fluoren-2-amine (8.58 g, 23.76 mmol) were completely dissolved in 220 ml of xylene in a 500-ml round bottom flask under a nitrogen atmosphere, and then sodium tert-butoxide (2.61 g, 27.15 mmol) was added thereto, bis(tri-tert-butylphosphine) palladium(0) (0.12 g, 0.23 mmol) was put thereinto, and then the resulting mixture was heated and stirred for 2 hours. The temperature was lowered to room temperature, the resulting mixture was filtered to remove the salt, and then xylene was concentrated under reduced pressure, and the residue was recrystallized with 200 ml of ethyl acetate to prepare Compound 4 (13.87 g, yield: 84%).

MS[M+H]$^+$=768

PREPARATION EXAMPLE 5

Preparation of Compound 5

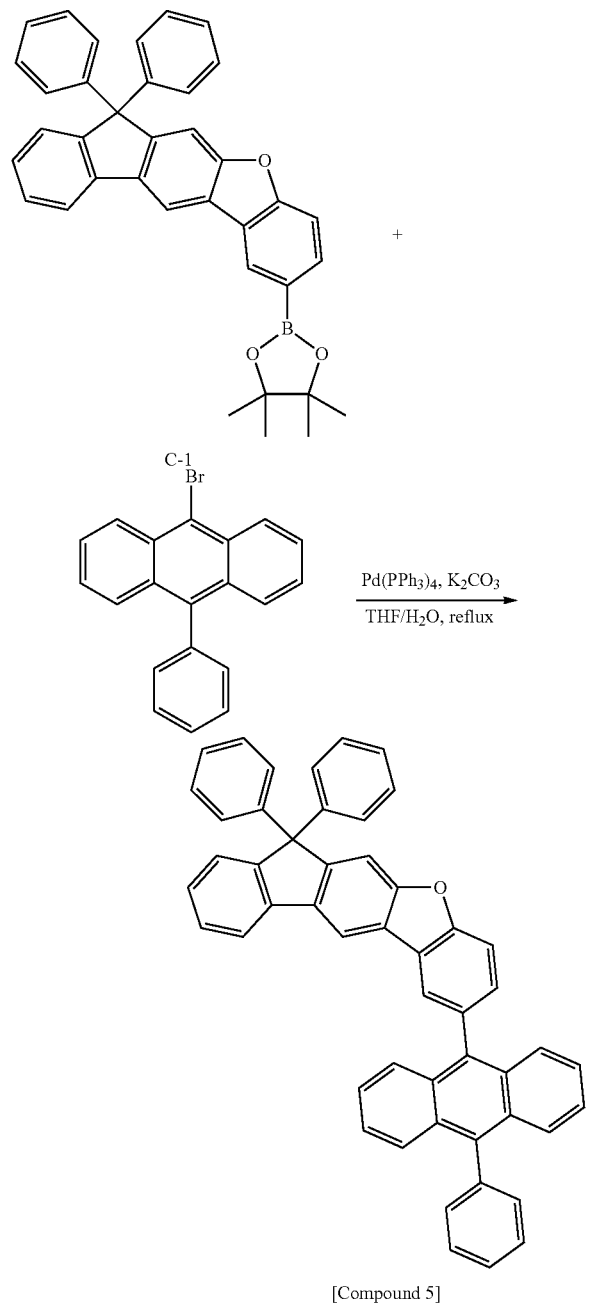

[Compound 5]

Compound C-1 (10.09 g, 33.13 mmol) and 9-bromo-10-phenylanthracene (10 g, 30.12 mmol) were completely dissolved in 240 ml of tetrahydrofuran in a 500-ml round bottom flask under a nitrogen atmosphere, and then an aqueous 2 M potassium carbonate solution (120 ml) was added thereto, tetrakis-(triphenylphosphine)palladium (0.19 g, 0.17 mmol) was put thereinto, and then the resulting mixture was heated and stirred for 8 hours. The temperature was lowered to room temperature, the aqueous layer was removed, and the residue was dried over anhydrous magnesium sulfate, and then concentrated under reduced pressure, and recrystallized with 220 ml of ethyl acetate to prepare Compound 5 (15.77 g, yield: 72%).

MS[M+H]$^+$=661

PREPARATION EXAMPLE 6

Preparation of Compound 6

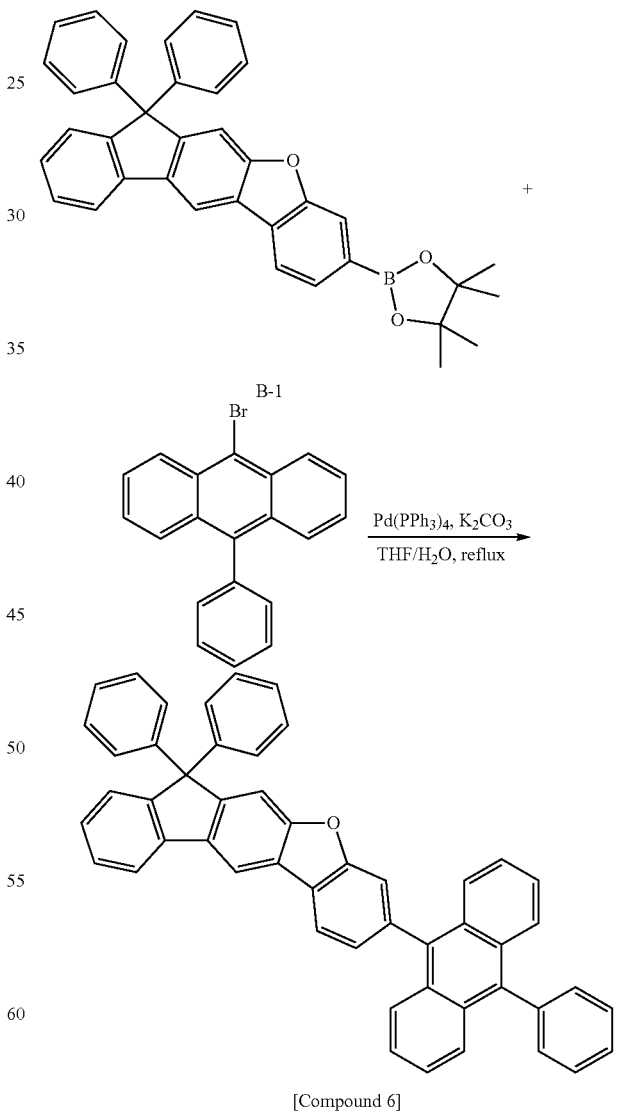

[Compound 6]

Compound B-1 (10.09 g, 33.13 mmol) and 9-bromo-10-phenylanthracene (10 g, 30.12 mmol) were completely dissolved in 240 ml of tetrahydrofuran in a 500-ml round bottom flask under a nitrogen atmosphere, and then an aqueous 2 M potassium carbonate solution (120 ml) was added thereto, tetrakis-(triphenylphosphine)palladium (0.19 g, 0.17 mmol) was put thereinto, and then the resulting mixture was heated and stirred for 8 hours. The temperature was lowered to room temperature, the aqueous layer was removed, and the residue was dried over anhydrous magnesium sulfate, and then concentrated under reduced pressure, and recrystallized with 260 ml of ethyl acetate to prepare Compound 6 (17.56 g, yield: 80%).

MS[M+H]$^+$=661

PREPARATION EXAMPLE 7

Preparation of Compound 7

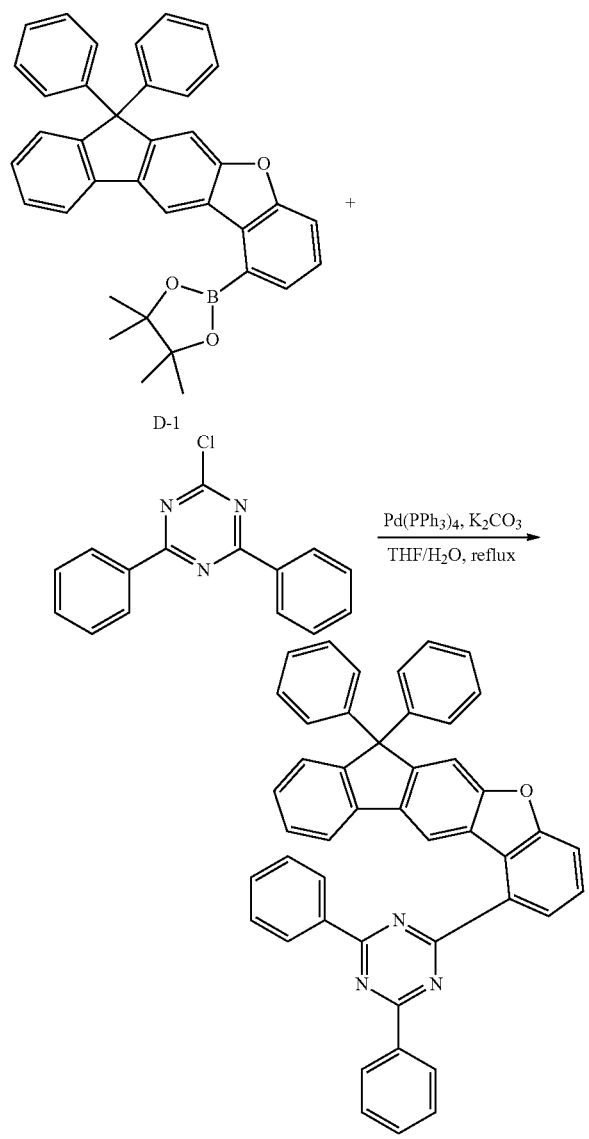

[Compound 7]

Compound D-1 (22.49 g, 41.20 mmol) and 2-chloro-4,6-diphenyl-1,3,5-triazine (10 g, 37.45 mmol) were completely dissolved in 280 ml of tetrahydrofuran in a 500-ml round bottom flask under a nitrogen atmosphere, and then an aqueous 2 M potassium carbonate solution (140 ml) was added thereto, tetrakis-(triphenylphosphine)palladium (1.30 g, 1.12 mmol) was put thereinto, and then the resulting mixture was heated and stirred for 4 hours. The temperature was lowered to room temperature, the aqueous layer was removed, and the residue was dried over anhydrous magnesium sulfate, and then concentrated under reduced pressure, and recrystallized with 340 ml of ethyl acetate to prepare Compound 7 (15.77 g, yield: 72%).

MS[M+H]$^+$=640

PREPARATION EXAMPLE 8

Preparation of Compound 8

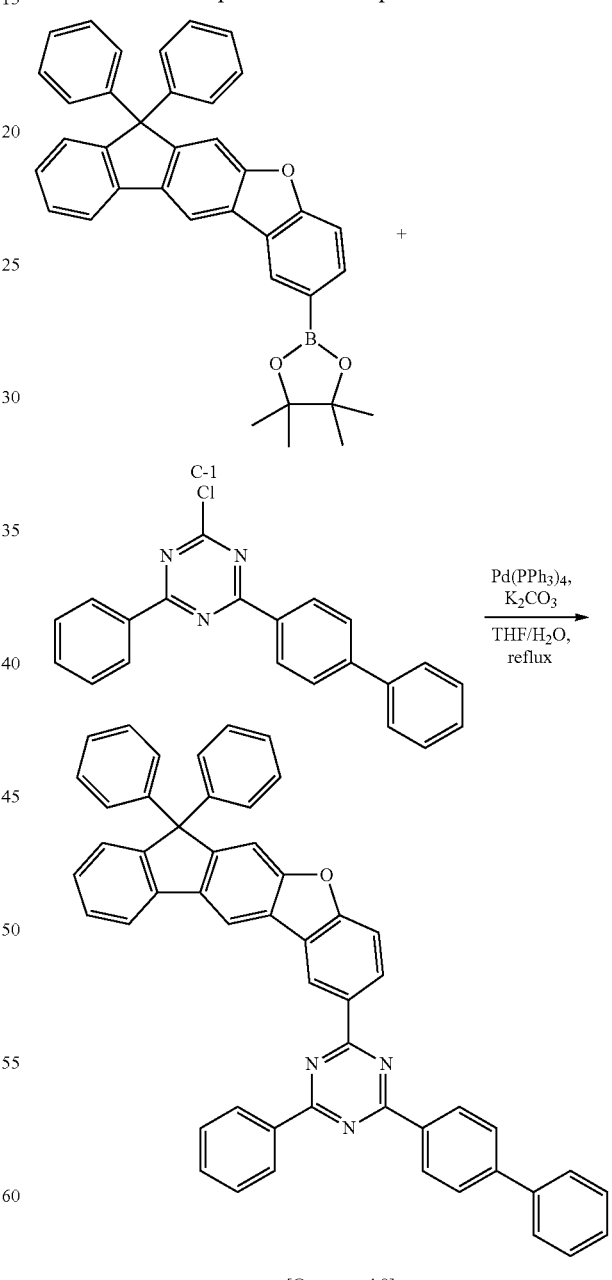

[Compound 8]

Compound C-1 (17.51 g, 32.07 mmol) and 2-([1,1'-biphenyl]-4-yl)-4-chloro-6-phenyl-1,3,5-triazine (10 g, 29.15 mmol) were completely dissolved in 280 ml of tetrahydrofuran in a 500-ml round bottom flask under a nitrogen atmosphere, and then an aqueous 2 M potassium carbonate solution (140 ml) was added thereto, tetrakis-(triphenylphosphine)palladium (1.30 g, 1.12 mmol) was put thereinto, and then the resulting mixture was heated and stirred for 4 hours. The temperature was lowered to room temperature, the aqueous layer was removed, and the residue was dried over anhydrous magnesium sulfate, and then concentrated under reduced pressure, and recrystallized with 260 ml of tetrahydrofuran to prepare Compound 8 (15.47 g, yield: 67%).

MS[M+H]$^+$=716

PREPARATION EXAMPLE 9

Preparation of Compound 9

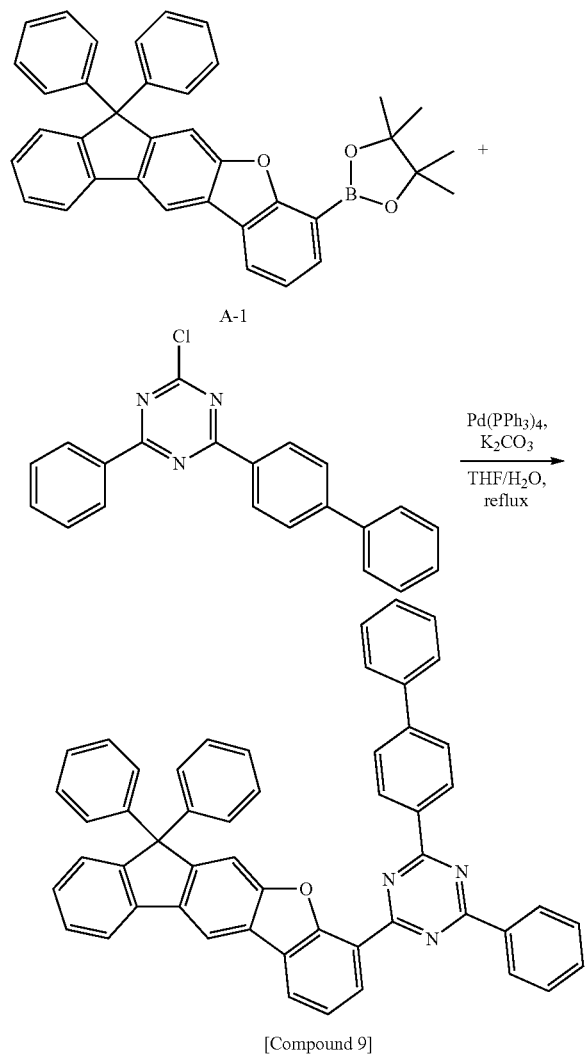

[Compound 9]

Compound A-1 (17.51 g, 32.07 mmol) and 2-([1,1'-biphenyl]-4-yl)-4-chloro-6-phenyl-1,3,5-triazine (10 g, 29.15 mmol) were completely dissolved in 280 ml of tetrahydrofuran in a 500-ml round bottom flask under a nitrogen atmosphere, and then an aqueous 2 M potassium carbonate solution (140 ml) was added thereto, tetrakis-(triphenylphosphine)palladium (1.30 g, 1.12 mmol) was put thereinto, and then the resulting mixture was heated and stirred for 3 hours. The temperature was lowered to room temperature, the aqueous layer was removed, and the residue was dried over anhydrous magnesium sulfate, and then concentrated under reduced pressure, and recrystallized with 310 ml of tetrahydrofuran to prepare Compound 9 (15.47 g, yield: 67%).

MS[M+H]$^+$=716

PREPARATION EXAMPLE 10

Preparation of Compound 10

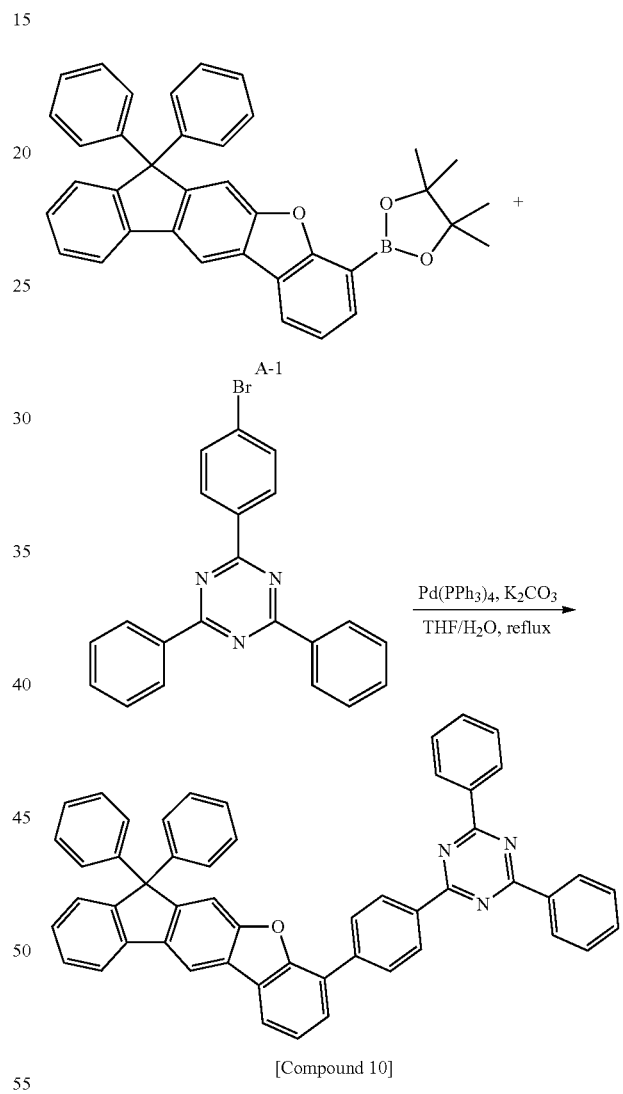

[Compound 10]

Compound A-1 (17.52 g, 28.42 mmol) and 2-(4-bromophenyl)-4,6-diphenyl-1,3,5-triazine (10 g, 25.84 mmol) were completely dissolved in 280 ml of tetrahydrofuran in a 500-ml round bottom flask under a nitrogen atmosphere, and then an aqueous 2 M potassium carbonate solution (140 ml) was added thereto, tetrakis-(triphenylphosphine)palladium (1.30 g, 1.12 mmol) was put thereinto, and then the resulting mixture was heated and stirred for 6 hours. The temperature was lowered to room temperature, the aqueous layer was removed, and the residue was dried over anhydrous magnesium sulfate, and then concentrated under reduced pressure, and recrystallized with 310 ml of tetrahydrofuran to prepare Compound 10 (17.23 g, yield: 85%).

MS[M+H]⁺=716

PREPARATION EXAMPLE 11

Preparation of Compound 11

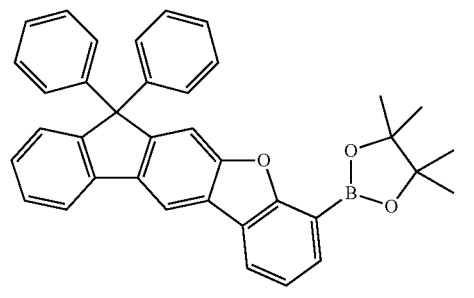

A-1

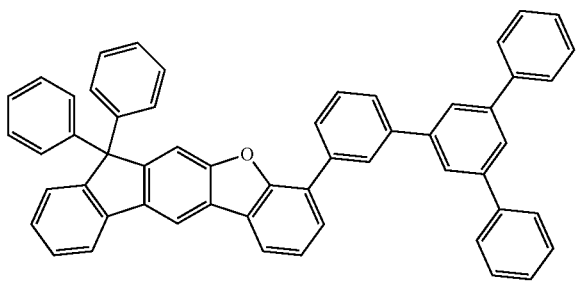

[Compound 11]

Compound A-1 (17.52 g, 28.42 mmol) and 2-(3-bromophenyl)-4,6-diphenyl-1,3,5-triazine (10 g, 25.84 mmol) were completely dissolved in 280 ml of tetrahydrofuran in a 500-ml round bottom flask under a nitrogen atmosphere, and then an aqueous 2 M potassium carbonate solution (140 ml) was added thereto, tetrakis-(triphenylphosphine)palladium (1.30 g, 1.12 mmol) was put thereinto, and then the resulting mixture was heated and stirred for 6 hours. The temperature was lowered to room temperature, the aqueous layer was removed, and the residue was dried over anhydrous magnesium sulfate, and then concentrated under reduced pressure, and recrystallized with 290 ml of tetrahydrofuran to prepare Compound 11 (16.95 g, yield: 83%).

MS[M+H]⁺=716

PREPARATION EXAMPLE 12

Preparation of Compound 12

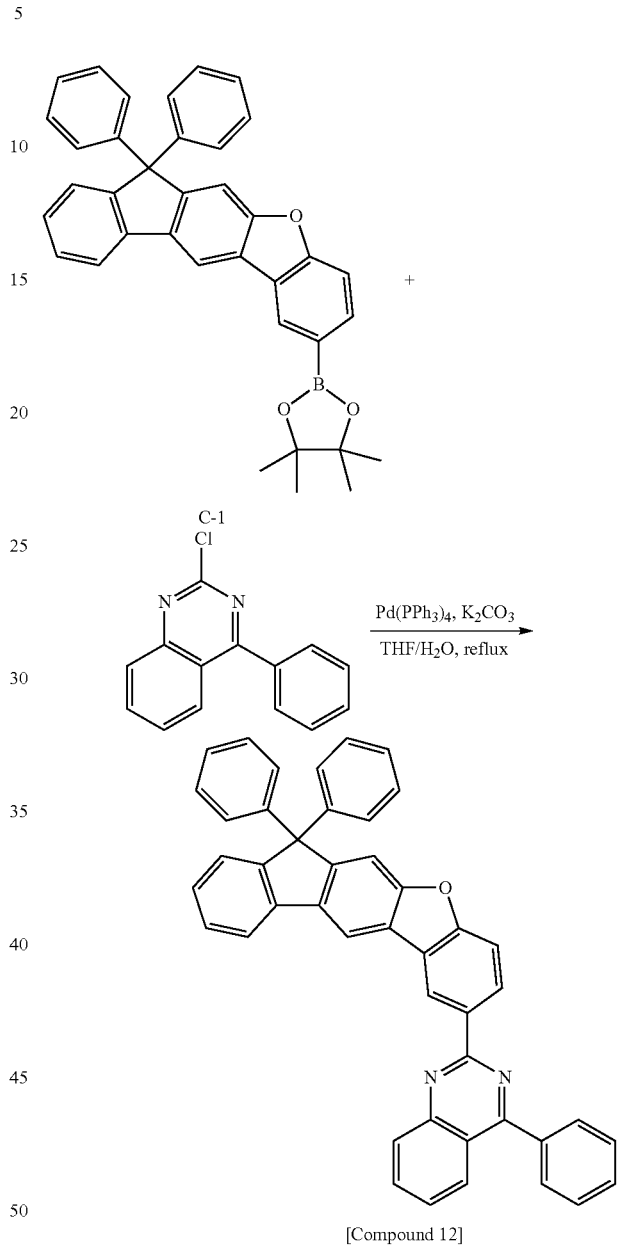

[Compound 12]

Compound C-1 (20.02 g, 36.67 mmol) and 2-chloro-4-phenylquinazoline (8.0 g, 33.33 mmol) were completely dissolved in 260 ml of tetrahydrofuran in a 500-ml round bottom flask under a nitrogen atmosphere, and then an aqueous 2 M potassium carbonate solution (130 ml) was added thereto, tetrakis-(triphenylphosphine)palladium (1.16 g, 1.00 mmol) was put thereinto, and then the resulting mixture was heated and stirred for 4 hours. The temperature was lowered to room temperature, the aqueous layer was removed, and the residue was dried over anhydrous magnesium sulfate, and then concentrated under reduced pressure, and recrystallized with 230 ml of tetrahydrofuran to prepare Compound 12 (21.45 g, yield: 67%).

MS[M+H]⁺=613

PREPARATION EXAMPLE 13

Preparation of Compound 13

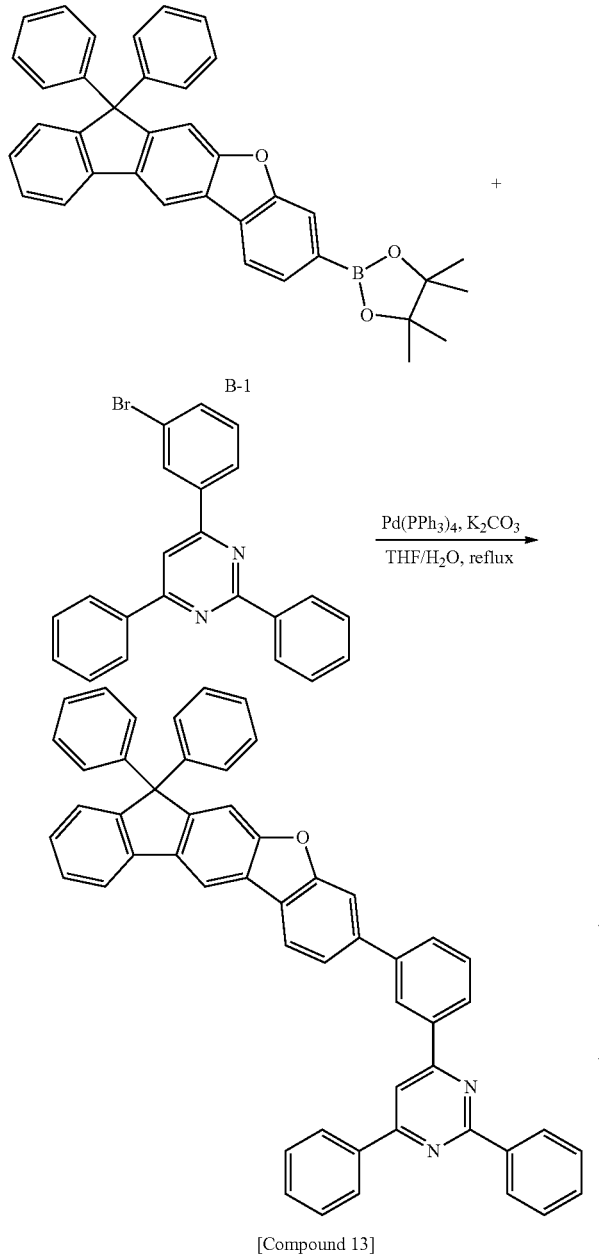

[Compound 13]

Compound B-1 (17.52 g, 28.42 mmol) and 4-(3-bromophenyl)-2,6-diphenylpyrimidine (10 g, 25.84 mmol) were completely dissolved in 280 ml of tetrahydrofuran in a 500-ml round bottom flask under a nitrogen atmosphere, and then an aqueous 2 M potassium carbonate solution (140 ml) was added thereto, tetrakis-(triphenylphosphine)palladium (1.30 g, 1.12 mmol) was put thereinto, and then the resulting mixture was heated and stirred for 6 hours. The temperature was lowered to room temperature, the aqueous layer was removed, and the residue was dried over anhydrous magnesium sulfate, and then concentrated under reduced pressure, and recrystallized with 310 ml of tetrahydrofuran to prepare Compound 13 (16.95 g, yield: 83%).
MS[M+H]$^+$=715

PREPARATION EXAMPLE 14

Preparation of Compound 14

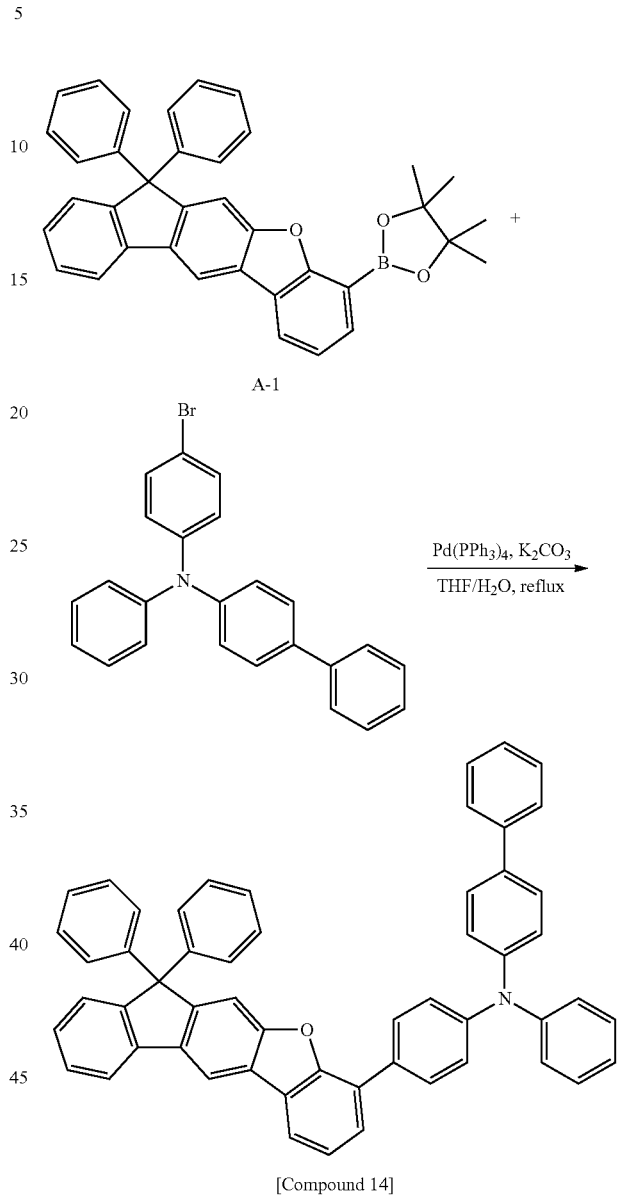

[Compound 14]

Compound A-1 (17.52 g, 28.42 mmol) and N-(4-bromophenyl)-N-phenyl-[1,1'-biphenyl]-4-amine (10 g, 25.84 mmol) were completely dissolved in 280 ml of tetrahydrofuran in a 500-ml round bottom flask under a nitrogen atmosphere, and then an aqueous 2 M potassium carbonate solution (140 ml) was added thereto, tetrakis-(triphenylphosphine)palladium (1.30 g, 1.12 mmol) was put thereinto, and then the resulting mixture was heated and stirred for 6 hours. The temperature was lowered to room temperature, the aqueous layer was removed, and the residue was dried over anhydrous magnesium sulfate, and then concentrated under reduced pressure, and recrystallized with 310 ml of tetrahydrofuran to prepare Compound 14 (17.23 g, yield: 85%).
MS[M+H]$^+$=728

PREPARATION EXAMPLE 15

Preparation of Compound 15

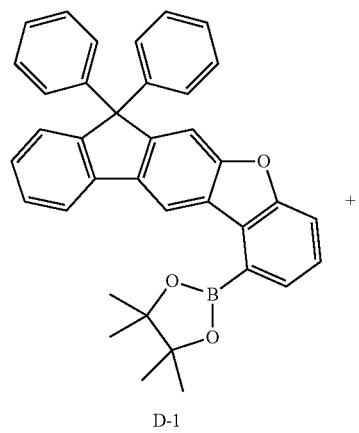

D-1

Compound D-1 (9.33 g, 17.09 mmol) and N-([1,1'-biphenyl]-4-yl)-N-(4-bromophenyl)-9,9-dimethyl-9H-fluoren-2-amine (8.0 g, 15.53 mmol) were completely dissolved in 280 ml of tetrahydrofuran in a 500-ml round bottom flask under a nitrogen atmosphere, and then an aqueous 2 M potassium carbonate solution (140 ml) was added thereto, tetrakis-(triphenylphosphine)palladium (1.30 g, 1.12 mmol) was put thereinto, and then the resulting mixture was heated and stirred for 8 hours. The temperature was lowered to room temperature, the aqueous layer was removed, and the residue was dried over anhydrous magnesium sulfate, and then concentrated under reduced pressure, and recrystallized with 180 ml of tetrahydrofuran to prepare Compound 15 (9.44 g, yield: 66%).

MS[M+H]$^+$=844

PREPARATION EXAMPLE 16

Preparation of Compound 16

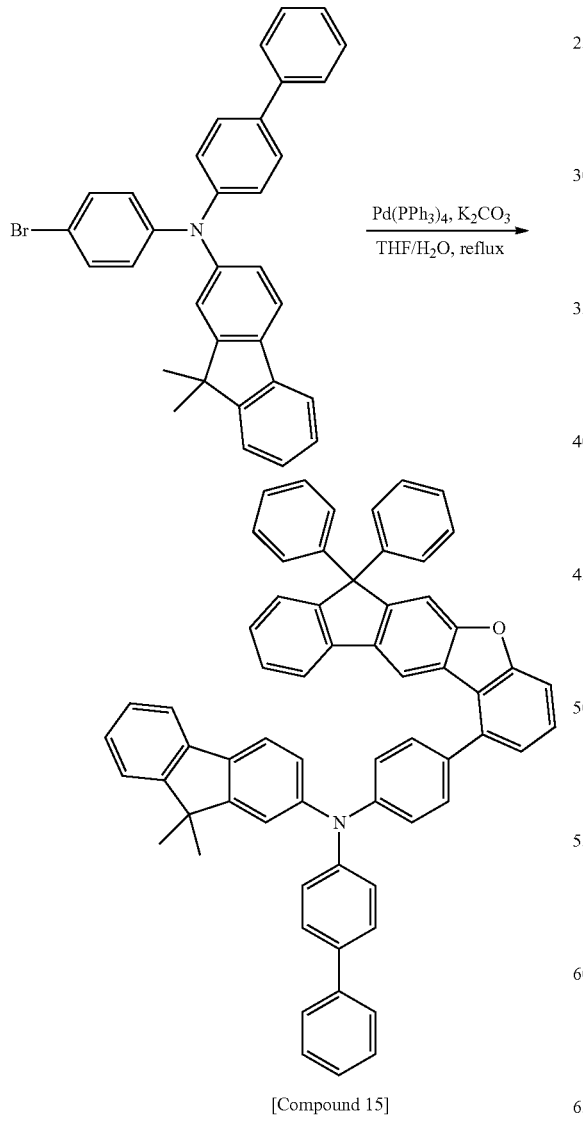

[Compound 15]

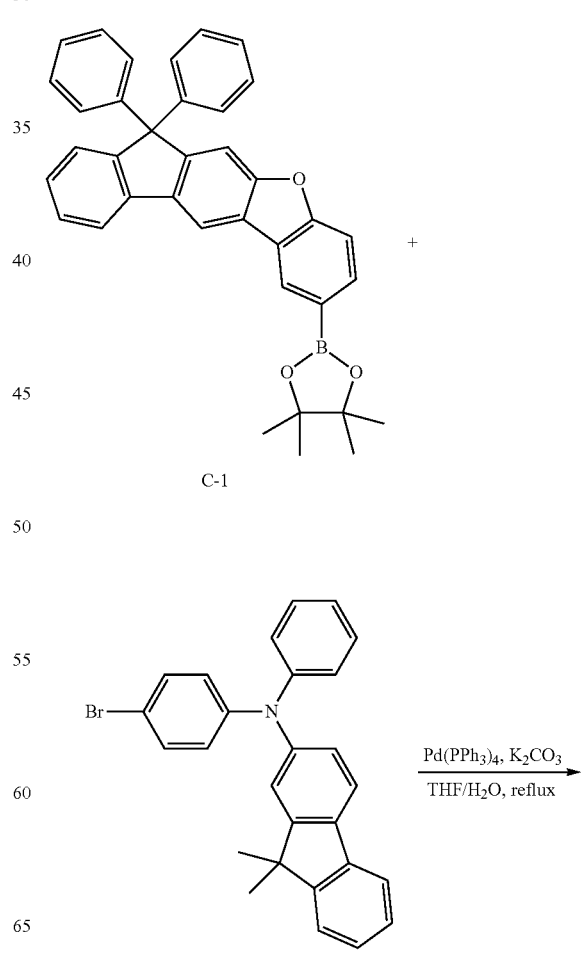

C-1

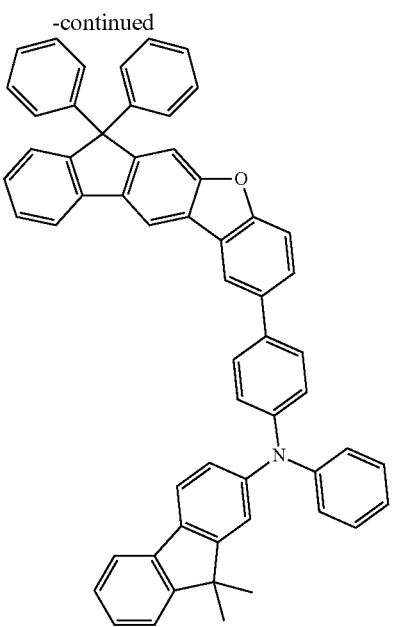

[Compound 16]

Compound C-1 (10.92 g, 20.01 mmol) and N-(4-bromophenyl)-9,9-dimethyl-N-phenyl-9H-fluoren-2-amine (8.0 g, 18.18 mmol) were completely dissolved in 280 ml of tetrahydrofuran in a 500-ml round bottom flask under a nitrogen atmosphere, and then an aqueous 2 M potassium carbonate solution (140 ml) was added thereto, tetrakis-(triphenylphosphine)palladium (1.30 g, 1.12 mmol) was put thereinto, and then the resulting mixture was heated and stirred for 8 hours. The temperature was lowered to room temperature, the aqueous layer was removed, and the residue was dried over anhydrous magnesium sulfate, and then concentrated under reduced pressure, and recrystallized with 180 ml of tetrahydrofuran to prepare Compound 16 (12.23 g, yield: 80%).

MS[M+H]$^+$=768

PREPARATION EXAMPLE 17

Preparation of Compound 17

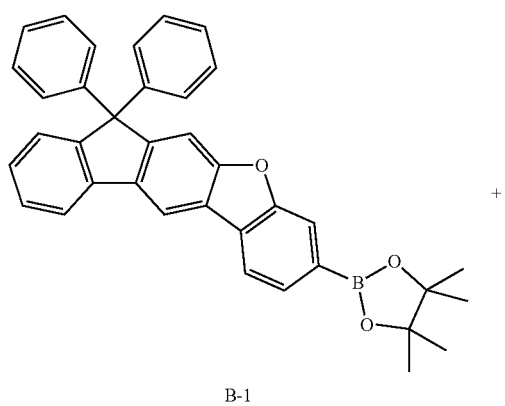

B-1

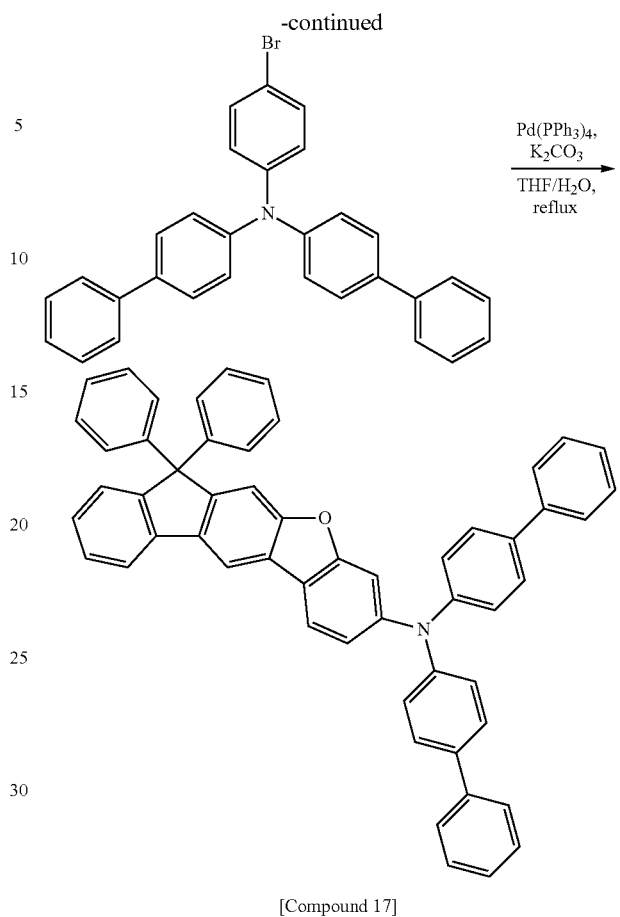

[Compound 17]

Compound B-1 (17.52 g, 28.42 mmol) and N-([1,1'-biphenyl]-4-yl)-N-(4-bromophenyl)-[1,1'-biphenyl]-4-amine (10 g, 25.84 mmol) were completely dissolved in 280 ml of tetrahydrofuran in a 500-ml round bottom flask under a nitrogen atmosphere, and then an aqueous 2 M potassium carbonate solution (140 ml) was added thereto, tetrakis-(triphenylphosphine)palladium (1.30 g, 1.12 mmol) was put thereinto, and then the resulting mixture was heated and stirred for 6 hours. The temperature was lowered to room temperature, the aqueous layer was removed, and the residue was dried over anhydrous magnesium sulfate, and then concentrated under reduced pressure, and recrystallized with 310 ml of tetrahydrofuran to prepare Compound 17 (17.23 g, yield: 85%).

MS[M+H]$^+$=804

PREPARATION EXAMPLE 18

Preparation of Compound 18

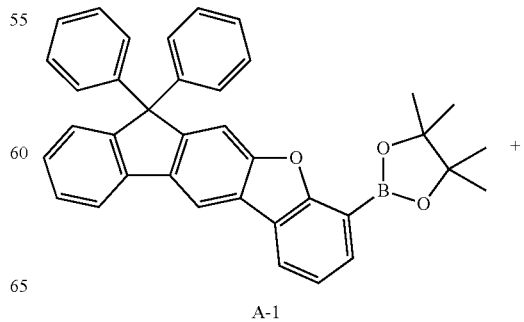

A-1

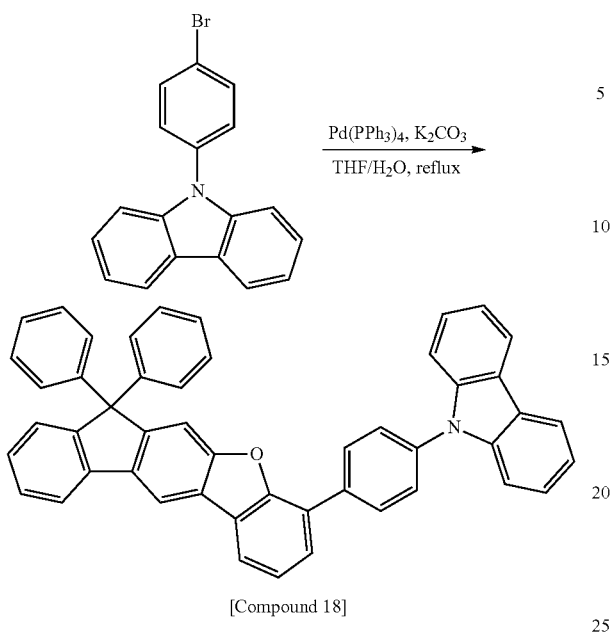

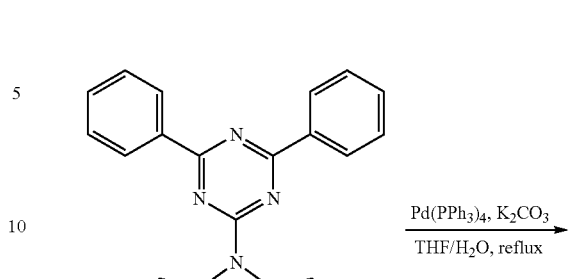

[Compound 18]

Compound A-1 (17.52 g, 28.42 mmol) and 9-(4-bromophenyl)-9H-carbazole (10 g, 25.84 mmol) were completely dissolved in 280 ml of tetrahydrofuran in a 500-ml round bottom flask under a nitrogen atmosphere, and then an aqueous 2 M potassium carbonate solution (140 ml) was added thereto, tetrakis-(triphenylphosphine)palladium (1.30 g, 1.12 mmol) was put thereinto, and then the resulting mixture was heated and stirred for 6 hours. The temperature was lowered to room temperature, the aqueous layer was removed, and the residue was dried over anhydrous magnesium sulfate, and then concentrated under reduced pressure, and recrystallized with 310 ml of tetrahydrofuran to prepare Compound 18 (17.23 g, yield: 85%).

MS[M+H]$^+$=650

PREPARATION EXAMPLE 19

Preparation of Compound 19

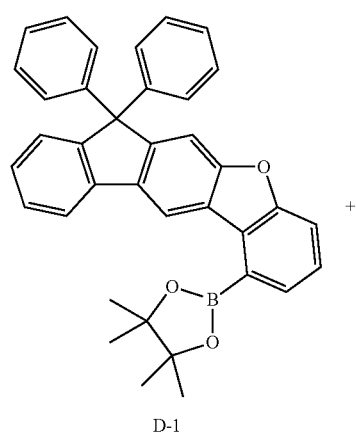

D-1

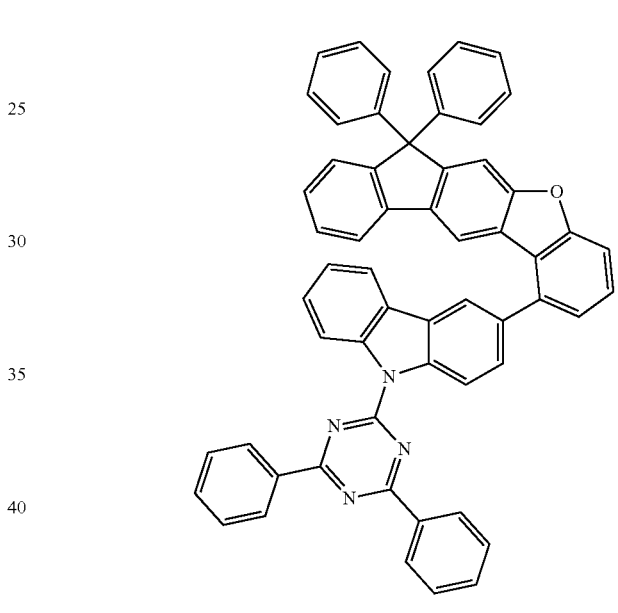

[Compound 19]

Compound D-1 (10.09 g, 18.49 mmol) and 3-bromo-9-(4,6-diphenyl-1,3,5-triazin-2-yl)-9H-carbazole (8.0 g, 16.81 mmol) were completely dissolved in 350 ml of tetrahydrofuran in a 500-ml round bottom flask under a nitrogen atmosphere, and then an aqueous 2 M potassium carbonate solution (175 ml) was added thereto, tetrakis-(triphenylphosphine)palladium (1.30 g, 1.12 mmol) was put thereinto, and then the resulting mixture was heated and stirred for 2 hours. The temperature was lowered to room temperature, the aqueous layer was removed, and the residue was dried over anhydrous magnesium sulfate, and then concentrated under reduced pressure, and recrystallized with 310 ml of tetrahydrofuran to prepare Compound 19 (16.47 g, yield: 90%).

MS[M+H]$^+$=805

PREPARATION EXAMPLE 20

Preparation of Compound 20

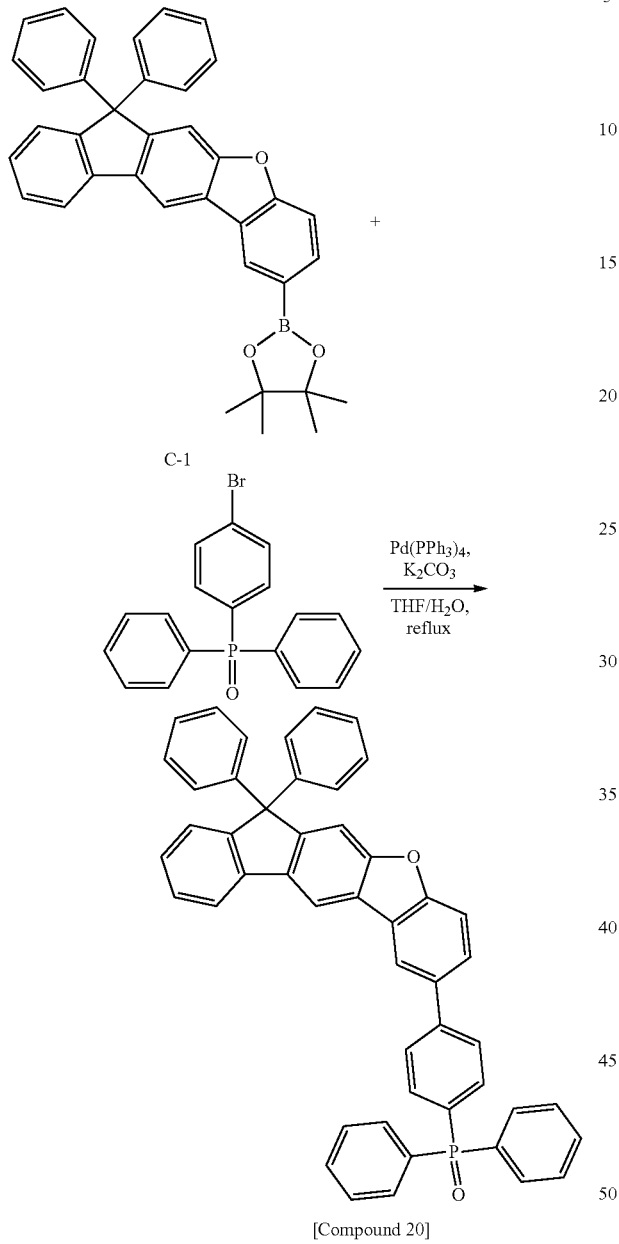

[Compound 20]

Compound C-1 (13.50 g, 24.72 mmol) and (4-bromophenyl)diphenylphosphine oxide (8.0 g, 22.47 mmol) were completely dissolved in 260 ml of tetrahydrofuran in a 500-ml round bottom flask under a nitrogen atmosphere, and then an aqueous 2 M potassium carbonate solution (130 ml) was added thereto, tetrakis-(triphenylphosphine)palladium (0.78 g, 0.67 mmol) was put thereinto, and then the resulting mixture was heated and stirred for 4 hours. The temperature was lowered to room temperature, the aqueous layer was removed, and the residue was dried over anhydrous magnesium sulfate, and then concentrated under reduced pressure, and recrystallized with 270 ml of tetrahydrofuran to prepare Compound 20 (11.18 g, yield: 66%).

MS[M+H]$^+$=685

PREPARATION EXAMPLE 21

Preparation of Compound 21

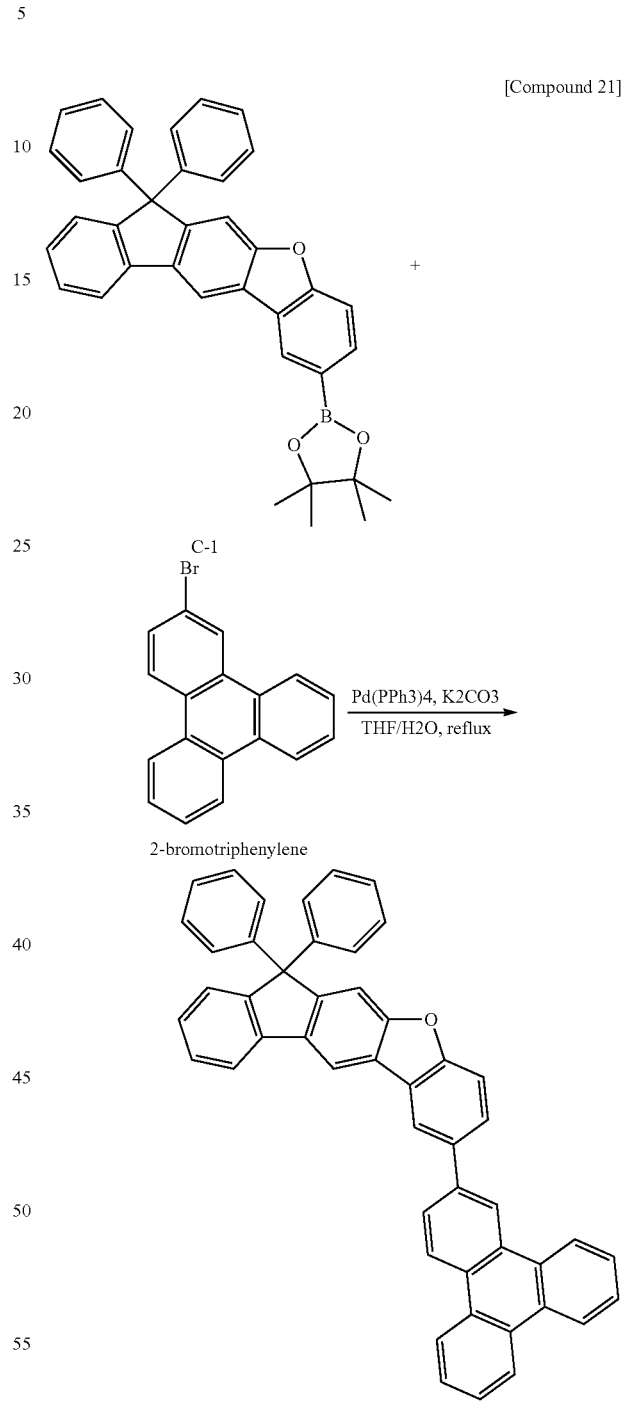

[Compound 21]

Compound C-1 (12.67 g, 24.72 mmol) and 2-bromotriphenylene (7.6 g, 22.47 mmol) were completely dissolved in 230 ml of tetrahydrofuran in a 500-ml round bottom flask under a nitrogen atmosphere, and then an aqueous 2 M potassium carbonate solution (160 ml) was added thereto, tetrakis-(triphenylphosphine)palladium (0.78 g, 0.67 mmol) was put thereinto, and then the resulting mixture was heated and stirred for 3 hours. The temperature was lowered to room temperature, the aqueous layer was removed, and the residue was dried over anhydrous magnesium sulfate, and then concentrated under reduced pressure, and recrystallized with 240 ml of tetrahydrofuran to prepare Compound 21 (10.78 g, yield: 67%).

MS[M+H]$^+$=635

PREPARATION EXAMPLE 22

Preparation of Compound 22

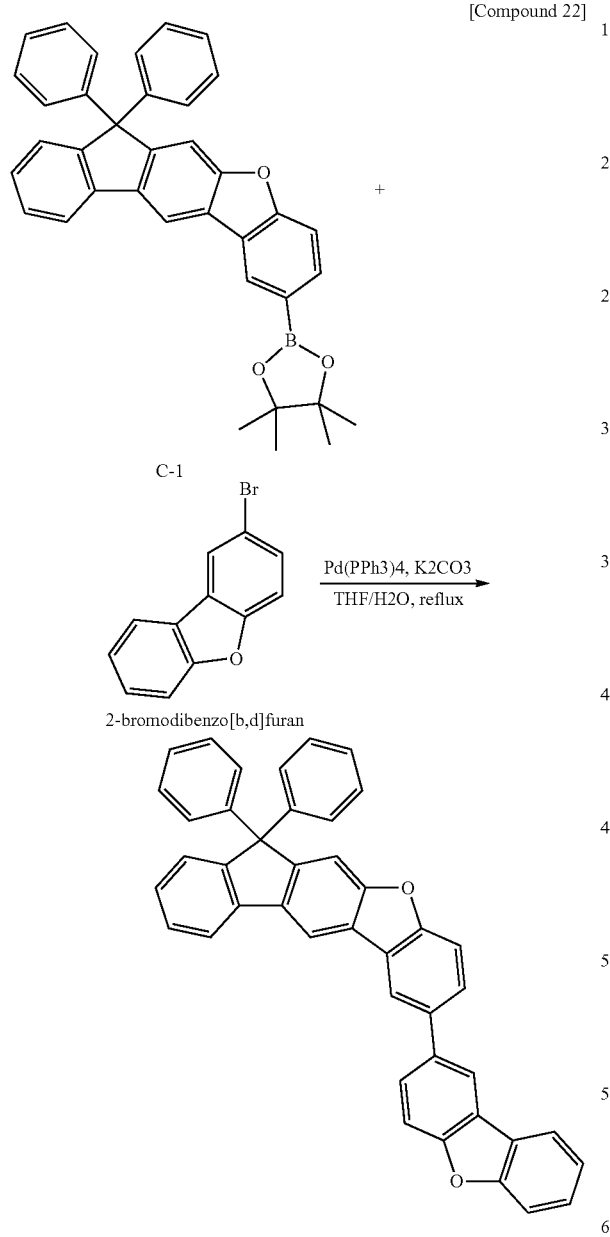

PREPARATION EXAMPLE 23

Preparation of Compound 23

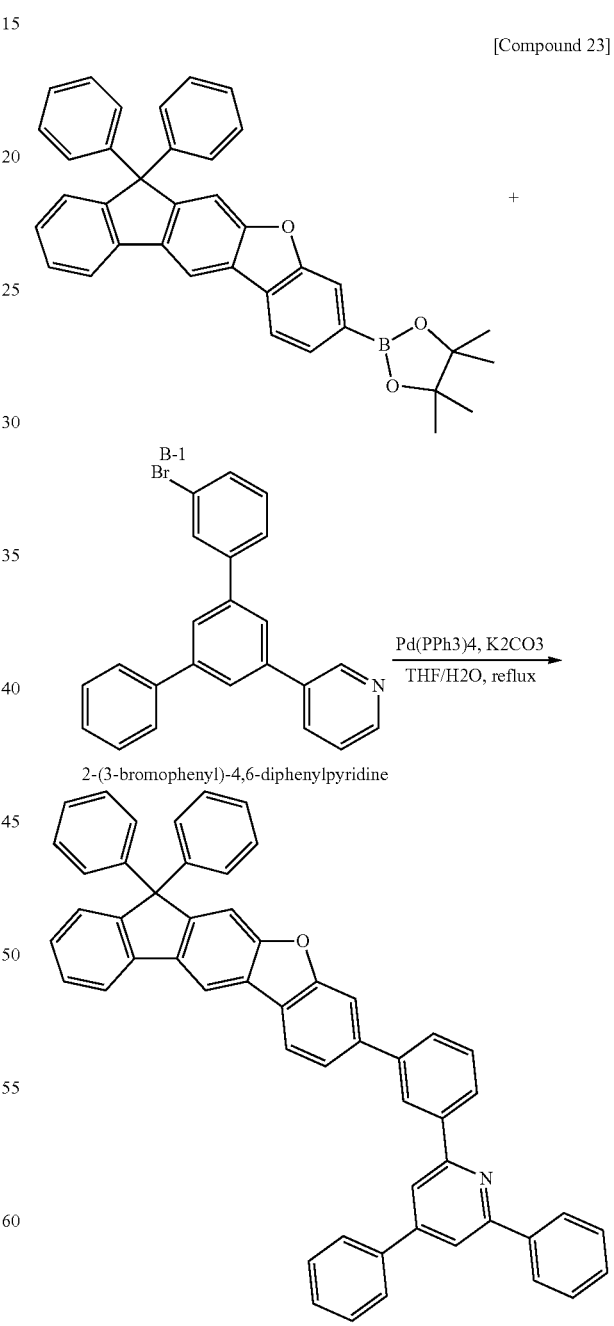

g, 0.67 mmol) was put thereinto, and then the resulting mixture was heated and stirred for 4 hours. The temperature was lowered to room temperature, the aqueous layer was removed, and the residue was dried over anhydrous magnesium sulfate, and then concentrated under reduced pressure, and recrystallized with 240 ml of tetrahydrofuran to prepare Compound 22 (11.05 g, yield: 64%).

MS[M+H]$^+$=575

Compound C-1 (13.50 g, 24.72 mmol) and 2-bromodibenzo[b,d]furan (8.0 g, 22.47 mmol) were completely dissolved in 260 ml of tetrahydrofuran in a 500-ml round bottom flask under a nitrogen atmosphere, and then an aqueous 2 M potassium carbonate solution (130 ml) was added thereto, tetrakis-(triphenylphosphine)palladium (0.78

Compound B-1 (17.52 g, 28.42 mmol) and 2-(3-bromophenyl)-4,6-diphenylpyridine (10 g, 25.84 mmol) were completely dissolved in 280 ml of tetrahydrofuran in a 500-ml round bottom flask under a nitrogen atmosphere, and then an aqueous 2 M potassium carbonate solution (140 ml) was added thereto, tetrakis-(triphenylphosphine)palladium (1.30 g, 1.12 mmol) was put thereinto, and then the resulting mixture was heated and stirred for 6 hours. The temperature was lowered to room temperature, the aqueous layer was removed, and the residue was dried over anhydrous magnesium sulfate, and then concentrated under reduced pressure, and recrystallized with 220 ml of tetrahydrofuran to prepare Compound 23 (13.74 g, yield: 66%).

MS[M+H]$^+$=714

PREPARATION EXAMPLE 24

Preparation of Compound 24

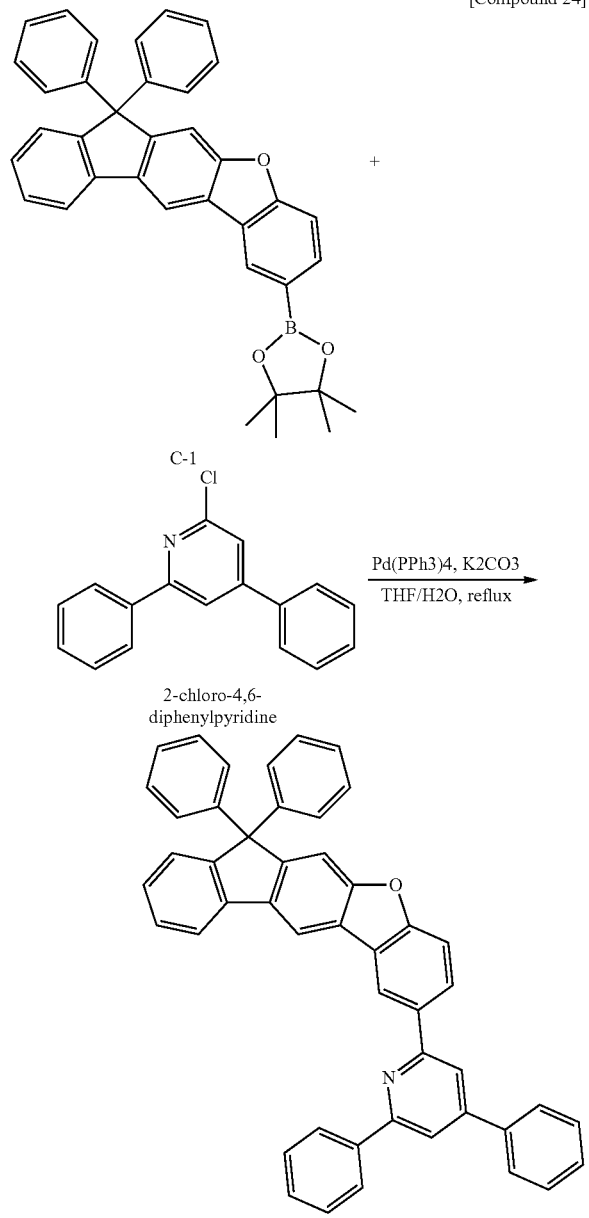

Compound C-1 (17.51 g, 32.07 mmol) and 2-chloro-4,6-diphenylpyridine (10 g, 29.15 mmol) were completely dissolved in 280 ml of tetrahydrofuran in a 500-ml round bottom flask under a nitrogen atmosphere, and then an aqueous 2 M potassium carbonate solution (140 ml) was added thereto, tetrakis-(triphenylphosphine)palladium (1.30 g, 1.12 mmol) was put thereinto, and then the resulting mixture was heated and stirred for 4 hours. The temperature was lowered to room temperature, the aqueous layer was removed, and the residue was dried over anhydrous magnesium sulfate, and then concentrated under reduced pressure, and recrystallized with 260 ml of tetrahydrofuran to prepare Compound 24 (15.47 g, yield: 67%).

MS[M+H]$^+$=638

EXPERIMENTAL EXAMPLE 1-1

A glass substrate on which a thin film of indium tin oxide (ITO) was coated to have a thickness of 1,000 Å was placed into distilled water in which a detergent was dissolved, and washed using ultrasonic waves. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine. Hexanitrile hexaazatriphenylene (HAT) of the following Chemical Formula was thermally vacuum deposited to have a thickness of 500 Å on the thus prepared ITO transparent electrode, thereby forming a hole injection layer.

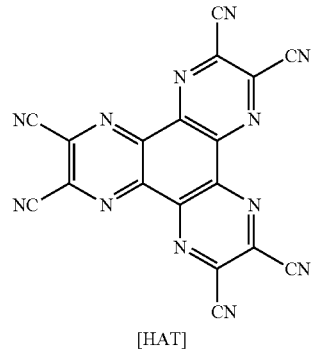

[HAT]

The following compound 4-4'-bis[N-(1-naphthyl)-N-phenylamino]biphenyl (NPB) (300 Å), which is a material for transporting holes, was vacuum deposited on the hole injection layer, thereby forming a hole transporting layer.

[NPB]

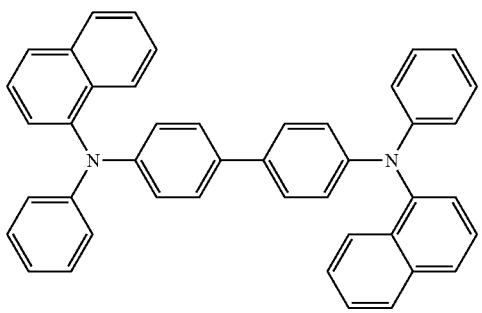

Subsequently, the following Compound 1 was vacuum deposited to have a film thickness of 100 Å on the hole transporting layer, thereby forming an electron blocking layer.

[Compound 1]

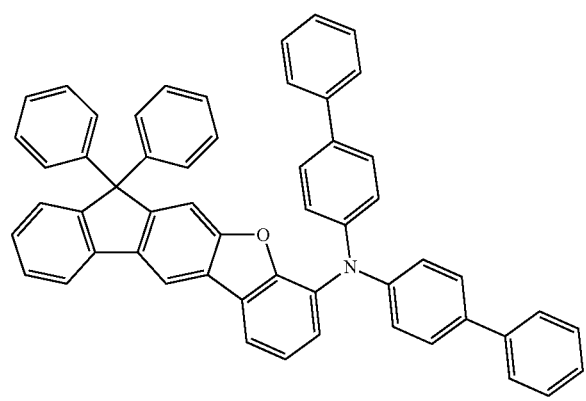

Subsequently, the following BH and BD were vacuum deposited at a weight ratio of 25:1 to have a film thickness of 300 Å on the electron blocking layer, thereby forming a light emitting layer.

[BH]

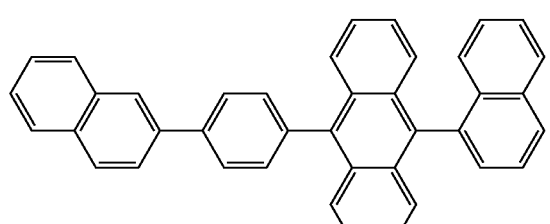

[BD]

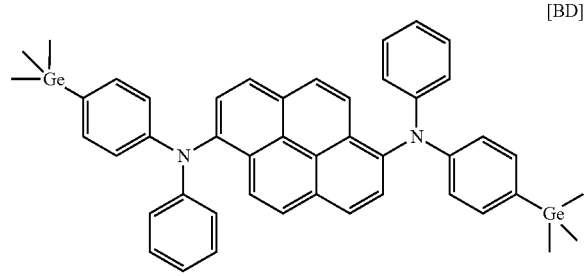

[ET1]

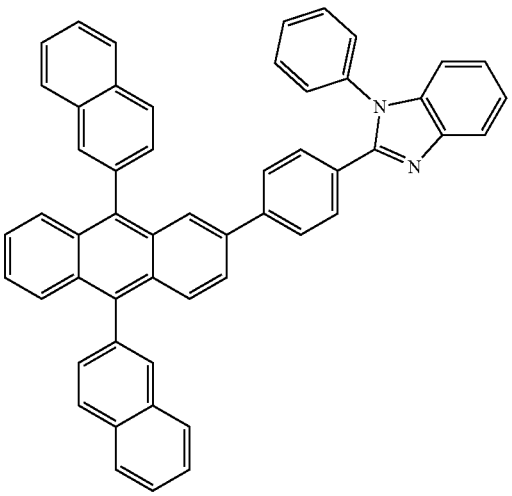

[LiQ]

Compound ET1 and Compound LiQ (lithium quinolate) were vacuum deposited at a weight ratio of 1:1 on the light emitting layer, thereby forming an electron injection and transporting layer having a thickness of 300 Å. Lithium fluoride (LiF) and aluminum were sequentially deposited on the electron injection and transporting layer to have a thickness of 12 Å and 2,000 Å, respectively, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2\times10^{-7}$ to $5\times10^{-6}$ torr, thereby manufacturing an organic light emitting device.

EXPERIMENTAL EXAMPLE 1-2

An organic light emitting device was manufactured in the same manner as in Experimental Example 1-1, except that as the electron blocking layer, Compound 2 was used instead of Compound 1 in Experimental Example 1-1.

EXPERIMENTAL EXAMPLE 1-3

An organic light emitting device was manufactured in the same manner as in Experimental Example 1-1, except that as the electron blocking layer, Compound 3 was used instead of Compound 1 in Experimental Example 1-1.

EXPERIMENTAL EXAMPLE 1-4

An organic light emitting device was manufactured in the same manner as in Experimental Example 1-1, except that as the electron blocking layer, Compound 4 was used instead of Compound 1 in Experimental Example 1-1.

EXPERIMENTAL EXAMPLE 1-5

An organic light emitting device was manufactured in the same manner as in Experimental Example 1-1, except that as the electron blocking layer, Compound 14 was used instead of Compound 1 in Experimental Example 1-1.

EXPERIMENTAL EXAMPLE 1-6

An organic light emitting device was manufactured in the same manner as in Experimental Example 1-1, except that as the electron blocking layer, Compound 15 was used instead of Compound 1 in Experimental Example 1-1.

EXPERIMENTAL EXAMPLE 1-7

An organic light emitting device was manufactured in the same manner as in Experimental Example 1-1, except that as the electron blocking layer, Compound 16 was used instead of Compound 1 in Experimental Example 1-1.

EXPERIMENTAL EXAMPLE 1-8

An organic light emitting device was manufactured in the same manner as in Experimental Example 1-1, except that as the electron blocking layer, Compound 17 was used instead of Compound 1 in Experimental Example 1-1.

EXPERIMENTAL EXAMPLE 1-9

An organic light emitting device was manufactured in the same manner as in Experimental Example 1-1, except that as the electron blocking layer, Compound 18 was used instead of Compound 1 in Experimental Example 1-1.

COMPARATIVE EXAMPLE 1-11

An organic light emitting device was manufactured in the same manner as in Experimental Example 1-1, except that as the electron blocking layer, a compound of the following EB1 was used instead of Compound 1 in Experimental Example 1-1.

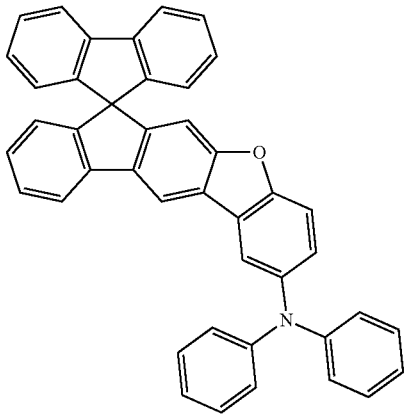

[EB1]

COMPARATIVE EXAMPLE 1-12

An organic light emitting device was manufactured in the same manner as in Experimental Example 1-1, except that as the electron blocking layer, a compound of the following EB2 was used instead of Compound 1 in Experimental Example 1-1.

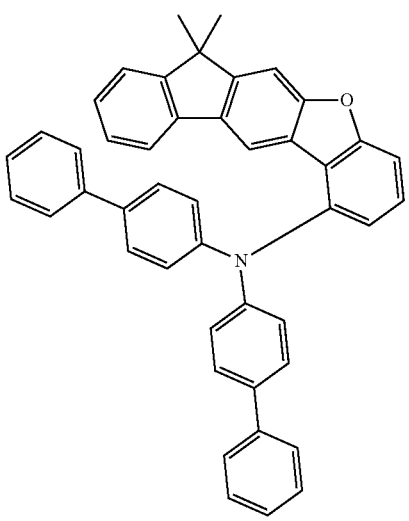

[EB2]

When current was applied to the organic light emitting devices manufactured in Experimental Examples 1-1 to 1-9 and Comparative Examples 1-11 and 1-12, the results of Table 1 were obtained.

TABLE 1

| | Compound (Electron blocking layer) | Voltage (V@10 mA/cm$^2$) | Efficiency (cd/A@10 mA/cm$^2$) | Color coordinate (x, y) |
|---|---|---|---|---|
| Experimental Example 1-1 | Compound 1 | 3.63 | 6.45 | (0.138, 0.127) |
| Experimental Example 1-2 | Compound 2 | 3.61 | 6.46 | (0.139, 0.127) |
| Experimental Example 1-3 | Compound 3 | 3.62 | 6.38 | (0.138, 0.126) |
| Experimental Example 1-4 | Compound 4 | 3.65 | 6.37 | (0.138, 0.127) |
| Experimental Example 1-5 | Compound 14 | 3.66 | 6.35 | (0.137, 0.126) |
| Experimental Example 1-6 | Compound 15 | 3.84 | 6.13 | (0.137, 0.126) |
| Experimental Example 1-7 | Compound 16 | 3.83 | 6.12 | (0.137, 0.127) |
| Experimental Example 1-8 | Compound 17 | 3.82 | 6.08 | (0.136, 0.126) |
| Experimental Example 1-9 | Compound 18 | 3.81 | 6.07 | (0.137, 0.126) |
| Comparative Example 1-11 | EB1 | 4.65 | 5.46 | (0.136, 0.127) |
| Comparative Example 1-12 | EB2 | 4.87 | 5.23 | (0.136, 0.127) |

As seen in Table 1, the organic light emitting device manufactured by using the hetero-cyclic compound represented by Chemical Formula 1 according to the present specification as the electron blocking layer exhibits excellent characteristics in terms of efficiency, driving voltage, and/or stability of the organic light emitting device.

The hetero-cyclic compound represented by Chemical Formula 1 according to the present specification exhibits lower voltage and higher efficiency characteristics than the organic light emitting devices manufactured by using the compounds in Comparative Examples 1-11 and 1-12, in which a ring is formed to have a structure similar to the core of Chemical Formula 1, as an electron blocking layer.

As in the result in Table 1, it could be confirmed that the hetero-cyclic compound represented by Chemical Formula 1 according to the present specification has an excellent electron blocking capability, and thus can be applied to an organic light emitting device.

EXPERIMENTAL EXAMPLES 2-1 TO 2-9

An experiment was performed in the same manner as in Experimental Example 1-1, except that the compounds in Experimental Examples 1-1 to 1-9 were used instead of NPB as the hole transporting layer, and the following compound TCTA was used instead of Compound 1 as the electron blocking layer.

[TCTA]

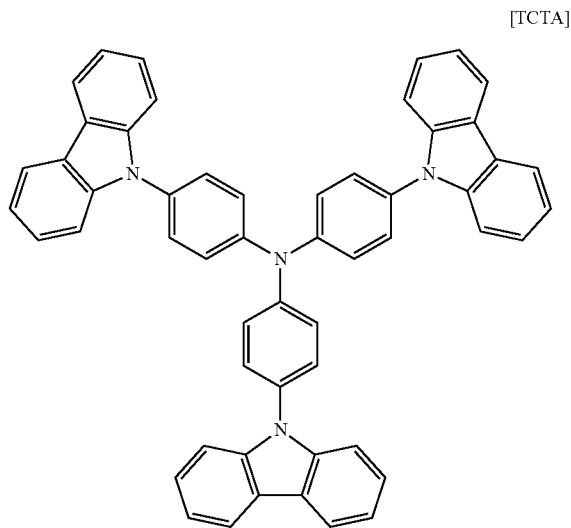 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1]

COMPARATIVE EXAMPLE 2-1

An organic light emitting device was manufactured in the same manner as in Experimental Example 2-1, except that a compound of the following HT 1 was used instead of Compound 1 in Experimental Example 2-1.

[HT 1]

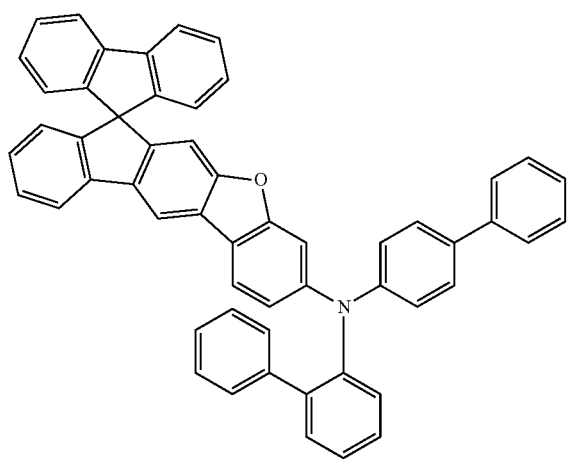

COMPARATIVE EXAMPLE 2-2

An organic light emitting device was manufactured in the same manner as in Experimental Example 2-1, except that a compound of the following HT 2 was used instead of Compound 1 in Experimental Example 2-1.

[HT 2]

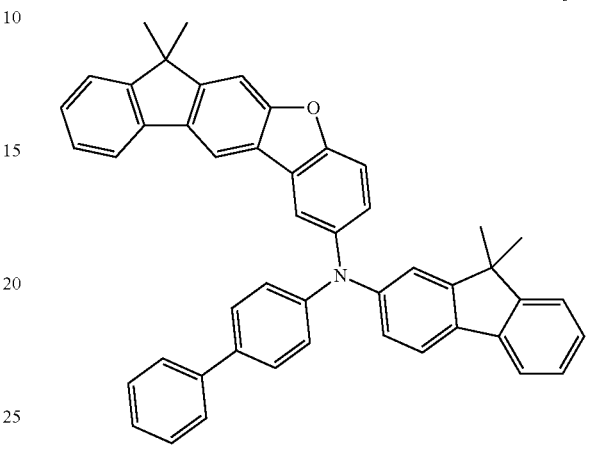

When current was applied to the organic light emitting devices manufactured in Experimental Examples 2-1 to 2-9 and Comparative Examples 2-1 and 2-2, the results of Table 2 were obtained.

TABLE 2

| | Compound (Hole transporting layer) | Voltage (V@10 mA/cm$^2$) | Efficiency (cd/A@10 mA/cm$^2$) | Color coordinate (x, y) |
|---|---|---|---|---|
| Experimental Example 2-1 | Compound 1 | 3.35 | 5.42 | (0.136, 0.126) |
| Experimental Example 2-2 | Compound 2 | 3.44 | 5.23 | (0.136, 0.126) |
| Experimental Example 2-3 | Compound 3 | 3.41 | 5.28 | (0.136, 0.127) |
| Experimental Example 2-4 | Compound 4 | 3.31 | 5.40 | (0.136, 0.126) |
| Experimental Example 2-5 | Compound 14 | 3.32 | 5.3/ | (0.136, 0.127) |
| Experimental Example 2-6 | Compound 15 | 3.44 | 5.22 | (0.136, 0.126) |
| Experimental Example 2-7 | Compound 16 | 3.54 | 5.1/ | (0.136, 0.127) |
| Experimental Example 2-8 | Compound 17 | 3.51 | 5.25 | (0.136, 0.126) |
| Experimental Example 2-9 | Compound 18 | 3.53 | 5.1* | (0.137, 0.126) |
| Comparative Example 2-11 | HT 1 | 4.11 | 4.53 | (0.136, 0.127) |
| Comparative Example 2-12 | HT 2 | 4.35 | 4.32 | (0.136, 0.127) |

As seen in Table 2, the organic light emitting device manufactured by using the hetero-cyclic compound represented by Chemical Formula 1 according to the present specification as a hole transporting layer exhibits better characteristics in terms of the efficiency, driving voltage, and/or stability of the organic light emitting device than the organic light emitting devices manufactured by using the compounds in Comparative Examples 2-11 and 2-12, in which a ring is formed to have a structure similar to Chemical Formula 1, as an electron transporting layer.

As in the result in Table 2, it could be confirmed that the compound according to the present invention has excellent hole transporting capability and thus can be applied to an organic light emitting device.

As in the results in Tables 1 and 2, it could be confirmed that the compound according to the present invention has not only an excellent electron blocking capability but also an excellent hole transporting capability and thus can be applied to an organic light emitting device.

COMPARATIVE EXAMPLE 3-11

The compounds prepared in the Preparation Examples were subjected to high-purity sublimation purification by a typically known method, and then a green organic light emitting device was manufactured by the following method.

A glass substrate on which a thin film of indium tin oxide (ITO) was coated to have a thickness of 1,000 Å was placed into distilled water in which a detergent was dissolved, and washed using ultrasonic waves. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

An organic EL device was manufactured by configuring the light emitting device in the order of m-MTDATA (60 nm)/TCTA (80 nm)/CBP+10% Ir(ppy)$_3$ (300 nm)/BCP (10 nm)/Alq$_3$ (30 nm)/LiF (1 nm)/Al (200 nm) on the thus prepared ITO transparent electrode by using CBP as a host.

The structures of m-MTDATA, TCTA, Ir(ppy)$_3$, CBP, and BCP are as follows.

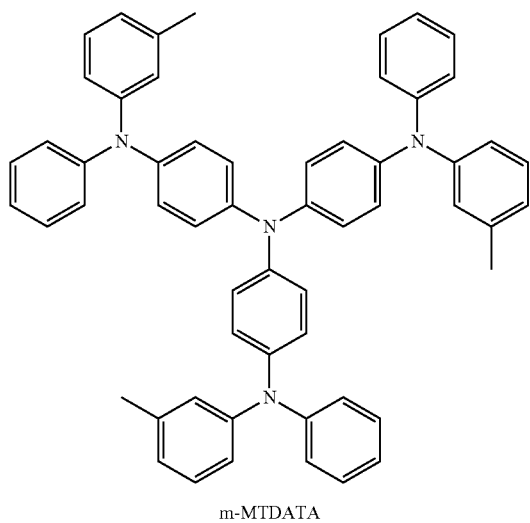

m-MTDATA

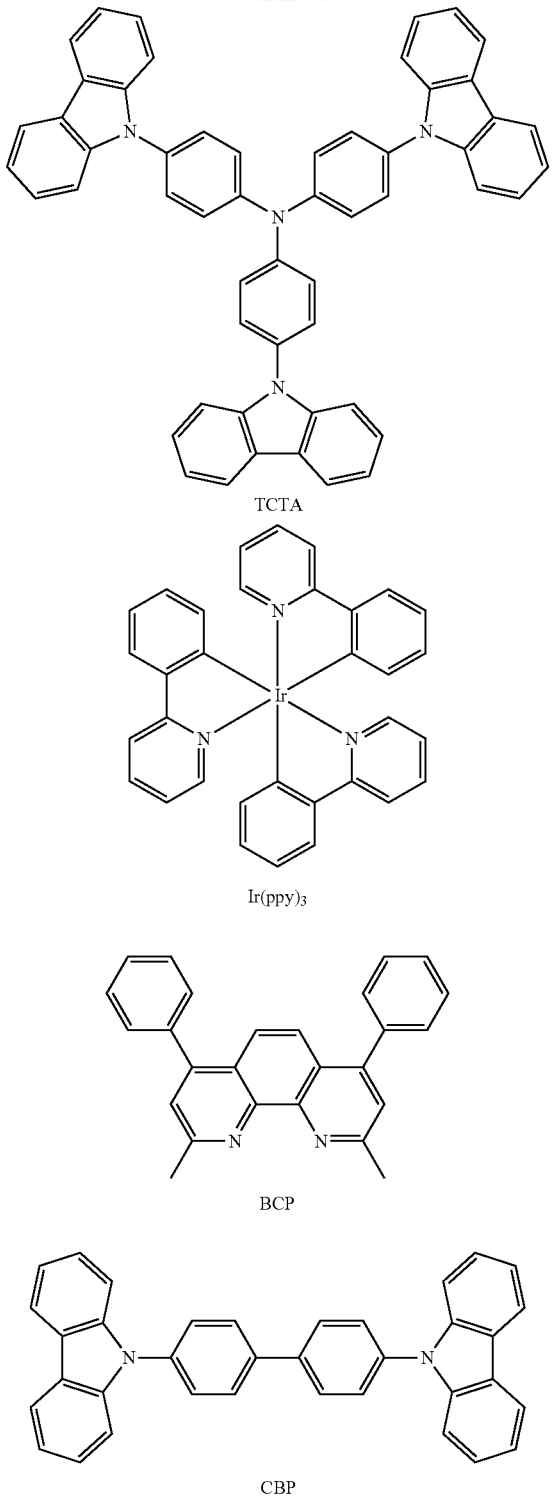

TCTA

Ir(ppy)$_3$

BCP

CBP

EXPERIMENTAL EXAMPLE 3-1

An organic light emitting device was manufactured in the same manner as in Comparative Example 3-11, except that Compound 7 was used instead of CBP in Comparative Example 3-11.

EXPERIMENTAL EXAMPLE 3-2

An organic light emitting device was manufactured in the same manner as in Comparative Example 3-11, except that Compound 8 was used instead of Compound CBP in Comparative Example 3-11.

EXPERIMENTAL EXAMPLE 3-3

An organic light emitting device was manufactured in the same manner as in Comparative Example 3-11, except that Compound 9 was used instead of Compound CBP in Comparative Example 3-11.

EXPERIMENTAL EXAMPLE 3-4

An organic light emitting device was manufactured in the same manner as in Comparative Example 3-11, except that Compound 10 was used instead of Compound CBP in Comparative Example 3-11.

EXPERIMENTAL EXAMPLE 3-5

An organic light emitting device was manufactured in the same manner as in Comparative Example 3-11, except that Compound 11 was used instead of Compound CBP in Comparative Example 3-11.

EXPERIMENTAL EXAMPLE 3-6

An organic light emitting device was manufactured in the same manner as in Comparative Example 3-11, except that Compound 13 was used instead of Compound CBP in Comparative Example 3-11.

EXPERIMENTAL EXAMPLE 3-7

An organic light emitting device was manufactured in the same manner as in Comparative Example 3-11, except that Compound 19 was used instead of Compound CBP in Comparative Example 3-11.

EXPERIMENTAL EXAMPLE 3-8

An organic light emitting device was manufactured in the same manner as in Comparative Example 3-11, except that Compound 23 was used instead of Compound CBP in Comparative Example 3-11.

EXPERIMENTAL EXAMPLE 3-9

An organic light emitting device was manufactured in the same manner as in Comparative Example 3-11, except that Compound 24 was used instead of Compound CBP in Comparative Example 3-11.

COMPARATIVE EXAMPLE 3-12

An organic light emitting device was manufactured in the same manner as in Comparative Example 3-11, except that a compound of the following GH 1 was used instead of Compound CBP in Comparative Example 3-11.

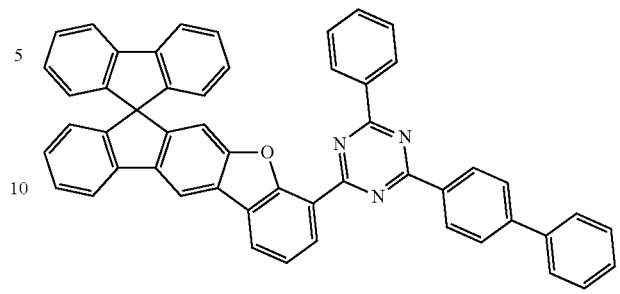

[GH 1]

COMPARATIVE EXAMPLE 3-13

An organic light emitting device was manufactured in the same manner as in Comparative Example 3-11, except that a compound of the following GH 2 was used instead of Compound CBP in Comparative Example 3-11.

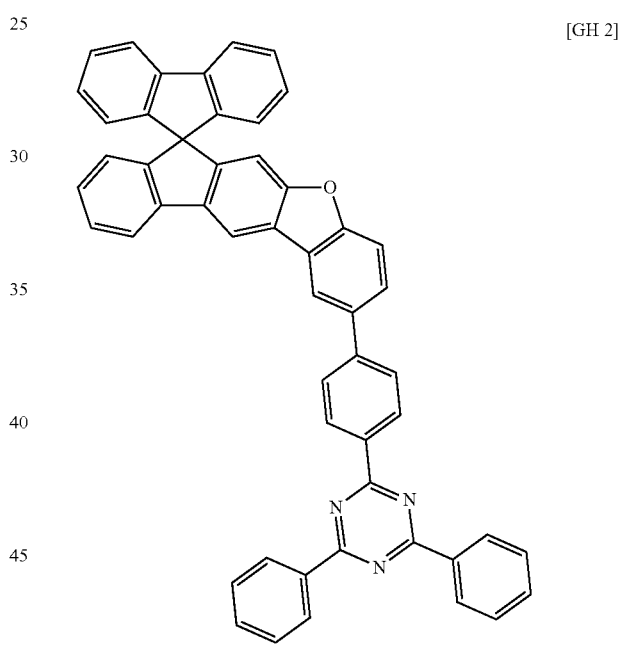

[GH 2]

When current was applied to the organic light emitting devices manufactured in Experimental Examples 3-1 to 3-9 and Comparative Examples 3-11 to 3-13, the results of Table 3 were obtained.

TABLE 3

| | Compound (Host) | Voltage (V@10 mA/cm$^2$) | Efficiency (cd/A@10 mA/cm$^2$) | EL peak (nm) |
|---|---|---|---|---|
| Comparative Example 3-11 | CBP | 7.62 | 35.32 | 516 |
| Experimental Example 3-1 | Compound 7 | 6.60 | 44.93 | 517 |
| Experimental Example 3-2 | Compound 8 | 6.56 | 45.24 | 516 |
| Experimental Example 3-3 | Compound 9 | 6.61 | 44.72 | 517 |

TABLE 3-continued

| | Compound (Host) | Voltage (V@10 mA/cm$^2$) | Efficiency (cd/A@10 mA/cm$^2$) | EL peak (nm) |
|---|---|---|---|---|
| Experimental Example 3-4 | Compound 10 | 6.59 | 44.75 | 518 |
| Experimental Example 3-5 | Compound 11 | 6.68 | 44.41 | 517 |
| Experimental Example 3-6 | Compound 13 | 6.53 | 44.63 | 517 |
| Experimental Example 3-7 | Compound 19 | 6.57 | 44.60 | 517 |
| Experimental Example 3-8 | Compound 23 | 6.72 | 44.31 | 516 |
| Experimental Example 3-9 | Compound 24 | 6.60 | 44.55 | 517 |
| Comparative Example 3-12 | GH 1 | 7.25 | 38.52 | 517 |
| Comparative Example 3-13 | GH 2 | 7.36 | 38.41 | 516 |

As seen in Table 3, it could be confirmed that the green organic light emitting devices in Experimental Examples 3-1 to 3-9, in which the hetero-cyclic compound represented by Chemical Formula 1 according to the present specification was used as a host material of a light emitting layer, exhibited better performances in terms of current efficiency and driving voltage than the organic light emitting devices manufactured by using the compounds in Comparative Example 3-11, in which CBP in the related art was used, and Comparative Examples 3-12 and 3-13, in which a ring was formed to have a structure similar to the core of Chemical Formula 1, as a host material. It can be seen that the compounds having triazine, pyrimidine, or pyridine as the substituent are suitable for a green organic light emitting device.

EXPERIMENTAL EXAMPLES 4-1 AND 4-2

The compounds prepared in the Preparation Examples were subjected to high-purity sublimation purification by a typically known method, and then red organic light emitting devices were manufactured by the following method.

An ITO glass was patterned and then washed, such that the light emitting area of the ITO glass became 2 mm×2 mm. The substrate was mounted on a vacuum chamber, and then the base pressure was allowed to be 1×10$^{-6}$ torr, and then for the organic material, DNTPD (700 Å), α-NPB (300 Å), and Compound 12 or Compound 19 prepared by the present invention were used as a host (90 wt %) on the ITO, the following (piq)$_2$Ir(acac) (10 wt %) was co-deposited (300 Å) as a dopant, films were formed in the order of Alq$_3$ (350 Å), LiF (5 Å), and Al (1,000 Å), and measurements were made at 0.4 mA.

The structures of DNTPD, α-NPB, (piq)$_2$Ir(acac), and Alq$_3$ are as follows.

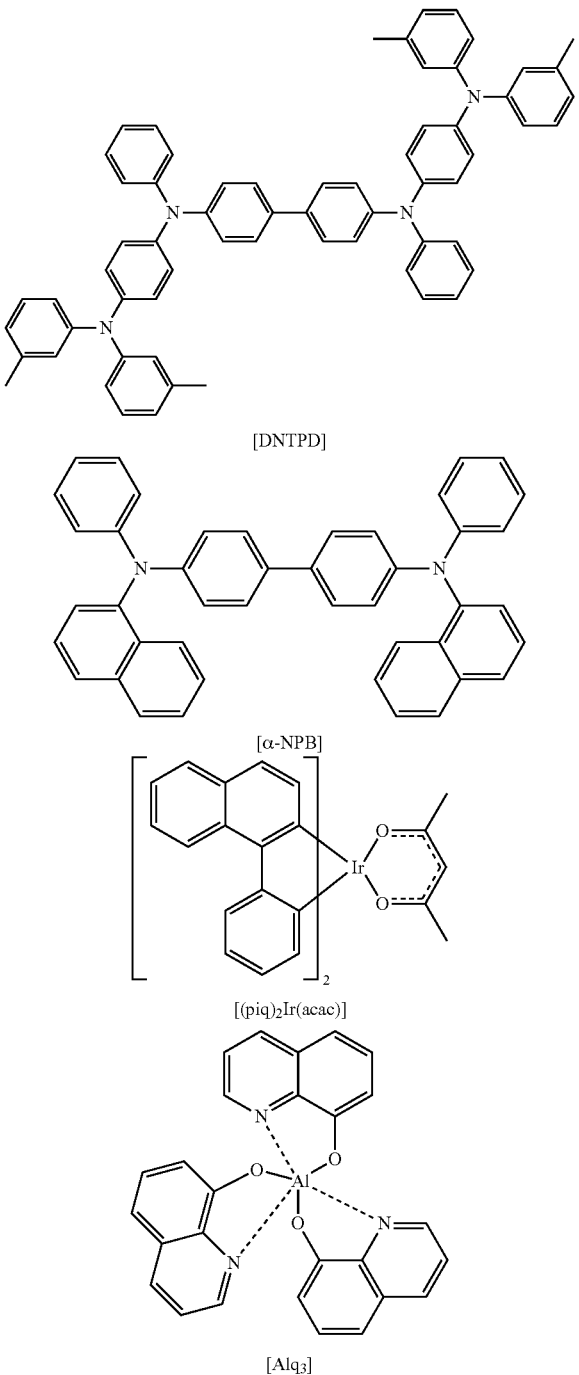

[DNTPD]

[α-NPB]

[(piq)$_2$Ir(acac)]

[Alq$_3$]

COMPARATIVE EXAMPLE 4-11

An organic light emitting device was manufactured in the same manner as in Experimental Example 4-1, except that as a host of the light emitting layer, CBP was used instead of Compound 12 in Experimental Example 4-1.

For the organic light emitting devices manufactured according to Experimental Examples 4-1 and 4-2 and Comparative Example 4-11, the voltages, current densities, luminances, color coordinates, and service lives were measured, and the results are shown in the following Table 4. T95 means the time taken for the luminance to be reduced to 95% of the initial luminance (5,000 nit).

TABLE 4

| Classification | Host | Dopant | Voltage | Luminance (cd/m$^2$) | CIE$x$ | CIE$y$ | T95 (hr) |
|---|---|---|---|---|---|---|---|
| Experimental Example 4-1 | Compound 12 | [(piq)$_2$Ir(acac)] | 4.4 | 1860 | 0.673 | 0.326 | 465 |
| Experimental Example 4-2 | Compound 19 | [(piq)$_2$Ir(acac)] | 4.2 | 1950 | 0.674 | 0.325 | 445 |
| Comparative Example 4-11 | CBP | [(piq)$_2$Ir(acac)] | 5.7 | 1420 | 0.670 | 0.331 | 280 |

As seen in Table 4, it could be confirmed that the red organic light emitting devices in Experimental Examples 4-1 and 4-2 in which the hetero-cyclic compound represented by Chemical Formula 1 according to the present specification was used as a host material of the light emitting layer exhibited better performances in terms of current efficiency, driving voltage, and service life than the red organic light emitting device in Comparative Example 4-11 in which CBP in the related art was used. It can be seen that the compounds having triazine and quinazoline as the substituent are suitable for a red organic light emitting device.

EXPERIMENTAL EXAMPLE 5-1

An organic light emitting device was manufactured in the same manner as in Experimental Example 1-1, except that Compound 7 was used instead of ET1 as the electron transporting layer, and the following compound TCTA was used instead of Compound 1 as the electron blocking layer in Experimental Example 1-1.

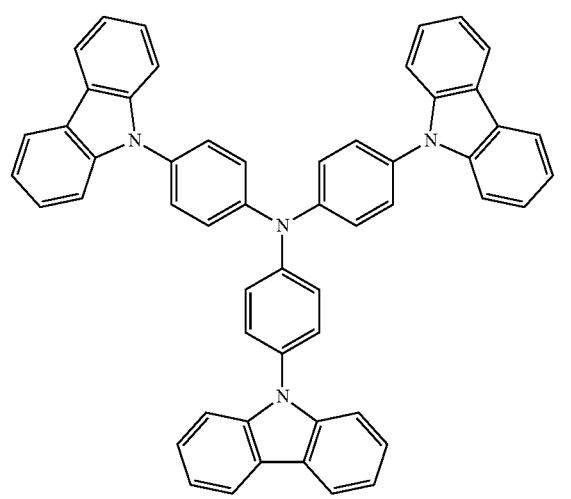

[TCTA]

EXPERIMENTAL EXAMPLE 5-2

An organic light emitting device was manufactured in the same manner as in Experimental Example 5-1, except that as the electron transporting layer, Compound 8 was used instead of Compound 7 in Experimental Example 5-1.

EXPERIMENTAL EXAMPLE 5-3

An organic light emitting device was manufactured in the same manner as in Experimental Example 5-1, except that as the electron transporting layer, Compound 9 was used instead of Compound 7 in Experimental Example 5-1.

EXPERIMENTAL EXAMPLE 5-4

An organic light emitting device was manufactured in the same manner as in Experimental Example 5-1, except that as the electron transporting layer, Compound 10 was used instead of Compound 7 in Experimental Example 5-1.

EXPERIMENTAL EXAMPLE 5-5

An organic light emitting device was manufactured in the same manner as in Experimental Example 5-1, except that as the electron transporting layer, Compound 11 was used instead of Compound 7 in Experimental Example 5-1.

EXPERIMENTAL EXAMPLE 5-6

An organic light emitting device was manufactured in the same manner as in Experimental Example 5-1, except that as the electron transporting layer, Compound 13 was used instead of Compound 7 in Experimental Example 5-1.

EXPERIMENTAL EXAMPLE 5-7

An organic light emitting device was manufactured in the same manner as in Experimental Example 5-1, except that as the electron transporting layer, Compound 19 was used instead of Compound 7 in Experimental Example 5-1.

EXPERIMENTAL EXAMPLE 5-8

An organic light emitting device was manufactured in the same manner as in Experimental Example 5-1, except that as the electron transporting layer, Compound 20 was used instead of Compound 7 in Experimental Example 5-1.

COMPARATIVE EXAMPLE 5-11

An organic light emitting device was manufactured in the same manner as in Experimental Example 5-1, except that as the electron transporting layer, a compound of the following ET2 was used instead of Compound 7 in Experimental Example 5-1.

[ET2]

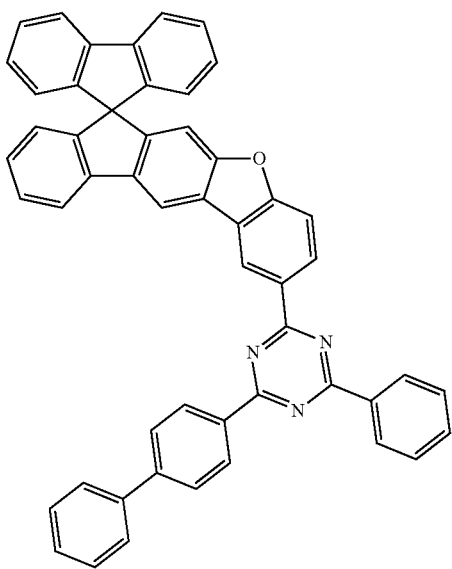

COMPARATIVE EXAMPLE 5-12

An organic light emitting device was manufactured in the same manner as in Experimental Example 5-1, except that as the electron transporting layer, a compound of the following ET3 was used instead of Compound 7 in Experimental Example 5-1.

[ET3]

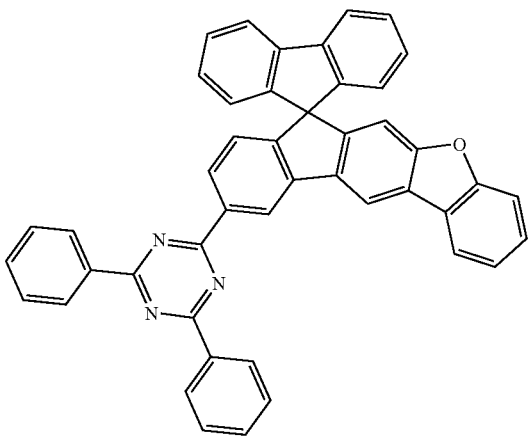

For the organic light emitting devices manufactured according to Experimental Examples 5-1 to 5-8 and Comparative Examples 5-11 and 5-12, the voltages, current densities, luminances, color coordinates, and service lives were measured, and the results are shown in the following Table 5.

TABLE 5

| | Compound | Voltage (V@10 mA/cm$^2$) | Efficiency (cd/A@10 mA/cm$^2$) | Color coordinate (x, y) |
|---|---|---|---|---|
| Experimental Example 5-1 | Compound 7 | 3.98 | 4.91 | (0.138, 0.127) |
| Experimental Example 5-2 | Compound 8 | 3.75 | 5.15 | (0.139, 0.122) |

TABLE 5-continued

| | Compound | Voltage (V@10 mA/cm$^2$) | Efficiency (cd/A@10 mA/cm$^2$) | Color coordinate (x, y) |
|---|---|---|---|---|
| Experimental Example 5-3 | Compound 9 | 3.86 | 5.04 | (0.138, 0.126) |
| Experimental Example 5-4 | Compound 10 | 3.85 | 4.92 | (0.138, 0.127) |
| Experimental Example 5-5 | Compound 11 | 3.89 | 4.65 | (0.137, 0.129) |
| Experimental Example 5-6 | Compound 13 | 3.95 | 4.64 | (0.138, 0.128) |
| Experimental Example 5-7 | Compound 19 | 3.90 | 4.62 | (0.138, 0.129) |
| Experimental Example 5-8 | Compound 20 | 3.96 | 4.55 | (0.136, 0.128) |
| Comparative Example 5-11 | ET2 | 4.22 | 3.95 | (0.136, 0.130) |
| Comparative Example 5-12 | ET3 | 4.43 | 3.87 | (0.136, 0.128) |

As a result of the experiment, it could be confirmed that the organic light emitting devices in Experimental Examples 5-1 to 5-8 in which the hetero-cyclic compound represented by Chemical Formula 1 according to the present specification was used as the electron transporting layer exhibited better performances in terms of current efficiency and driving voltage than the organic light emitting devices in Comparative Examples 5-11 and 5-12.

Although the preferred exemplary embodiments (an electron blocking layer, a hole transporting layer, a green light emitting layer, a red light emitting layer, and an electron transporting layer) of the present invention have been described above, the present invention is not limited thereto, and various modifications can be made and carried out within the scope of the claims and the detailed description of the invention, and also fall within the scope of the invention.

EXPERIMENTAL EXAMPLE 6-1

A glass substrate on which a thin film of indium tin oxide (ITO) was coated to have a thickness of 1,000 Å was placed into distilled water in which a detergent was dissolved, and washed using ultrasonic waves. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

Hexanitrile hexaazatriphenylene (HAT) of the following Chemical Formula was thermally vacuum deposited to have a thickness of 100 Å on the thus prepared ITO transparent electrode, thereby forming a hole injection layer.

[HAT]

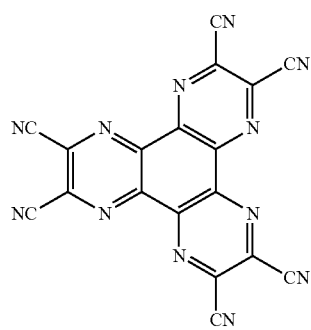

The following compound N-([1,1'-biphenyl]-4-yl)-9,9-dimethyl-N-(4-(9-phenyl-9H-carbazol-3-yl)phenyl)-9H-fluoren-2-amine [HT1] (1,100 Å), which is a material for transporting holes, was vacuum deposited on the hole injection layer, thereby forming a hole transporting layer.

[HT1]

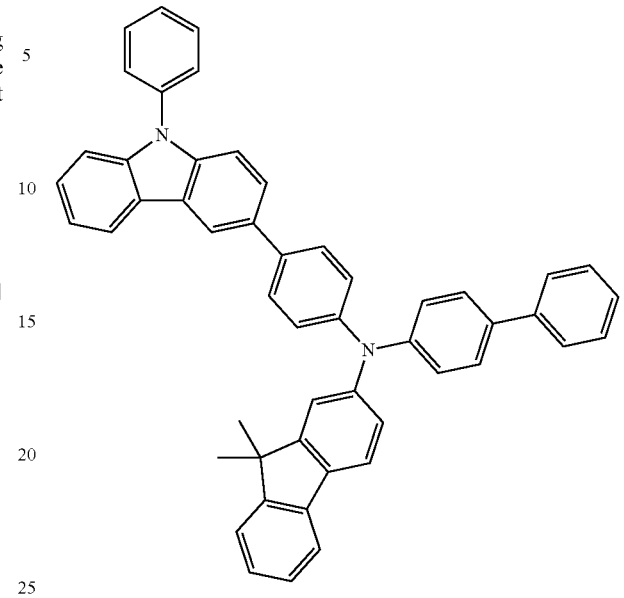

Subsequently, the following Compound 1 was vacuum deposited to have a film thickness of 150 Å on the hole transporting layer, thereby forming an electron blocking layer.

Subsequently, the following BH and BD were vacuum deposited at a weight ratio of 25:1 to have a film thickness of 300 Å on the electron blocking layer, thereby forming a light emitting layer.

[BH]

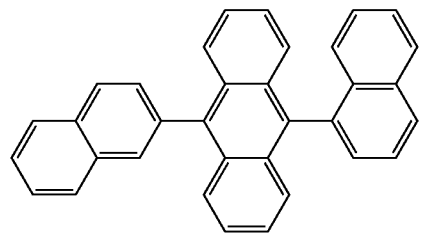

[BD]

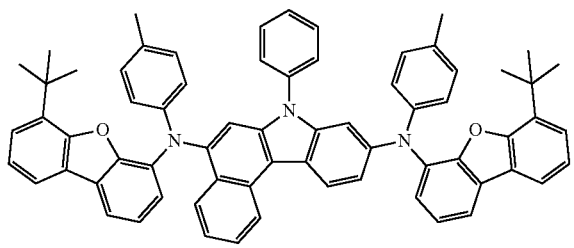

[ET1]

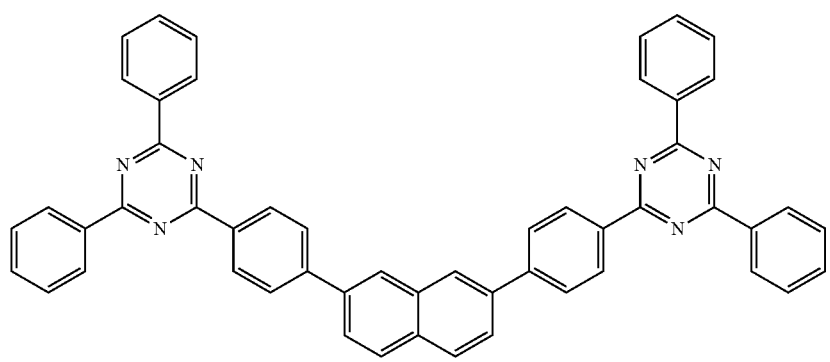

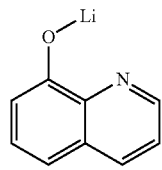
[LiQ]

Compound ET1 and Compound LiQ (lithium quinolate) were vacuum deposited at a weight ratio of 1:1 on the light emitting layer, thereby forming an electron injection and transporting layer having a thickness of 300 Å. Lithium fluoride (LiF) and aluminum were sequentially deposited on the electron injection and transporting layer to have a thickness of 12 Å and 2,000 Å, respectively, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

EXPERIMENTAL EXAMPLE 6-2

An organic light emitting device was manufactured in the same manner as in Experimental Example 6-1, except that Compound 2 was used instead of Compound 1 in Experimental Example 6-1.

EXPERIMENTAL EXAMPLE 6-3

An organic light emitting device was manufactured in the same manner as in Experimental Example 6-1, except that Compound 3 was used instead of Compound 1 in Experimental Example 6-1.

EXPERIMENTAL EXAMPLE 6-4

An organic light emitting device was manufactured in the same manner as in Experimental Example 6-1, except that Compound 4 was used instead of Compound 1 in Experimental Example 6-1.

EXPERIMENTAL EXAMPLE 6-5

An organic light emitting device was manufactured in the same manner as in Experimental Example 6-1, except that Compound 14 was used instead of Compound 1 in Experimental Example 6-1.

EXPERIMENTAL EXAMPLE 6-6

An organic light emitting device was manufactured in the same manner as in Experimental Example 6-1, except that Compound 15 was used instead of Compound 1 in Experimental Example 6-1.

EXPERIMENTAL EXAMPLE 6-7

An organic light emitting device was manufactured in the same manner as in Experimental Example 6-1, except that Compound 16 was used instead of Compound 1 in Experimental Example 6-1.

EXPERIMENTAL EXAMPLE 6-8

An organic light emitting device was manufactured in the same manner as in Experimental Example 6-1, except that Compound 17 was used instead of Compound 1 in Experimental Example 6-1.

EXPERIMENTAL EXAMPLE 6-9

An organic light emitting device was manufactured in the same manner as in Experimental Example 6-1, except that Compound 18 was used instead of Compound 1 in Experimental Example 6-1.

COMPARATIVE EXAMPLE 6-11

An organic light emitting device was manufactured in the same manner as in Experimental Example 6-1, except that a compound of the following EB2 was used instead of Compound 1 in Experimental Example 6-1.

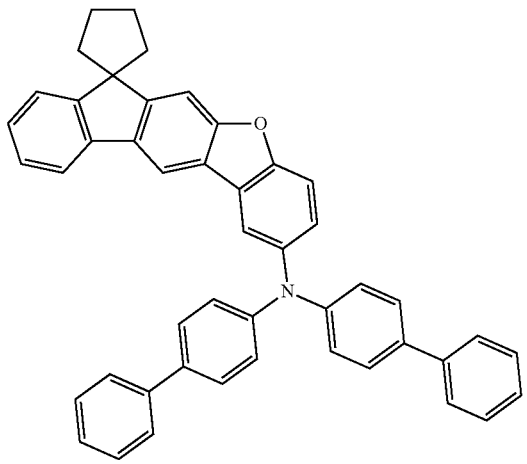
[EB2]

COMPARATIVE EXAMPLE 6-12

An organic light emitting device was manufactured in the same manner as in Experimental Example 6-1, except that a compound of the following EB3 was used instead of Compound 1 in Experimental Example 6-1.

[EB3]

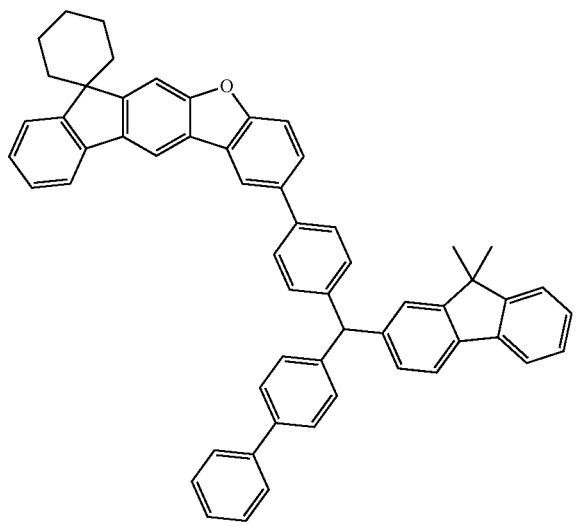

COMPARATIVE EXAMPLE 6-13

An organic light emitting device was manufactured in the same manner as in Experimental Example 6-1, except that a compound of the following EB1 was used instead of Compound 1 in Experimental Example 6-1.

[EB1]

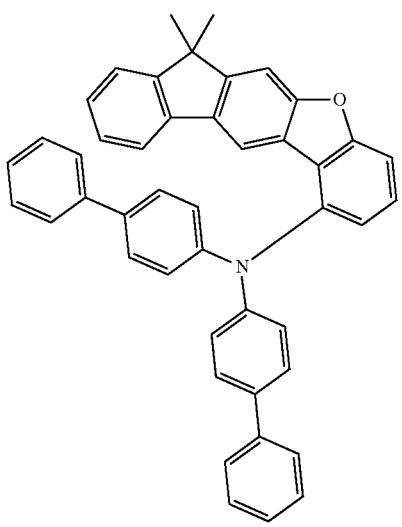

COMPARATIVE EXAMPLE 6-14

An organic light emitting device was manufactured in the same manner as in Experimental Example 6-1, except that a compound of the following EB4 was used instead of Compound 1 in Experimental Example 6-1.

[EB4]

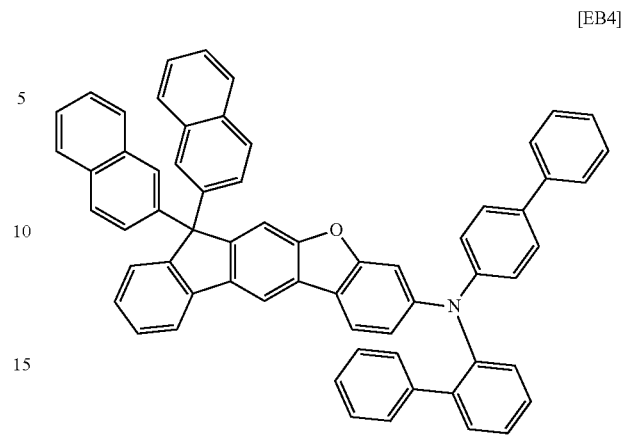

When current was applied to the organic light emitting devices manufactured in Experimental Examples 6-1 to 6-9 and Comparative Examples 6-11 to 6-14, the voltages, efficiencies, color coordinates, and service lives were measured, and the results are shown in the following [Table 6]. T90 means the time taken for the luminance to be reduced to 90% of the initial luminance (1,300 nit).

TABLE 6

| | Compound (Electron blocking layer) | Voltage (V@ 10 mA/ cm$^2$) | Efficiency (cd/A@10 mA/cm$^2$) | Color coordinate (x, y) | T90 (hr) |
|---|---|---|---|---|---|
| Experimental Example 6-1 | Compound 1 | 3.40 | 6.60 | (0.141, 0.053) | 165 |
| Experimental Example 6-2 | Compound 2 | 3.42 | 6.63 | (0.142, 0.051) | 155 |
| Experimental Example 6-3 | Compound 3 | 3.43 | 6.51 | (0.140, 0.050) | 160 |
| Experimental Example 6-4 | Compound 4 | 3.41 | 6.55 | (0.140, 0.050) | 155 |
| Experimental Example 6-5 | Compound 14 | 3.46 | 6.56 | (0.141, 0.051) | 150 |
| Experimental Example 6-6 | Compound 15 | 3.69 | 6.34 | (0.140, 0.052) | 150 |
| Experimental Example 6-7 | Compound 16 | 3.67 | 6.39 | (0.142, 0.052) | 155 |
| Experimental Example 6-8 | Compound 17 | 3.68 | 6.28 | (0.143, 0.050) | 165 |
| Experimental Example 6-9 | Compound 18 | 3.64 | 6.25 | (0.140, 0.055) | 175 |
| Comparative Example 6-11 | EB2 | 4.25 | 4.82 | (0.145, 0.051) | 50 |
| Comparative Example 6-12 | EB3 | 4.11 | 4.95 | (0.144, 0.048) | 65 |
| Comparative Example 6-13 | EB1 | 3.86 | 5.67 | (0.144, 0.053) | 110 |
| Comparative Example 6-14 | EB4 | 3.96 | 5.85 | (0.144, 0.045) | 125 |

As seen in Table 6, the organic light emitting device manufactured by using the compound of the present invention as an electron blocking layer exhibits excellent characteristics in terms of the efficiency, driving voltage, and/or stability of the organic light emitting device.

The organic light emitting device exhibits higher voltage and higher efficiency characteristics than the organic light emitting devices manufactured by using the compounds in Comparative Examples 6-11 to 6-14, in which a ring is formed to have a structure different from the core of the present invention, as an electron blocking layer. Further, the organic light emitting device exhibits a result that the service life is increased by 10 to 50% or more.

In the case of Comparative Example 6-13, since the structure of the core is a methyl group, it is determined that the stability of the core itself deteriorates as compared to the compound of the present invention, to which an aryl group (phenyl) is linked.

Even in the case of Comparative Examples 6-11 and 6-12, the stability of cycloalkyl itself significantly deteriorates as compared to an OLED material which is composed of most of the aromatic compounds in the organic light emitting device. Furthermore, the material is highly likely to be broken during the sublimation purification process.

In the case of Comparative Example 6-14, there was obtained a result that the structure of the core was naphthalene, and the efficiency was decreased because a T1 value of naphthalene was relatively decreased as compared to that of phenyl. Typically, a material used for an electron blocking layer attached to a light emitting layer has a T1 value of 2.5 eV or more. For example, a material such as carbazole, phenyl, triphenylene, and dibenzofuran is used. In addition, when the T1 value is low, excitons produced from a light emitting layer are transferred, and as a result, the service life is affected.

As in the result in Table 6, it could be confirmed that the compound according to the present invention has an excellent hole blocking capability and thus can be applied to an organic light emitting device.

EXPERIMENTAL EXAMPLES 7-1 TO 7-11

An experiment was performed in the same manner as in Experimental Example 6-1, except that the compounds, Compound 21, and Compound 22 used as the electron blocking layer in Experimental Examples 6-1 to 6-9 were used instead of HT1 as the hole transporting layer, and the following Compound EB1 was used as the electron blocking layer in Experimental Example 6-1.

[EB1]

COMPARATIVE EXAMPLE 7-21

An organic light emitting device was manufactured in the same manner as in Experimental Example 7-1, except that a compound of the following HT 2 was used instead of Compound 1 in Experimental Example 7-1.

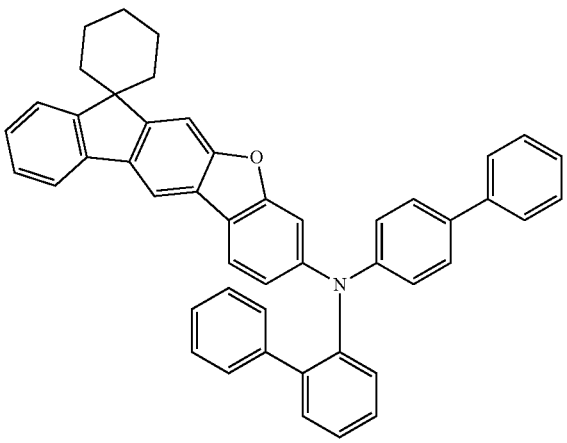

[HT2]

COMPARATIVE EXAMPLE 7-22

An organic light emitting device was manufactured in the same manner as in Experimental Example 7-1, except that a compound of the following HT 1 was used instead of Compound 1 in Experimental Example 7-1.

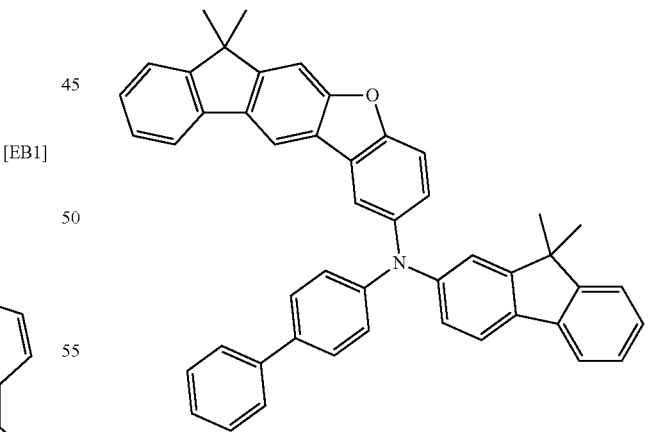

[HT 1]

COMPARATIVE EXAMPLE 7-23

An organic light emitting device was manufactured in the same manner as in Experimental Example 7-1, except that a compound of the following HT 3 was used instead of Compound 1 in Experimental Example 7-1.

[HT3]

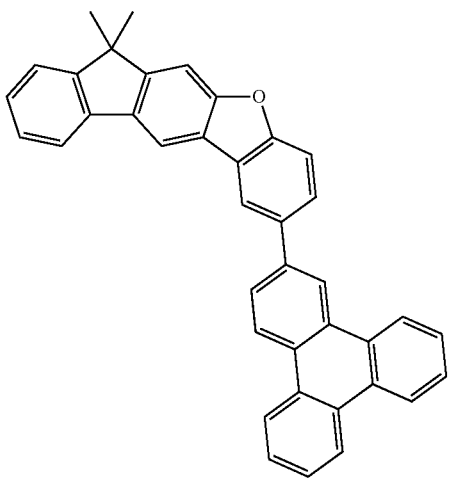

COMPARATIVE EXAMPLE 7-24

An organic light emitting device was manufactured in the same manner as in Experimental Example 7-1, except that a compound of the following HT 4 was used instead of Compound 1 in Experimental Example 7-1.

[HT4]

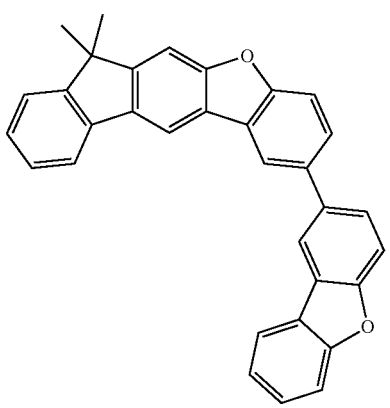

When current was applied to the organic light emitting devices manufactured in Experimental Examples 7-1 to 7-11 and Comparative Examples 7-21 to 7-24, the voltages, efficiencies, color coordinates, and service lives were measured, and the results are shown in the following [Table 7]. T95 means the time taken for the luminance to be reduced to 95% of the initial luminance (1,300 nit).

TABLE 7

|  | Compound (Hole transporting layer) | Voltage (V@ 10 Ma/ cm$^2$) | Efficiency (cd/A@10 mA/cm$^2$) | Color coordinate (x, y) | T95 (hr) |
| --- | --- | --- | --- | --- | --- |
| Experimental Example 7-1 | Compound 1 | 3.41 | 6.21 | (0.141, 0.053) | 190 |
| Experimental Example 7-2 | Compound 2 | 3.45 | 6.25 | (0.142, 0.051) | 185 |
| Experimental Example 7-3 | Compound 3 | 3.44 | 6.14 | (0.140, 0.050) | 190 |

TABLE 7-continued

|  | Compound (Hole transporting layer) | Voltage (V@ 10 Ma/ cm$^2$) | Efficiency (cd/A@10 mA/cm$^2$) | Color coordinate (x, y) | T95 (hr) |
| --- | --- | --- | --- | --- | --- |
| Experimental Example 7-4 | Compound 4 | 3.41 | 6.10 | (0.140, 0.050) | 185 |
| Experimental Example 7-5 | Compound 14 | 3.48 | 6.16 | (0.141, 0.051) | 185 |
| Experimental Example 7-6 | Compound 15 | 3.67 | 5.94 | (0.140, 0.052) | 180 |
| Experimental Example 7-7 | Compound 16 | 3.69 | 5.98 | (0.142, 0.052) | 185 |
| Experimental Example 7-8 | Compound 17 | 3.65 | 5.88 | (0.143, 0.050) | 195 |
| Experimental Example 7-9 | Compound 18 | 3.64 | 5.84 | (0.140, 0.055) | 200 |
| Experimental Example 7-10 | Compound 21 | 3.82 | 5.48 | (0.143, 0.050) | 155 |
| Experimental Example 7-11 | Compound 22 | 3.81 | 5.44 | (0.140, 0.055) | 160 |
| Comparative Example 7-21 | HT 2 | 4.28 | 4.45 | (0.145, 0.051) | 85 |
| Comparative Example 7-22 | HT 1 | 3.95 | 5.21 | (0.144, 0.053) | 140 |
| Comparative Example 7-23 | HT 3 | 4.11 | 4.53 | (0.144, 0.048) | 105 |
| Comparative Example 7-24 | HT 4 | 3.96 | 4.82 | (0.144, 0.045) | 130 |

As seen in Table 7, the organic light emitting device manufactured by using the compound of the present invention as a hole transporting layer exhibits better characteristics in terms of the efficiency, driving voltage, and/or service life (stability) of the organic light emitting device than the organic light emitting devices manufactured by using the compounds in Comparative Examples 7-21 to 7-24, in which a ring is formed to have a structure similar to the core of the present invention, as a hole transporting layer.

A result significantly improved particularly in terms of service life was obtained, and it appears that the thickness of the hole transporting layer is relatively larger than that of the electron blocking layer, and as a result, the stability aspect of the material is significantly affected.

In the case of Comparative Example 7-22, since the structure of the core is a methyl group, it is determined that the stability of the core itself deteriorates as compared to the compound of the present invention, to which an aryl group (phenyl) is linked.

Even in the case of Comparative Examples 7-21, the stability of cycloalkyl itself significantly deteriorates as compared to an OLED material which is composed of most of the aromatic compounds in the organic light emitting device. Furthermore, the material is highly likely to be broken during the sublimation purification process.

In the case of Comparative Examples 7-23 and 7-24, a material in which a triphenylenyl group and dibenzofuran are substituted had a significantly increased voltage. It appears that the capability of providing holes is insufficient due to the absence of an arylamine group, and the homo value is 5.5 eV or less, and accordingly, the barrier with a hole injection layer is increased, thereby affecting an increase in voltage. Even in terms of service life, the service life is almost at the level of sudden death, and accordingly, it appears that a material having no arylamine group in an OLED device is not suitable as an electron blocking layer.

As in the result in Table 7, it could be confirmed that the compound according to the present invention has an excellent hole transporting capability and thus can be applied to an organic light emitting device.

As in the results in Tables 6 and 7, it could be confirmed that the compound according to the present invention has not only an excellent electron blocking capability but also an excellent hole transporting capability, and thus can be applied to an organic light emitting device.

EXPERIMENTAL EXAMPLE 8-1

An experiment was performed in the same manner as in Experimental Example 6-1, except that as the electron injection and transporting layer, Compound 7 was used instead of ET1.

EXPERIMENTAL EXAMPLE 8-2

An experiment was performed in the same manner as in Experimental Example 8-1, except that as the electron transporting layer, Compound 8 was used instead of Compound 7.

EXPERIMENTAL EXAMPLE 8-3

An experiment was performed in the same manner as in Experimental Example 8-1, except that as the electron transporting layer, Compound 9 was used instead of Compound 7.

EXPERIMENTAL EXAMPLE 8-4

An experiment was performed in the same manner as in Experimental Example 8-1, except that as the electron transporting layer, Compound 10 was used instead of Compound 7.

EXPERIMENTAL EXAMPLE 8-5

An experiment was performed in the same manner as in Experimental Example 8-1, except that as the electron transporting layer, Compound 11 was used instead of Compound 7.

EXPERIMENTAL EXAMPLE 8-6

An experiment was performed in the same manner as in Experimental Example 8-1, except that as the electron transporting layer, Compound 13 was used instead of Compound 7.

EXPERIMENTAL EXAMPLE 8-7

An experiment was performed in the same manner as in Experimental Example 8-1, except that as the electron transporting layer, Compound 19 was used instead of Compound 7.

EXPERIMENTAL EXAMPLE 8-8

An experiment was performed in the same manner as in Experimental Example 8-1, except that as the electron transporting layer, Compound 20 was used instead of Compound 7.

COMPARATIVE EXAMPLE 8-11

An organic light emitting device was manufactured in the same manner as in Experimental Example 8-1, except that as the electron transporting layer, a compound of the following ET2 was used instead of Compound 7 in Experimental Example 8-1.

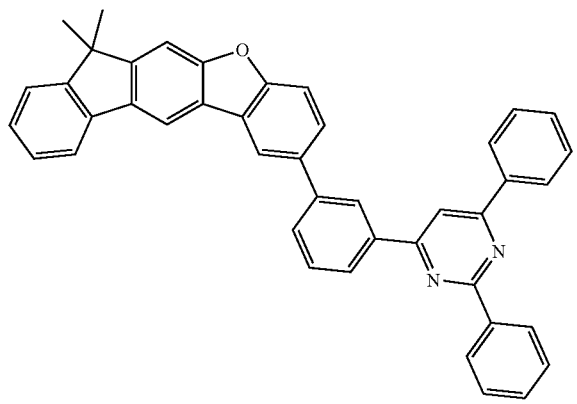

[ET2]

COMPARATIVE EXAMPLE 8-12

An organic light emitting device was manufactured in the same manner as in Experimental Example 8-1, except that as the electron transporting layer, a compound of the following ET3 was used instead of Compound 7 in Experimental Example 8-1.

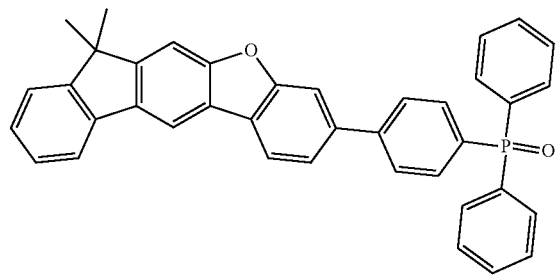

[ET3]

COMPARATIVE EXAMPLE 8-13

An organic light emitting device was manufactured in the same manner as in Experimental Example 8-1, except that as the electron transporting layer, a compound of the following ET1 was used instead of Compound 7 in Experimental Example 8-1.

[ET1]

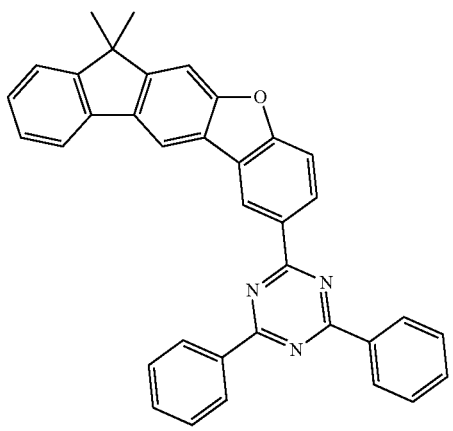

When current was applied to the organic light emitting devices manufactured in Experimental Examples 8-1 to 8-9 and Comparative Examples 8-11 to 8-13, the voltages, efficiencies, color coordinates, and service lives were measured, and the results are shown in the following [Table 8]. T90 means the time taken for the luminance to be reduced to 90% of the initial luminance (3,000 nit).

TABLE 8

| | Compound | Voltage (V@ 10 mA/ cm$^2$) | Efficiency (cd/A@10 mA/cm$^2$) | T90 (hr) | Color coordinate (x, y) |
|---|---|---|---|---|---|
| Experimental Example 8-1 | Compound 7 | 3.88 | 5.05 | 185 | (0.141, 0.053) |
| Experimental Example 8-2 | Compound 8 | 3.75 | 5.15 | 175 | (0.142, 0.052) |
| Experimental Example 8-3 | Compound 9 | 3.86 | 5.04 | 180 | (0.140, 0.055) |
| Experimental Example 8-4 | Compound 10 | 3.85 | 4.92 | 165 | (0.140, 0.054) |
| Experimental Example 8-5 | Compound 11 | 3.89 | 4.85 | 165 | (0.141, 0.053) |
| Experimental Example 8-6 | Compound 13 | 3.95 | 4.64 | 170 | (0.140, 0.055) |
| Experimental Example 8-7 | Compound 19 | 4.05 | 5.35 | 165 | (0.142, 0.056) |
| Experimental Example 8-8 | Compound 20 | 3.96 | 4.87 | 285 | (0.143, 0.054) |
| Comparative Example 8-11 | ET2 | 4.15 | 4.18 | 115 | (0.145, 0.052) |
| Comparative Example 8-12 | ET3 | 4.43 | 3.87 | 150 | (0.145, 0.053) |
| Comparative Example 8-13 | ET1 | 4.16 | 4.27 | 85 | (0.144, 0.053) |

As a result of the experiments, it could be confirmed that the organic light emitting devices in Experimental Examples 8-1 to 8-8 in which the compound prepared according to the present invention was used as an electron transporting layer exhibited excellent performances as a whole in terms of current efficiency, driving voltage, and service life as compared to the organic light emitting devices in Comparative Examples 8-11 to 8-13, in which the core structure was a methyl group.

When the characteristics according to the substituent of the compound of the present invention are observed, the case where the compound of the present invention is substituted with triazine has the highest efficiency in Experimental Examples 8-1 to 8-4, and when a phenyl group is linked via a linking group, the efficiency is decreased, and the case where the compound of the present invention is substituted with pyrimidine also exhibits a tendency that the efficiency is decreased.

In Experimental Example 8-8 where a material in which phosphine oxide was substituted was applied, the efficiency was slightly decreased, but the highest service life was measured. However, when Comparative Example 11 in which the core was composed of a methyl group of which the stability relatively deteriorates was observed, characteristics in which the service life was significantly increased were not exhibited.

EXPERIMENTAL EXAMPLE 9-1

A glass substrate on which a thin film of indium tin oxide (ITO) was coated to have a thickness of 1,000 Å was placed into distilled water in which a detergent was dissolved, and washed using ultrasonic waves. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

The following compound N4,N4,N4',N4'-tetra([1,1'-biphenyl]-4-yl)-[1,1'-biphenyl]-4,4'-diamine was thermally vacuum deposited to have a thickness of 100 Å on the thus prepared ITO transparent electrode, thereby forming a hole injection layer.

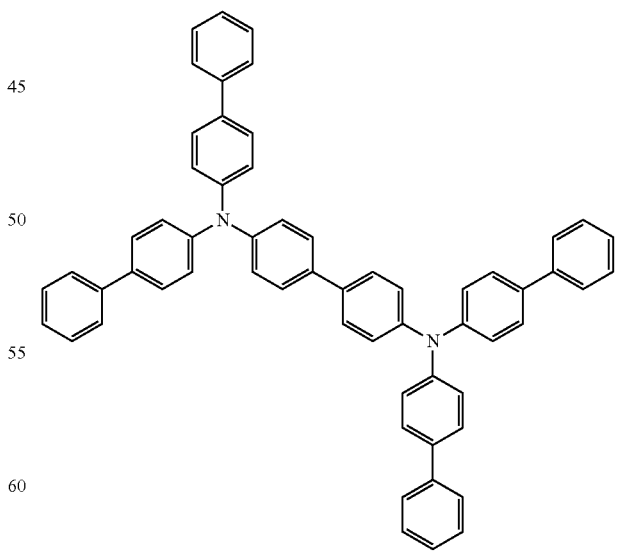

The following compound N-([1,1'-biphenyl]-4-yl)-9,9-dimethyl-N-(4-(9-phenyl-9H-carbazol-3-yl)phenyl)-9H-fluoren-2-amine (1,250 Å), which is a material for transporting holes, was vacuum deposited on the hole injection layer, thereby forming a hole transporting layer.

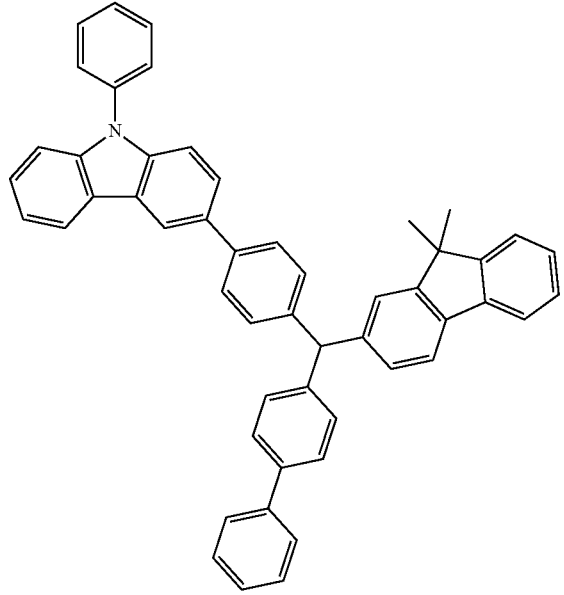 [SMILES: CC1(C)c2ccccc2-c2ccc(C(c3ccc(-c4ccccc4)cc3)c3ccc(-c4ccc5c(c4)c4ccccc4n5-c4ccccc4)cc3)cc21]

Subsequently, the following compound N,N-di([1,1'-biphenyl]-4-yl)-4'-(9H-carbazol-9-yl)-[1,1'-biphenyl]-4-amine was vacuum deposited to have a film thickness of 150 Å on the hole transporting layer, thereby forming an electron blocking layer.

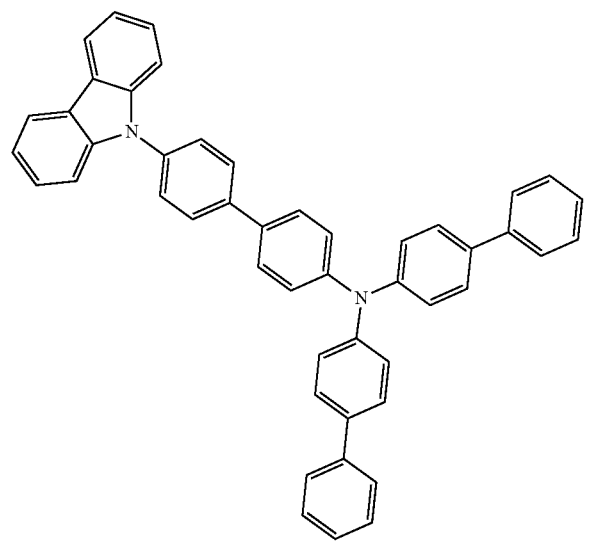

[EBL]

Subsequently, the following BH and BD were vacuum deposited at a weight ratio of 25:1 to have a film thickness of 300 Å on the electron blocking layer, thereby forming a light emitting layer.

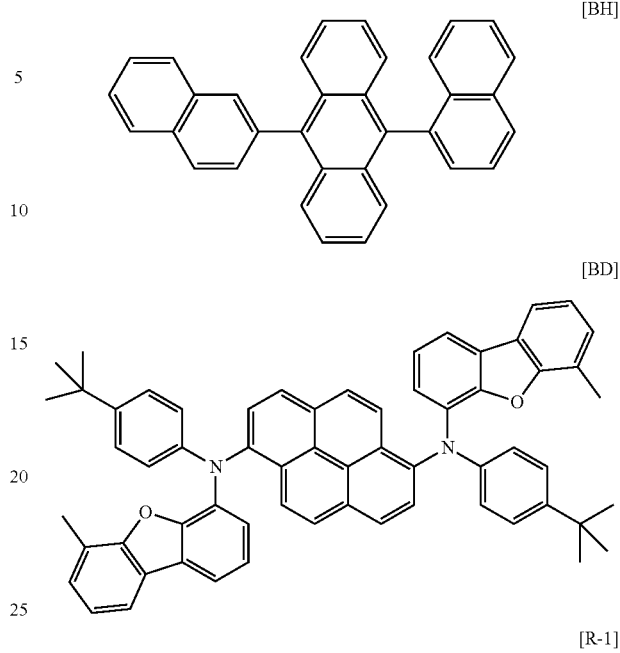

[BH]

[BD]

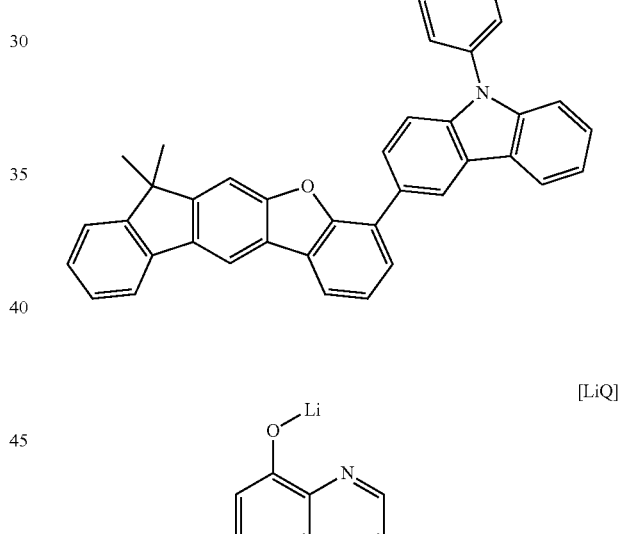

[R-1]

[LiQ]

Compound R-1 and Compound LiQ (lithium quinolate) were vacuum deposited at a weight ratio of 1:1 on the light emitting layer, thereby forming an electron injection and transporting layer having a thickness of 360 Å. Lithium fluoride (LiF) and aluminum were sequentially deposited on the electron injection and transporting layer to have a thickness of 12 Å and 2,000 Å, respectively, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

COMPARATIVE EXAMPLE 9-11

An organic light emitting device was manufactured in the same manner as in Experimental Example 9-1, except that the following compound R-2 was used instead of R-1 in Experimental Example 9-1.

[R-2]

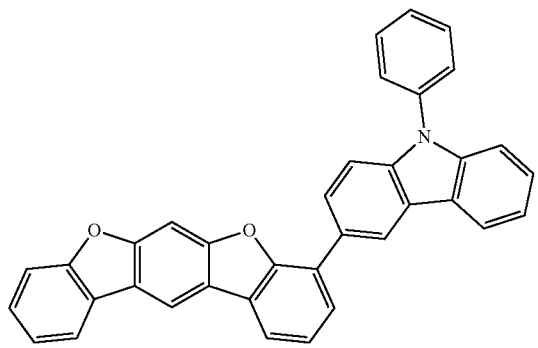

For the organic light emitting devices manufactured according to Experimental Example 9-1 and Comparative Example 9-11, the voltages, current densities, luminances, color coordinates, and service lives were measured, and the results are shown in the following [Table 9]. T95 means the time taken for the luminance to be reduced to 95% of the initial luminance (5,000 nit).

TABLE 9

| | Compound | Voltage (V@10 mA/cm$^2$) | Efficiency (cd/A@10 mA/cm$^2$) | Color coordinate (x, y) | T95 (hr) |
|---|---|---|---|---|---|
| Experimental Example 9-1 | R-1 | 4.20 | 6.15 | (0.142, 0.046) | 330 |
| Comparative Example 9-11 | R-2 | 4.76 | 5.34 | (0.141, 0.047) | 215 |

When a compound having a dibenzofuran core, in which benzofuran is fused, is used through Experimental Example 9-1 and Comparative Example 9-11, driving voltage, efficiency, and service life characteristics deteriorate as compared to the case of using a compound having a fluorene core in which benzofuran, in which a methyl group is bonded to a No. 9 position of fluorene, is fused, and accordingly, it can be confirmed that the effects significantly deteriorate as compared to the compound corresponding to Chemical Formula 1 of the present invention.

The invention claimed is:

1. A hetero-cyclic compound represented by the following Chemical Formula 1:

[Chemical Formula 1]

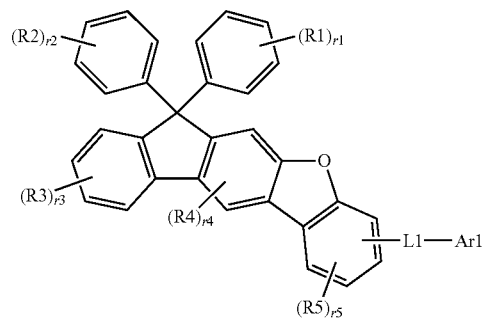

in Chemical Formula 1,

R1 to R3 and R5 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, R4 is hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; an unsubstituted amine group; a substituted or unsubstituted arylphosphine group; a substituted or unsubstituted phosphine oxide group; a substituted or unsubstituted aryl group; or a substituted or unsubstituted heteroaryl group, L1 is a direct bond; a substituted or unsubstituted arylene group; or a substituted or unsubstituted heteroarylene group, wherein the arylene group in L1 is not an anthracenylene group, Ar1 is a substituted or unsubstituted amine group; a substituted or unsubstituted phosphine oxide group; a substituted or unsubstituted aryl group; or a substituted or unsubstituted heteroaryl group, wherein the aryl group in Ar1 is not an anthracenyl group, r1 and r2 are each an integer from 1 to 5, r3 is an integer from 1 to 4, r4 is 1 or 2, r5 is an integer from 1 to 3, and when r1 to r5 are each present in a plural number, a plurality of structures in the parenthesis is the same as or different from each other.

2. The hetero-cyclic compound of claim 1, wherein Chemical Formula 1 is represented by any one of the following Chemical Formulae 2 to 5:

[Chemical Formula 2]

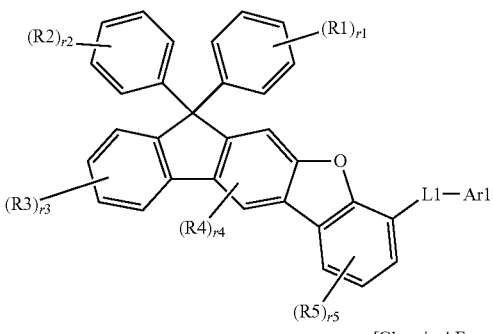

[Chemical Formula 3]

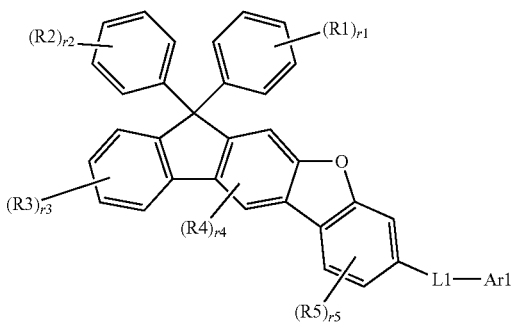

[Chemical Formula 4]

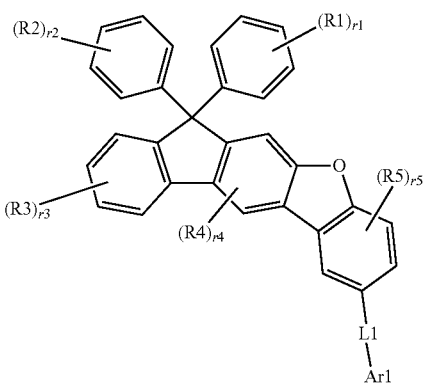

[Chemical Formula 5]

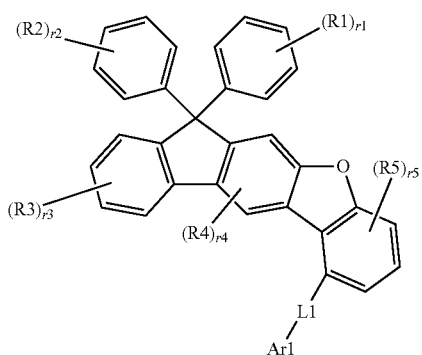

in Chemical Formulae 2 to 5,
the definitions of R1 to R5, r1 to r5, L1, and Ar1 are the same as those in Chemical Formula 1.

3. The hetero-cyclic compound of claim 1, wherein L1 is a direct bond; an unsubstituted arylene group; or an unsubstituted heteroarylene group.

4. The hetero-cyclic compound of claim 1, wherein Ar1 is an arylamine group which is unsubstituted or substituted with an alkyl group or a heteroaryl group; an N-arylheteroarylamine group which is unsubstituted or substituted with an aryl group; a phosphine oxide group which is substituted with an aryl group; an aryl group which is unsubstituted or substituted with an alkyl group or an aryl group; or a heteroaryl group which is unsubstituted or substituted with an aryl group.

5. An organic light emitting device comprising:
a first electrode;
a second electrode disposed to face the first electrode; and
an organic material layer having one or more layers disposed between the first electrode and the second electrode,
wherein the one or more layers of the organic material layer comprise the hetero-cyclic compound of claim 1.

6. The organic light emitting device of claim 5, wherein the organic material layer comprises an electron blocking layer, and the electron blocking layer comprises the hetero-cyclic compound.

7. The organic light emitting device of claim 5, wherein the organic material layer comprises a light emitting layer, and the light emitting layer comprises the hetero-cyclic compound.

8. The organic light emitting device of claim 5, wherein the organic material layer comprises a light emitting layer, and the light emitting layer comprises the hetero-cyclic compound as a host of the light emitting layer.

9. The organic light emitting device of claim 5, wherein the organic material layer comprises an electron transporting layer, and the electron transporting layer comprises the hetero-cyclic compound.

10. An organic light emitting device comprising:
a first electrode;
a second electrode disposed to face the first electrode; and
an organic material layer having one or more layers disposed between the first electrode and the second electrode,
wherein the organic material layer comprises at least one of a hole transporting layer, an electron blocking layer, or an electron transporting layer, and the at least one of the hole transporting layer the electron blocking layer, or the electron transporting layer comprises a hetero-cyclic compound represented by the following Chemical Formula 1:

[Chemical Formula 1]

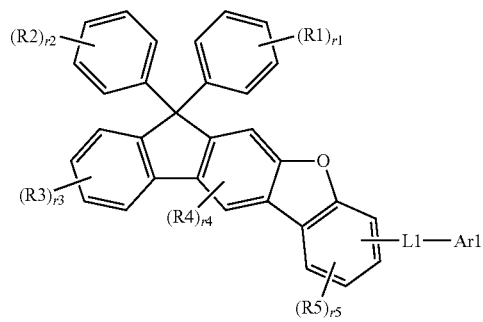

in Chemical Formula 1,

R1 to R5 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, L1 is a direct bond; a substituted or unsubstituted arylene group; or a substituted or unsubstituted heteroarylene group, Ar1 is a substituted or unsubstituted amine group; a substituted or unsubstituted phosphine oxide group; a substituted or unsubstituted aryl group; or a substituted or unsubstituted heteroaryl group, r1 and r2 are each an integer from 1 to 5, r3 is an integer from 1 to 4, r4 is 1 or 2, r5 is an integer from 1 to 3, and when r1 to r5 are each present in a plural number, a plurality of structures in the parenthesis is the same as or different from each other.

11. A hetero-cyclic compound selected from the following compounds:

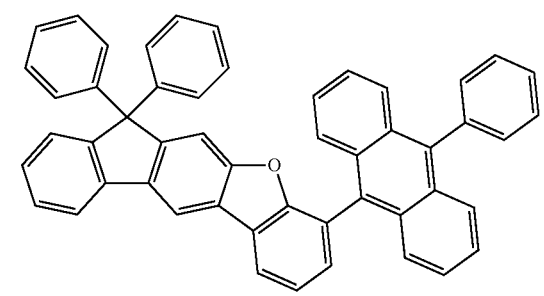

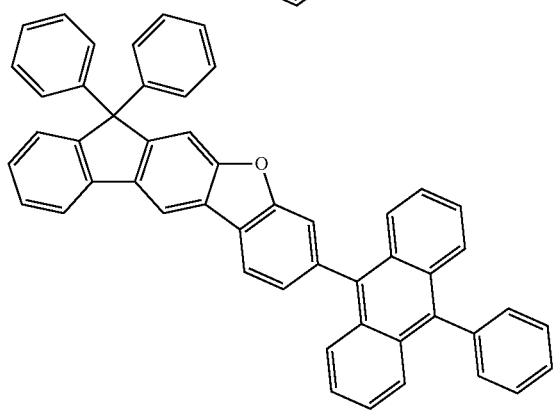

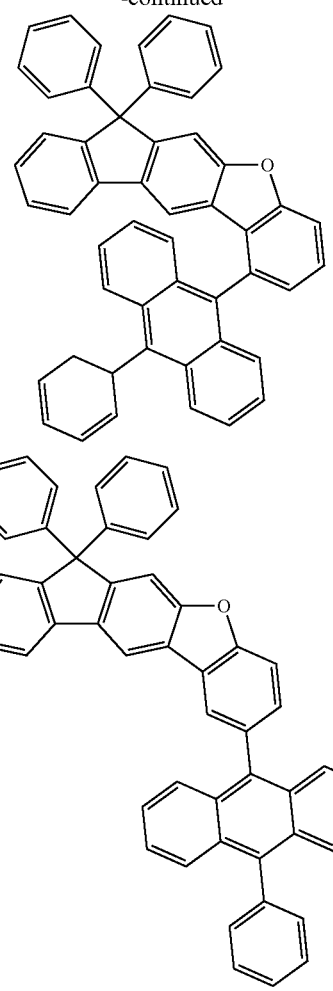

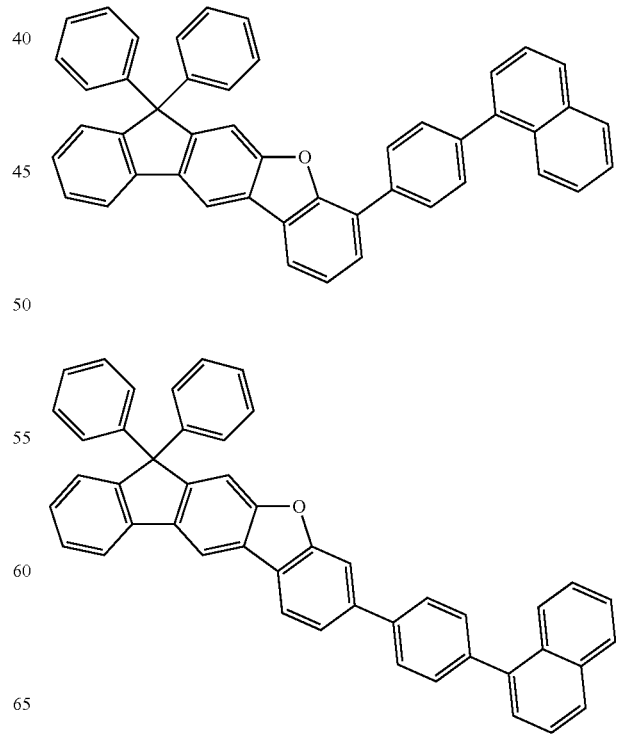

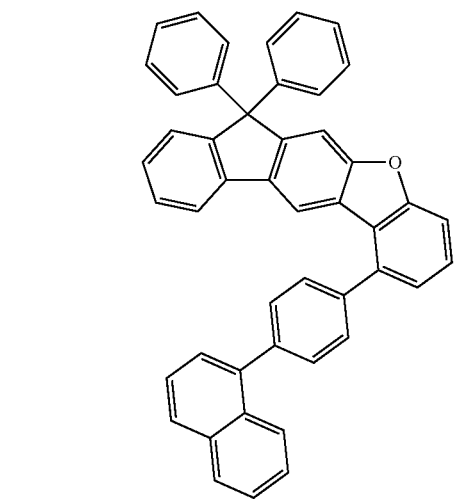
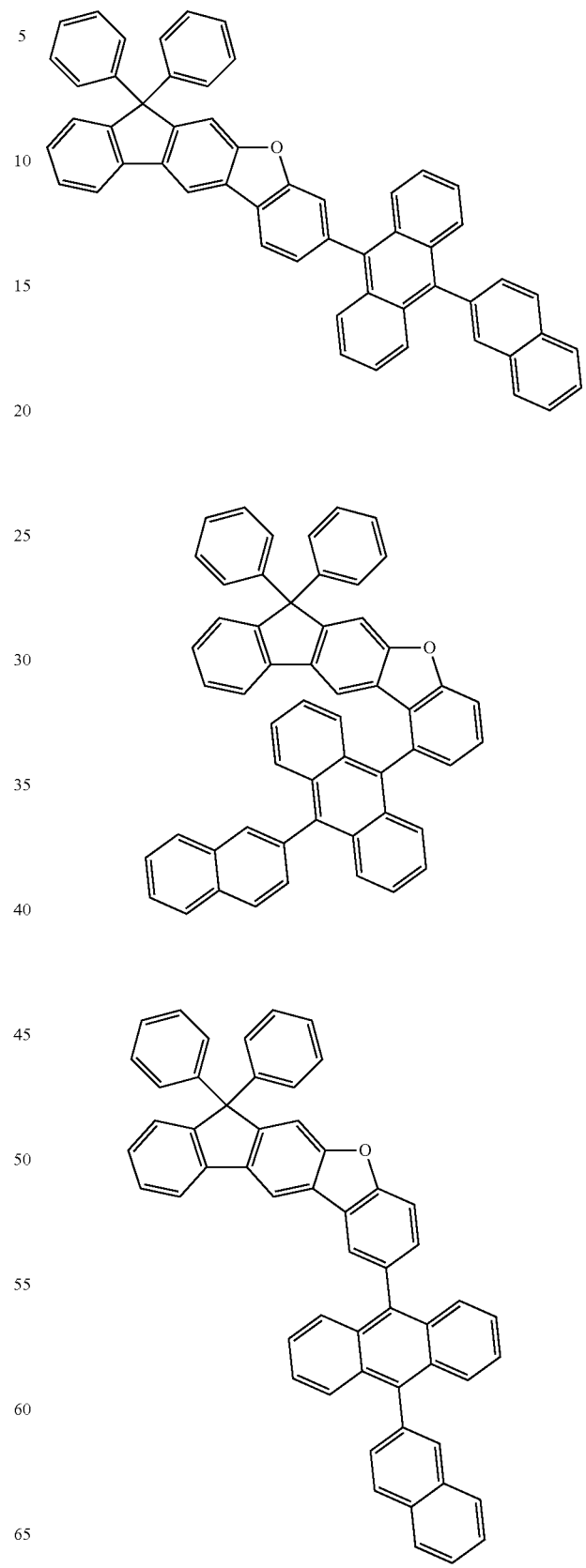

249
-continued
250
-continued
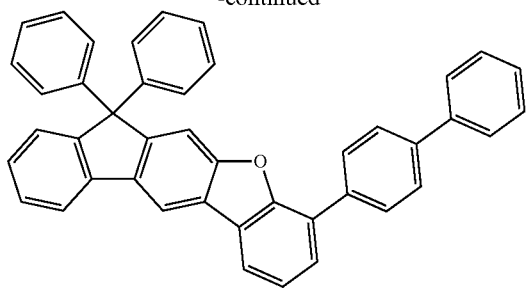
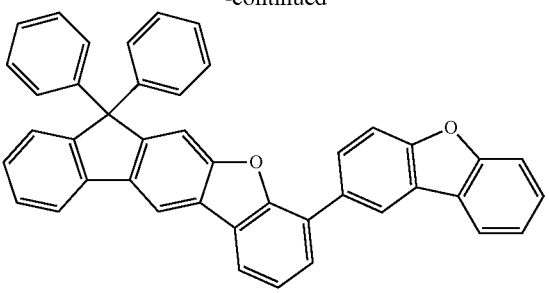

251
-continued
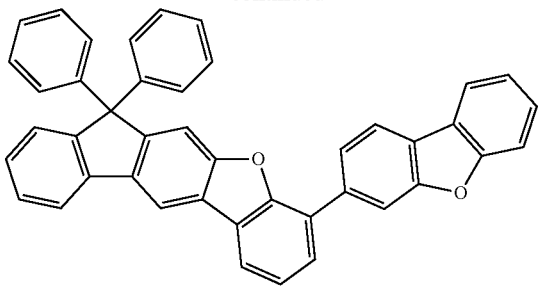
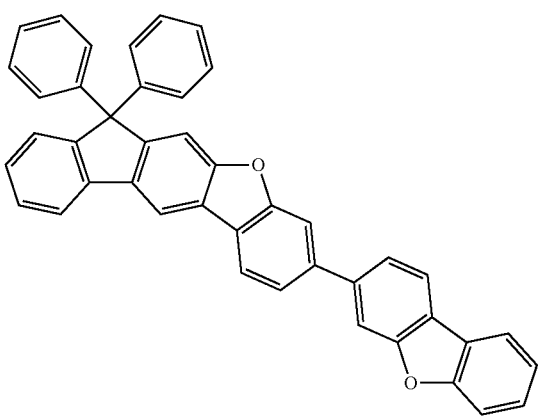
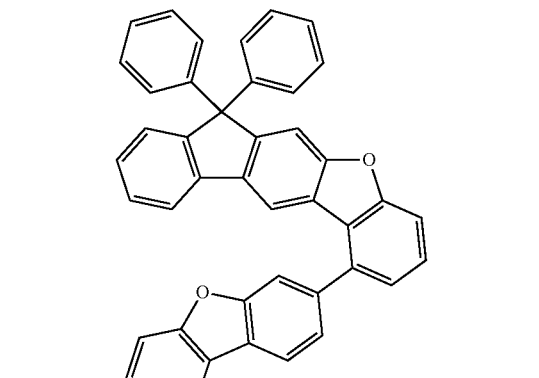
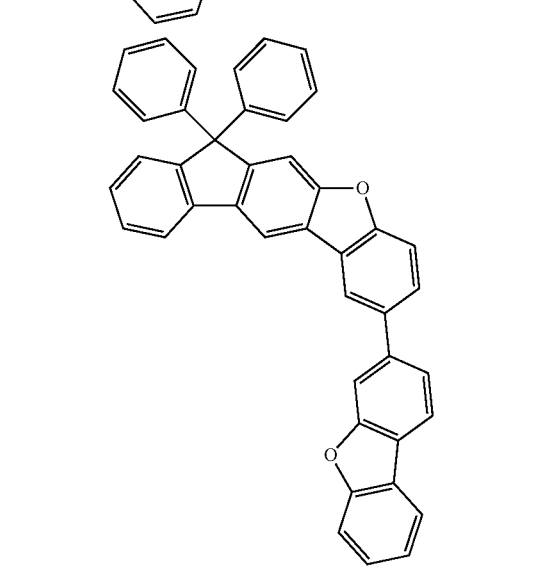
252
-continued
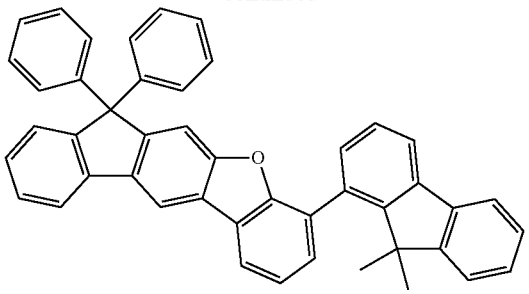
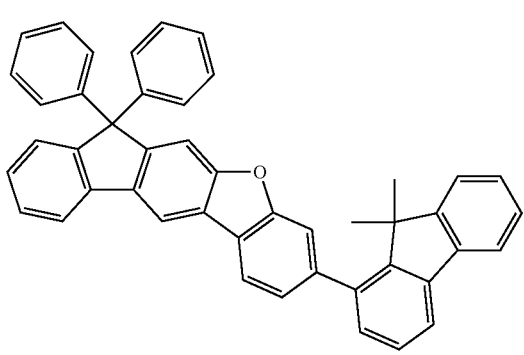
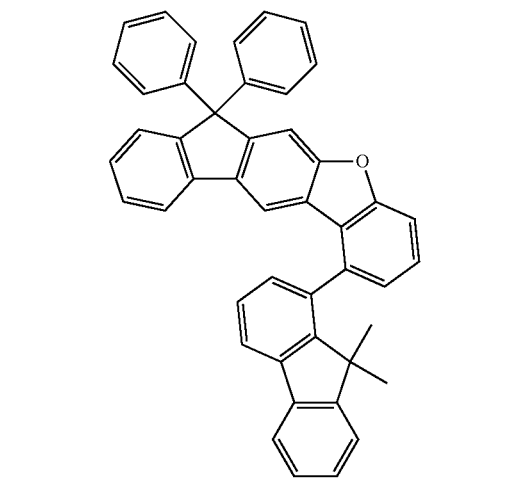
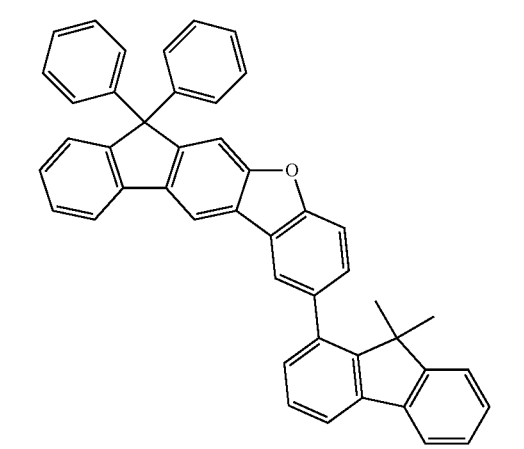

253
-continued
254
-continued
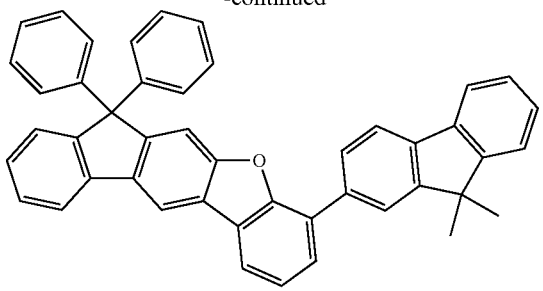
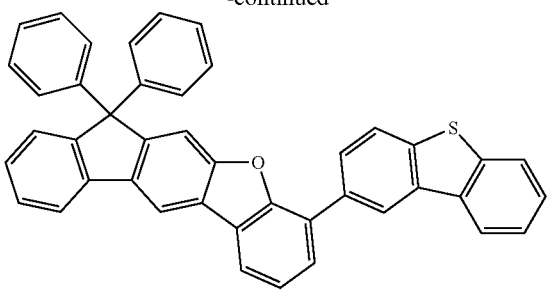

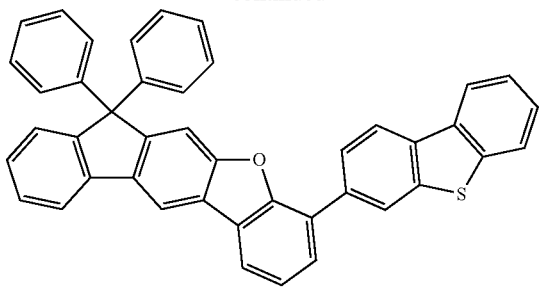
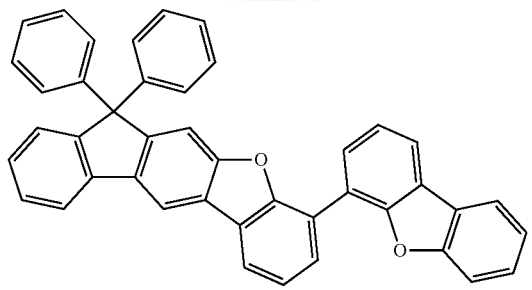

257
-continued
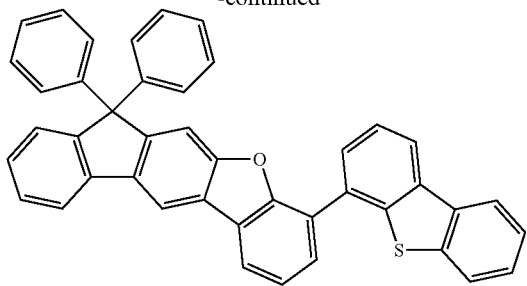
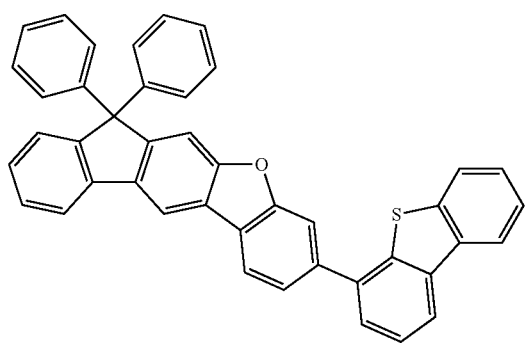
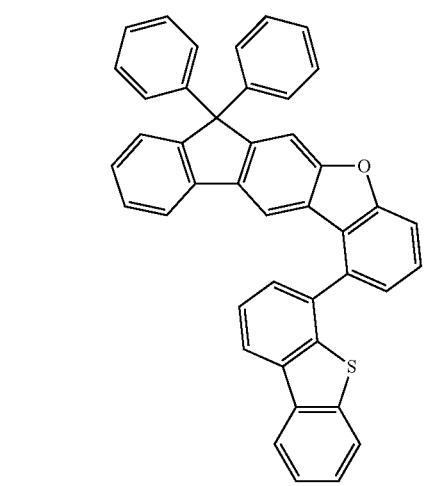
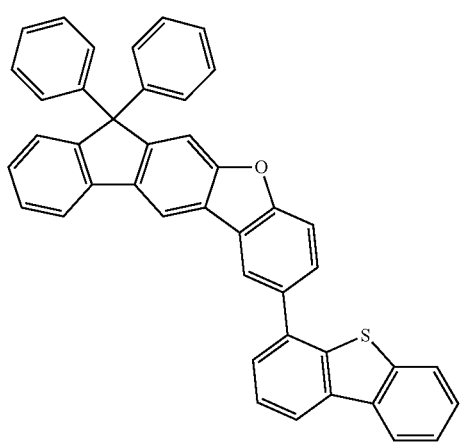
258
-continued
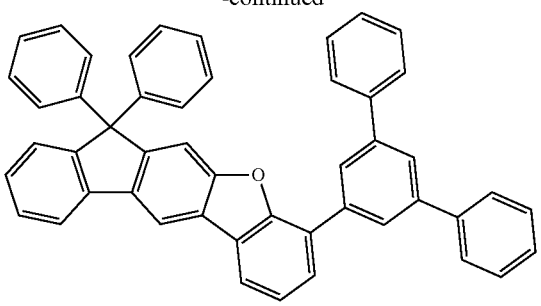
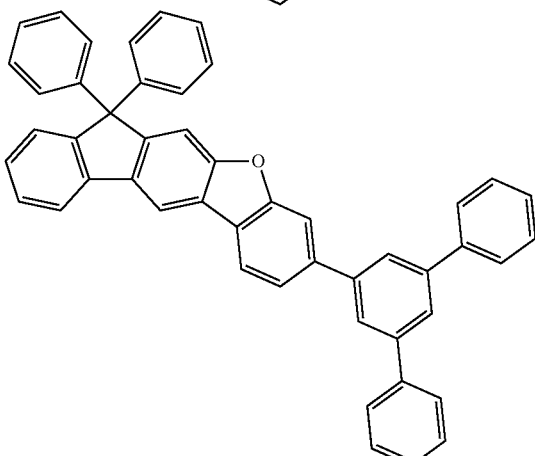
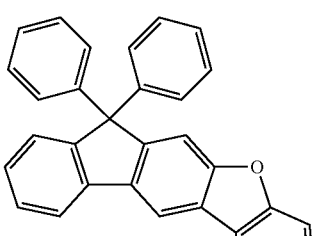
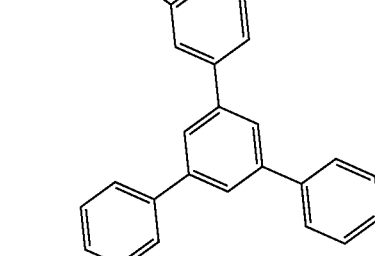
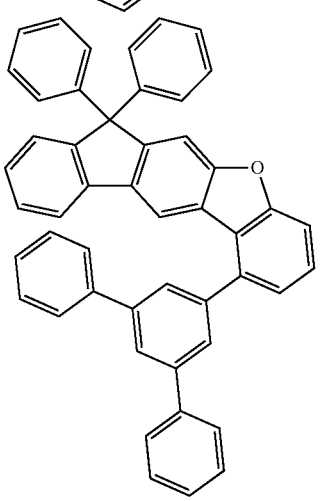

259
-continued
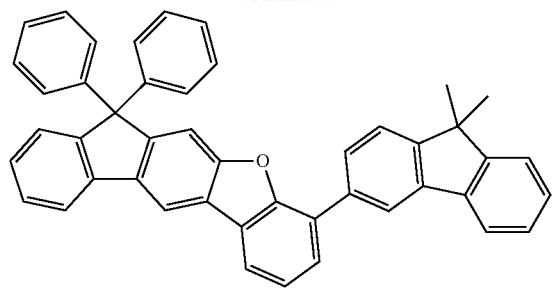
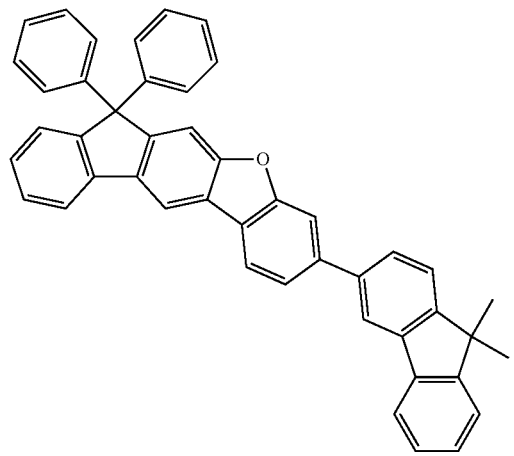
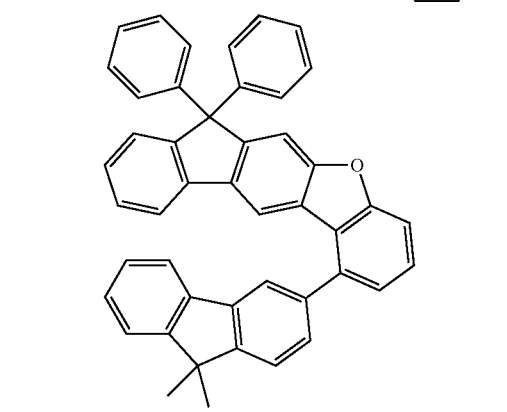
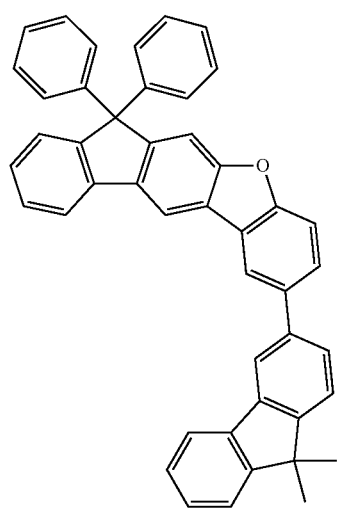
260
-continued
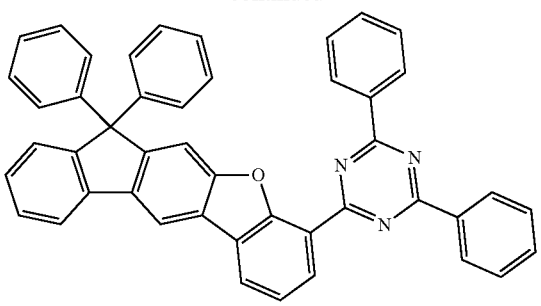
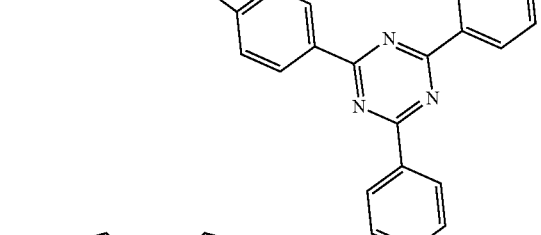
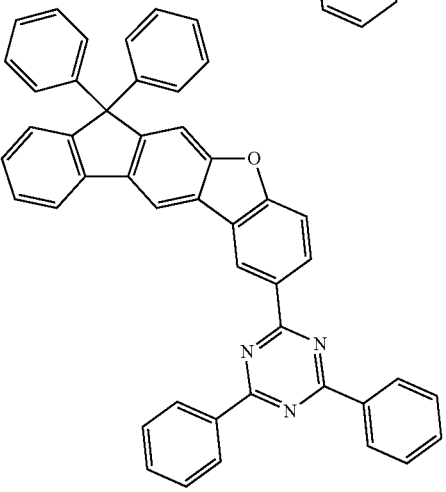
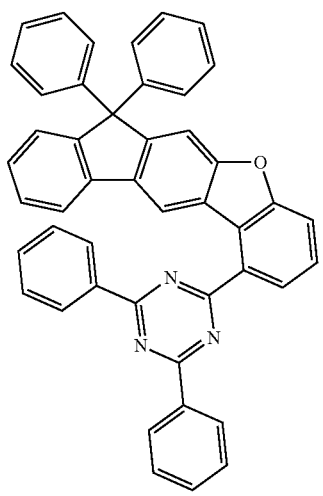

261
-continued
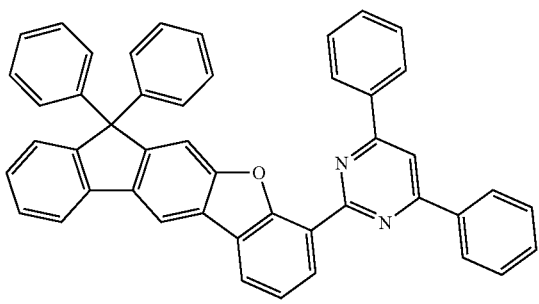
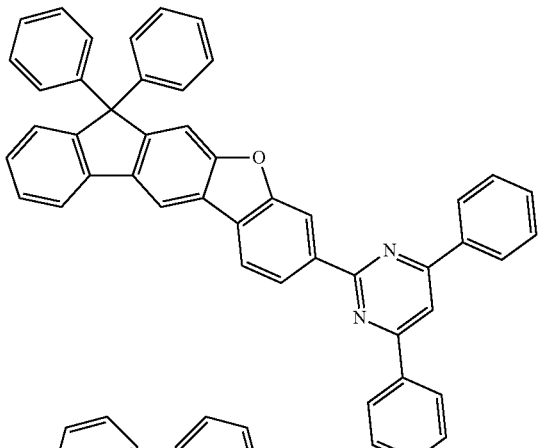
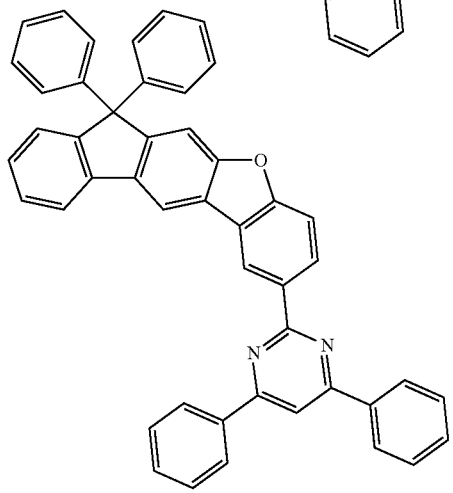
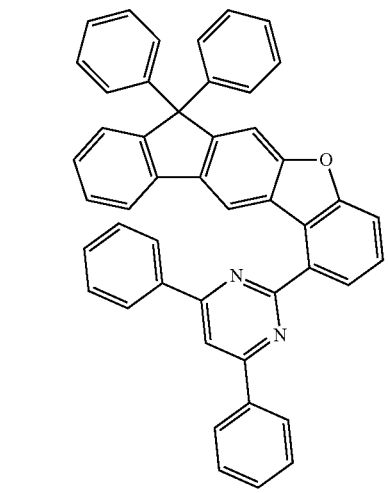
262
-continued
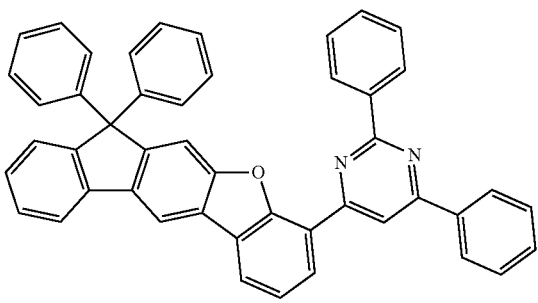
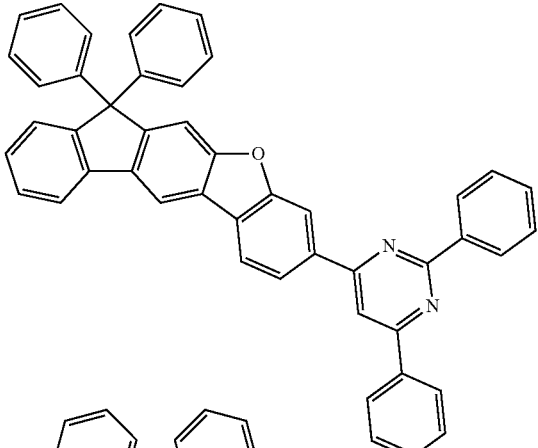
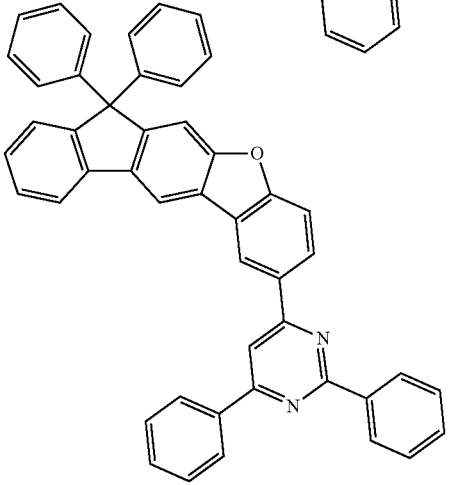
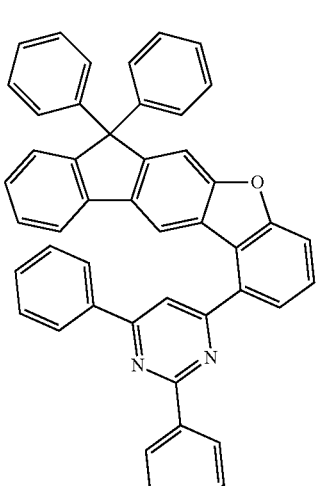

263
-continued
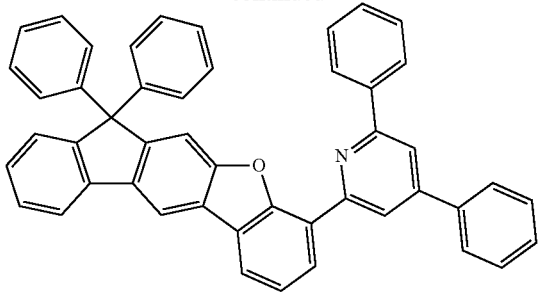
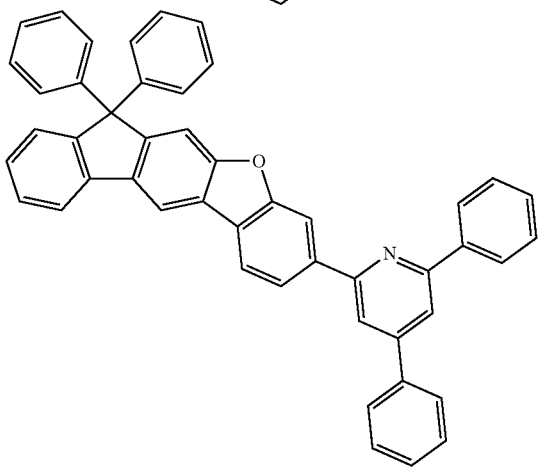
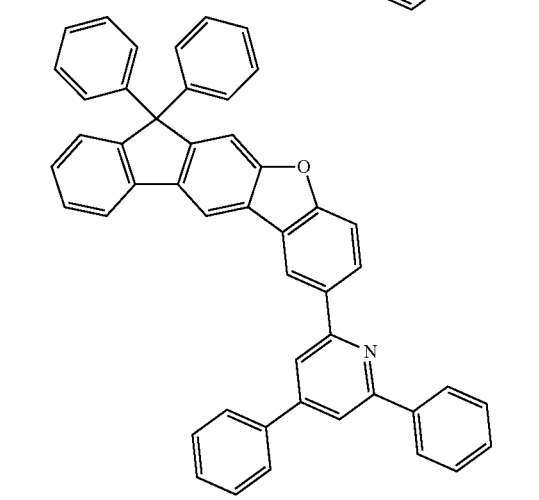
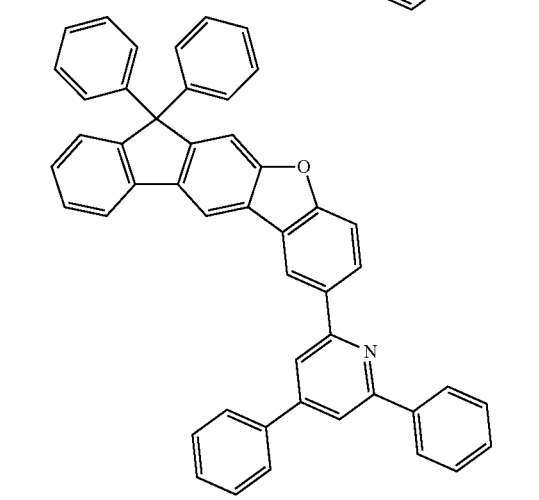
264
-continued
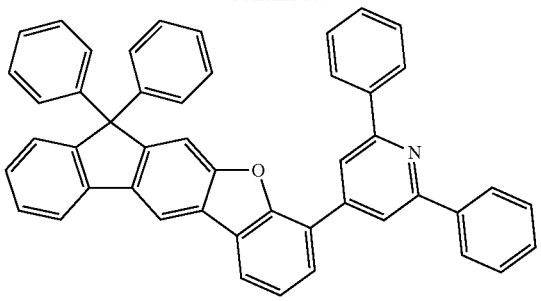
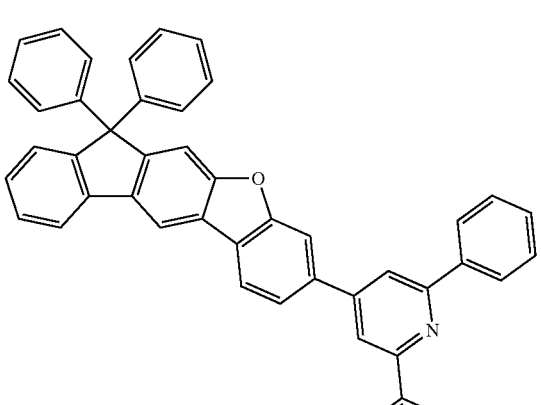
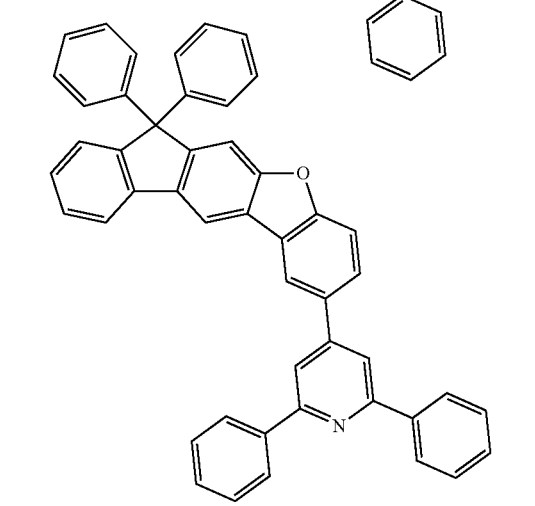
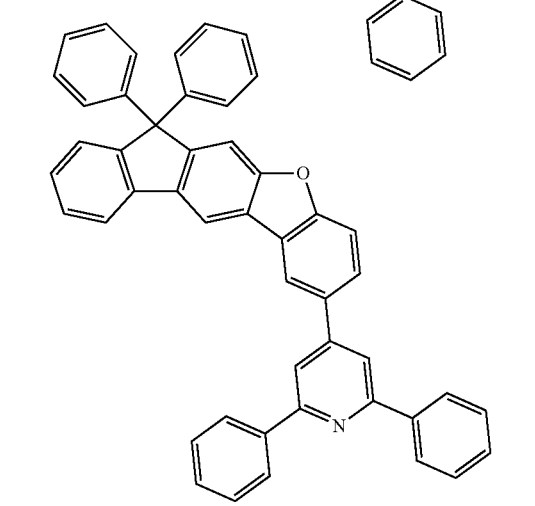

265
-continued
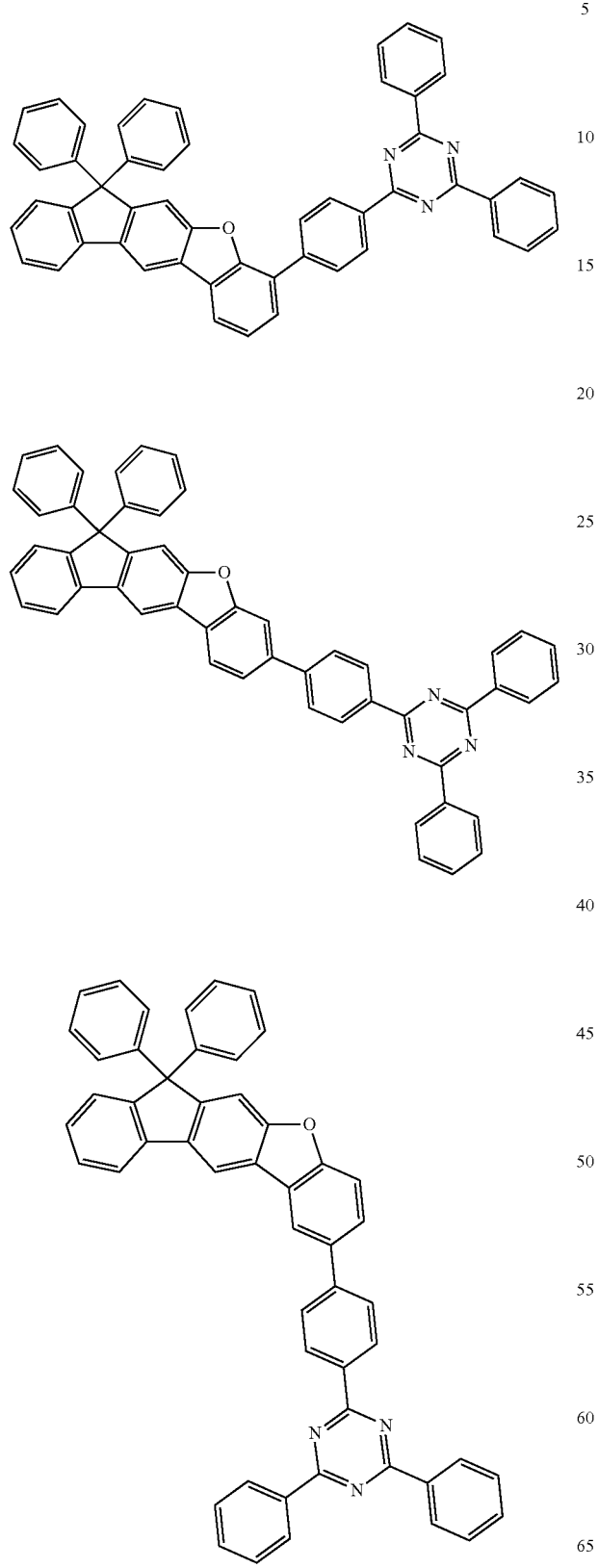
266
-continued
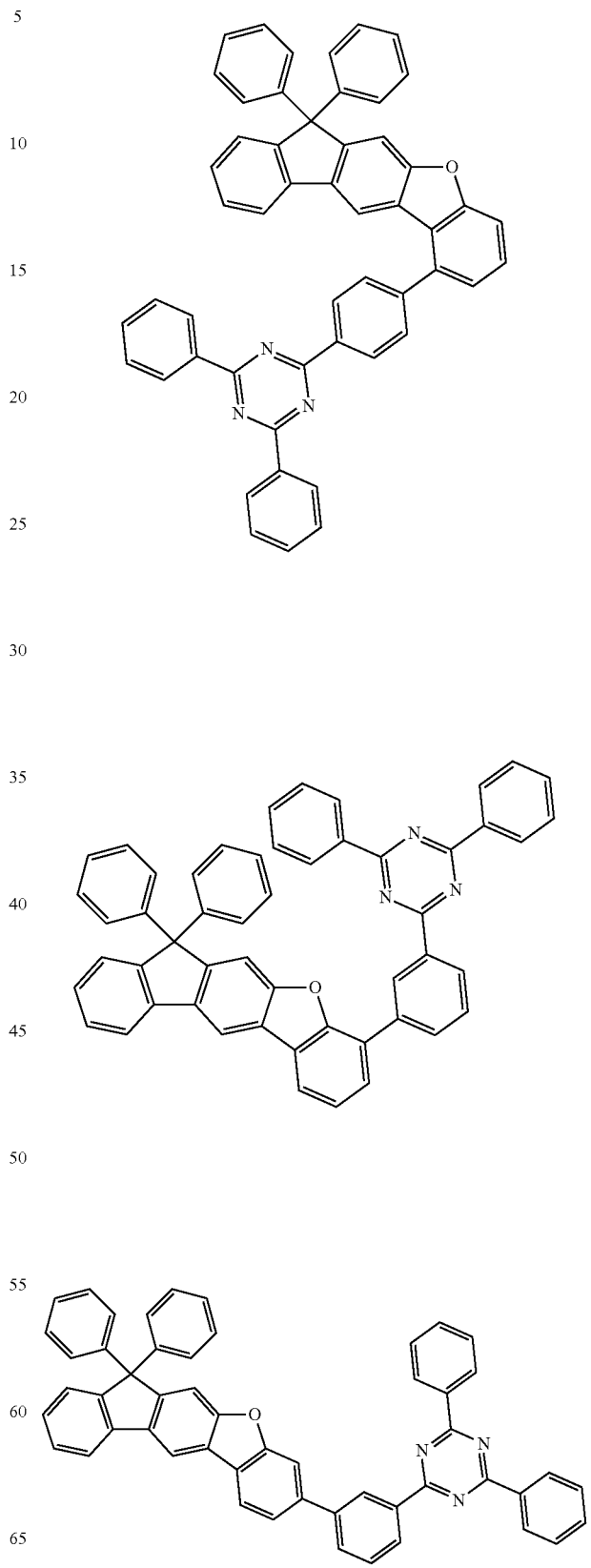

267
-continued
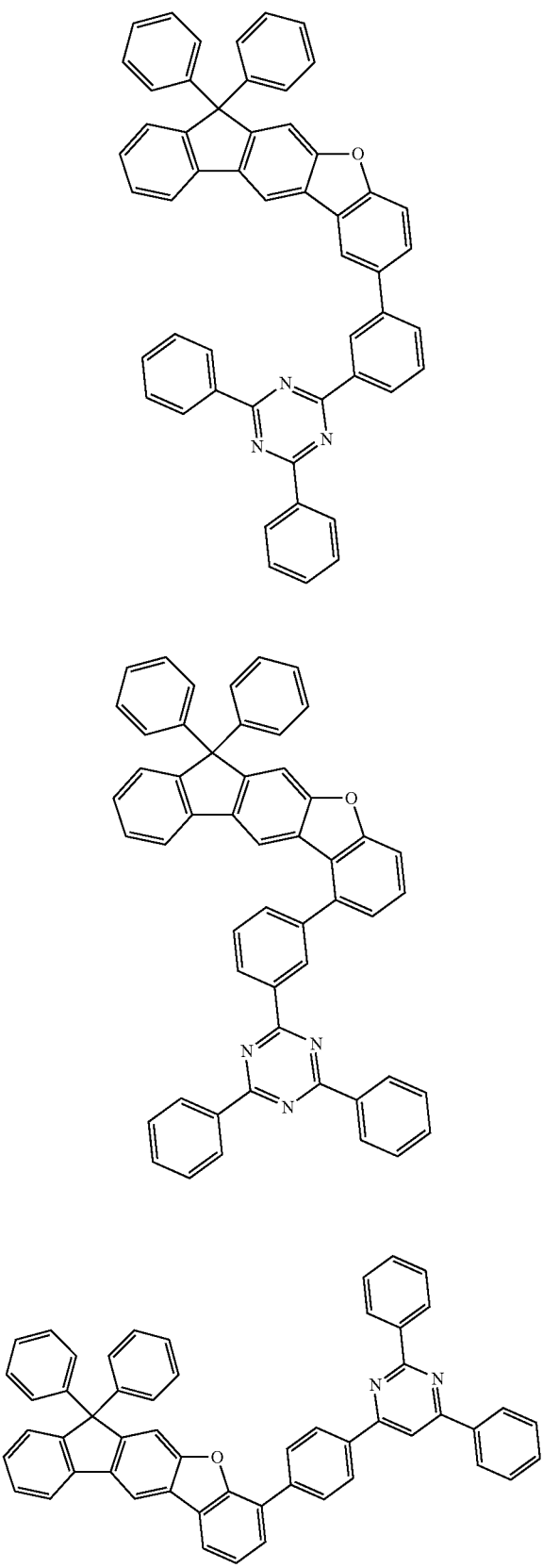
268
-continued
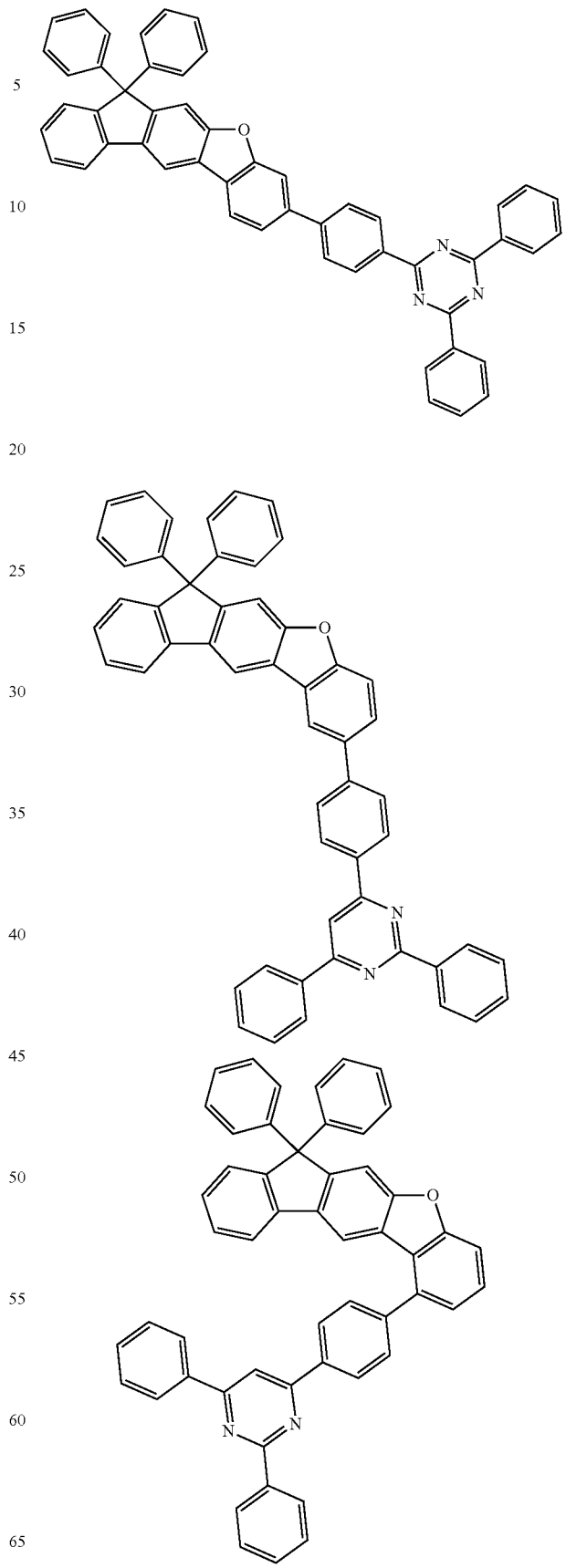

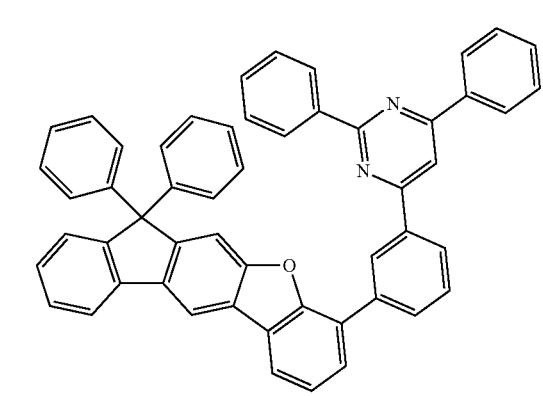
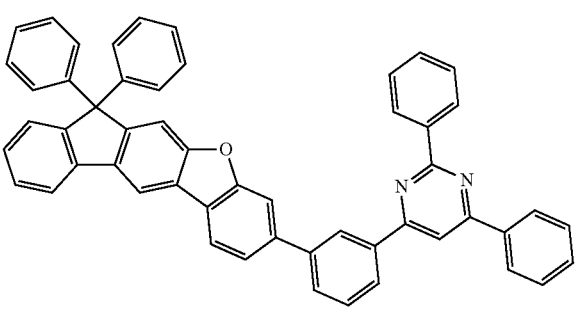
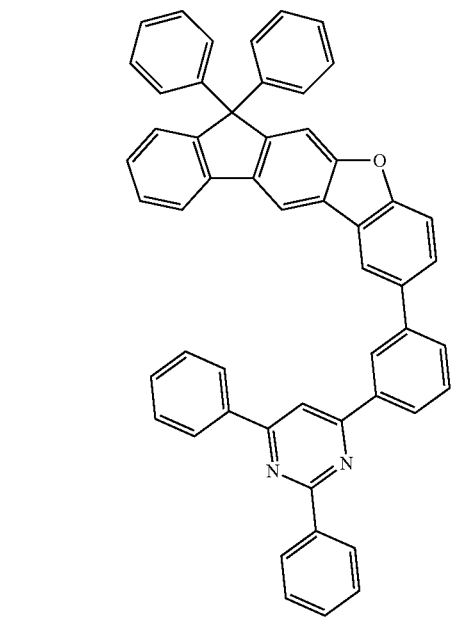
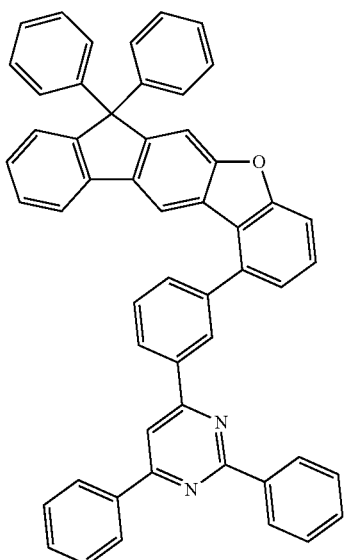
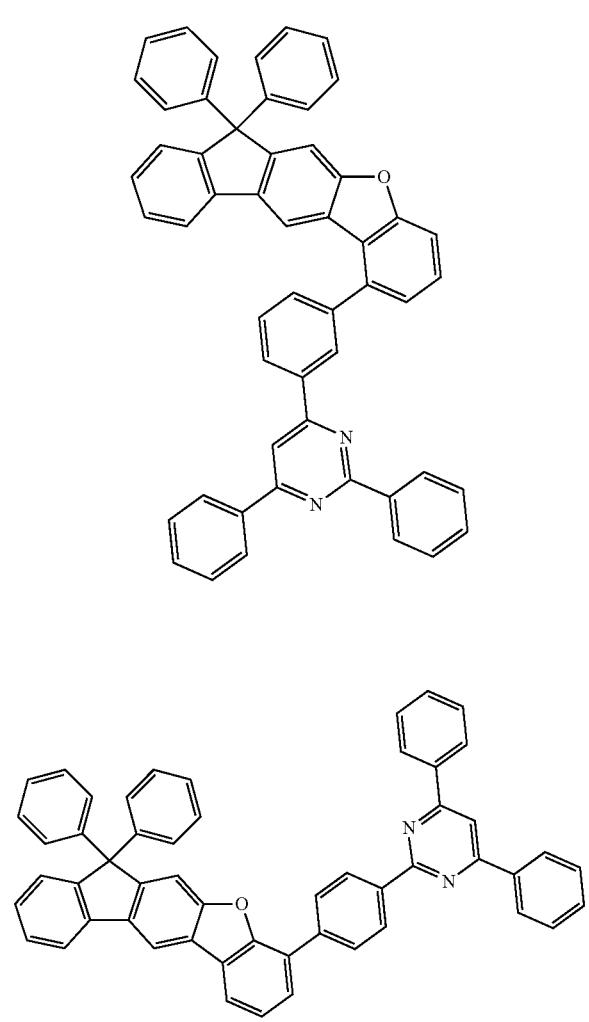

271
-continued
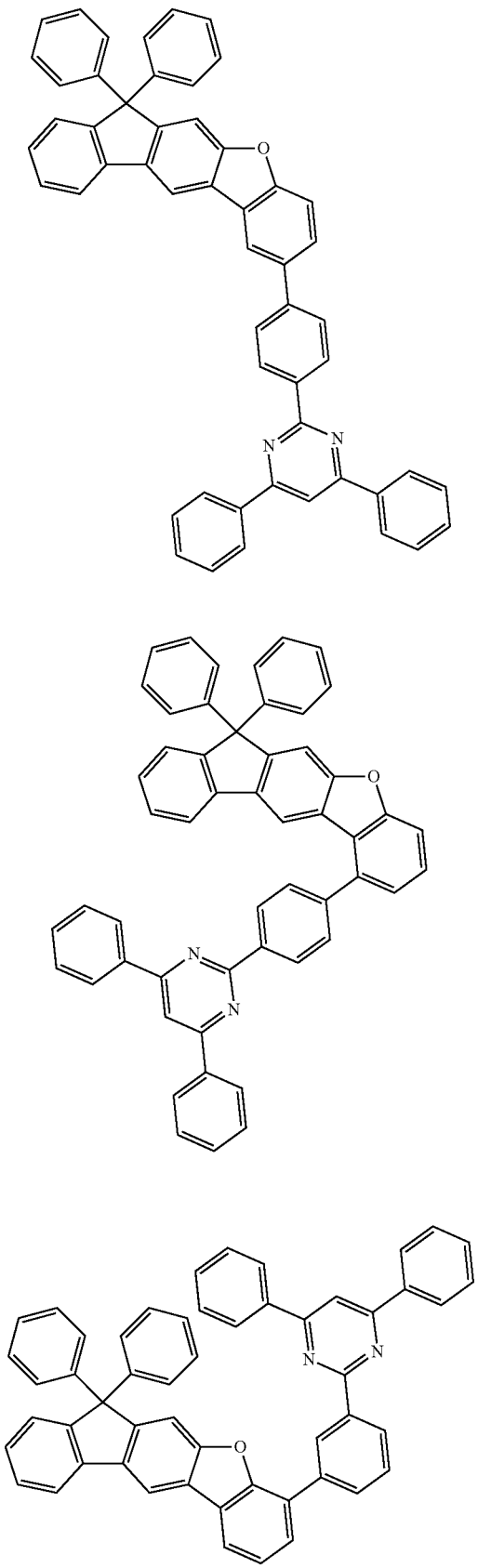
272
-continued
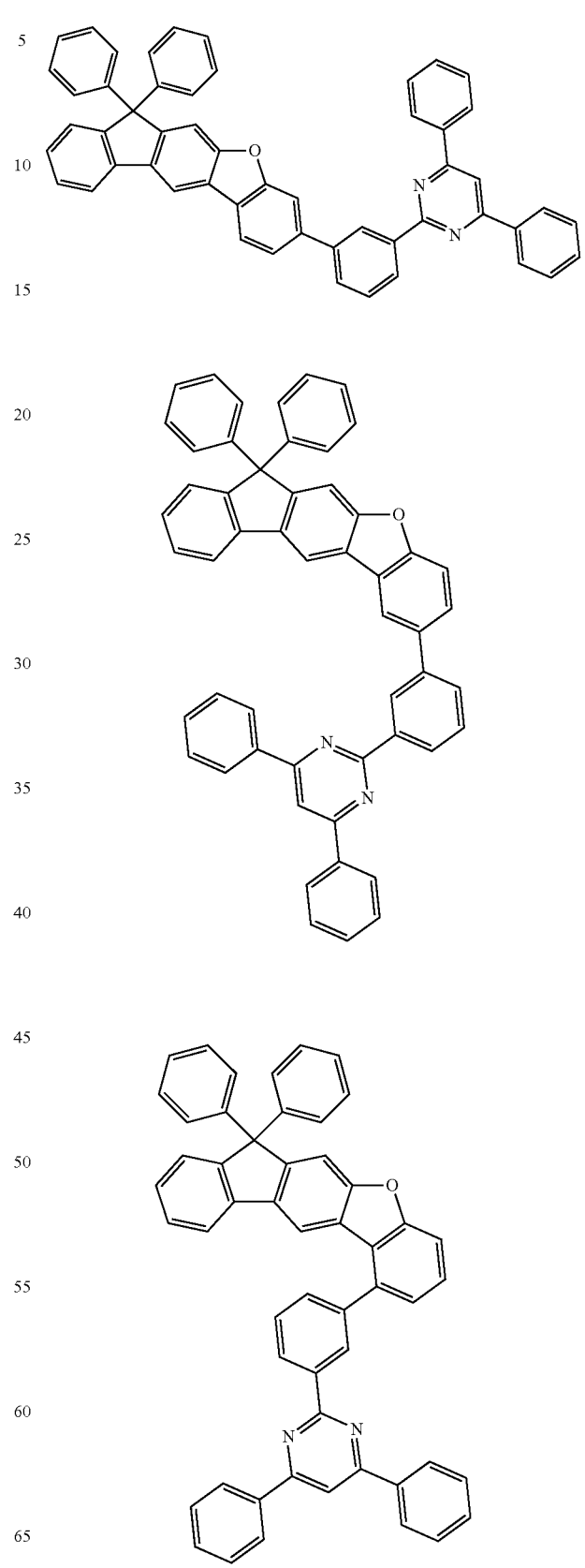

273
-continued
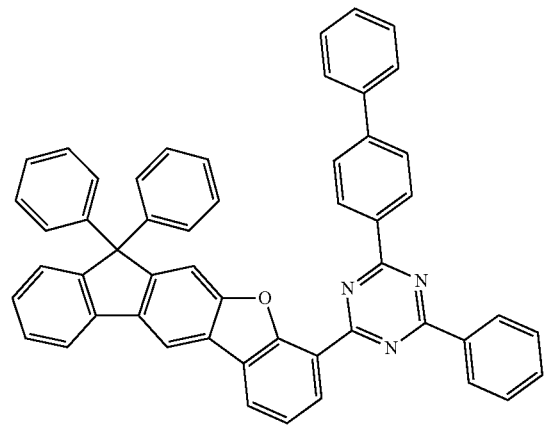
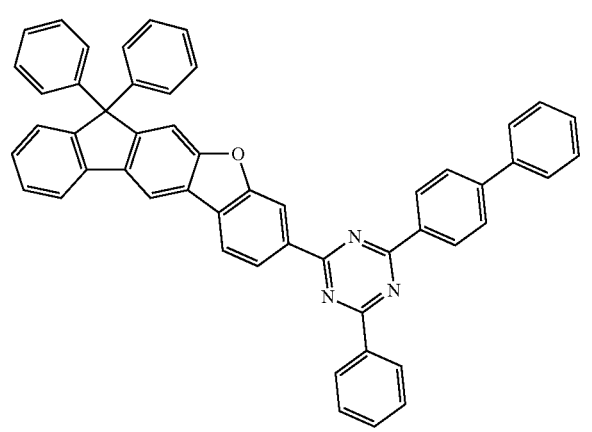
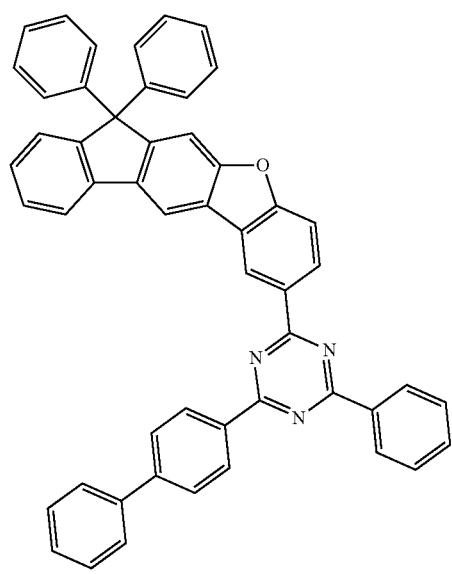
274
-continued
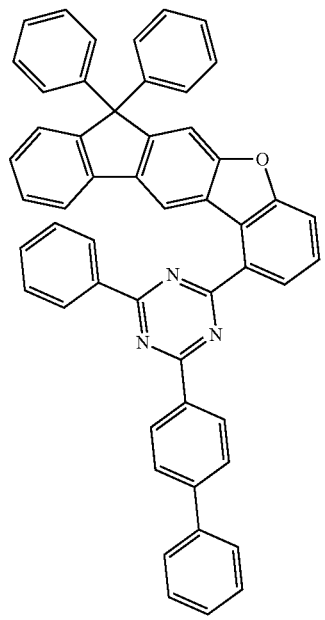
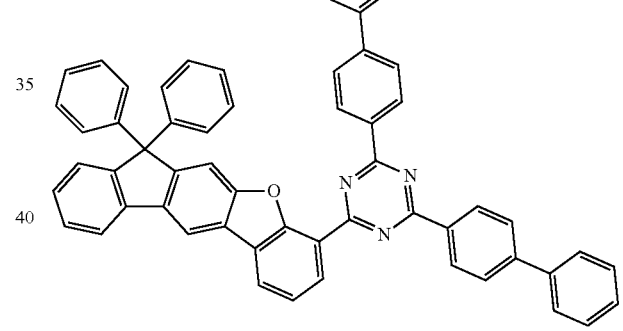
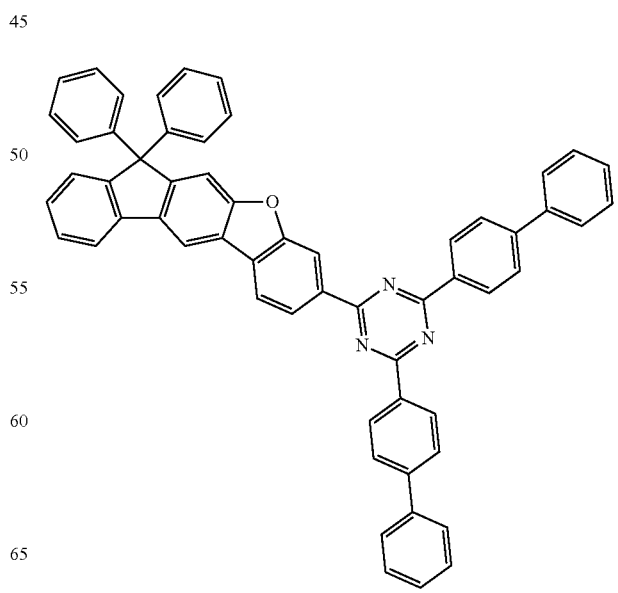

275
-continued
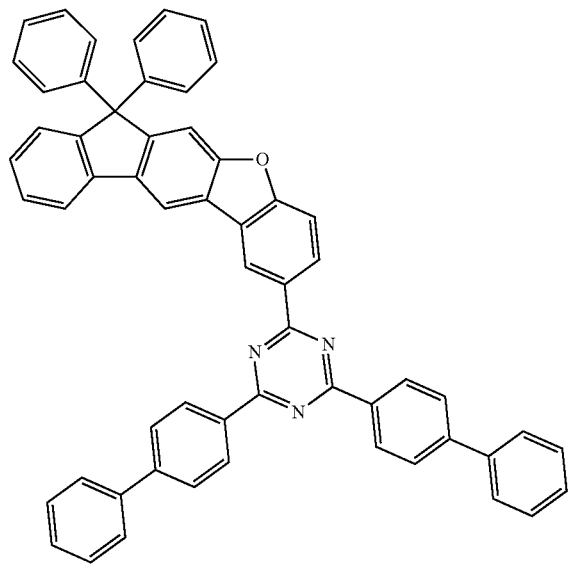
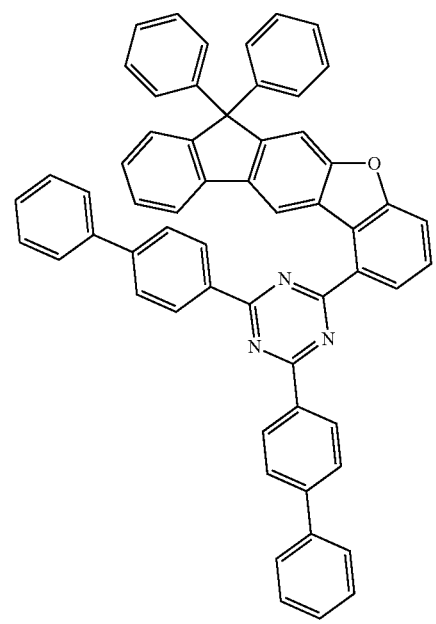
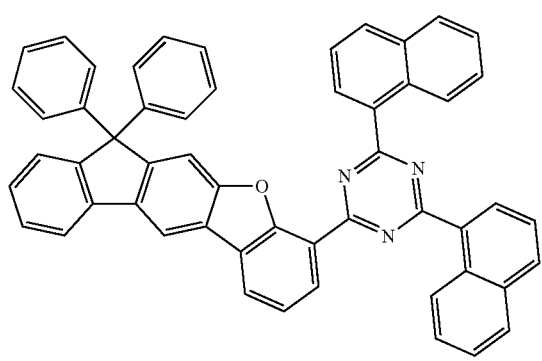
276
-continued
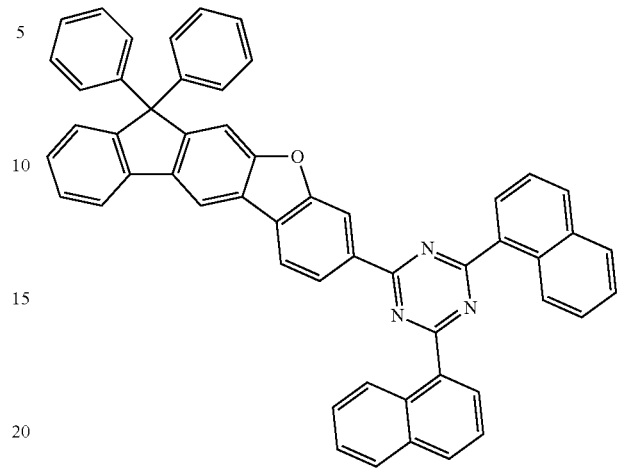
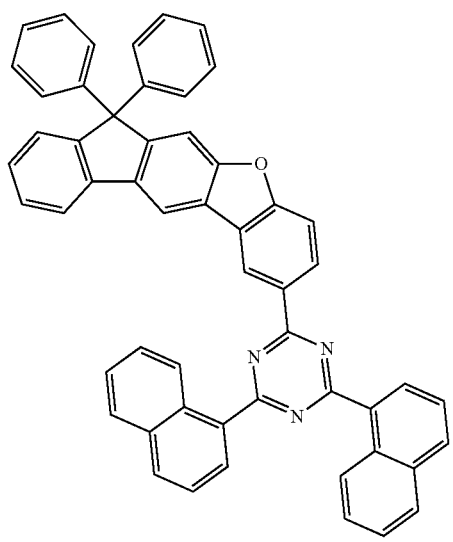
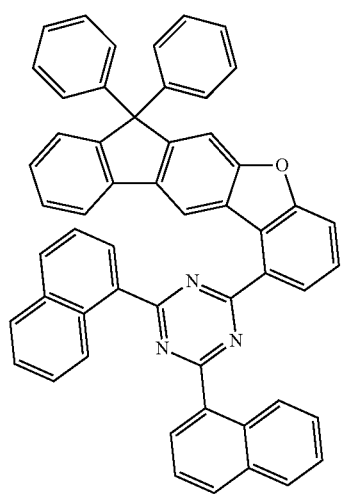

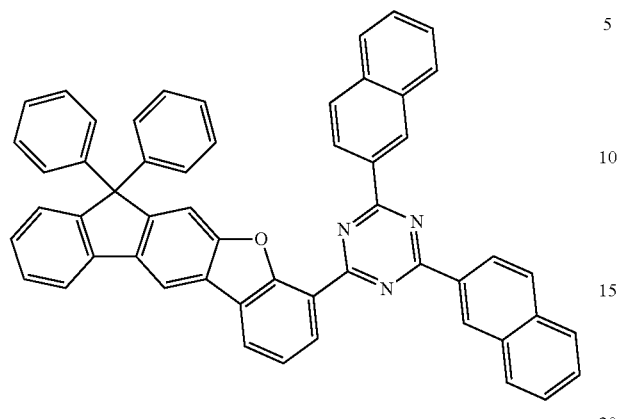
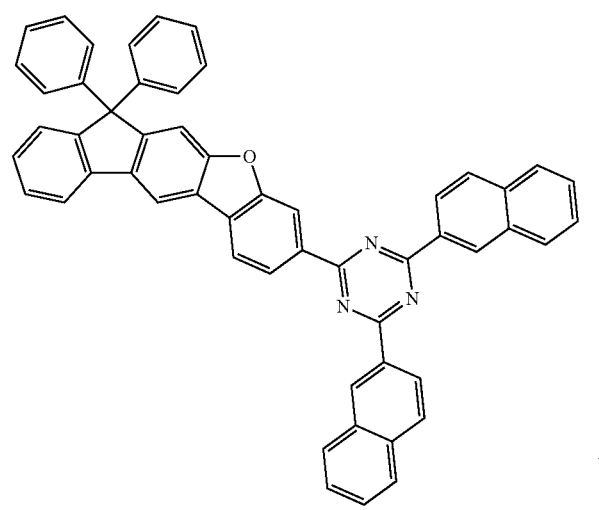
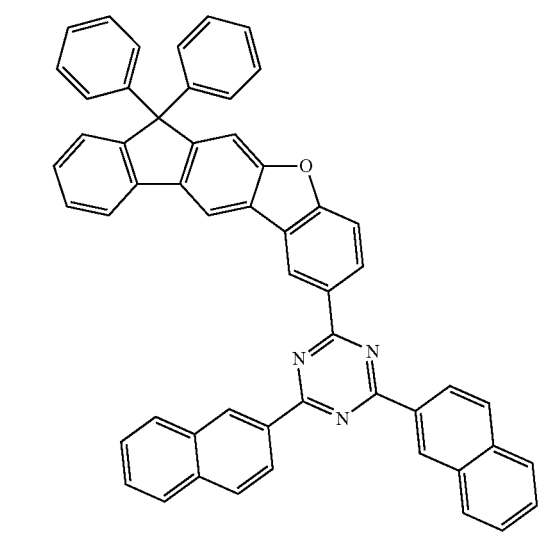
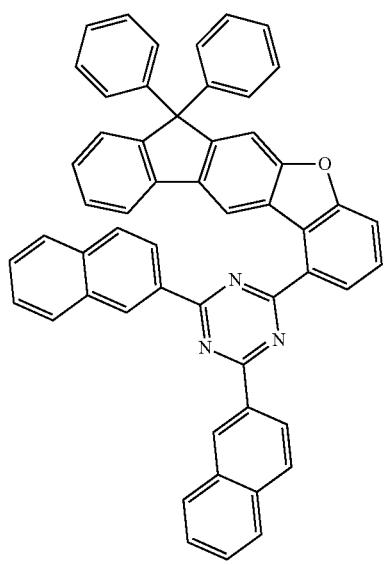
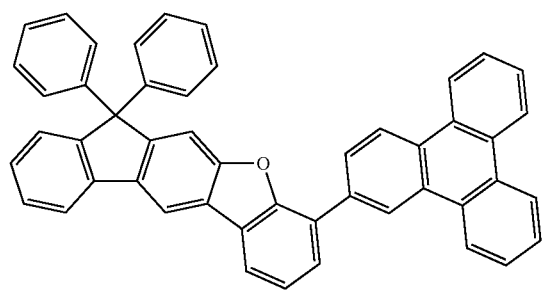
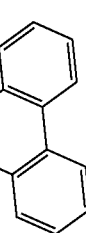

279
-continued
280
-continued
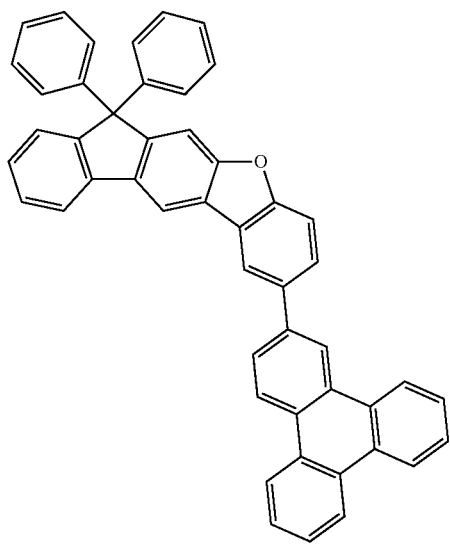
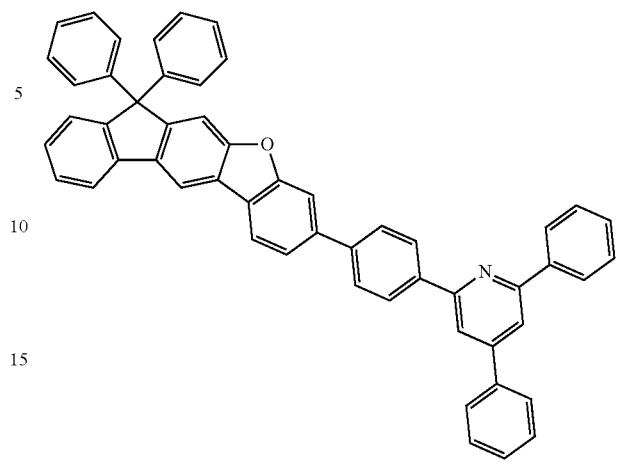
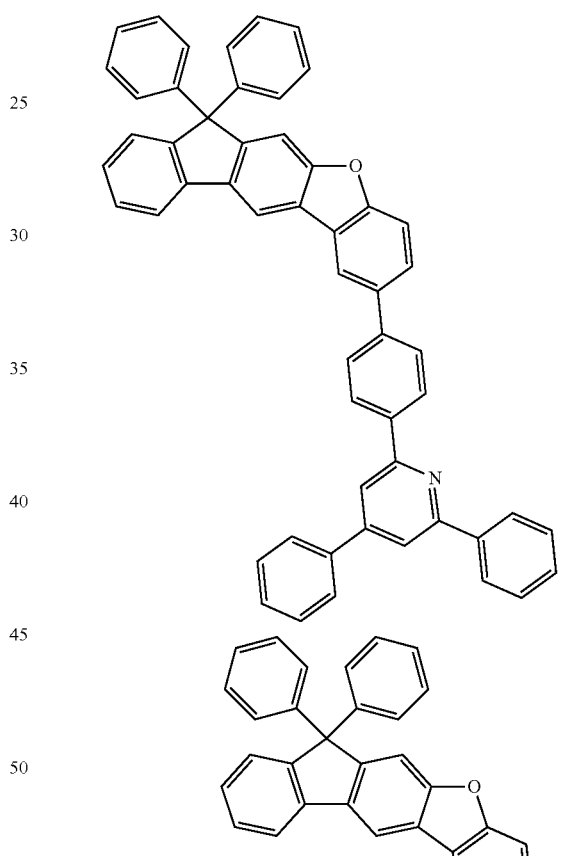
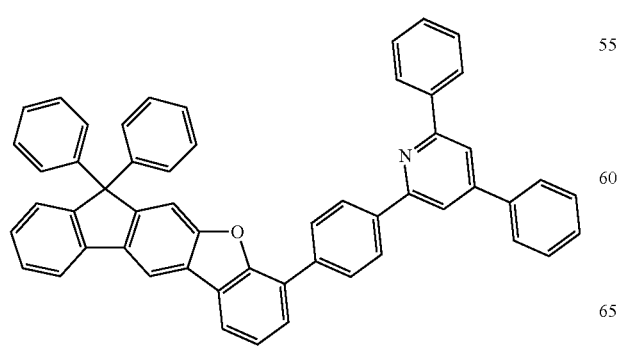
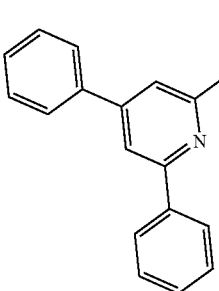

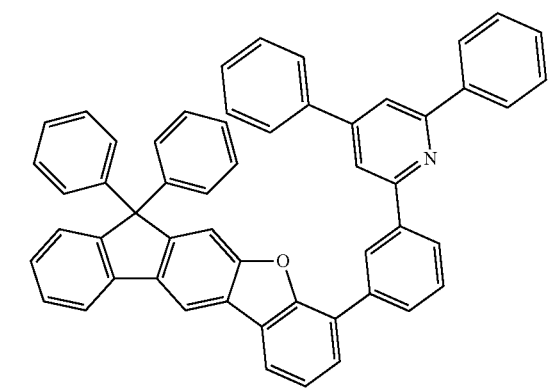
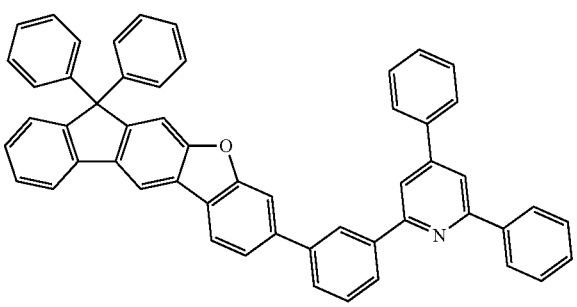
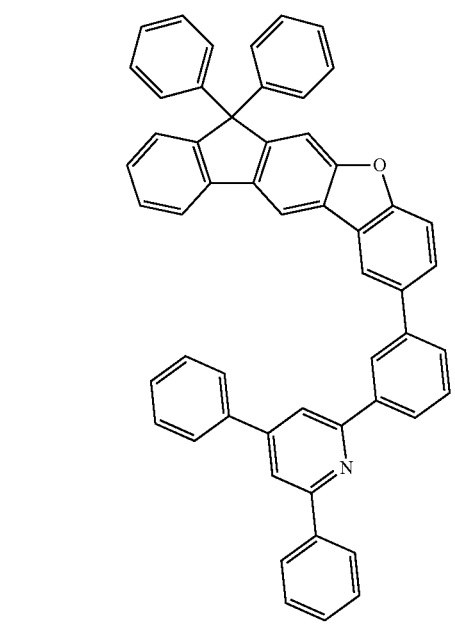
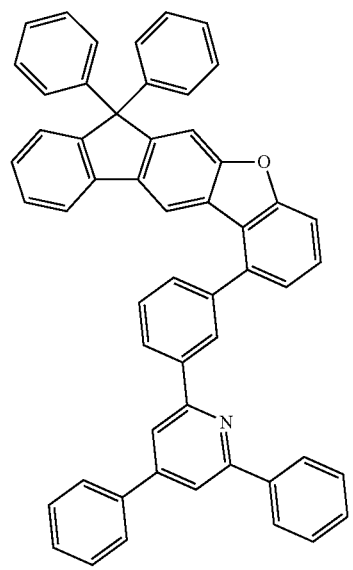
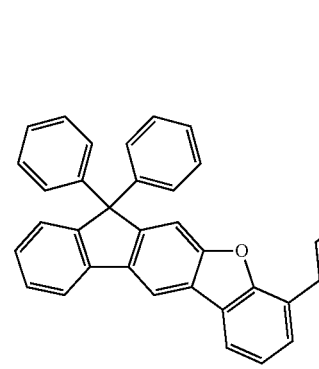
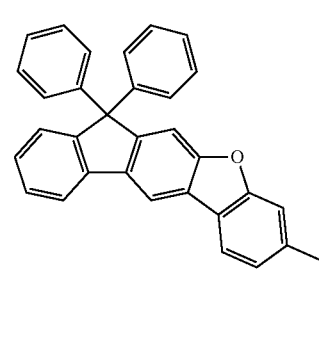

283
-continued
284
-continued
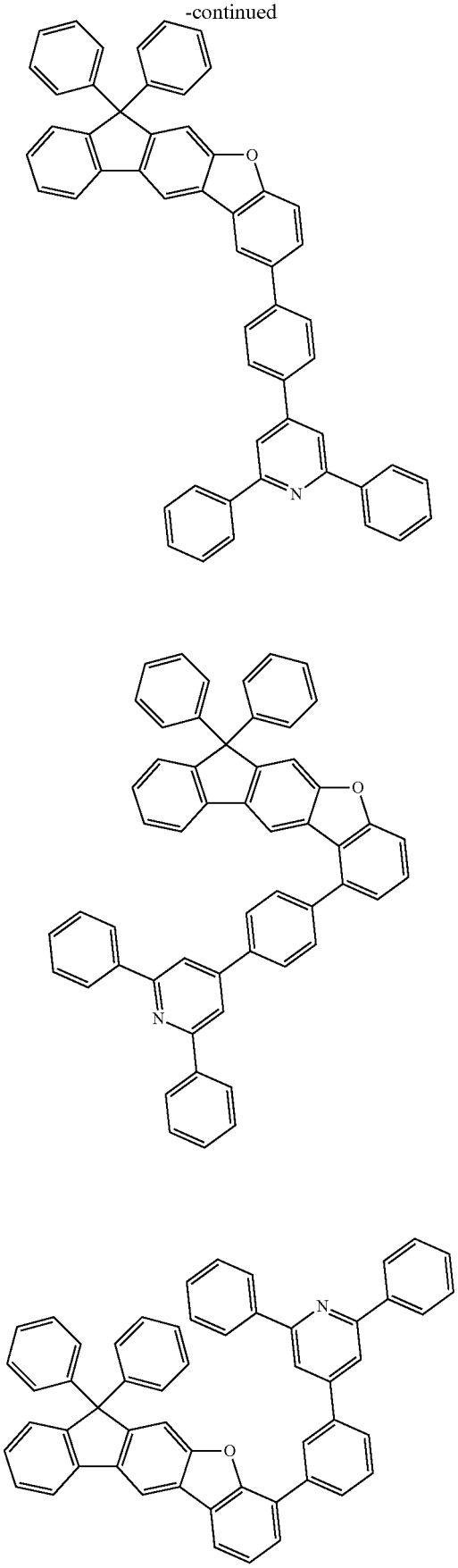
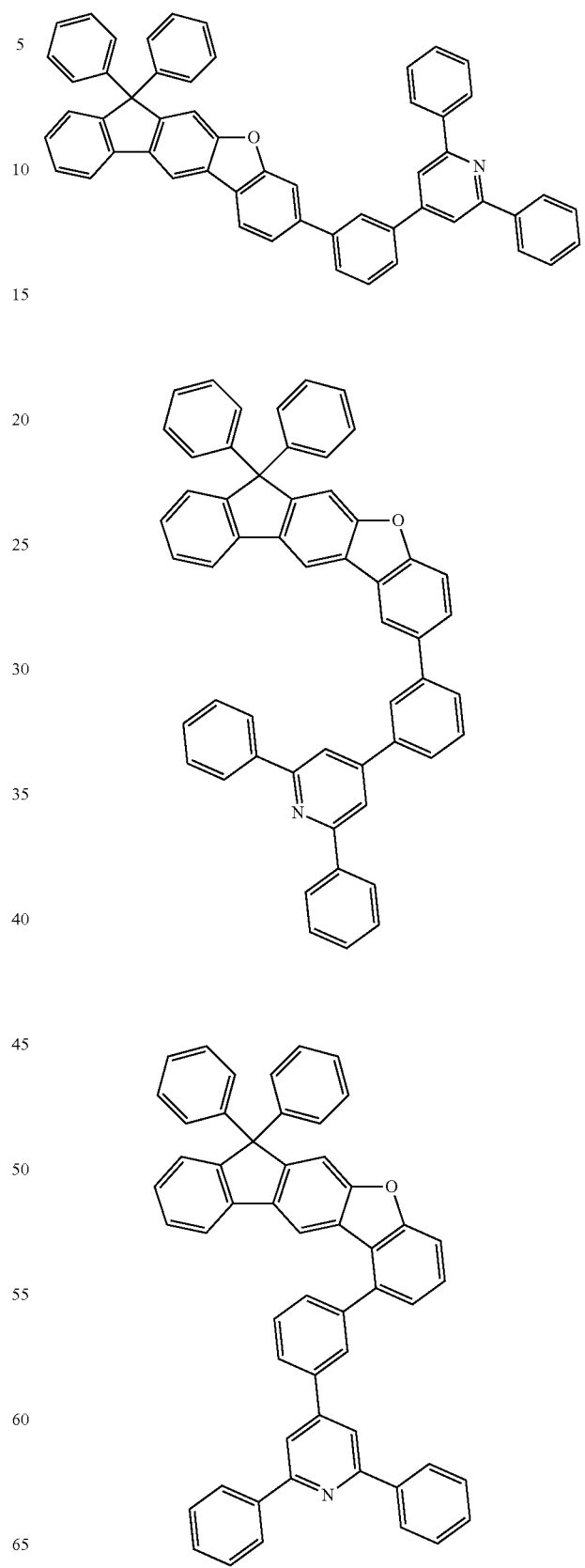

285
-continued
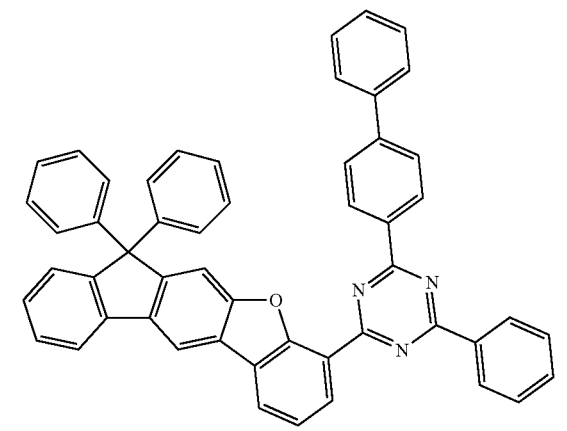
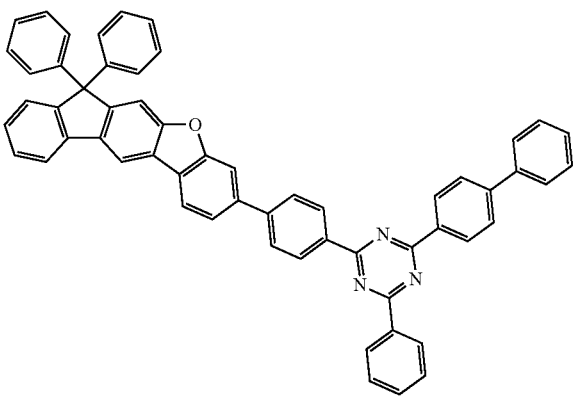
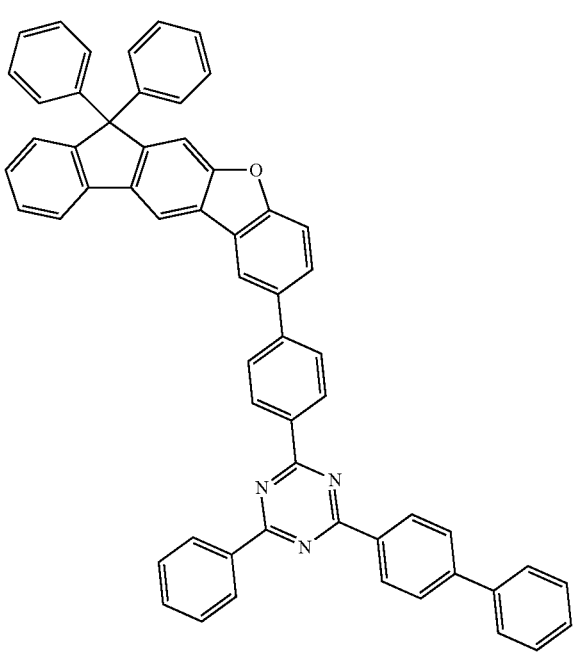
286
-continued
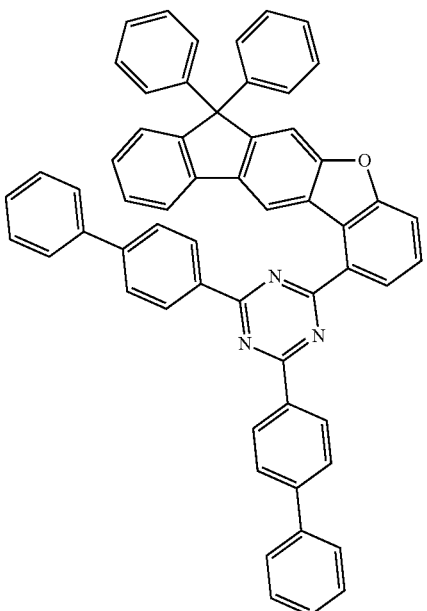
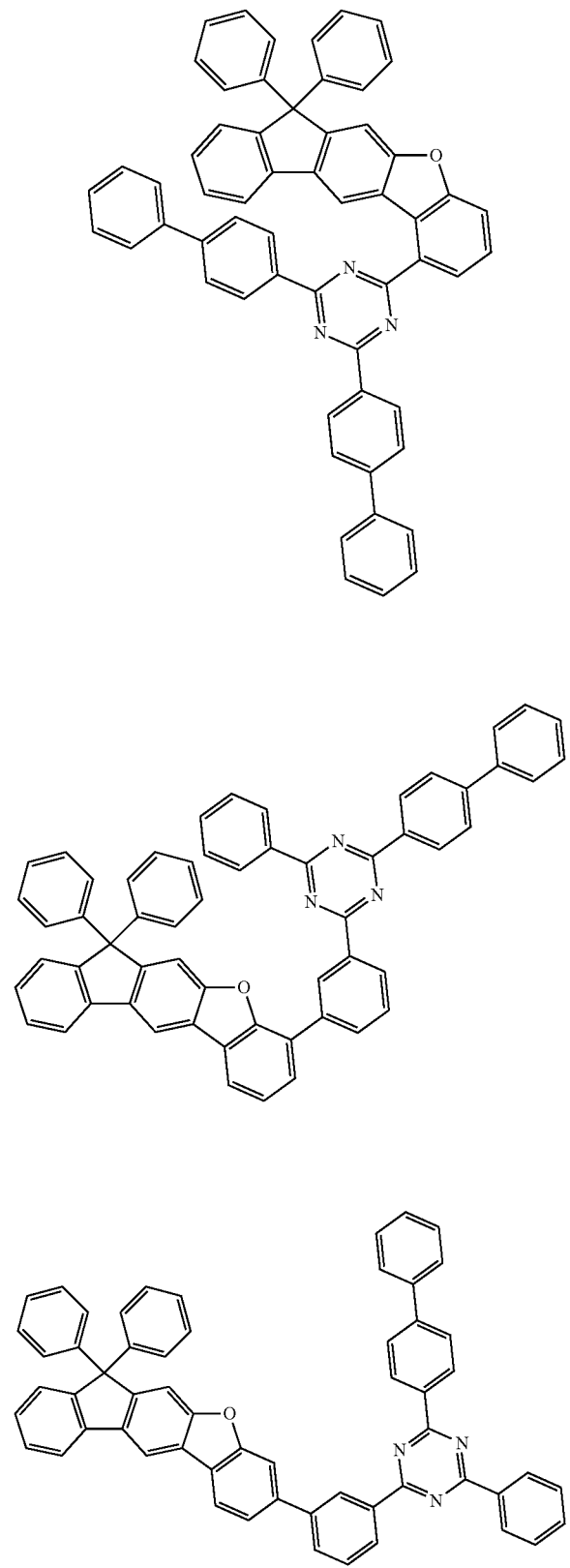

287
-continued
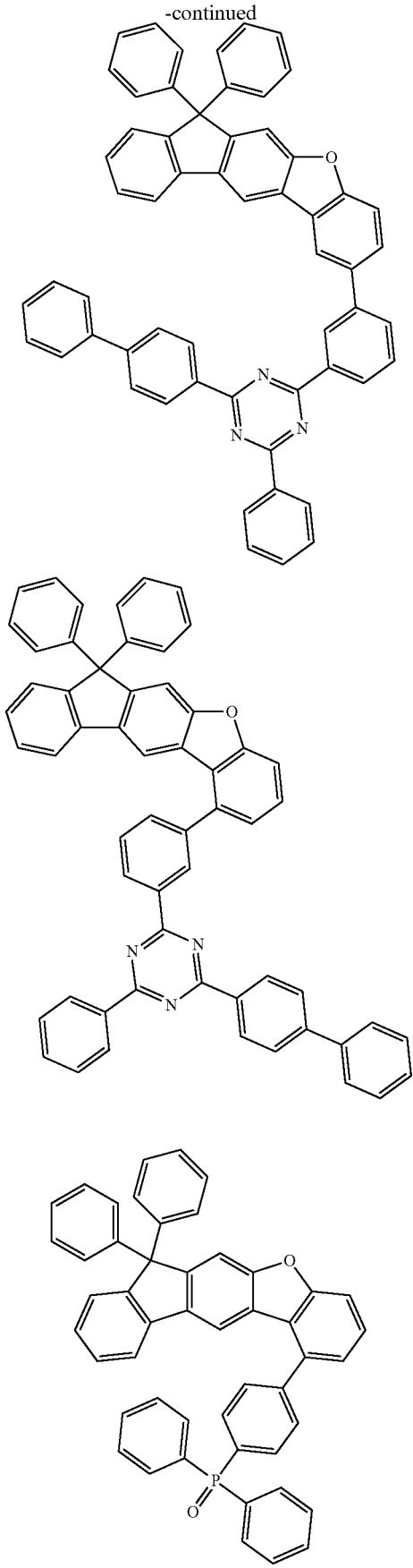
288
-continued
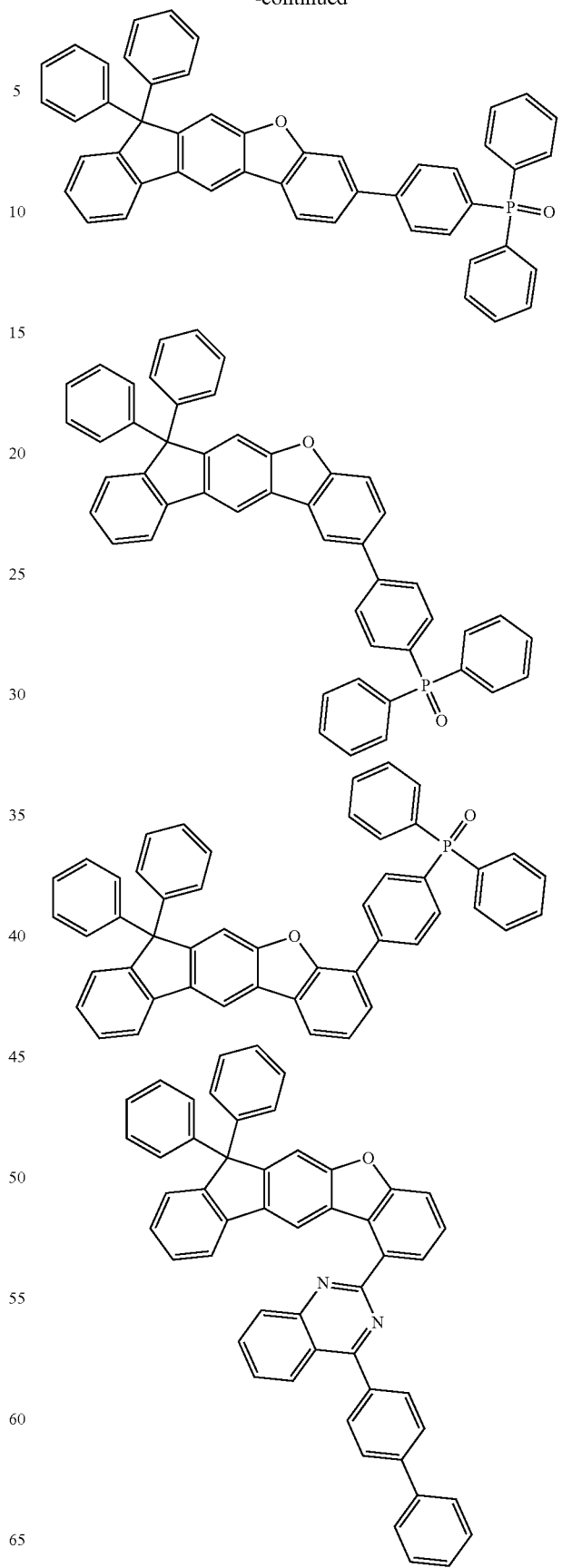

289
-continued
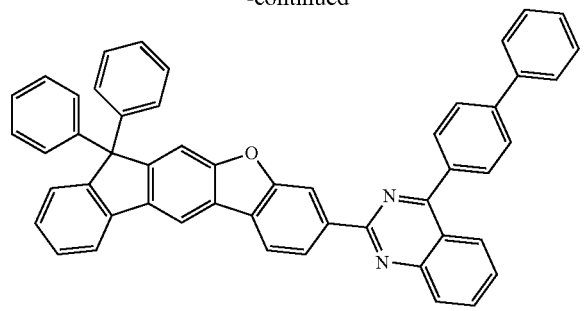
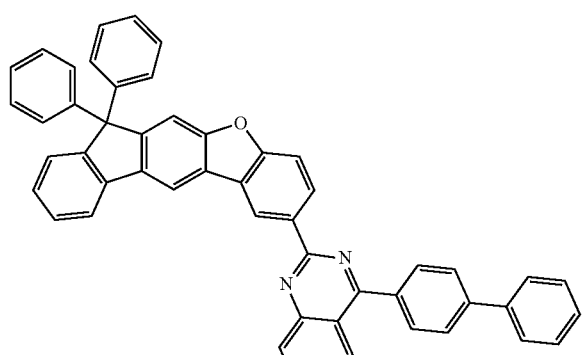
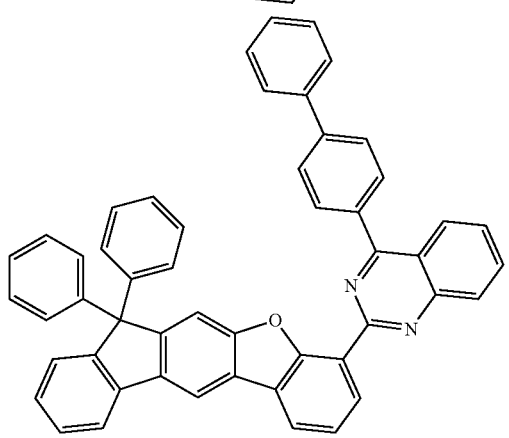
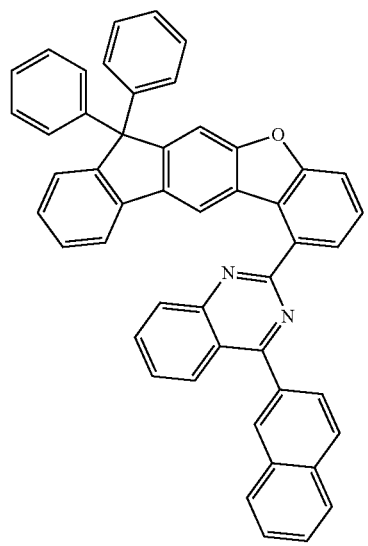
290
-continued
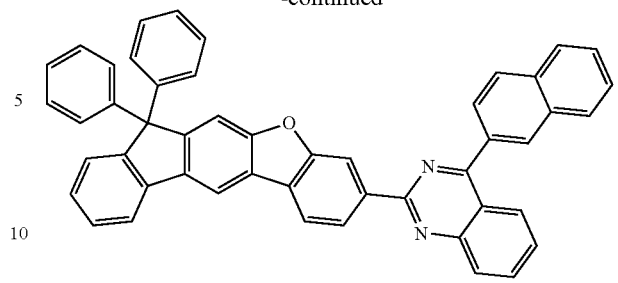
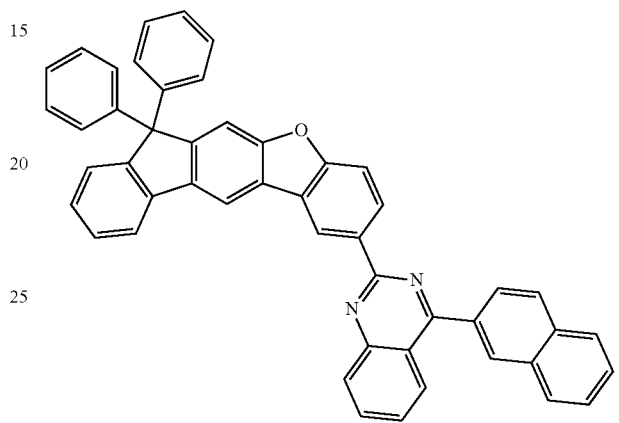
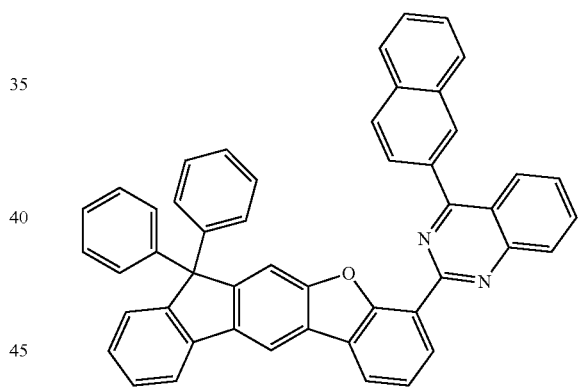
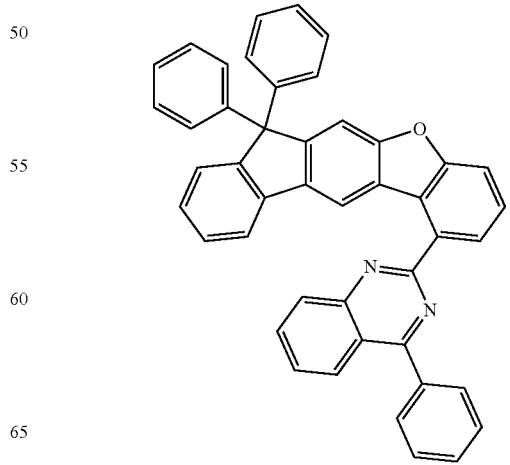

291
-continued
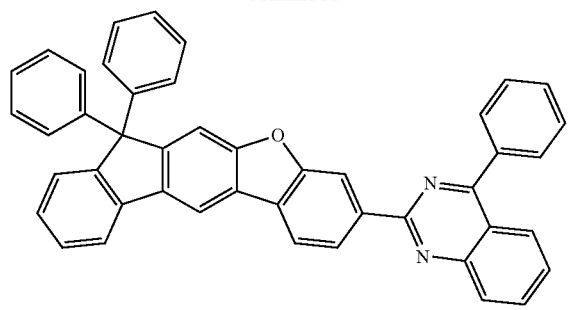
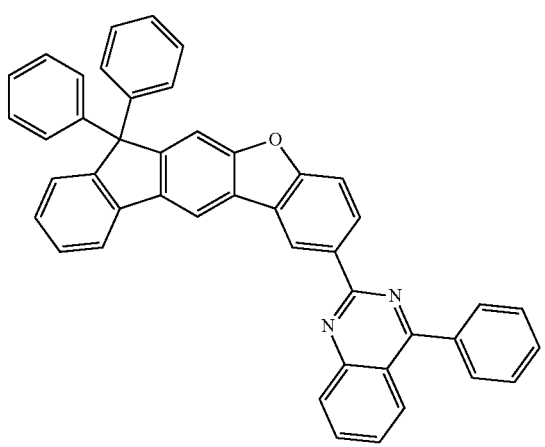
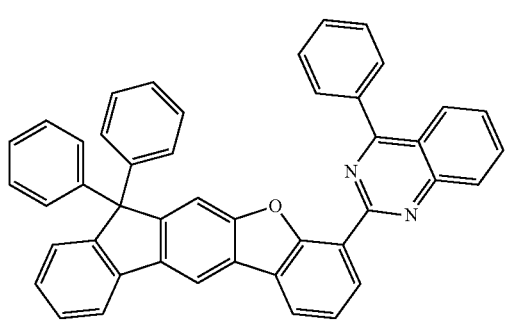
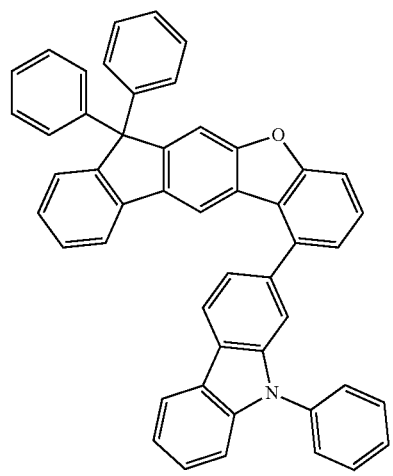
292
-continued
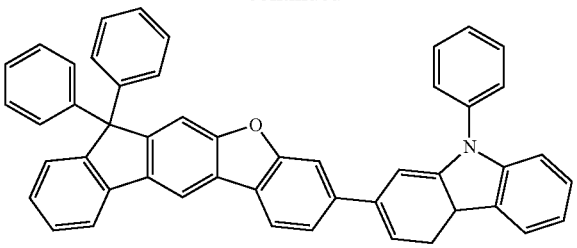
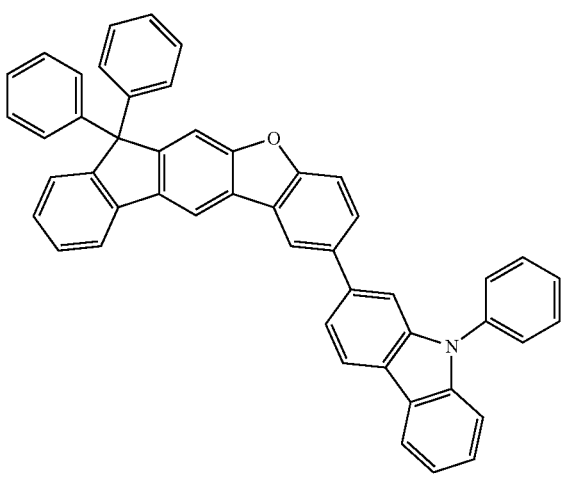
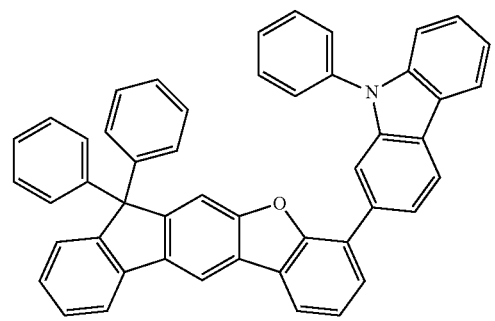
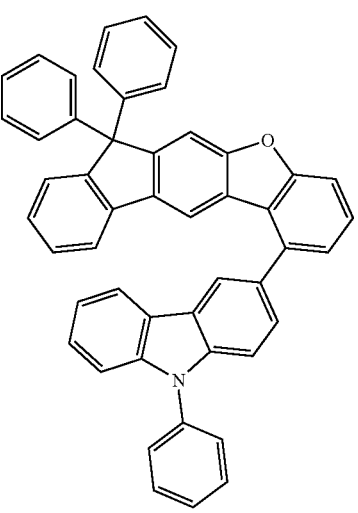

293
-continued
294
-continued
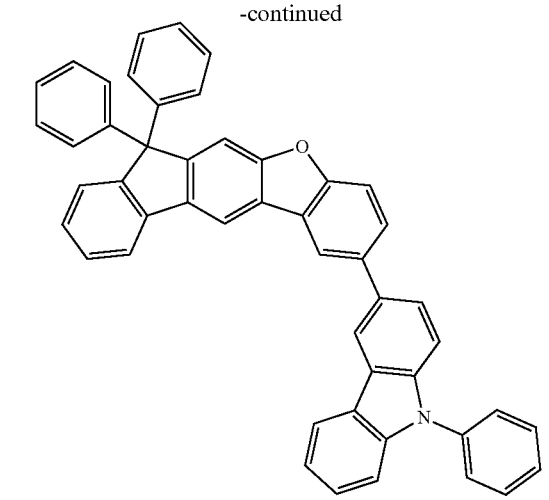
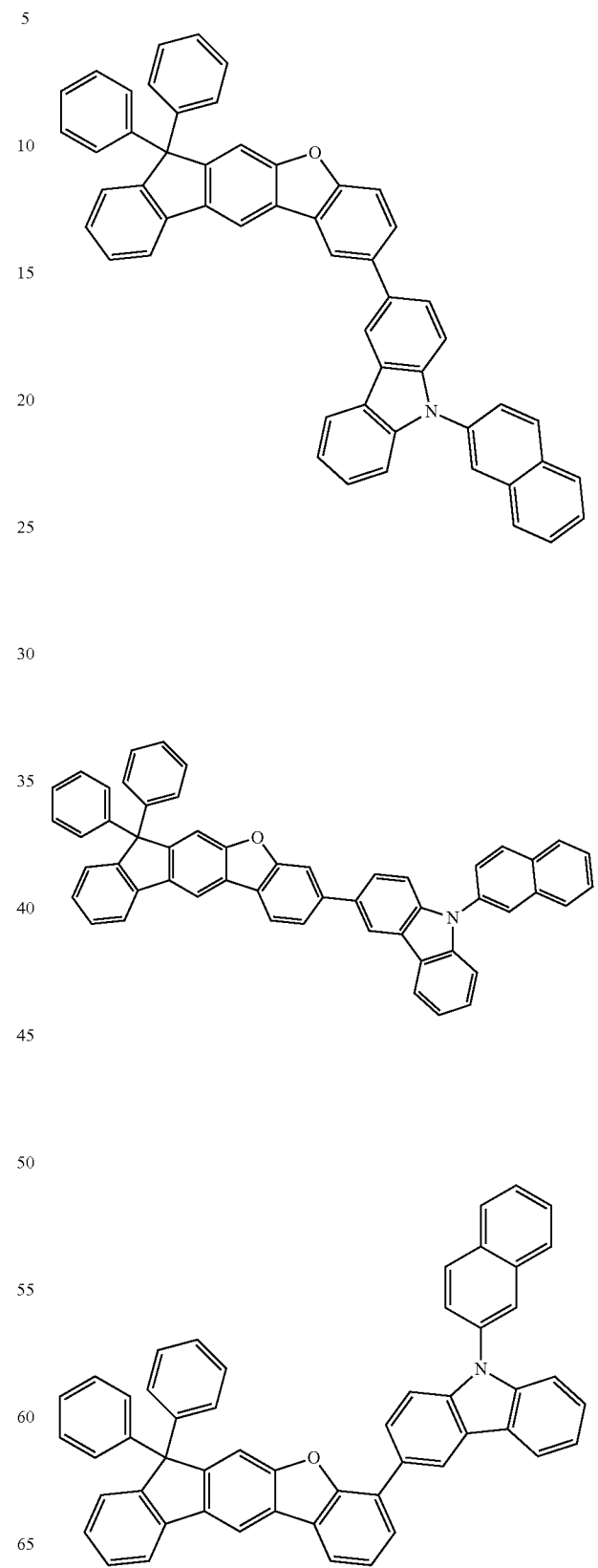

295
-continued
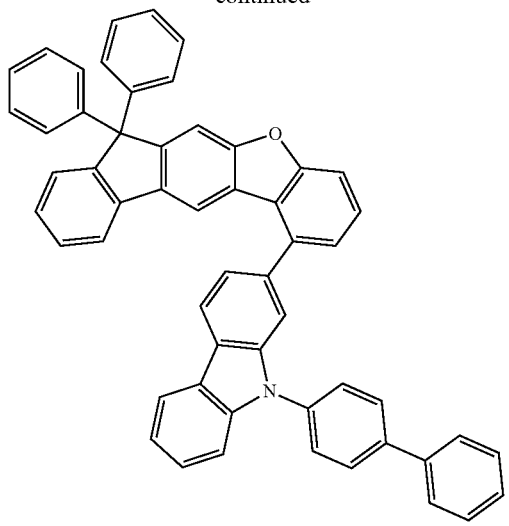
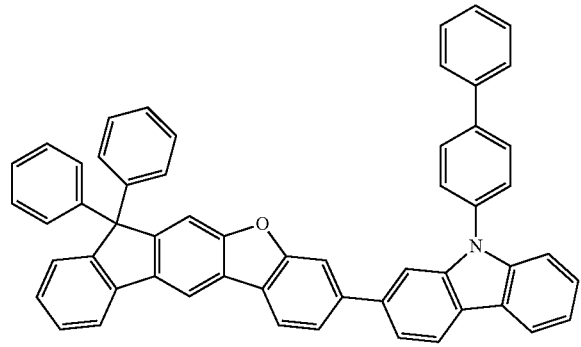
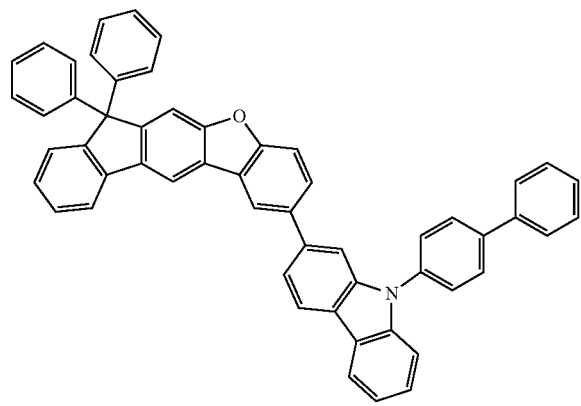
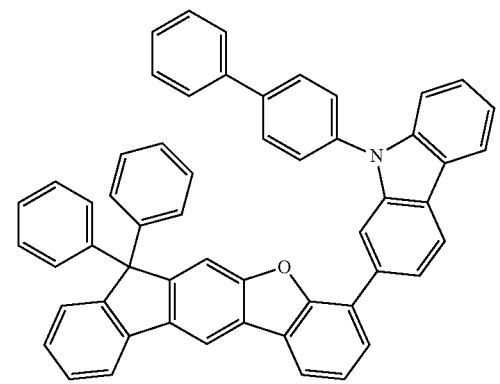
296
-continued
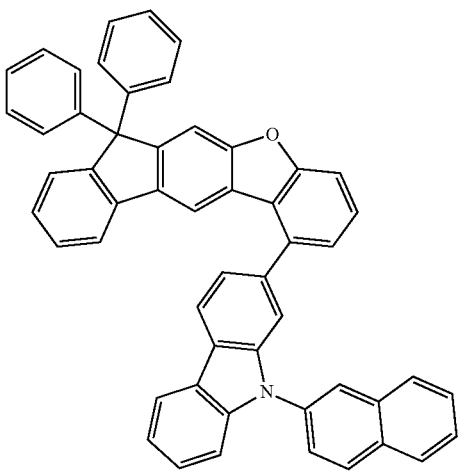
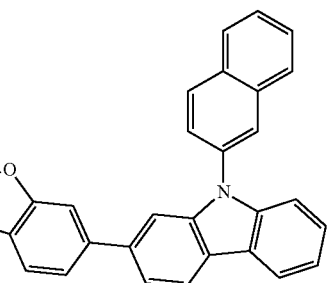
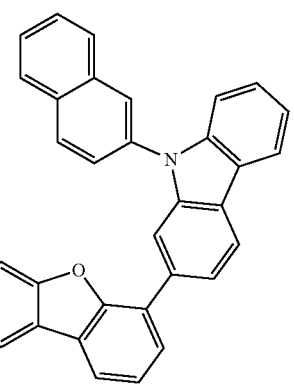

297
-continued
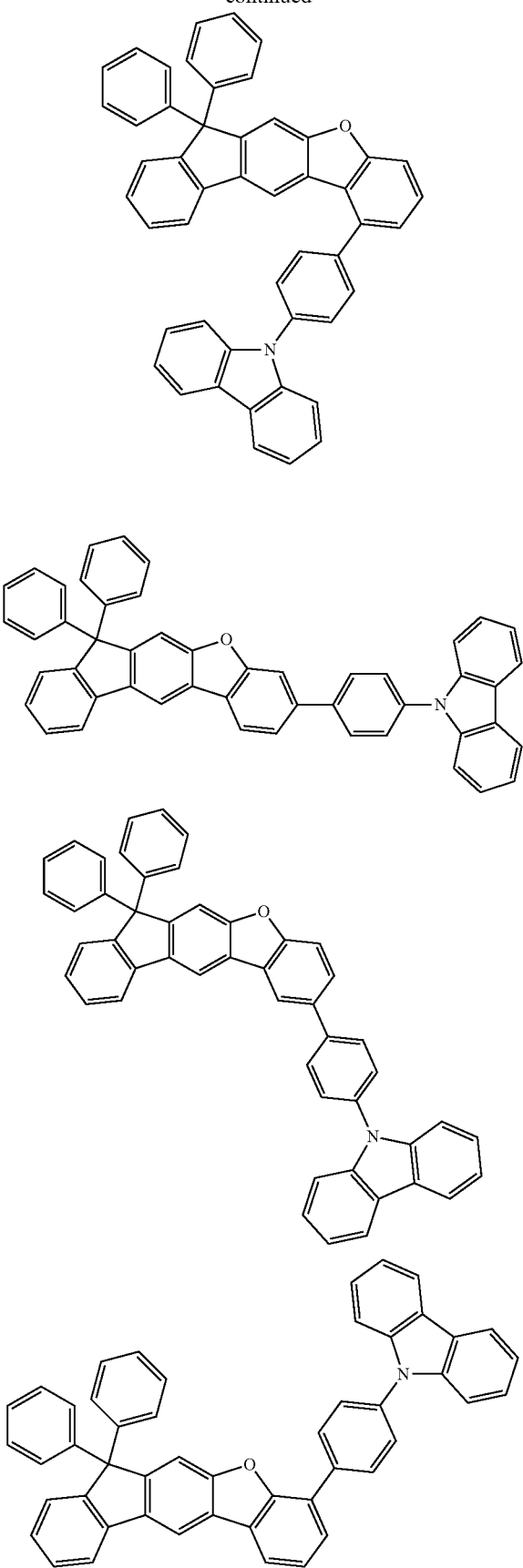
298
-continued
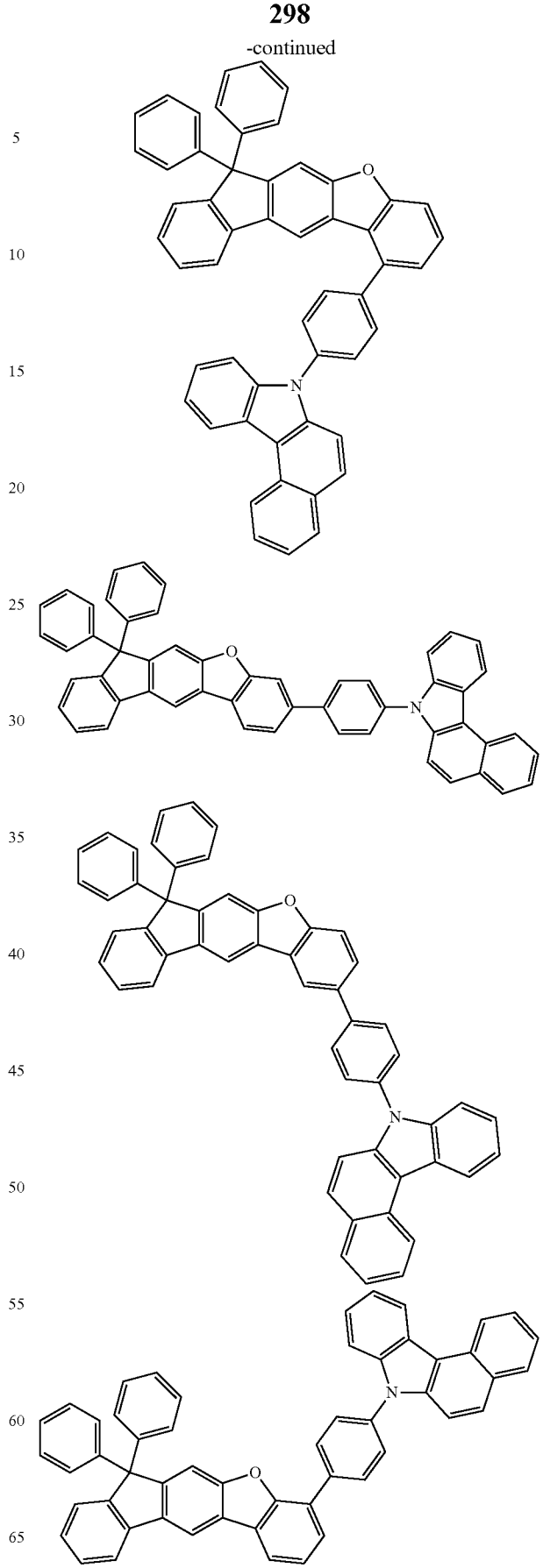

299
-continued
300
-continued
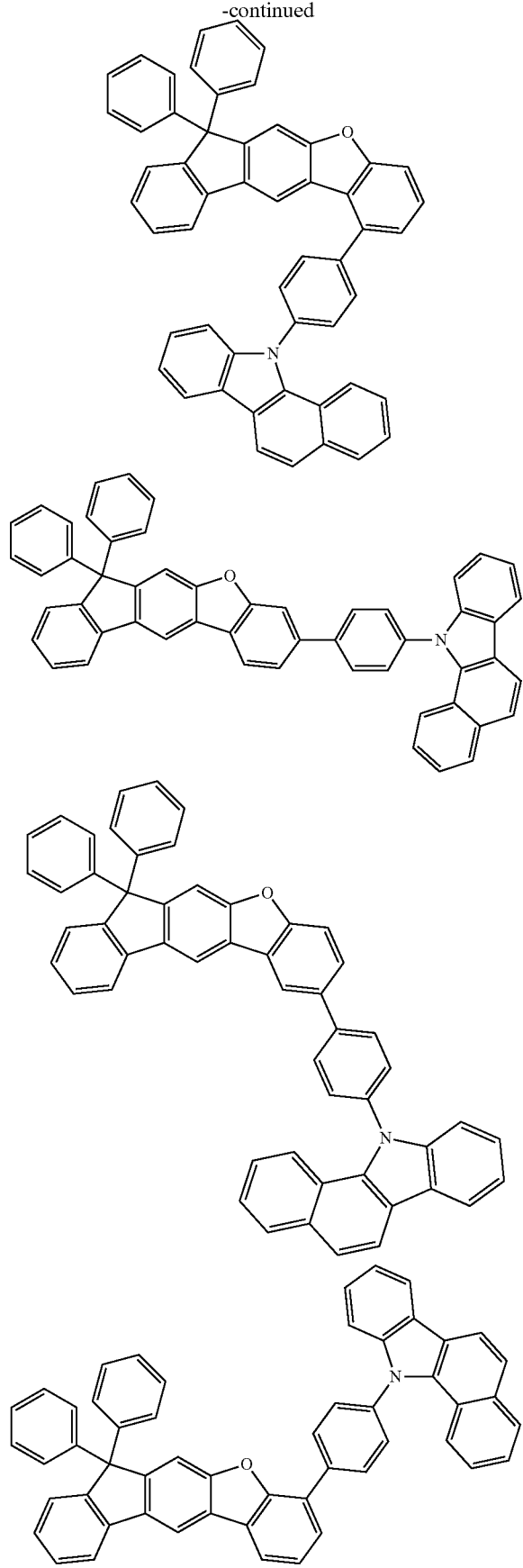
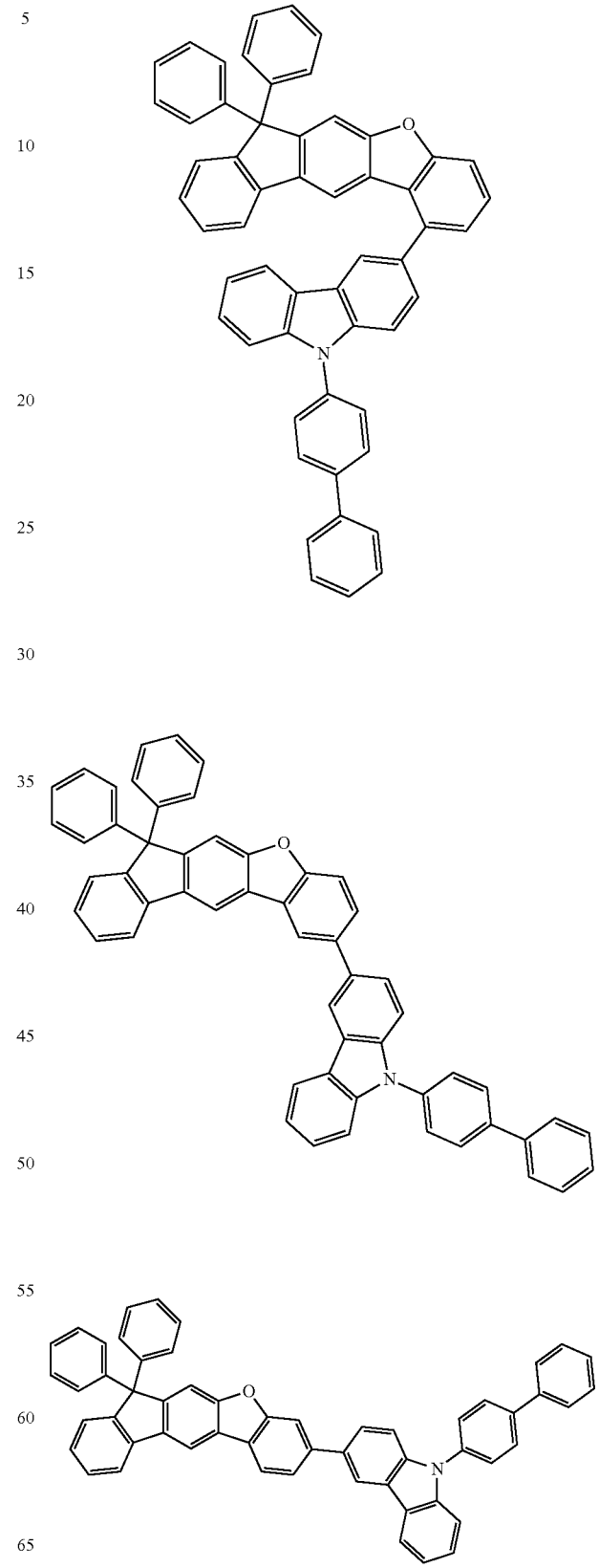

301
-continued
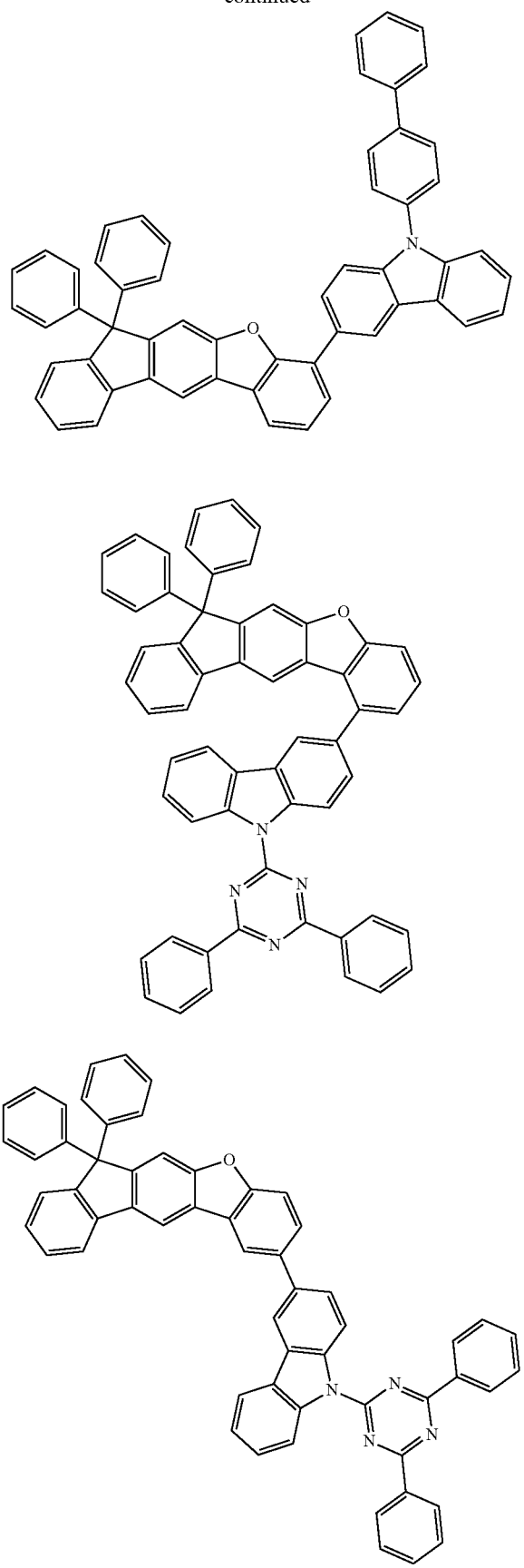
302
-continued
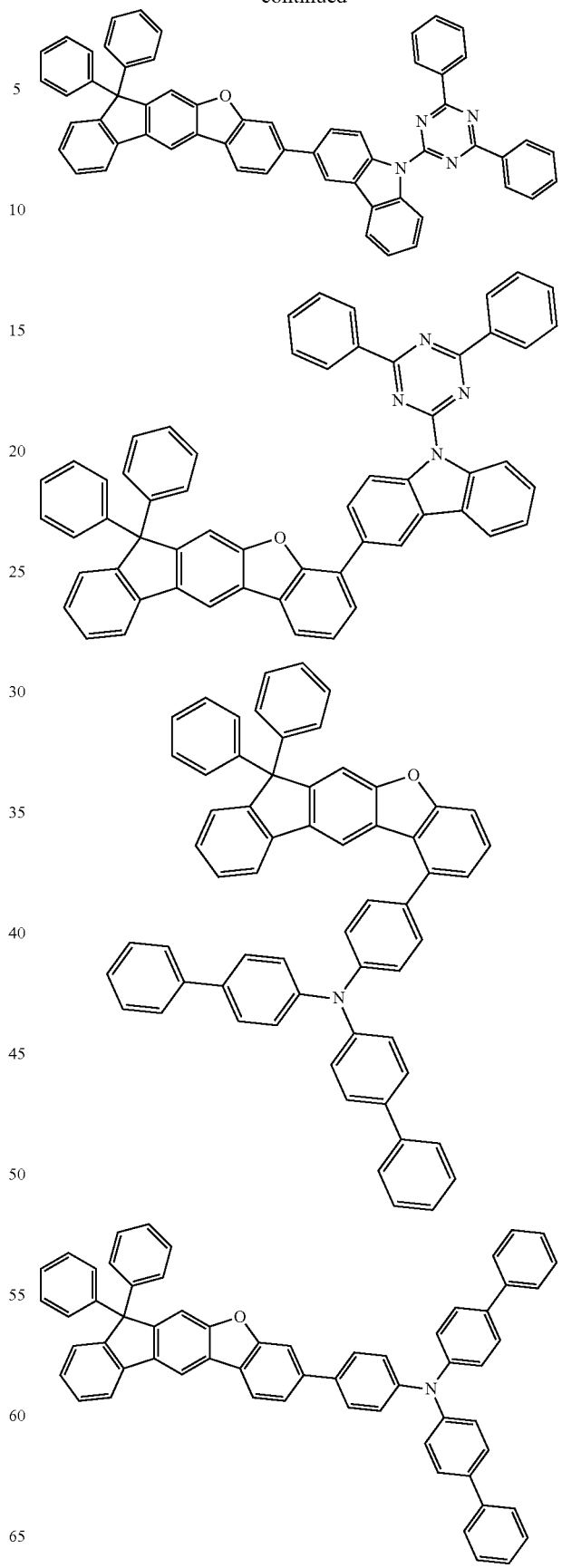

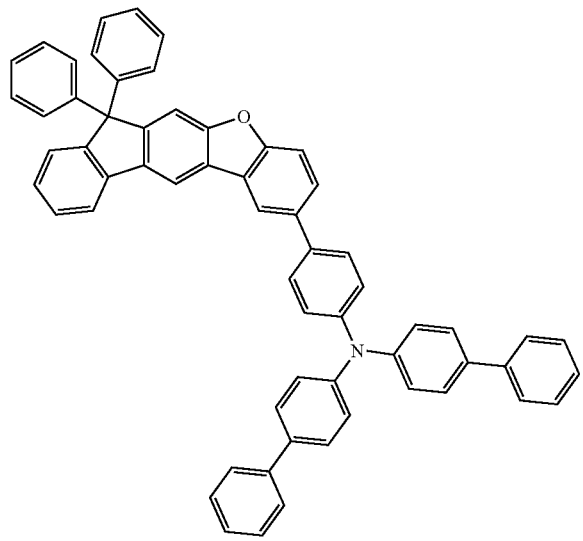
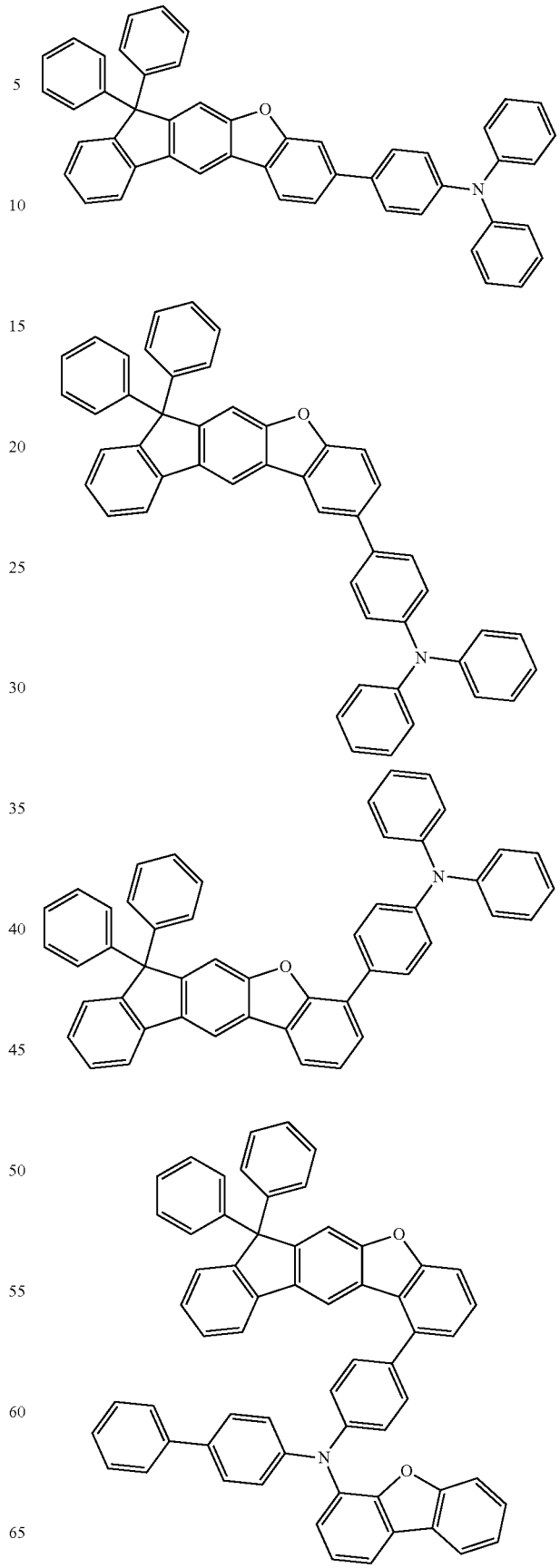

305
-continued

306
-continued

307
-continued
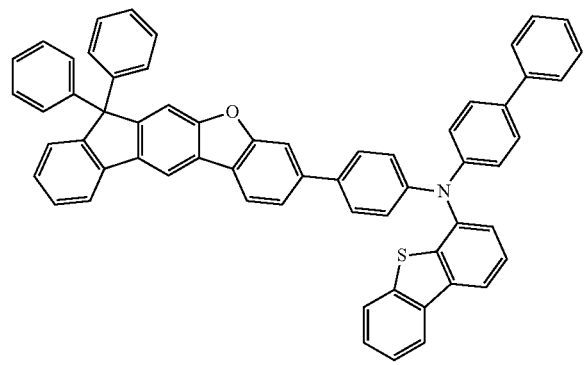
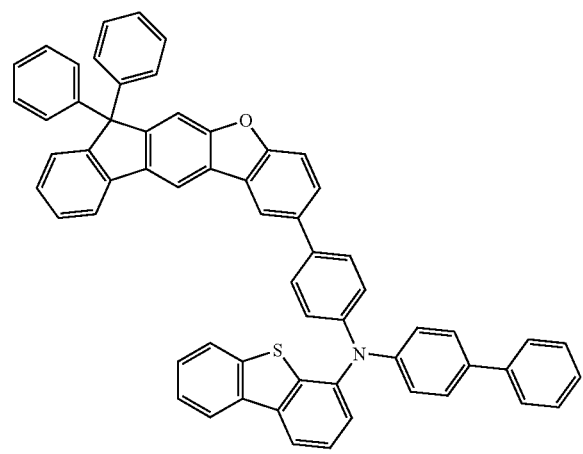
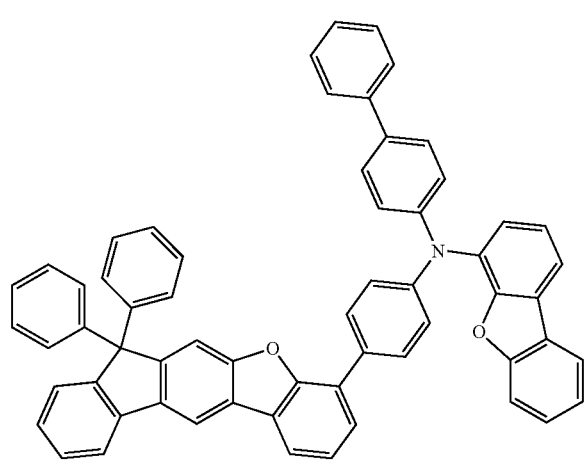
308
-continued
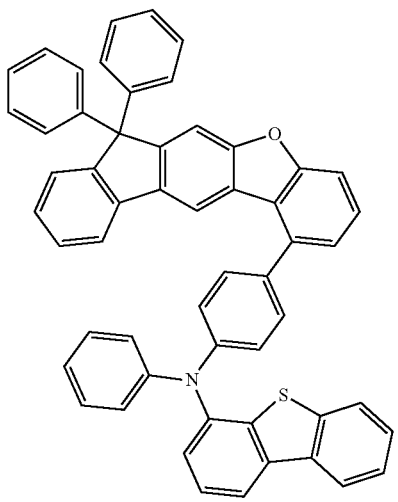
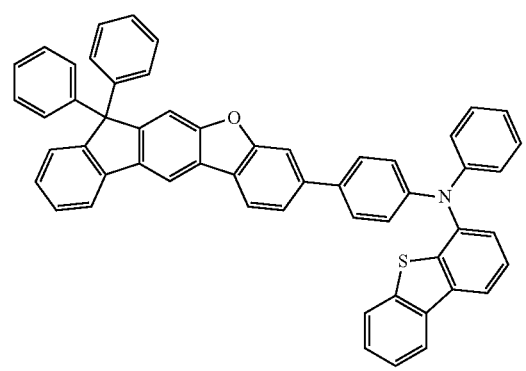
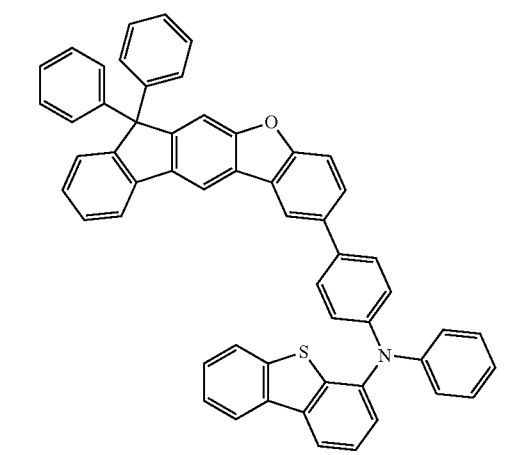
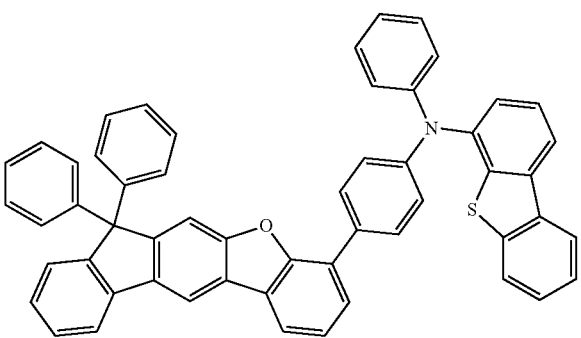

309
-continued
310
-continued
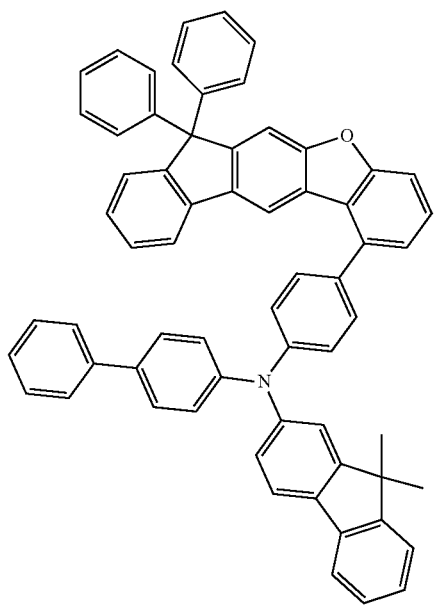
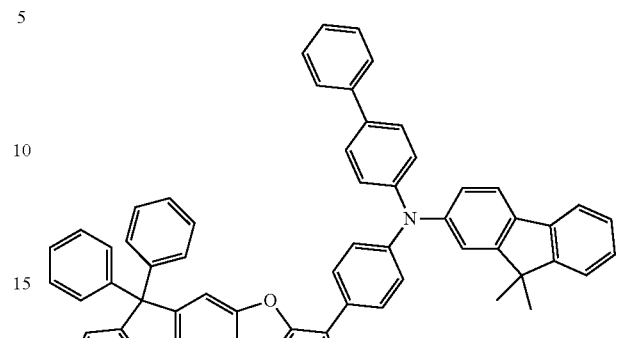
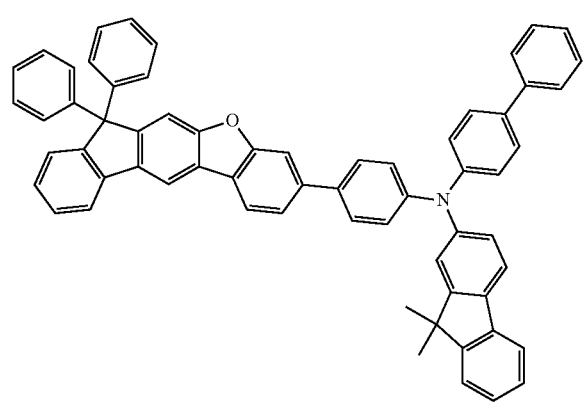
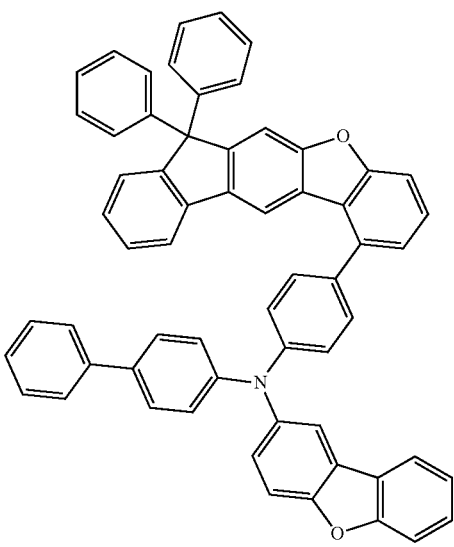
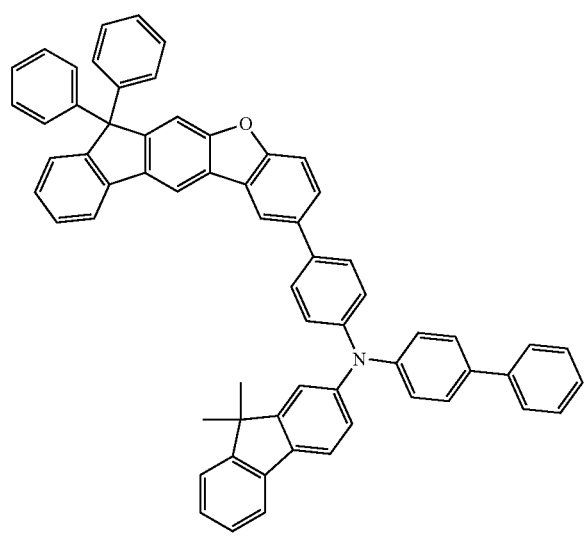
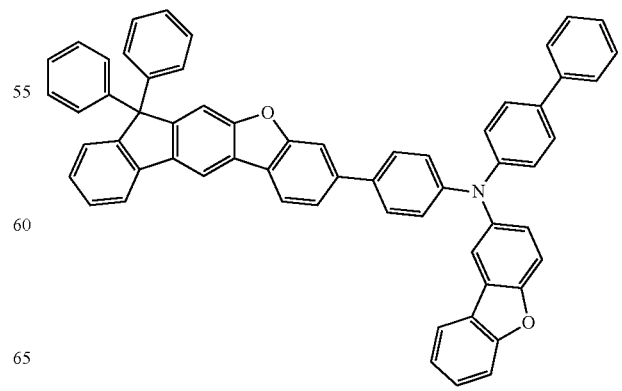

311
-continued
312
-continued
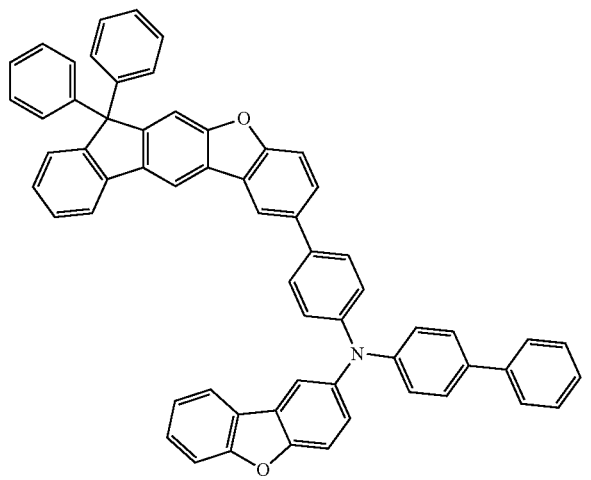
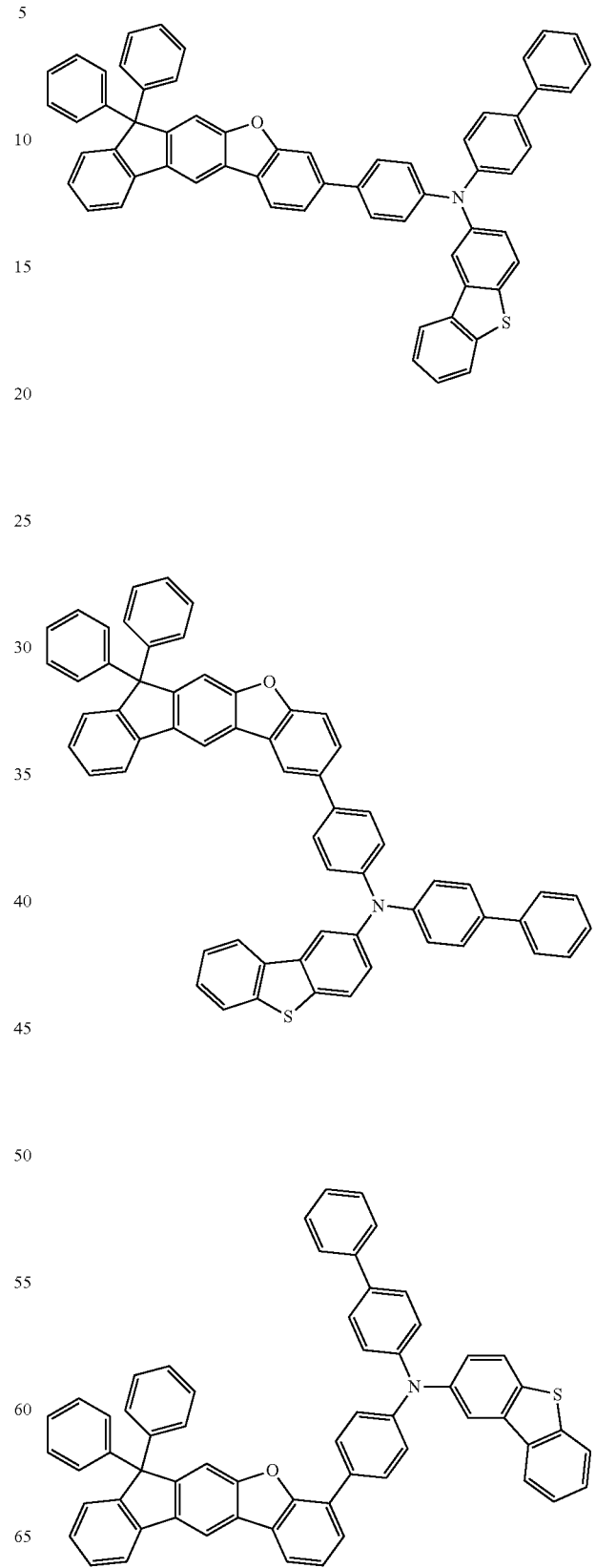

313
-continued
314
-continued
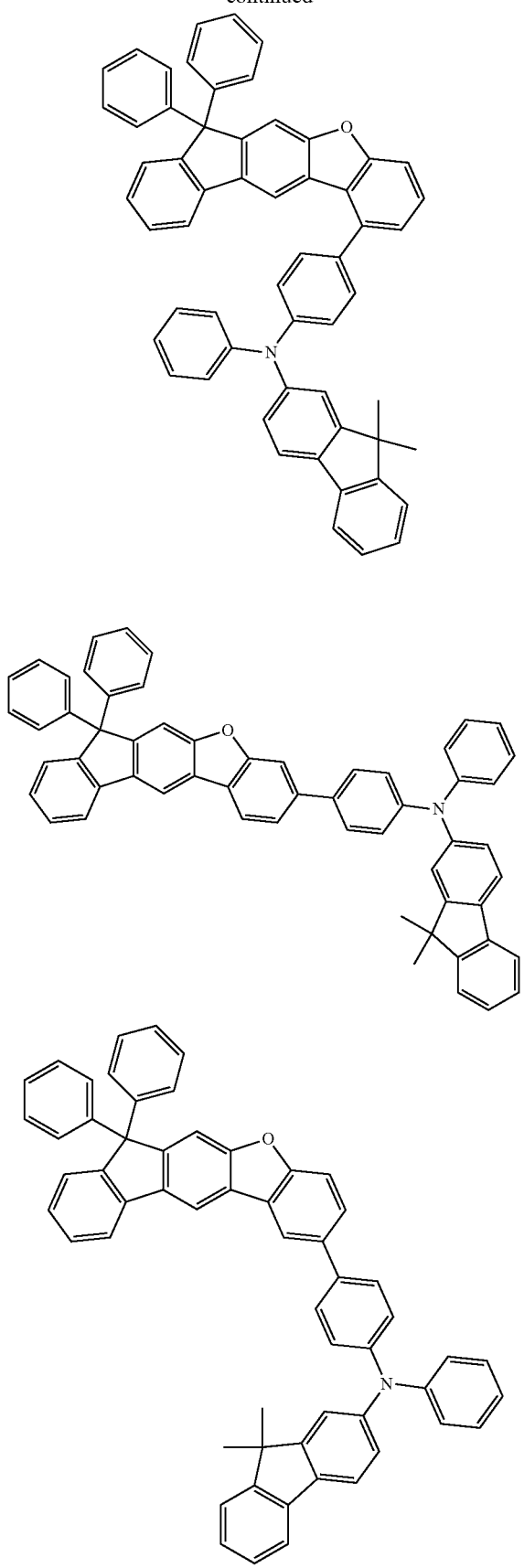
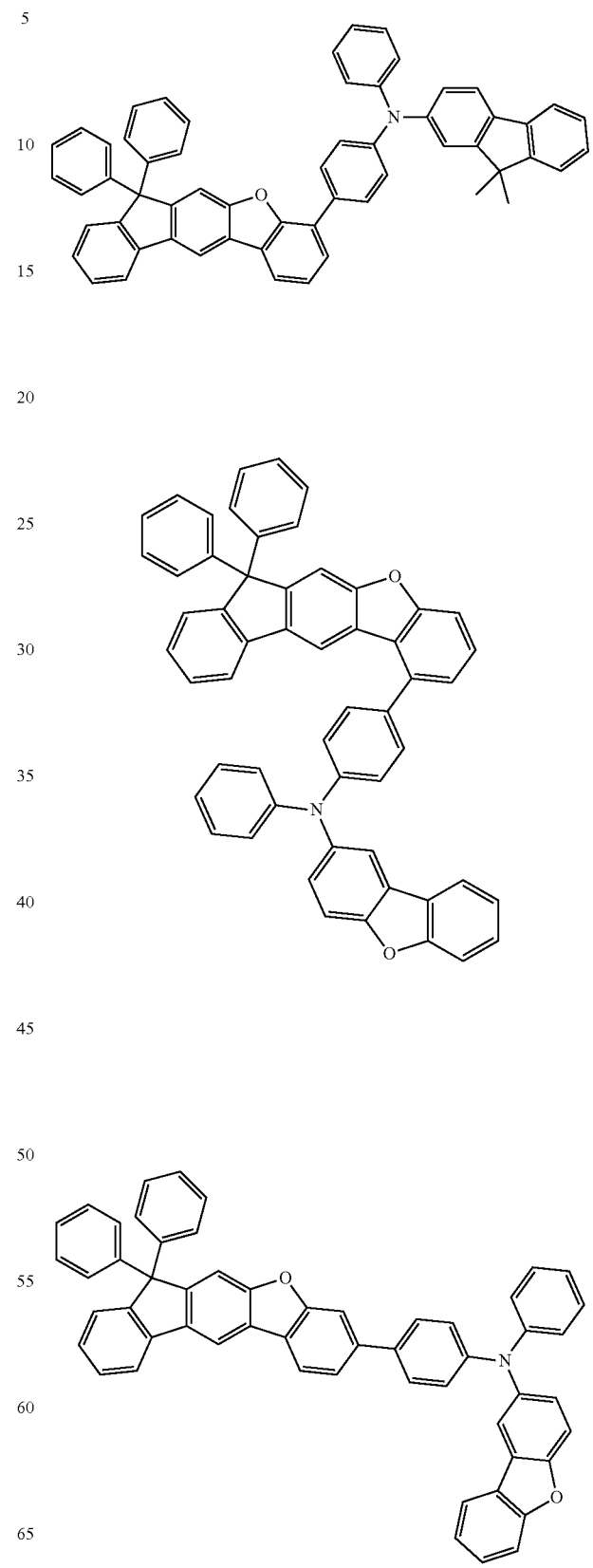

315
-continued
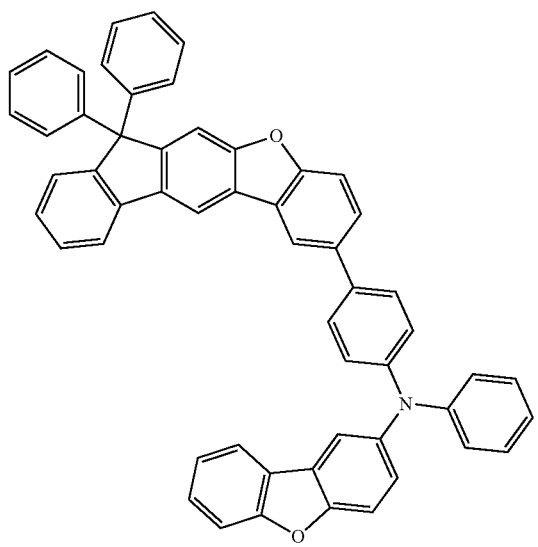
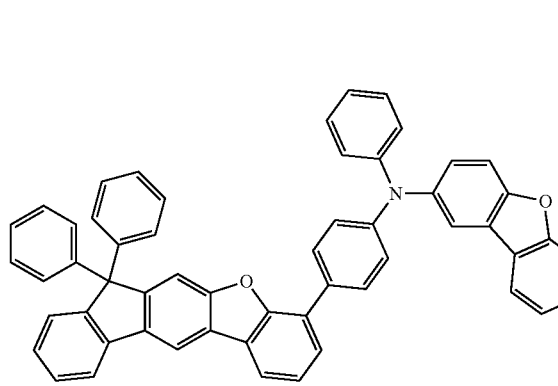
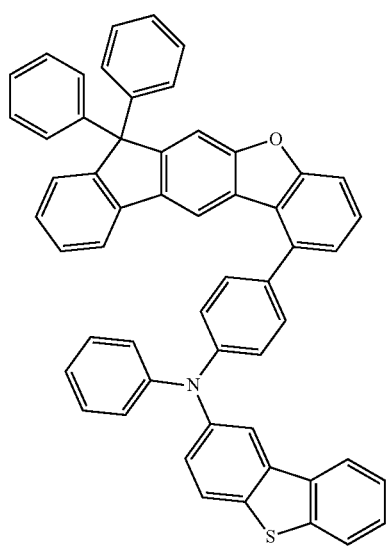
316
-continued
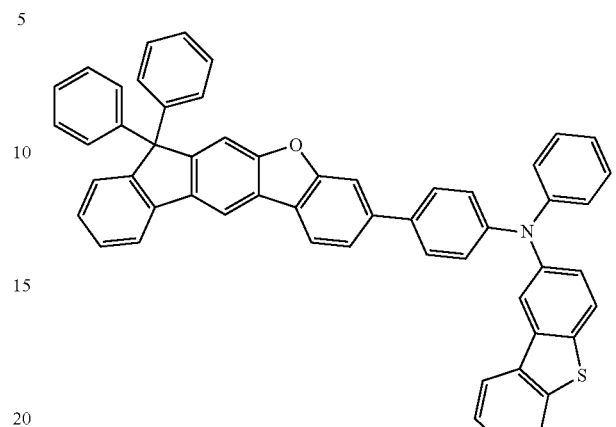
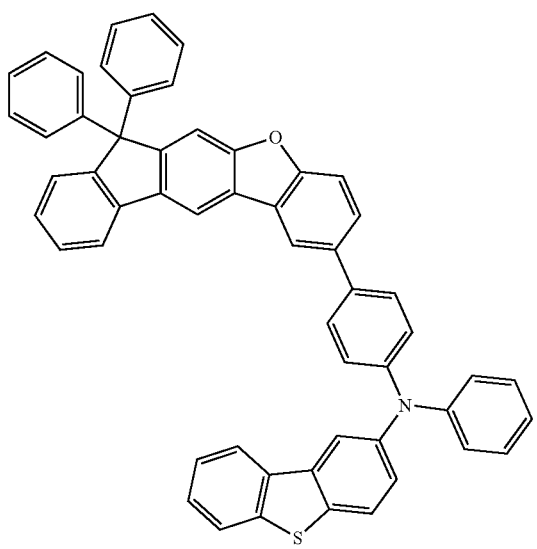
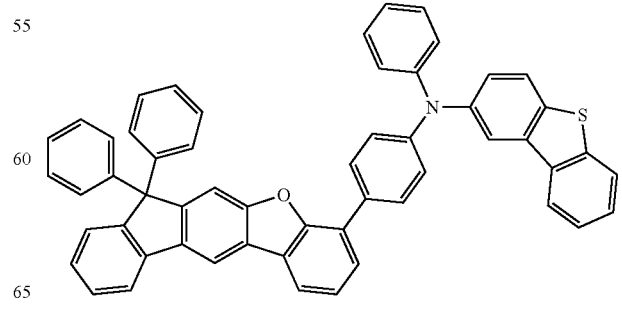

317
-continued
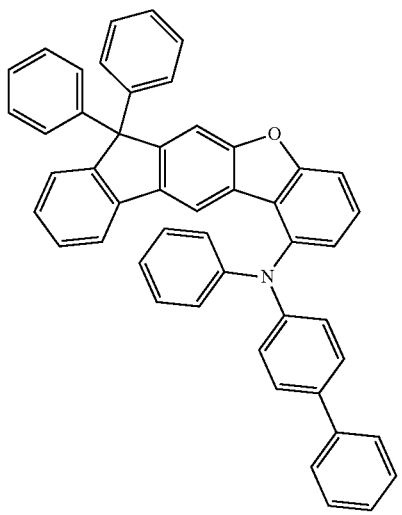
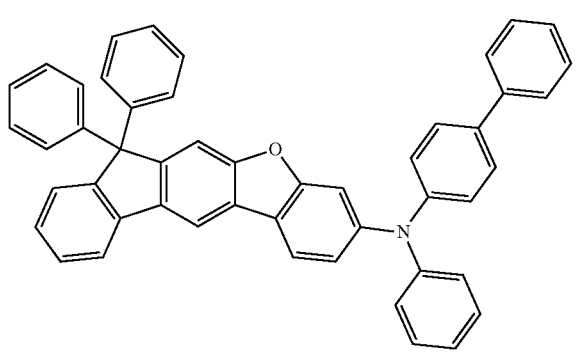
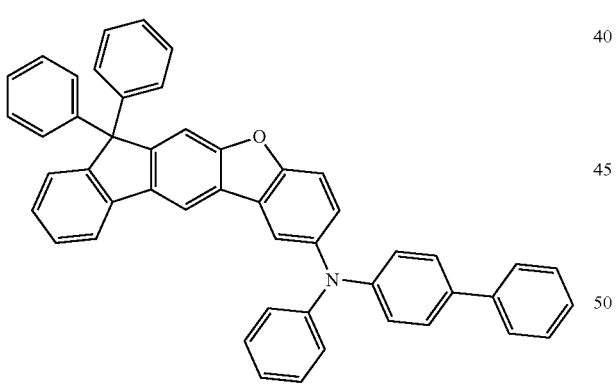
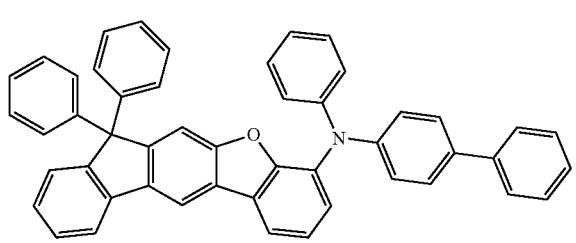
318
-continued
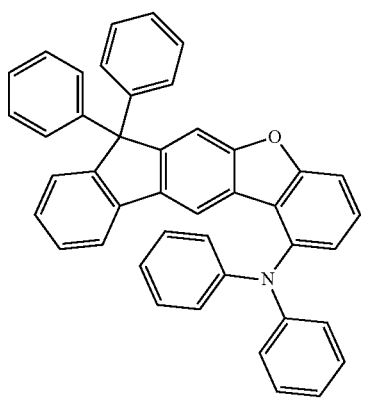
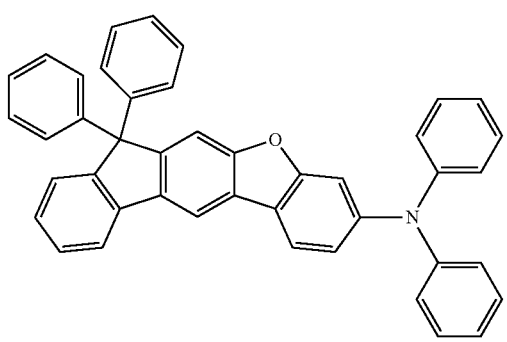
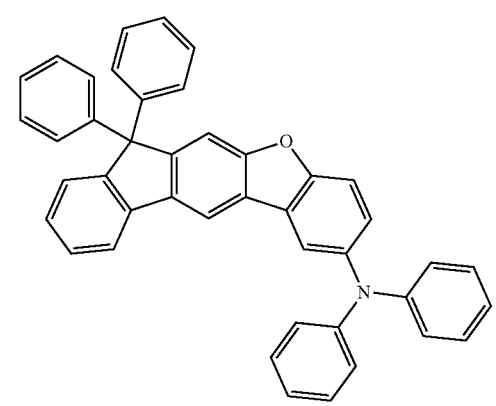
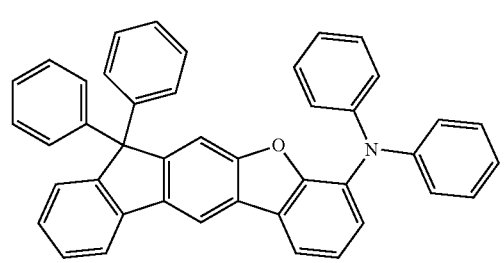

319
-continued
320
-continued
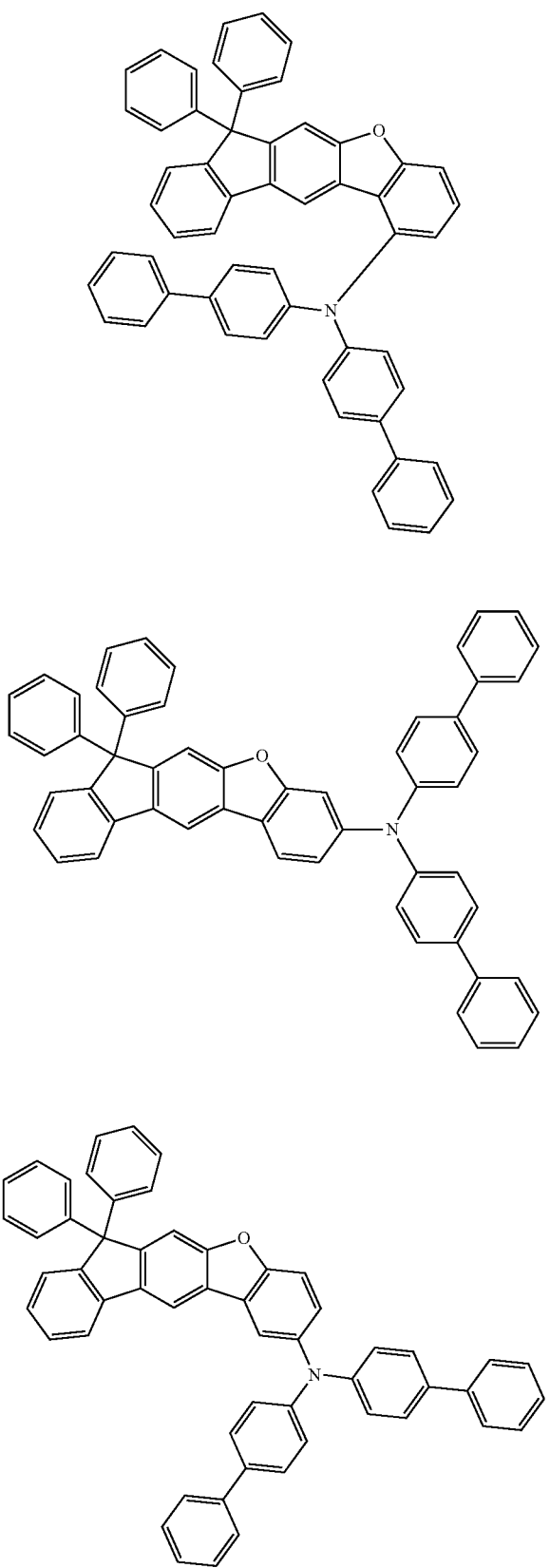
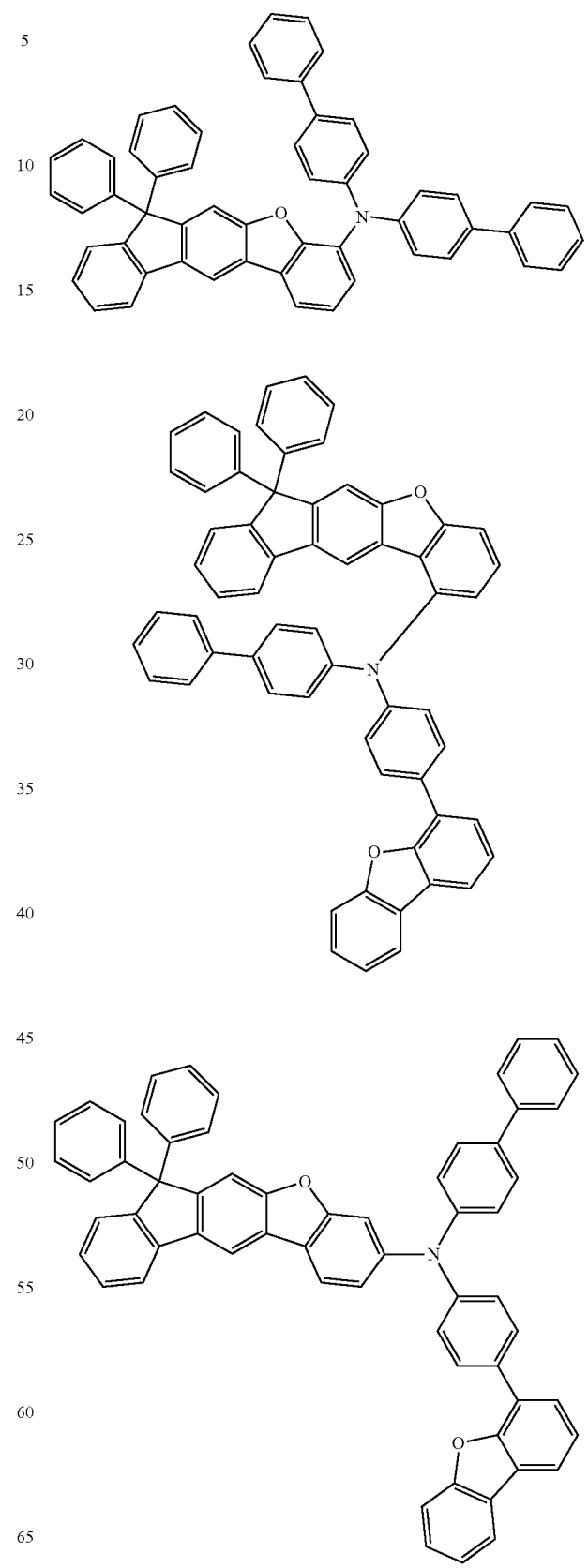

321
-continued
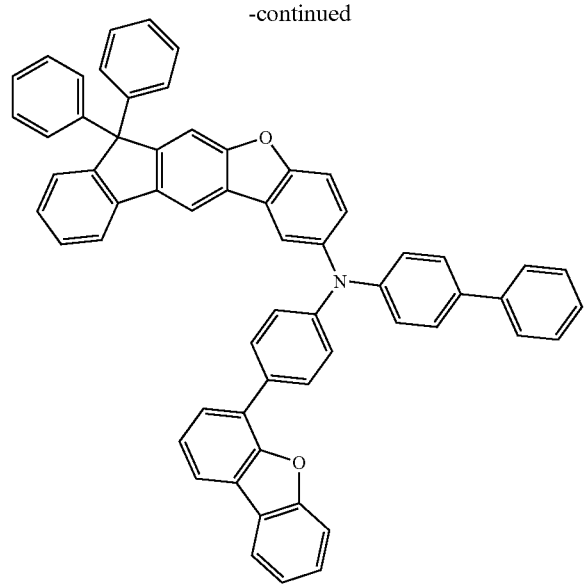
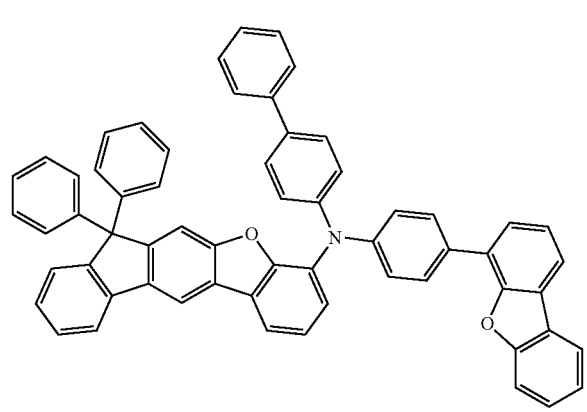
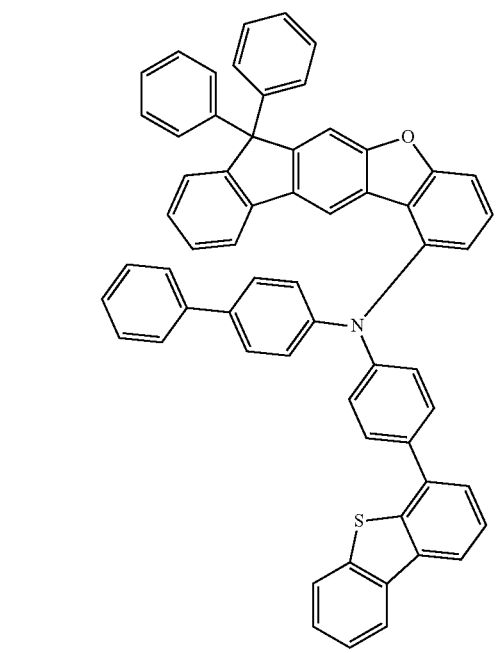
322
-continued
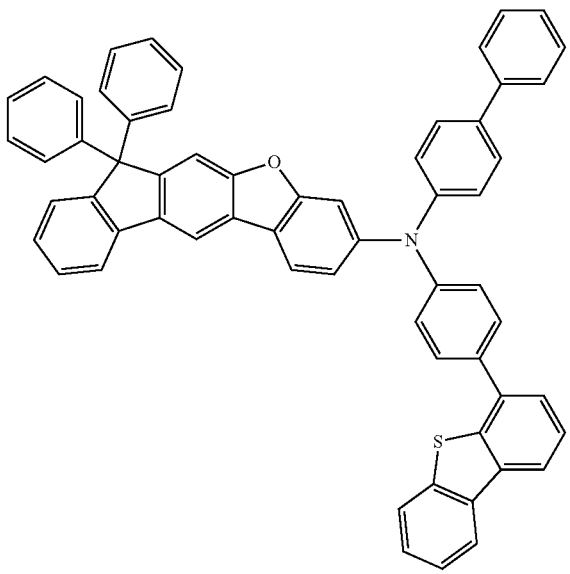
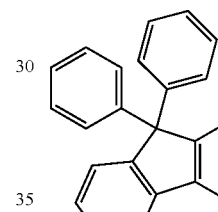
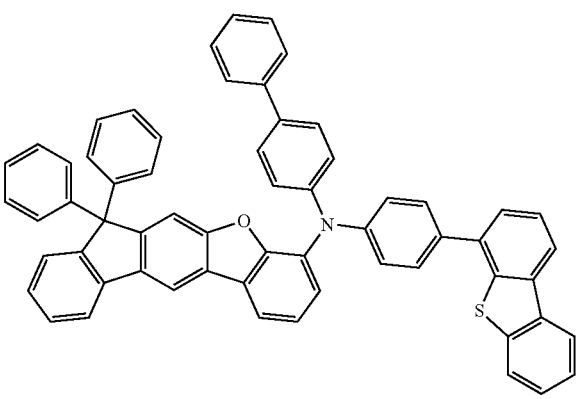

323
-continued
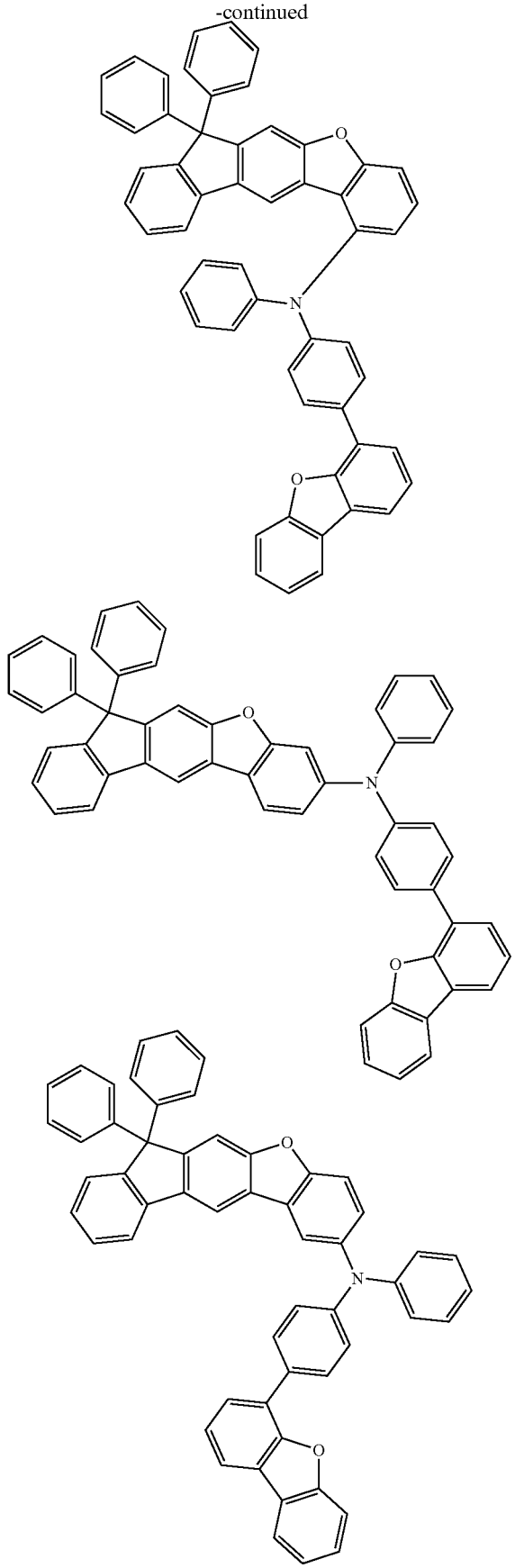
324
-continued
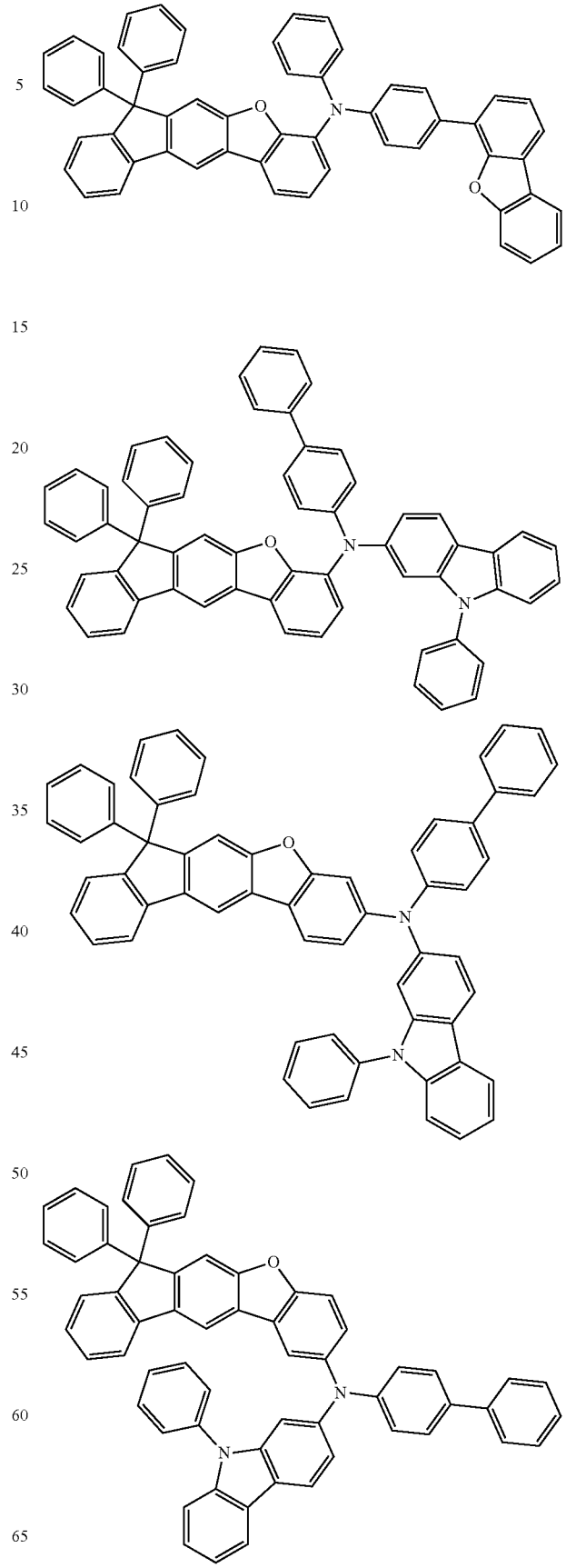

325
-continued
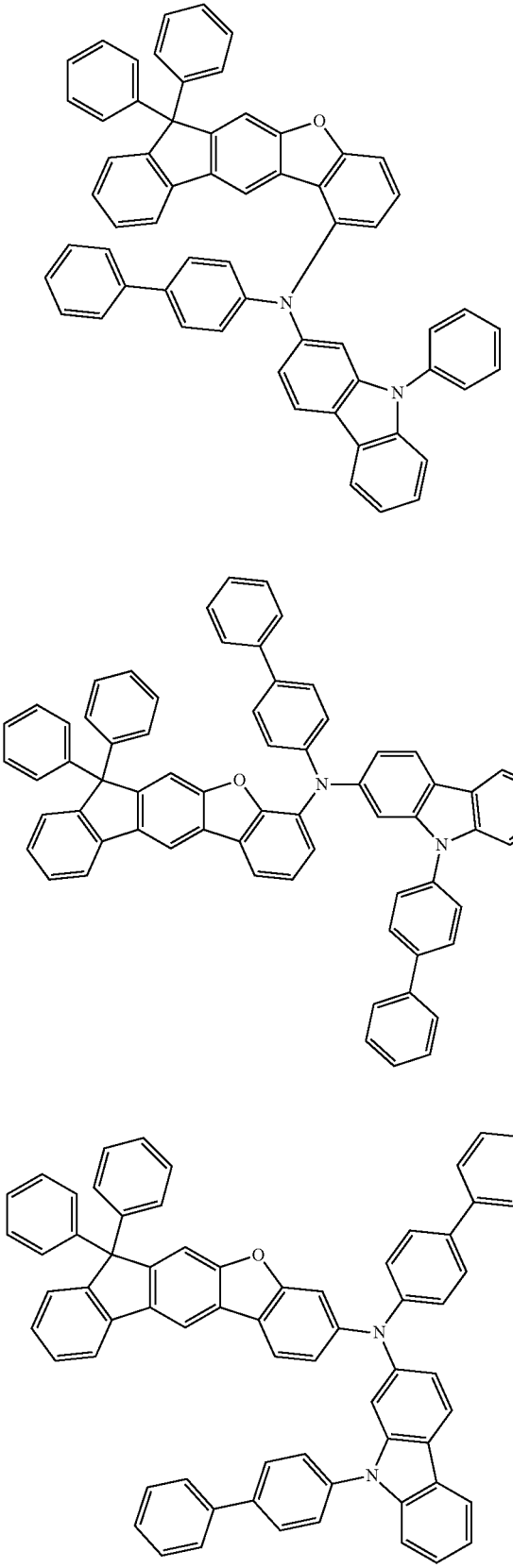
326
-continued
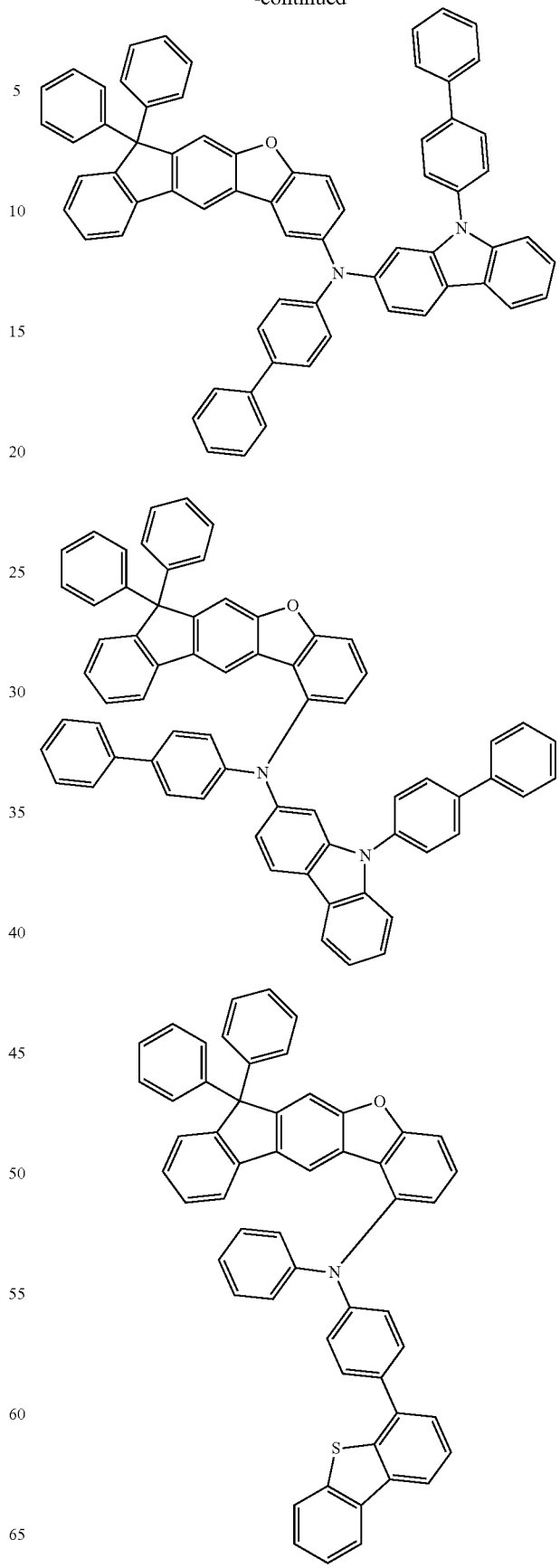

327
-continued
328
-continued
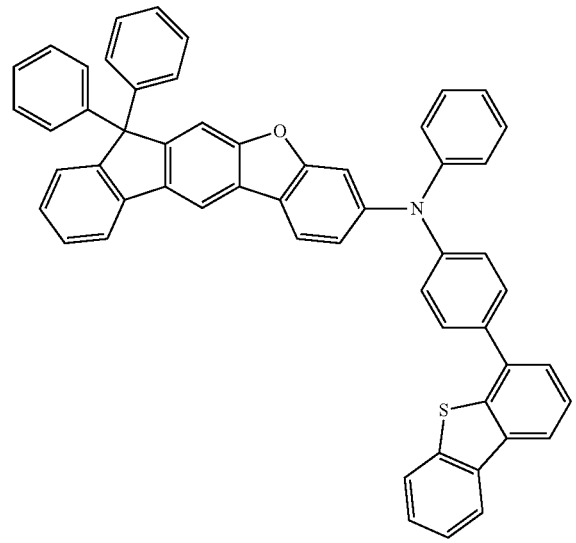
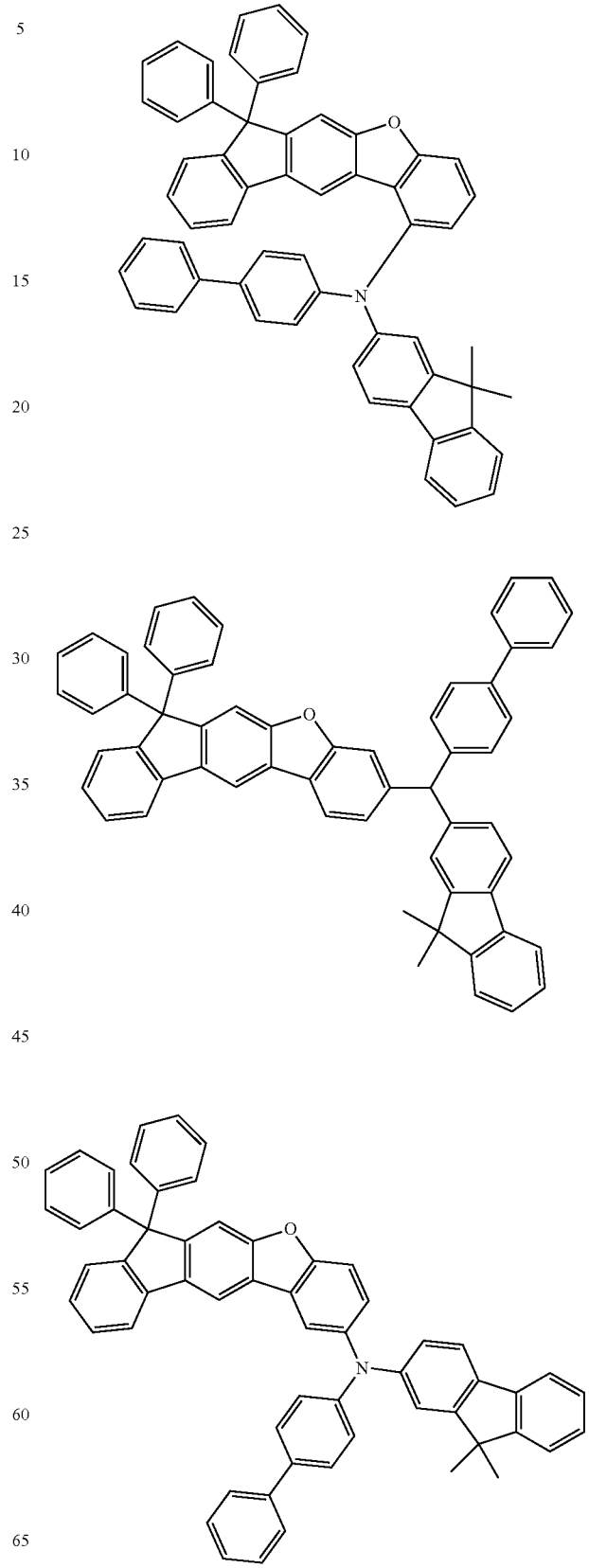

329
-continued
330
-continued
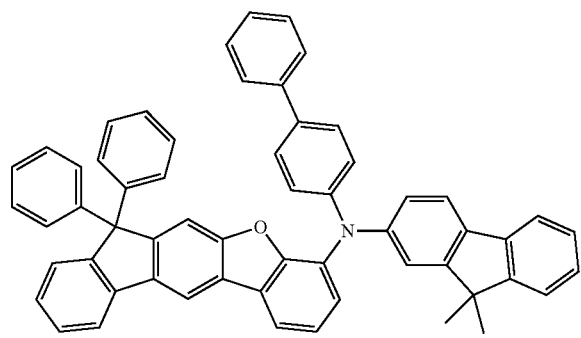
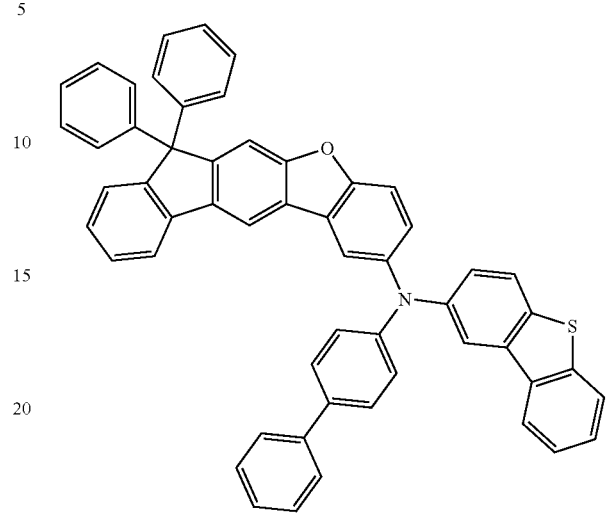
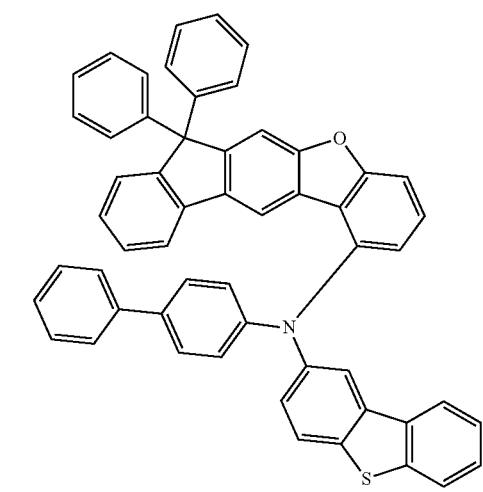
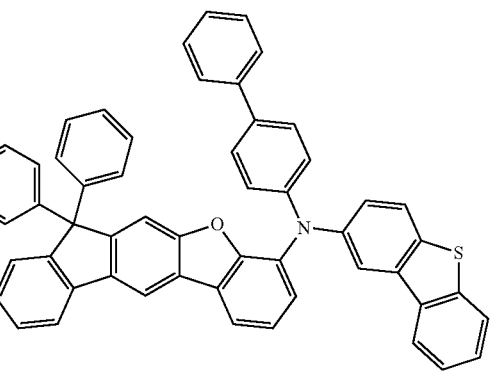
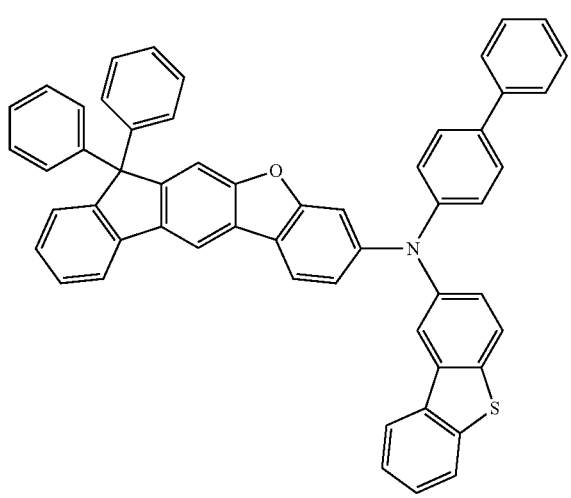
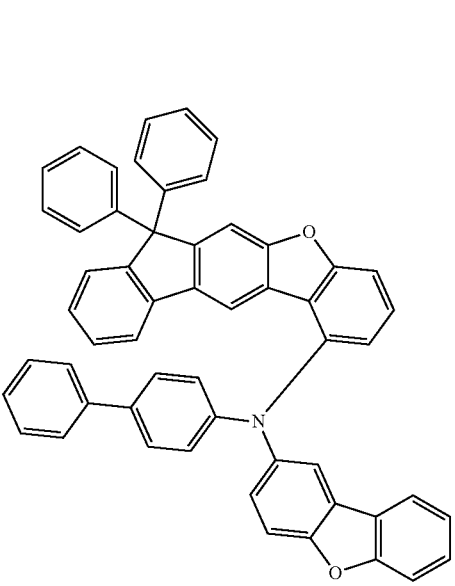

331
-continued
332
-continued
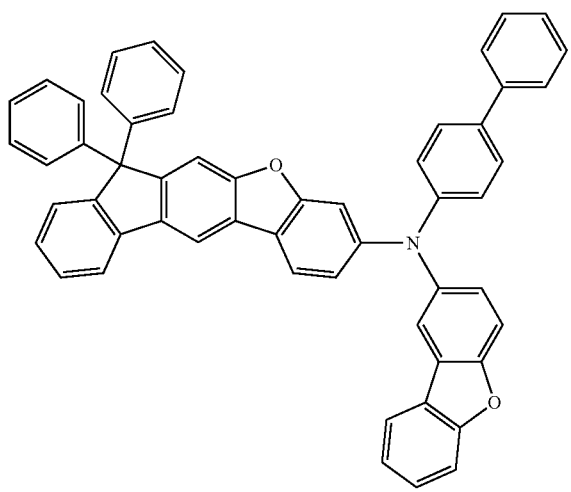
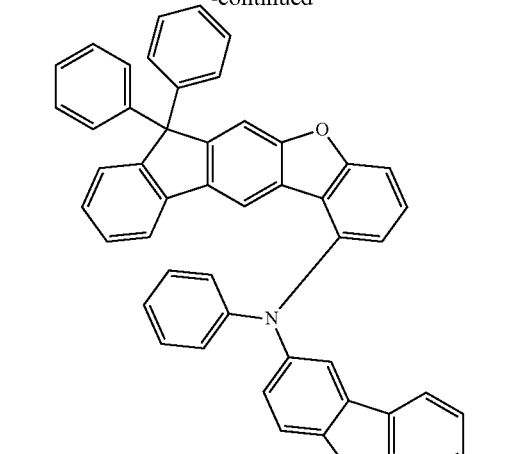
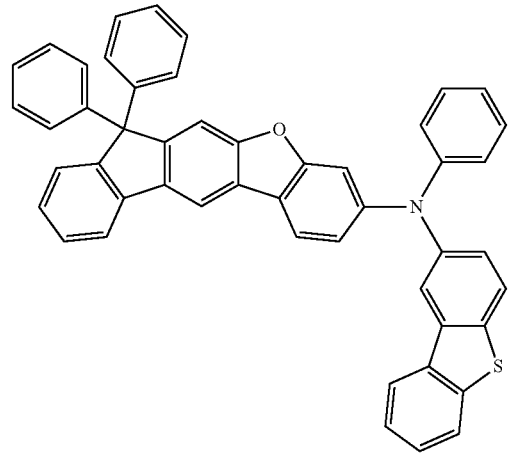
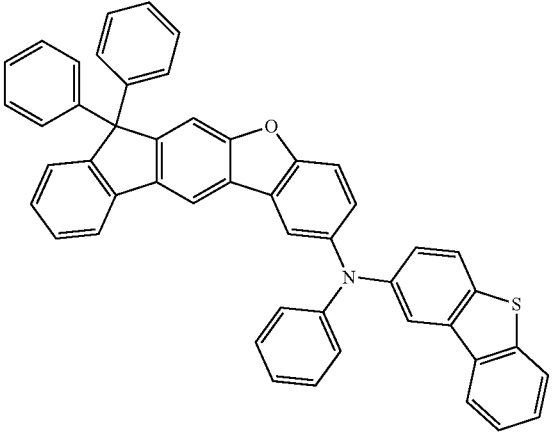
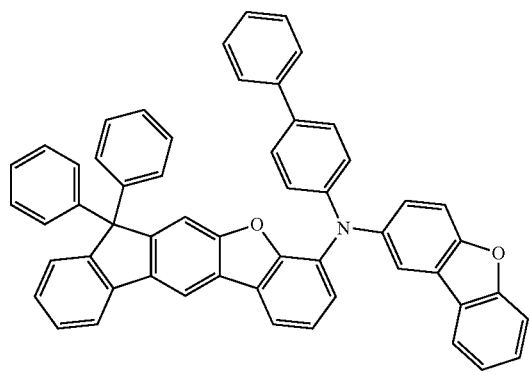
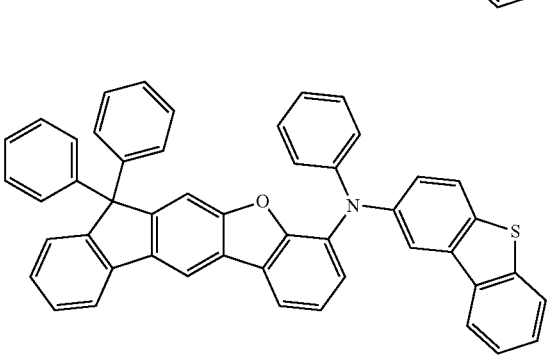

333
-continued
334
-continued
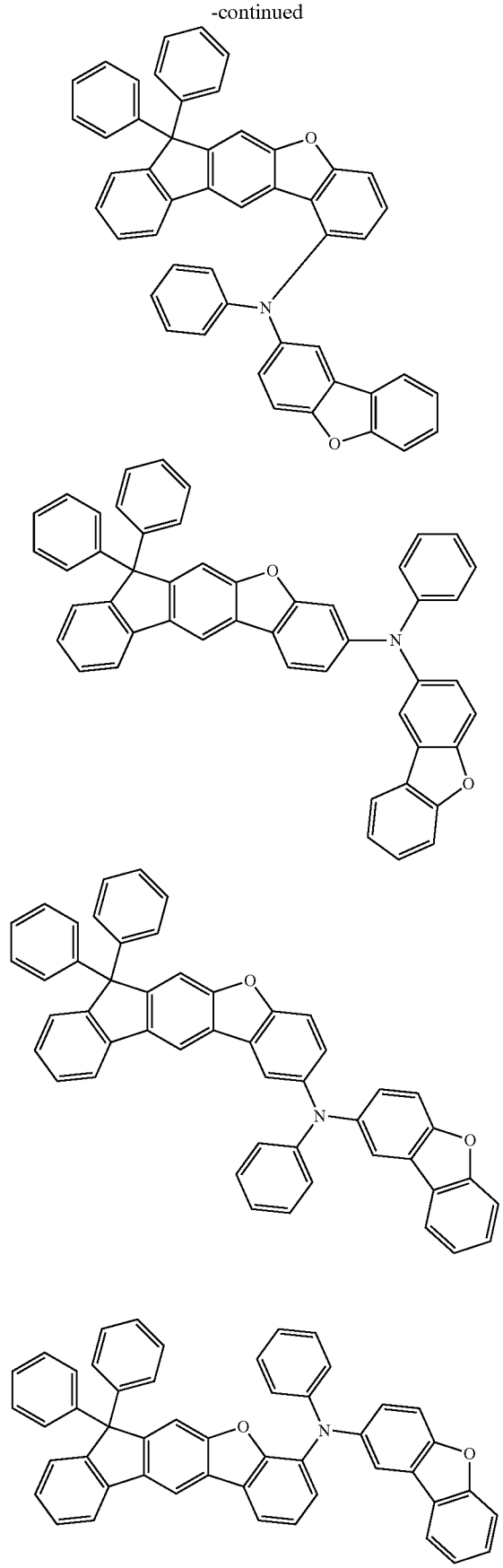
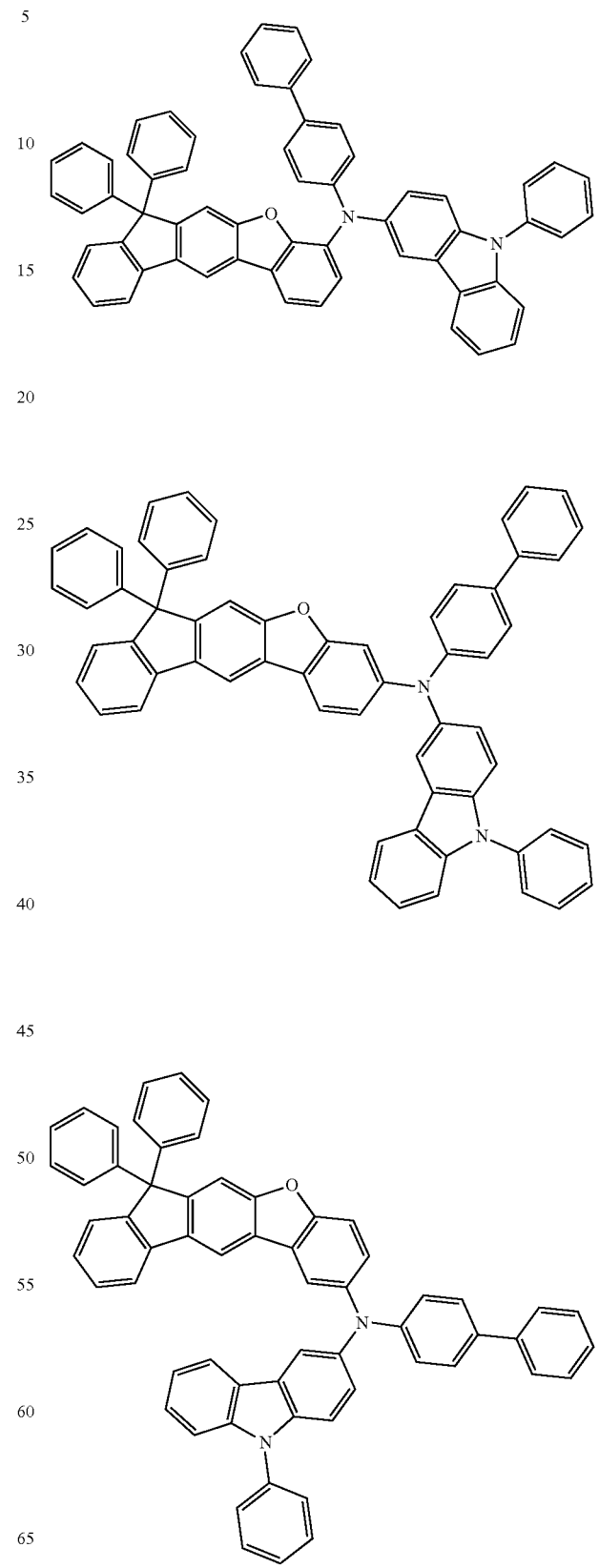

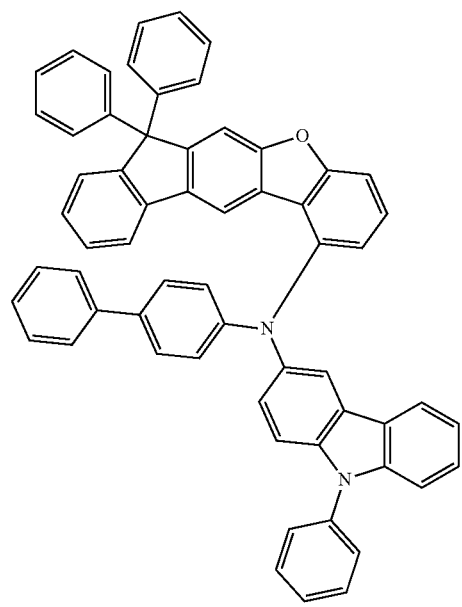

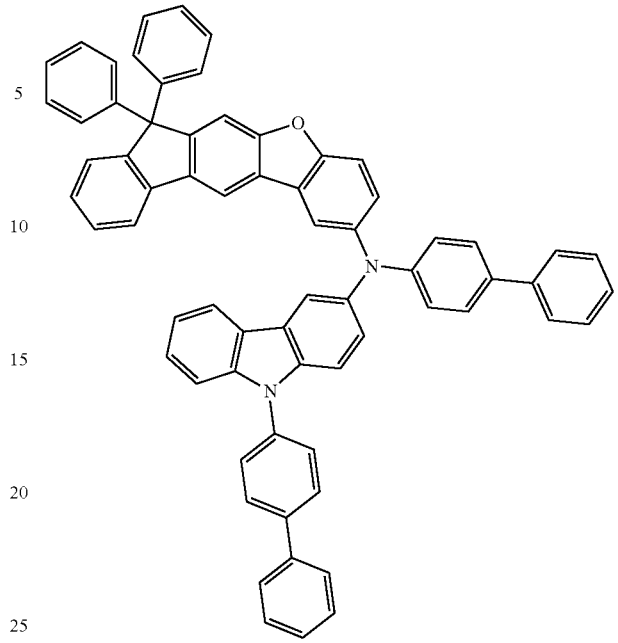

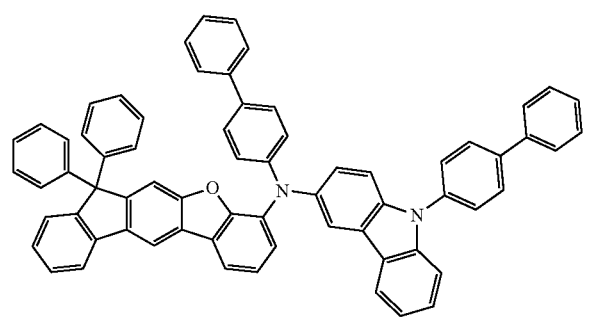

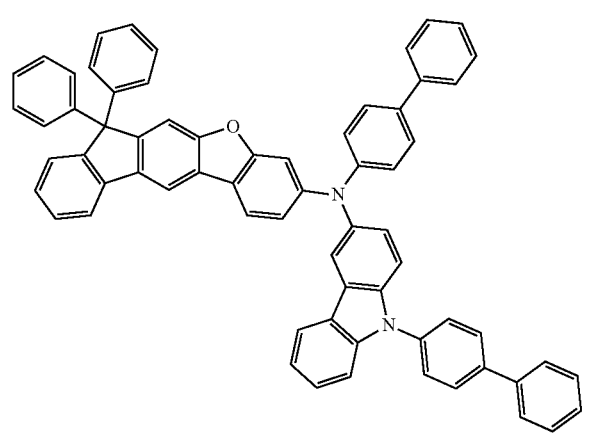

12. The organic light emitting device of claim 5, wherein the organic material layer comprises a hole transporting layer, and the hole transporting layer comprises the heterocyclic compound.

13. The organic light emitting device of claim 10, wherein the organic material layer comprises a hole transporting layer, and the hole transporting layer comprises the heterocyclic compound.

14. The organic light emitting device of claim 10, wherein the organic material layer comprises an electron blocking layer, and the electron blocking layer comprises the heterocyclic compound.

15. The organic light emitting device of claim 10, wherein the organic material layer comprises an electron transporting layer, and the electron transporting layer comprises the hetero-cyclic compound.

\* \* \* \* \*